(12) United States Patent
Shinagawa et al.

(10) Patent No.: US 7,304,174 B2
(45) Date of Patent: Dec. 4, 2007

(54) CASR ANTAGONIST

(75) Inventors: Yuko Shinagawa, Takatsuki (JP);
Teruhiko Inoue, Takatsuki (JP);
Toshihiro Kiguchi, Takatsuki (JP);
Taku Ikenogami, Takatsuki (JP); Naoki Ogawa, Takatsuki (JP); Kenji Fukuda, Takatsuki (JP); Takashi Nakagawa, Takatsuki (JP); Masanori Shindo, Takatsuki (JP); Yuki Soejima, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 519 days.

(21) Appl. No.: 10/830,480

(22) Filed: Apr. 23, 2004

(65) Prior Publication Data

US 2005/0032796 A1 Feb. 10, 2005

(30) Foreign Application Priority Data

Apr. 23, 2003 (JP) ............................. 2003-119131

(51) Int. Cl.
*C07C 560/102* (2006.01)
*C07C 562/469* (2006.01)

(52) U.S. Cl. ...................................... 560/102; 562/469
(58) Field of Classification Search .................. 564/88, 564/165, 220, 346, 451; 560/9, 11, 12, 17, 560/19, 43, 45, 48; 562/426, 429, 430, 433, 562/442, 443, 444, 452, 465, 488
See application file for complete search history.

(56) References Cited

U.S. PATENT DOCUMENTS

| | | | |
|---|---|---|---|
| 6,022,894 A | 2/2000 | Del Mar et al. | |
| 6,291,459 B1 | 9/2001 | Bhatnagar et al. | |
| 6,294,531 B1 | 9/2001 | Barmore et al. | |
| 6,334,338 B1 | 1/2002 | Mandich et al. | |
| 6,395,919 B1 | 5/2002 | Bhatnagar et al. | |
| 6,417,215 B1 | 7/2002 | Largo | |
| 6,521,667 B1 | 2/2003 | Del Mar et al. | |
| 6,916,956 B2 * | 7/2005 | Shinagawa et al. | 564/88 |
| 2002/0052509 A1 | 5/2002 | Bhatnagar et al. | |
| 2002/0099220 A1 | 7/2002 | Del Mar et al. | |
| 2003/0018203 A1 | 1/2003 | Lago et al. | |
| 2003/0212110 A1 | 11/2003 | Bhatnagar et al. | |
| 2004/0006130 A1 | 1/2004 | Shinagawa et al. | |
| 2004/0009980 A1 | 1/2004 | Bhatnagar et al. | |
| 2004/0014723 A1 | 1/2004 | Bhatnagar et al. | |
| 2004/0180912 A1 | 9/2004 | Beerti et al. | |
| 2004/0192741 A1 | 9/2004 | Lago et al. | |

FOREIGN PATENT DOCUMENTS

| | | |
|---|---|---|
| JP | 2001-501584 A | 2/2001 |
| JP | 2001-523223 A | 11/2001 |
| JP | 2002-510636 A | 4/2002 |
| JP | 2002-510671 A | 4/2002 |
| JP | 2002-522499 A | 7/2002 |
| JP | 2002-522532 A | 7/2002 |
| JP | 2002-536330 A | 10/2002 |
| WO | WO 97/37967 A1 | 10/1997 |
| WO | WO 98/45255 A1 | 10/1998 |
| WO | WO 99/51241 A1 | 10/1999 |
| WO | WO 99/51569 A1 | 10/1999 |
| WO | WO 00/09132 A1 | 2/2000 |
| WO | WO 00/09491 A1 | 2/2000 |
| WO | WO 00/45816 A1 | 8/2000 |
| WO | WO 01/53254 A1 | 7/2001 |
| WO | WO 02/07673 A2 | 1/2002 |
| WO | WO 02/14259 A1 | 2/2002 |
| WO | WO 02/34204 A2 | 5/2002 |
| WO | WO 02/38106 A2 | 5/2002 |
| WO | WO 02/102782 A1 | 12/2002 |
| WO | WO 2004/106280 | 12/2004 |

OTHER PUBLICATIONS

Brown, E.M., "Homeostatic Mechanisms Regulating Extracellular and Intracellular Calcium Metabolism, The Parathyroid," p. 19, (1994), Raven press, New York.
Tam et al., "Parathyroid Hormone Stimulates the Bone Apposition Rate Independently of its Resorptive Action: Differential Effects of Intermittent and Continuous Administration," Endocrinology, The Endocrine Society, vol. 110, No. 2, pp. 506-512, (1982).
Uzawa et al., "Comparison of the Effect of Intermittent and Continuous Administration of Human Parathyroid Hormone (1-34) on Rat Bone," Bone, Elsevier, vol. 16, No. 4, pp. 477-484, (1995).
Scutt et al., "Time-Dependent Effects of Parathyroid Hormone and Prostaglandin $E_2$ on DNA Synthesis by Periosteal Cells From Embryonic Chick Calvaria," Calcified Tissue Int., vol. 55, pp. 208-215 (1994).

(Continued)

Primary Examiner—Karl Puttlitz
(74) Attorney, Agent, or Firm—Fitzpatrick, Cella, Harper & Scinto

(57) ABSTRACT

A compound represented by the following formula (1), a pharmaceutically acceptable salt thereof or an optically active form thereof:

$$R^1 \underset{R^2}{\overset{O}{\diagdown}} \underset{R^3}{\overset{X^1}{\diagdown}} (Z)n \overset{X^2}{\diagdown} \underset{OR^5}{\overset{R^4}{\diagdown}} O \underset{H}{\overset{H_3C}{\diagdown}} \underset{CH_3}{\overset{CH_3}{\diagdown}} N(CH_2)p \underset{R^8}{\overset{Y}{\diagdown}} \underset{R^7}{\overset{R^6}{\diagdown}} \quad (1)$$

wherein each symbol is as defined in the specification. A compound having a calcium-sensing receptor antagonistic action, a pharmaceutical composition comprising the compound, particularly a calcium receptor antagonist and a therapeutic drug for osteoporosis are provided.

13 Claims, No Drawings

OTHER PUBLICATIONS

Wronski et al., "Parathyroid Hormone is More Effective Than Estrogen or Bisphosphonates for Restoration of Lost Bone Mass in Ovariectomized Rats," Endocrinology, The Endocrine Society, vol. 132, No. 2, pp. 823-831 (1993).

Wronski et al., "Anabolic Effects of Parathyroid Hormone on Cortical Bone in Ovariectomized Rats," Bone, vol. 15, No. 1, pp. 51-58, (1994).

Mosekilde et al., "The Anabolic Effects of Human Parathyroid Hormone (hPTH) on Rat Vertebral Body Mass Are Also Reflected in the Quality of Bone, Assessed by Biomechanical Testing: A Comparison Study Between hPTH-(1-34) and hPTH-(1-84)," Endocrinology, The Endocrine Society, vol. 129, No. 1, pp. 421-428 (1991).

Ejersted et al., "Human Parathyroid Hormone (1-34) and (1-84) Increase The Mechanical Strength and Thickness of Cortical Bone in Rats," Journal of Bone and Mineral Research, vol. 8, No. 9, pp. 1097-1101, (1993).

Brown et al., "Cloning and Characterization of an Extracellular $Ca^{2+}$-Sensing Receptor From Bovine Parathyroid," Letters to Nature, vol. 366, No. 9, pp. 575-580, (1993).

Gowen et al., "Antagonizing the Parathyroid Calcium Receptor Stimulates Parathyroid Hormone Secretion and Bone Formation in Osteopenic Rats," The Journal of Clinical Investigation, vol. 105, No. 11, pp. 1595-1604 (2000).

* cited by examiner

CASR ANTAGONIST

TECHNICAL FIELD

The present invention relates to a compound having a calcium-sensing receptor (CaSR, hereinafter to be simply referred to as a calcium receptor) antagonistic action, a pharmaceutical composition containing the compound, particularly a calcium receptor antagonist and a therapeutic agent of osteoporosis.

BACKGROUND ART

Calcium receptors sense extracellular $Ca^{2+}$ concentration and increase intracellular $Ca^{2+}$, thereby acting to suppress the production of parathyroid hormone (PTH) involved in the control of $Ca^{2+}$ metabolism and bone metabolism.

The serum calcium concentration of healthy mammal is strictly maintained at about 9-10 mg/100 ml (ca. 2.5 mM), which is referred to as calcium homeostasis of living organisms. When this value falls to not more than 50%, tetania occurs, and conversely, when it increases by 50%, consciousness is clouded, both cases threatening the lives. For maintaining calcium homeostasis, duodenum acts as a $Ca^{2+}$ uptake organ, bone acts as a $Ca^{2+}$ storage organ, and kidney acts as a $Ca^{2+}$ excretory organ. These $Ca^{2+}$ kinetics are controlled by various hormones generally referred to as "calcium controlling hormone". Representative hormone includes active vitamin D [$1_\alpha$, $25(OH)_2D_3$], PTH, calcitonin, Parathyroid Hormone-Related Protein (PTH-related Protein (PTHrP)) and the like.

Bone plays an important role not only as a supporting framework and motor organ of the body, but also as a storage organ of $Ca^{2+}$, which is its constituent component. To fulfill such functions, bone tissues repeat formation thereof (osteogenesis) and absorption thereof (bone resorption) throughout the entire life. For osteogenesis, osteoblast derived from mesenchymal cell plays a major role, and for bone resorption, osteoclast derived from hematopoietic cell plays a major role. The mechanism of osteogenesis includes osteoid formation by bone organic matrix (bone matrix proteins such as type I collagen and the like) produced by osteoblast present on the osteogenesis surface, and subsequent calcification. On the other hand, the mechanism of bone resorption includes adhesion of osteoclast to the bone surface, intracellular absorption of $Ca^{2+}$ via protease acid secretion and ion transport, and excretion of absorbed $Ca^{2+}$ to the bone marrow side, thereby releasing $Ca^{2+}$ into blood. The deficient part of the bone absorbed by osteoclast is repaired by osteogenesis by osteoblast. This series of phenomena are called remodeling of bone, and by the remodeling, old bones are replaced by new bones, thus maintaining the strength of the entire bone while maintaining calcium homeostasis.

When blood $Ca^{2+}$ concentration increases, calcium receptor senses it, immediately suppresses secretion of PTH from the parathyroid gland to decrease the amount of $Ca^{2+}$ to be supplied into the blood [Brown, E. M., Homeostatic mechanisms regulating extracellular and intracellular calcium metabolism, in the parathyroids, p. 19, (1994), Raven press, New York]. Secretion of PTH is also suppressed by active vitamin D [$1_\alpha$, $25(OH)_2D_3$].

Because PTH is a hormone assuming an important role in controlling $Ca^{2+}$ metabolism and bone metabolism, attempts have been made to apply PTH to the treatment of osteoporosis. In 1982, Tam et al. found that sustained administration of bovine PTH (1-84) to thyroid/parathyroid gland enucleated rat results in promotion of both osteogenesis and bone resorption of femoral cancellous bone, leading to a decrease in net bone mass, but subcutaneous intermittent administration thereof does not result in promotion of bone resorption but in promotion of osteogenesis alone, leading to an increase in the bone mass [Endocrinology, 110, 506-512 (1982)]. Furthermore, Uzawa et al. compared the actions of sustained administration and intermittent administration of PTH with regard to epiphyseal long bone and metaphyseal cancellous bone of young rat. As a result, they clarified that sustained administration of PTH results in remarkable increase in bone mass in metaphyseal cancellous bone highly susceptible to the effect of enchondral ossification, though associated with abnormal findings such as hyperplasia of epiphyseal plate cartilage, fibrous ostitis and the like, and in marked promotion of bone resorption and decrease in bone mass accompanied by rarefaction of cortical bone, in epiphyseal cancellous bone where the effect is small [Bone, 16, 477-484 (1995)]. In addition, it has been reported that intermittent administration of PTH results in significant increases in bone mass and bone trabecula in both epiphyseal and metaphyseal cancellous bones without increase in osteoclast or decrease of cortical bone.

Moreover, Scutt et al. have reported that, in chicken calvaria derived osteoblast, a short time (10-20 min) treatment with PTH promotes cell growth as compared to a long time (18 hr) treatment [Calcif. Tissue Int., 55, 208-215 (1994)]. This suggests that some of the actions of PTH on osteoblast are temporary and that expression of the action by the treatment for an extremely short time may be related to the fact that sustained administration and intermittent administration of PTH in vivo show different actions on bone tissues.

Ishizuya et al. further clarified through investigation of the action of PTH on differentiation of osteoblast using an in vitro experiment system that the action of PTH varies depending on the treatment time. They have reported that sustained action of PTH on osteoblast derived from rat calvaria resulted in strong inhibition of differentiation of osteoblast and nearly complete inhibition of osteogenesis in vitro, but repeated PTH action for the first 6 hr of 48 hr as one cycle resulted in significant promotion of differentiation of osteoblast and promotion of osteogenesis in vitro.

PTH is considered to not only prevent decrease in bone mass of osteoporosis model, but also has a bone mass recovery effect even on an animal already suffering from marked decrease in bone mass. Wronski et al. intermittently administered human PTH (1-34) to 90-day-old SD rat at 4 weeks post-ovariectomy and showing an obvious decrease in cancellous bone, for 15 weeks from 4 weeks post-ovariectomy. As a result, promotion of osteogenesis and inhibition of bone resorption were observed during the period of from week 5 to week 10 after the start of the administration, showing increased bone mass of about twice the bone mass of sham operation group [Endocrinology, 132, 823-831 (1993)]. They have also reported that, in this experiment, estrogen and bisphosphonate prevented decrease in bone mass caused by ovariectomy but did not show increase in bone mass, unlike PTH. They analyzed in detail the cortical bone of this experiment system and found images showing promoted osteogenesis and bone mass increase on the periost side and endosteum side by intermittent administration of human PTH (1-34), based on which they have clarified that the increase in cancellous bone due to PTH did not accompany decrease in cortical bone [Bone, 15, 51-58 (1994)].

Furthermore, Mosekilde et al. have reported that intermittent administration of human PTH (1-34) or human PTH (1-84) causes not only an increase in bone mass but also a dose-dependent increase in compression strength and bending strength, which are indices of bone substance, of cancellous bone [Endocrinology, 129, 421-428 (1991)] and cortical bone [J. Bone Miner. Res., 8, 1097-1101 (1993)] of rat vertebral bone. As discussed above, since PTH shows an obvious bone mass increasing action in experimental animals, various investigations are ongoing as regards the restrictive conditions expected in actual clinical applications. Mizoguchi studied whether or not a pharmacological effect is observed by intermittent administration of PTH, even when PTH in blood, which is considered to be one of the factors responsible for osteoporosis, has significantly increased, and concluded that the bone mass increased as usual [Journal of Japanese Society of Bone Morphometry, vol. 5, pp. 33-39 (1995)]. Takao et al. have studied the frequency of PTH administration and reported that administration of once a week for 12 weeks to healthy rat scarcely promoted bone resorption but dose-dependently increased the bone mass [Japanese Journal of Bone Metabolism, vol. 12 (Suppl.), p. S343 (1994)], suggesting possible effectiveness of clinically useful low frequency administration. The foregoing achievements suggest the possibility of PTH for making a potent and promising therapeutic drug for the treatment of postmenopausal osteoporosis or postovariectomy osteoporosis, which increases bone mass and decreases bone fracture rate.

These results clearly indicate that intermittent administration of PTH would enable treatment of osteoporosis. On the other hand, PTH problematically requires injection as an administration route, which is painful for many patients. However, an orally administrable pharmaceutical agent that can intermittently increase PTH concentration in blood is greatly expected to become a therapeutic drug of osteoporosis, which is based on a new action mechanism different from that of the above-mentioned PTH and conventional calcitonin.

Calcium receptor is a G protein coupled receptor, which is cloned as a molecule essential for controlling PTH secretion, and which penetrates cell membrane 7 times. Human calcium receptor consists of 1078 amino acids, and shows 93% amino acid homology with bovine calcium receptor. Human calcium receptor consists of a large N terminal extracellular region consisting of 612 amino acids, a cell membrane penetration region consisting of 250 amino acids and a C terminal intracellular region consisting of 216 amino acids.

Expression of calcium receptor has been found in parathyroid gland, kidney, thyroid C cell, brain and the like, as well as in bone (bone marrow cells).

When calcium receptor is bound with a ligand such as $Ca^{2+}$ and the like, it activates phospholipase C in conjugation with G protein, causes production of inositol triphosphate and increase in intracellular $Ca^{2+}$ concentration, and as a result, suppresses secretion of PTH [Nature, 366, 575-580 (1993)].

As mentioned above, a pharmaceutical agent that inhibits activation of calcium receptor, or a pharmaceutical agent that antagonizes calcium receptor, removes suppression of PTH secretion in parathyroid gland cells, and promotes secretion of PTH. It is considered that, if the antagonistic action can increase blood PTH concentration discontinuously and intermittently, its antagonist is expected to show the same effect as that provided by intermittent administration of PTH, and a pharmaceutical agent extremely effective for the treatment of osteoporosis can be provided.

In contrast, cytochrome (cytochrome P450, hereinafter P450) is a protein having a molecular weight of about 50,000, which contains protoheme, and its physical functions vary over a wide range. For example, it has a function of an enzyme catalyzing various reactions in the drug metabolism. CYP2D6 belonging to the family of P450 (CYP) is an important enzyme for human drug metabolism, and is involved in the metabolism of many compounds. When a drug inhibiting the metabolic function of CYP2D6 is administered, the drug is accumulated in the body and may exert a strong influence. Accordingly, a compound having a weak inhibitory action on the metabolic function of CYP2D6 is desirable as a drug.

Heretofore, various compounds useful as CaSR antagonists have been reported.

Specifically, for example, a compound represented by the following formula

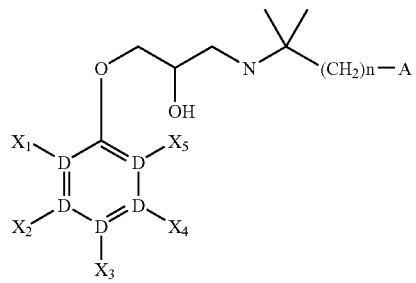

wherein A is aryl etc., D is C or N, $X_1$ and $X_5$ are each hydrogen, cyano etc., and $X_2$, $X_3$ and $X_4$ are each hydrogen, halogen, $C_{1-4}$ alkyl etc. (WO 02/38106) is mentioned.

In addition, a compound represented by the following formula

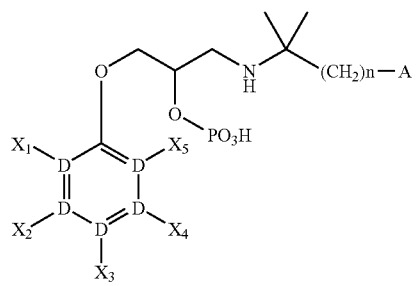

wherein A is aryl etc., D is C or N, $X_1$ and $X_5$ are each hydrogen, cyano etc., $X_2$ is hydrogen etc., and $X_3$ and $X_4$ are each hydrogen, $C_{1-4}$ alkyl etc. (WO 02/34204) is mentioned.

Furthermore, a compound represented by the following formula

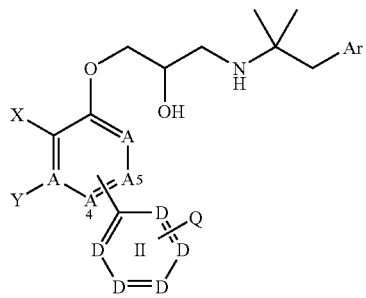

wherein A is C or N, D is C or N, X is cyano, nitro etc., Y is chlorine, fluorine etc., and Ar is phenyl, naphthyl etc. (WO 02/07673) is mentioned.

In addition, a compound represented by the following formula

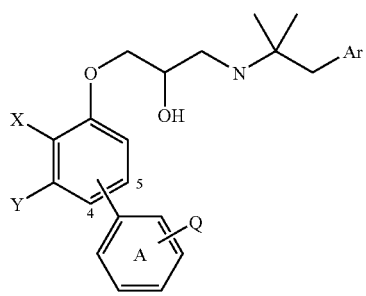

wherein X is cyano, nitro etc., Y is chlorine, fluorine etc., and Ar is phenyl, naphthyl etc. (JP 2002-536330-T, WO 00/45816, EP 1148876-A, U.S. Pat. No. 6,417,215), and a compound represented by the following formula

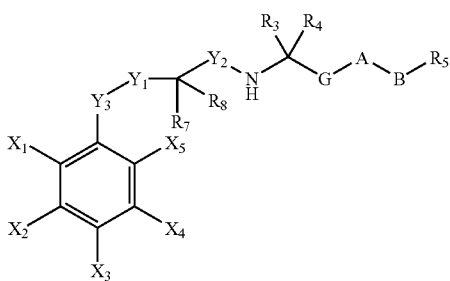

wherein $X_1$, $X_2$, $X_3$, $X_4$ and $X_5$ are each H, halogen and the like, $Y_1$ is a covalent bond, or a non-substituted or a substituted alkylene, etc., $Y_2$ is a non-substituted or a substituted methylene, $C_{1-4}$ alkyl etc., $Y_3$ is a covalent bond, O etc., $R_3$ and $R_4$ are each independently methyl, ethyl etc., $R_5$ is aryl, fused aryl etc., $R_7$ is H, OH etc., $R_8$ is H, $C_{1-4}$ alkyl etc., A and B are independently a bond, $CH_2$ etc., G is a covalent bond, $CHR_6$ ($R_6$ is H etc.) etc. (JP 2002-510671-T, WO 99/51569, EP 1070048-A, U.S. Pat. No. 6,395,919) are described.

As a CaSR antagonist, a compound represented by the following formula

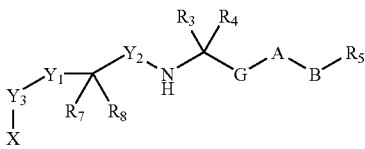

wherein X is a compound represented by the following formula

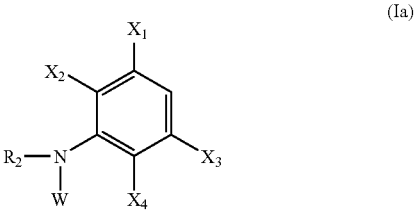

(Ia)

wherein $X_1$, $X_2$, $X_3$ and $X_4$ are each independently CN, $NO_2$ etc., then W is $R_1$, $SO_2R_1$ etc., $R_2$ is H, $C_{1-4}$ alkyl etc., and the like, $Y_1$ is a covalent bond, or a non-substituted or a substituted alkylene etc., $Y_2$ is a non-substituted or a substituted methylene etc., $Y_3$ is a covalent bond, O etc., $R_3$ and $R_4$ are independently methyl, ethyl etc., $R_5$ is heteroaryl, fused heteroaryl etc., $R_7$ is H, OH etc., $R_8$ is H, $C_{1-4}$ alkyl etc., A and B are each independently a bond, $CH_2$ etc., and G is a covalent bond, $CHR_6$ ($R_6$ is H etc.) etc. (JP 2002-510636-T, WO 99/51241, EP 1069901-A, US 2002052509-A) is described.

As a CaSR antagonist, a compound represented by the following formula

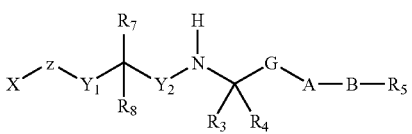

wherein $Y_1$ is a covalent bond, alkylene etc., $Y_2$ is a non-substituted or a substituted methylene, $C_{1-4}$ alkyl etc., Z is a covalent bond, O etc., $R_3$ and $R_4$ are each independently methyl, ethyl etc., $R_5$ is phenyl, naphthyl etc., G is a covalent bond or C—$R_6$ wherein $R_6$ is H, OH etc., $R_7$ is H, OH etc., $R_8$ is H, $C_{1-4}$ alkyl etc., A-B moiety is $CH_2CH_2$, a covalent bond etc., and X is a following formula

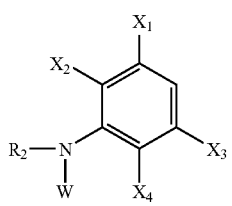

wherein W is $R_1$, $SO_2R_1$ wherein $R_1$ is hydrogen, $C_{1-4}$ alkyl etc., and the like, $X_1$, $X_2$, $X_3$ and $X_4$ are each independently CN, $NO_2$ etc., $R_2$ is hydrogen, $C_{1-4}$ alkyl etc., and the like (JP 2001-523223-T, WO 98/45255, EP 973730-A, U.S. Pat. No. 6,294,531), a compound represented by the following formula

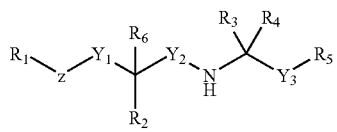

wherein $R_1$ is aryl etc., $R_2$ is hydroxyl group etc., $R_3$ and $R_4$ are each lower alkyl etc., $R_5$ is substituted naphthyl, substituted phenyl etc., $Y_1$ is alkylene etc., $Y_2$ is alkylene, $Y_3$ is alkylene and Z is oxygen etc. (JP 2001-501584-T, WO 97/37967, EP 901459-A, U.S. Pat. No. 6,022,894), a compound represented by the following formula

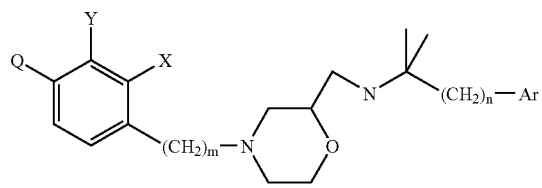

wherein X is nitro etc., Y is hydrogen etc., Q is $C_{1-4}$ alkyl etc., Ar is phenyl, naphthyl etc., m is 0-2 and n is 1-3 (JP 2002-522499-T, WO 00/09132, EP 1112073-A), and a compound represented by the following formula

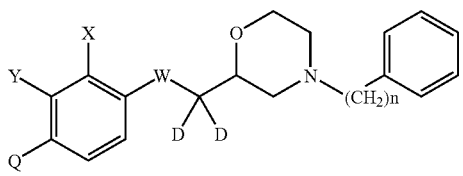

wherein X is cyano etc., Y is chlorine etc., Q is hydrogen etc., W is oxygen etc., D is hydrogen etc. and n is 2-4 (JP 2002-522532-T, WO 00/09491, EP 1104411-A) are described.

Maxine Gowen et al. administered a compound having a CaSR antagonistic action, which is called NPS-2143,

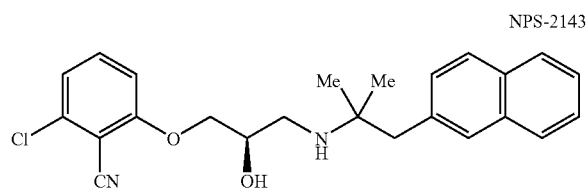

NPS-2143 to OVX rats orally and measured blood concentration and bone density thereof, thereby testing the effect of NPS-2143 on osteogenesis, and reported the results thereof (The Journal of Clinical Investigation, vol. 105, pp. 1595-1604 (2000)).

According to the report, NPS-2143 significantly promotes release of PTH, but it did not show any direct effect on osteoblast and osteoclast in vitro and was free of bone decrease or bone increase. One of the reasons pointed out therefor is too long a half-life of NPS-2143 in blood. That is, when rat PTH (1-34) was administered to OVX rat at the dose of 5 μg/kg, blood PTH concentration reached the peak of about 175 pg/ml in 30 minutes and returned to the original level in 2 hours, but when NPS-2143 was administered at the dose of 100 μmol/kg, the blood PTH concentration reached about 115 pg/ml in 30 minutes and kept increasing and showed about 140 pg/ml even 4 hours later (The Journal of Clinical Investigation, vol. 105, p.1595-1604 (2000), especially p. 1598, FIG. 3).

At that time, the blood concentration of NPS-2143 itself was maintained at the level of not less than 100 ng/ml even 8 hours after the administration. It was 24 hours later when the concentration became 10 ng/ml or below the undetectable level.

The above-mentioned Maxine Gowen et al. reference teaches that a calcium receptor antagonist having a too long blood half-life provides results as in continuous administration of PTH, where a bone mass increase cannot be expected. Thus, most of the conventional calcium receptor antagonists continuously increase the blood PTH concentration and cannot be expected to provide a sufficient osteogenesis promoting action. Of the conventional calcium receptor antagonists, a compound represented by the following formula [I]

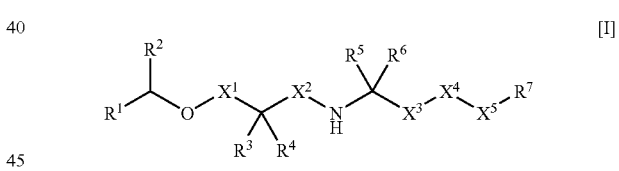

[I]

wherein $R^1$ is optionally substituted aryl group etc., $R^2$ is $C_{1-6}$ alkyl group, $C_{3-7}$ cycloalkyl group etc., $R^3$ is hydroxyl group etc., $R^4$ is hydrogen atom etc., $R^5$ and $R^6$ are $C_{1-6}$ alkyl group etc., $R^7$ is optionally substituted aryl group etc., $X^1$ is a single bond, $C_{1-6}$ alkylene etc., $X^2$ is optionally substituted $C_{1-6}$ alkylene, $X^3$ is a single bond or optionally substituted $C_{1-6}$ alkylene, and $X^4$ and $X^5$ are linked to form a single bond, methylene etc., which has a superior calcium receptor antagonistic action, which can be administered orally and intermittently, and which can increase blood PTH concentration discontinuously and intermittently, is disclosed (WO02/14259). By comparison of the activities of a compound within the scope disclosed in this publication and the compound of the present invention, the compound of the present invention was surprisingly found to have a higher activity and to be a compound having a lower inhibitory action on the metabolic enzyme CYP2D6.

However, there are not many reports on such an effective compound, and further study is desired.

DISCLOSURE OF THE INVENTION

The present invention aims at providing a compound having a superior calcium receptor antagonistic action, which can be administered orally and intermittently, and which can increase blood PTH concentration discontinuously and intermittently. The present invention also aims at providing a pharmaceutical composition permitting oral administration, which comprises this compound, and which is effective as a therapeutic drug for a disease accompanying abnormal calcium homeostasis, or osteoporosis, hypoparathyroidism, osteosarcoma, periodontitis, bone fracture, osteoarthrisis, chronic rheumatoid arthritis, Paget's disease, humoral hypercalcemia syndrome, autosomal dominant hypocalcemia and the like, particularly a therapeutic drug for osteoporosis.

It has reported that blood calcium concentration causes an increasing of dopamine in the brain and then improve a condition of Parkinson's disease and dementia. The compound of the present invention is also expected a therapeutic drug for Parkinson's disease and dementia because of increasing blood PTH concentration and consequently increasing blood calcium concentration.

To solve the above-mentioned problems, the present inventors have conducted intensive studies and, as a result, found that a compound represented by the following formula (1) has a superior calcium receptor antagonistic action, and can be administered orally and intermittently, which resulted in the completion of the present invention. A compound represented by the following formula (1) can surprisingly increase the blood PTH concentration discontinuously and intermittently, and is greatly expected to have practicality as a superior therapeutic drug for osteoporosis.

A compound represented by the following formula (1) of the present invention is characterized in that a carbon atom adjacent to an oxygen atom has a structure of

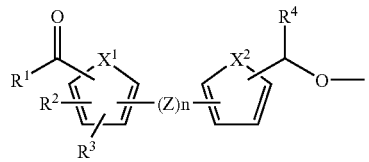

wherein each symbol is as defined above. As is clear from the following Experimental Examples, the compound of the present invention having this structure is superior in calcium receptor antagonistic action, and also has a noncontinuous and transitional PTH secretagogue action. Accordingly, by administration of the compound of the present invention, a similar effect as in the intermittent administration of the PTH can be achieved, which is considered to be extremely effective for the treatment of osteoporosis. In addition, as shown in the Experimental Examples below, the compound of the present invention shows a weak inhibitory action on the metabolic function of P450, especially CYP2D6, which is desirable as a pharmaceutical product. The PTH secretion action of the present invention was shown even low dose compared with a compound as known before. The compound of the present invention was improved a property of absorption and solubility. It is also clear that the compound of the present invention has a weak side effect.

The present invention relates to a compound represented by the following formula (1), a calcium receptor antagonist and a therapeutic drug for osteoporosis, which comprise this compound as an active ingredient. More particularly, the present invention provides the following [1] to [44].

[1] A compound represented by the following formula (1), a pharmaceutically acceptable salt thereof or an optically active form thereof (hereinafter sometimes to be collectively abbreviated as compound (1)):

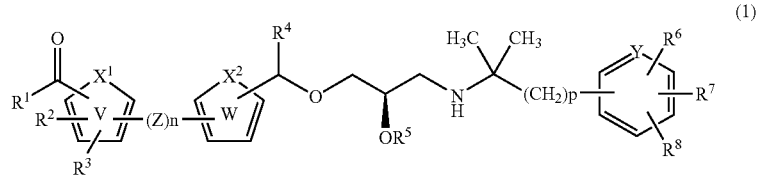

(1)

wherein n is 0 or 1, p is an integer of 1 to 3, $R^1$ is a hydroxyl group, a $C_{1-6}$ alkoxy group or $R_A$,
  wherein $R^A$ is $R^c$—OC(=O)O—$C_{1-4}$alkylene-O— or OH—NH—,
    wherein $R^C$ is a $C_{1-6}$ alkyl group or a $C_{3-6}$ cycloalkyl group, $R^2$ and $R^3$ are the same or different and each is a hydrogen atom, a hydroxyl group, a halogen atom, an amino group, a $C_{1-7}$ acylamino group, a halo $C_{1-6}$ alkyl group, a carboxyl group, a $C_{1-6}$ alkoxy-carbonyl group, a $C_{1-6}$ alkoxy group, a halo $C_{1-6}$ alkoxy group, a $C_{1-6}$ alkyl group, a hydroxy-$C_{1-6}$ alkyl group, a $C_{1-7}$ acylamino-$C_{1-6}$ alkyl group, a $C_{2-6}$ alkenyl group, an aralkyl group, a phenyl group, a $C_{1-6}$ alkylamino group, a di($C_{1-6}$ alkyl)amino group, a $C_{1-6}$ alkoxy-$C_{1-6}$ alkyl group, a mercapto group, a cyano group, a nitro group, a morpholino group, a piperidino group or a pyrrolidino group, or $R^2$ and $R^3$ are joined to form an ethyleneoxy group, $X^1$ is —C=C—, —C=N—, an oxygen atom or a sulfur atom, Z is —S—, —SO—, —SO$_2$—, —(CH$_2$)$_{m1}$—O—, —O—(CH$_2$)$_{m1}$—, —(CH$_2$)$_{m2}$—NH—, —NH—(CH$_2$)$_{m2}$—, —(CH$_2$)$_{m3}$—N(CH$_3$)—, —N(CH$_3$)—(CH$_2$)$_{m3}$—, a $C_{1-4}$ alkylene group, —SO$_2$—N(CH$_3$)—, —N(CH$_3$)—SO$_2$—, —NHCO—, —CONH— or a $C_{2-4}$ alkenylene group,
  wherein m1, m2 and m3 are each an integer of 0 to 2, $X^2$ is —C=C—, an oxygen atom or a sulfur atom, R[4] is a $C_{1-6}$ alkyl group or a $C_{3-6}$ cycloalkyl group, R[5] is a hydrogen atom or $R^B$,
   wherein $R^B$ is a $C_{1-7}$ acyl group optionally substituted by a carboxyl group, Y is a carbon atom or a nitrogen atom, and R[6], R[7] and R[8] are the same or different and each is a hydrogen atom, a halogen atom, a $C_{1-6}$ alkyl group, a $C_{1-6}$ alkoxy group, a halo $C_{1-6}$ alkyl group, a halo $C_{1-6}$ alkoxy group, a carboxyl group, a hydroxyl group, a cyano group, a nitro group, a phenyl group, a $C_{3-6}$ cycloalkyl group, a di($C_{1-6}$ alkyl)aminocarbonyl group or a hydroxy-$C_{1-6}$ alkyl group, or adjacent R[6] and R[7] are joined to form —CH=CH—CH=CH—, —C(OH)=CH—CH=CH—, —CH=C(OH)—CH=CH—, —O—$(CH_2)_{k1}$—O—, —O—$(CH_2)_{k2}$— or —$(CH_2)_{k3}$—,
   wherein k1 is an integer of 1 to 4, k2 is an integer of 2 to 5, k3 is an integer of 3 to 6, provided that when R[2] and R[3] are both hydrogen atoms and n is 1, then Z should be a group other than —$SO_2$—N($CH_3$)— wherein sulfur atom is bonded to ring V and a nitrogen atom is bonded to ring W, a pharmaceutically acceptable salt thereof or an optically active form thereof.

[2] The compound of the above-mentioned [1], which has a configuration represented by the following formula (1')

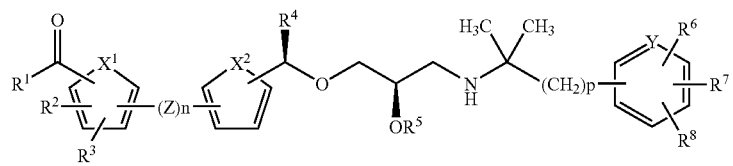

(1')

wherein each symbol is as defined above in [1], or a pharmaceutically acceptable salt thereof.

[3] The compound of the above-mentioned [1] or [2], wherein n is 1, or a pharmaceutically acceptable salt thereof or an optically active form thereof.

[4] The compound of the above-mentioned [3], wherein n is 1, p is 1

R[1] is a hydroxyl group or a $C_{1-6}$ alkoxy group,

R[2] and R[3] are the same or different and each is a hydrogen atom, a hydroxyl group, a halogen atom, an amino group, a $C_{1-7}$ acylamino group, a trifluoromethyl group, a $C_{1-6}$ alkoxy-carbonyl group, a $C_{1-6}$ alkoxy group, a $C_{1-6}$ alkyl group, a hydroxy-$C_{1-6}$ alkyl group, a $C_{2-6}$ alkenyl group, a phenyl group, a benzyl group, a di($C_{1-6}$alkyl)amino group or a nitro group, or R[2] and R[3] are joined to form an ethyleneoxy group, $X^1$ is —C=C— or —C=N—, $X^2$ is —C=C—, Z is —S—, —SO—, —$SO_2$—, —$(CH_2)_{m1}$—O—, —O—$(CH_2)_{m1}$—, —$(CH_2)_{m2}$—NH—, —NH—$(CH_2)_{m2}$—, —$(CH_2)_{m3}$—N($CH_3$)—, —N($CH_3$)—$(CH_2)_{m3}$—, a $C_{1-4}$ alkylene group or a $C_{2-4}$ alkenylene group,
   wherein m1, m2 and m3 are each an integer of 0 to 2, R[4] is a $C_{1-6}$ alkyl group or a $C_{3-6}$ cycloalkyl group, R[5] is a hydrogen atom, Y is a carbon atom or a nitrogen atom, and R[6], R[7] and R[8] are the same or different and each is a hydrogen atom, a halogen atom, a $C_{1-6}$ alkyl group or a $C_{1-6}$ alkoxy group, or adjacent R[6] and R[7] are joined to form —CH=CH—CH=CH—, a pharmaceutically acceptable salt thereof or an optically active form thereof.

[5] The compound of the above-mentioned [4], wherein n is 1, p is 1,

R[1] is a hydroxyl group or a $C_{1-6}$ alkoxy group,

R[2] and R[3] are the same or different and each is a hydrogen atom, a halogen atom, a $C_{1-6}$ alkoxy group or a $C_{1-6}$ alkyl group, $X^1$ is —C=C—, Z is —S—, —SO—, —$SO_2$—, —$(CH_2)_{m1}$—O—, —O—$(CH_2)_{m1}$, —$CH_2$—NH—, —NH—$CH_2$—, —N($CH_3$)—, methylene or vinylene,
   wherein m1 is 0 or 1, $X^1$ is —C=C—, R[4] is a methyl group or a cyclopropyl group, R[5] is a hydrogen atom, Y is a carbon atom or a nitrogen atom, and R[6], R[7] and R[8] are the same or different and each is a hydrogen atom, a halogen atom or a $C_{1-6}$ alkyl group, or adjacent R[6] and R[7] are joined to form —CH=CH—CH=CH—, a pharmaceutically acceptable salt thereof or an optically active form thereof.

[6] The compound of the above-mentioned [3], which is selected from the group consisting of
   4-[2-[1-[(2R)-3-[[1-(3-fluoro-4-methylphenyl)-2-methyl-propan-2-yl]amino]-2-hydroxypropoxy]ethyl]phenoxy]benzoic acid,
   4-[2-[1-[(2R)-3-[[1-(3-fluoro-4-methylphenyl)-2-methyl-propan-2-yl]amino]-2-hydroxypropoxy]ethyl]phenoxy]-3-methoxybenzoic acid,
   methyl 4-[2-[1-[(2R)-3-[[1-(naphthalen-2-yl)-2-methyl-propan-2-yl]amino]-2-hydroxypropoxy]ethyl]phenoxy]benzoate, 4-[2-[1-[(2R)-3-[[1-(naphthalen-2-yl)-2-methylpropan-2-yl]amino]-2-hydroxypropoxy]ethyl]phenoxy]benzoic acid, 4-[2-[1-[(2R)-3-[[1-(quinolin-3-yl)-2-methylpropan-2-yl]amino]-2-hydroxypropoxy]ethyl]phenoxy]benzoic acid, 4-[2-[1-[(2R)-3-[[1-(4-chloro-2-fluorophenyl)-2-methylpropan-2-yl]amino]-2-hydroxypropoxy]ethyl]phenoxy]benzoic acid, 4-[2-[1-[(2R)-3-[[1-(3-fluoro-4-methylphenyl)-2-methylpropan-2-yl]amino]-2-hydroxypropoxy]ethyl]phenoxy]benzoic acid, 3-[2-[1-[(2R)-3-[[1-(3-fluoro-4-methylphenyl)-2-methylpropan-2-yl]amino]-2-hydroxypropoxy]ethyl)phenoxy]benzoic acid, 4-[2-[2-[1-[(2R)-3-[[1-(naphthalen-2-yl)-2-methylpropan-2-yl]amino]-2-hydroxypropoxy]ethyl]phenyl]vinyl]benzoic acid, 3-[2-[1-[(2R)-3-[[1-(naphthalen-2-yl)-2-methylpropan-2-yl]amino]-2-hydroxypropoxy]ethyl]phenylthio]benzoic acid, 4-[2-[2-[1-[(2R)-3-[[1-(3-fluoro-4-methylphenyl)-2-methylpropan-2-yl]amino]-2-hydroxypropoxy]ethyl]phenyl]vinyl]benzoic acid, 4-[2-[1-[(2R)-3-[[1-(3-fluoro-4-methylphenyl)-2-methylpropan-2-yl]amino]-2-hydroxypropoxy]ethyl]phenoxy]-3,5-dimethylbenzoic acid, 4-[2-[1-[(2R)-3-[[1-(4-chloro-2-fluorophenyl)-2-methylpropan-2-yl]amino]-2-hydroxypropoxy]ethyl]phenoxy]-3,5-dimethylbenzoic acid, 4-[2-[1-[(2R)-3-[[1-(naphthalen-2-yl)-2-methylpropan-2-yl]amino]-2-hydroxypropoxy]ethyl]benzyl]benzoic acid, 3-[2-[1-[(2R)-3-[[1-(naphthalen-2-yl)-2-methylpropan-2-yl]amino]-2-hydroxypropoxy]ethyl]benzyl]benzoic acid, 4-[2-[1-[(2R)-3-[[1-(naphthalen-2-yl)-2-methylpropan-2-yl]amino]-2-hydroxypropoxy]ethyl]phenylthio]benzoic acid, 4-[2-[1-[(2R)-3-[[1-(naphthalen-2-yl)-2-methylpropan-2-yl]amino]-2-hydroxypropoxy]ethyl]phenylsulfinyl]benzoic acid, 4-[2-[1-[(2R)-3-[[1-(naphthalen-2-yl)-2-methylpropan-2-yl]amino]-2-hydroxypropoxy]ethyl]phenylsulfonyl]benzoic acid, 4-[[2-[1-[(2R)-3-[[1-(naphthalen-2-yl)-2-methylpropan-2-yl]amino]-2-hydroxypropoxy]ethyl]phenylamino]methyl]benzoic acid, 2-[[2-[1-[(2R)-3-[[1-(naphthalen-2-yl)-2-methylpropan-2-yl]amino]-2-hydroxypropoxy]ethyl]phenoxy]methyl]benzoic acid, 3-[[2-[1-[(2R)-3-[[1-(naphthalen-2-yl)-2-methylpropan-2-yl]amino]-2-hydroxypropoxy]ethyl]phenoxy]methyl]benzoic acid, 4-[[2-[1-[(2R)-3-[[1-(naphthalen-2-yl)-2-methylpropan-2-yl]amino]-2-hydroxypropoxy]ethyl]phenoxy]methyl]benzoic acid, 3-[[2-[1-[(2R)-3-[[1-(3-fluoro-4-methylphenyl)-2-methylpropan-2-yl]amino]-2-hydroxypropoxy]ethyl]phenoxy]methyl]benzoic acid, 4-[[2-[1-[(2R)-3-[[1-(3-fluoro-4-methylphenyl)-2-methylpropan-2-yl]amino]-2-hydroxypropoxy]ethyl]phenoxy]methyl]benzoic acid, 3-fluoro-4-[[2-[1-[(2R)-3-[[1-(3-fluoro-4-methylphenyl)-2-methylpropan-2-yl]amino]-2-hydroxypropoxy]ethyl]phenoxy]methyl]benzoic acid, 4-[[2-[1-[(2R)-3-[[1-(3-fluoro-4-methylphenyl)-2-methylpropan-2-yl]amino]-2-hydroxypropoxy]ethyl]phenoxy]methyl]-3-methylbenzoic acid, 4-[2-[1-[(2R)-3-[[1-(3-fluoro-4-methylphenyl)-2-methylpropan-2-yl]amino]-2-hydroxypropoxy]ethyl]phenoxy]-3,5-dimethoxybenzoic acid, 4-[2-[1-[(2R)-3-[[1-(3-fluoro-4-methylphenyl)-2-methylpropan-2-yl]amino]-2-hydroxypropoxy]ethyl]phenoxy]-3-nitrobenzoic acid, 4-[2-[1-[(2R)-3-[[1-(3-fluoro-4-methylphenyl)-2-methylpropan-2-yl]amino]-2-hydroxypropoxy]ethyl]phenoxy]-2-nitrobenzoic acid, 4-[2-[1-[(2R)-3-[[1-(3-fluoro-4-methylphenyl)-2-methylpropan-2-yl]amino]-2-hydroxypropoxy]ethyl]phenoxy]-3-chlorobenzoic acid, 4-[2-[1-[(2R)-3-[[1-(3-fluoro-4-methylphenyl)-2-methylpropan-2-yl]amino]-2-hydroxypropoxy]ethyl]phenoxy]-2-chlorobenzoic acid, 4-[2-[1-[(2R)-3-[[1-(3-fluoro-4-methylphenyl)-2-methylpropan-2-yl]amino]-2-hydroxypropoxy]ethyl]phenoxy]-2-trifluoromethylbenzoic acid, 4-[2-[1-[(2R)-3-[[1-(3-fluoro-4-methylphenyl)-2-methylpropan-2-yl]amino]-2-hydroxypropoxy]ethyl]phenoxy]-3-trifluoromethylbenzoic acid, 4-[2-[1-[(2R)-3-[[1-(3-fluoro-4-methylphenyl)-2-methylpropan-2-yl]amino]-2-hydroxypropoxy]ethyl]phenoxy]-3-fluorobenzoic acid, 4-[2-[1-[(2R)-3-[[1-(4-chloro-3-fluorophenyl)-2-methylpropan-2-yl]amino]-2-hydroxypropoxy]ethyl]phenoxy]benzoic acid, and 4-[2-[1-[(2R)-3-[[1-(4-chloro-3-fluorophenyl)-2-methylpropan-2-yl]amino]-2-hydroxypropoxy]ethyl]phenoxy]-5-methylbenzoic acid, a pharmaceutically acceptable salt thereof or an optically active form thereof.

[7] The compound of the above-mentioned [1] or [2], wherein n is 0, a pharmaceutically acceptable salt thereof or an optically active form thereof.

[8] The compound of the above-mentioned [7], wherein n is 0, p is 1, $R^1$ is a hydroxyl group or a $C_{1-6}$ alkoxy group, $R^2$ and $R^3$ are the same or different and each is a hydrogen atom, a hydroxyl group, a halogen atom, an amino group, a $C_{1-7}$ acylamino group, a trifluoromethyl group, a $C_{1-6}$ alkoxy-carbonyl group, a $C_{1-6}$ alkoxy group, a $C_{1-6}$ alkyl group, a hydroxy-$C_{1-6}$ alkyl group, a $C_{2-6}$ alkenyl group, a phenyl group, a benzyl group, a di($C_{1-6}$alkyl)amino group or a nitro group, or $R^2$ and $R^3$ are joined to form an ethyleneoxy group, $X^1$ is —C=C— or —C=N—, $X^2$ is —C=C—, $R^4$ is a $C_{1-6}$ alkyl group or a $C_{3-6}$ cycloalkyl group, $R^5$ is a hydrogen atom, Y is a carbon atom or a nitrogen atom, and, $R^6$, $R^7$ and $R^8$ are the same or different and each is a hydrogen atom, a halogen atom, a $C_{1-6}$ alkyl group or a $C_{1-6}$ alkoxy group, or adjacent $R^6$ and $R^7$ are joined to form —CH=CH—CH=CH—, a pharmaceutically acceptable salt thereof or an optically active form thereof.

[9] The compound of the above-mentioned [8], wherein n is 0, p is 1, $R^1$ is a hydroxyl group or a $C_{1-6}$ alkoxy group, $R^2$ and $R^3$ are the same or different and each is a hydrogen atom, a hydroxyl group, a halogen atom, an amino group, a $C_{1-7}$ acylamino group, a trifluoromethyl group, a $C_{1-6}$ alkoxy-carbonyl group, a $C_{1-6}$ alkoxy group, a $C_{1-6}$ alkyl group, a hydroxy-$C_{1-6}$ alkyl group, a $C_{2-6}$ alkenyl group, a phenyl group, a benzyl group, a di($C_{1-6}$ alkyl)amino group or a nitro group, or $R^2$ and $R^3$ are joined to form an ethyleneoxy group, $X^1$ is —C═C— or —C═N—, $X^2$ is —C═C—, $R^4$ is a methyl group or a cyclopropyl group, $R^5$ is a hydrogen atom, Y is a carbon atom, and $R^6$, $R^7$ and $R^8$ are the same or different and each is a hydrogen atom, a halogen atom, a $C_{1-6}$ alkyl group or a $C_{1-6}$ alkoxy group, or adjacent $R^6$ and $R^7$ are joined to form —CH═CH—CH═CH—, a pharmaceutically acceptable salt thereof or an optically active form thereof.

[10] The compound of the above-mentioned [7], which is selected from the group consisting of 2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-methylbiphenyl-4-carboxylic acid, 2'-[1-[(2R)-3-[[1-(3-chloro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-methylphenyl)-2-methylpropan-2-yl]amino]-2-hydroxypropoxy]ethyl]-3-methylbiphenyl-4-carboxylic acid, 2'-[1-[(2R)-3-[[1-(2,3-difluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-2-fluorophenyl)-2-methylpropan-2-yl]amino]-2-hydroxypropoxy]ethyl]-3-methylbiphenyl-4-carboxylic acid, 2'-[1-[(2R)-3-[[1-(2-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-ethyl-3-fluorophenyl)-2-methylpropan-2-yl]amino]-2-hydroxypropoxy]ethyl]-3-methylbiphenyl-4-carboxylic acid, 3-methyl-2'-[1-[(2R)-3-[[1-(naphthalen-2-yl)-2-methylpropan-2-yl]amino]-2-hydroxypropoxy]ethyl]biphenyl-5-carboxylic acid, methyl 2'-[1-[(2R)-3-[[1-(naphthalen-2-yl)-2-methylpropan-2-yl]amino]-2-hydroxypropoxy]ethyl]biphenyl-3,5-dicarboxylate, 2'-[(cyclopropyl)[(2R)-3-[[1-(naphthalen-2-yl)-2-methylpropan-2-yl]amino]-2-hydroxypropoxy]methyl]-3-methylbiphenyl-4-carboxylic acid, 2'-[1-[(2R)-3-[[1-(naphthalen-2-yl)-2-methylpropan-2-yl]amino]-2-hydroxypropoxy]ethyl]-3-methylbiphenyl-4-carboxylic acid, 2'-[(cyclopropyl)[(2R)-3-[[1-(3-fluoro-4-methylphenyl)-2-methylpropan-2-yl]amino]-2-hydroxypropoxy]methyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-methylbiphenyl-5-carboxylic acid, 2'-[(cyclopropyl)[(2R)-3-[[1-(4-chloro-2-fluorophenyl)-2-methylpropan-2-yl]amino]-2-hydroxypropoxy]methyl]-3-methylbiphenyl-4-carboxylic acid, 2'-[(cyclopropyl)[(2R)-3-[[1-(4-chloro-3-fluorophenyl)-2-methylpropan-2-yl]amino]-2-hydroxypropoxy]methyl]-3-methylbiphenyl-4-carboxylic acid, 2'-[1-[(2R)-3-[[1-(3-fluoro-4-methoxyphenyl)-2-methylpropan-2-yl]amino]-2-hydroxypropoxy]ethyl]-3-methylbiphenyl-4-carboxylic acid, 3-methyl-2'-[1-[(2R)-3-[[1-(3,4-dimethylphenyl)-2-methylpropan-2-yl]amino]-2-hydroxypropoxy]ethyl]biphenyl-4-carboxylic acid, 2'-[1-[(2R)-3-[[1-(4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-methoxyphenyl)-2-methylpropan-2-yl]amino]-2-hydroxypropoxy]ethyl]-3-methylbiphenyl-4-carboxylic acid, 2'-[1-[(2R)-3-[[1-(4-ethylphenyl)-2-methylpropan-2-yl]amino]-2-hydroxypropoxy]ethyl]-3-methylbiphenyl-4-carboxylic acid, 2'-(1-[(2R)-3-[(1-(4-chloro-2,5-difluorophenyl)-2-methylpropan-2-yl]amino]-2-hydroxypropoxy]ethyl]-3-methylbiphenyl-4-carboxylic acid, 2'-[1-[(2R)-3-[[1-(naphthalen-2-yl)-2-methylpropan-2-yl]amino]-2-hydroxypropoxy]ethyl]-3-methoxybiphenyl-4-carboxylic acid, 2'-[1-[(2R)-3-[[1-(naphthalen-2-yl)-2-methylpropan-2-yl]amino]-2-hydroxypropoxy]ethyl]-2-methoxybiphenyl-4-carboxylic acid, 2'-[1-[(2R)-3-[[1-(naphthalen-2-yl)-2-methylpropan-2-yl]amino]-2-hydroxypropoxy]ethyl]-3-(trifluoromethyl)biphenyl-4-carboxylic acid, 2'-[1-[(2R)-3-[[1-(2-fluoro-4-methoxyphenyl)-2-methylpropan-2-yl]amino]-2-hydroxypropoxy]ethyl]-3-(trifluoromethyl)biphenyl-4-carboxylic acid, 3-ethyl-2'-[1-[(2R)-3-[[1-(naphthalen-2-yl)-2-methylpropan-2-yl]amino]-2-hydroxypropoxy]ethyl]biphenyl-4-carboxylic acid, 2'-[1-[(2R)-3-[[1-(3,4-dichlorophenyl)-2-methylpropan-2-yl]amino]-2-hydroxypropoxy]ethyl]-3-(trifluoromethyl)biphenyl-4-carboxylic acid, 2'-[1-[(2R)-3-[[1-(naphthalen-2-yl)-2-methylpropan-2-yl]amino]-2-hydroxypropoxy]ethyl]-3-isopropylbiphenyl-4-carboxylic acid, 3-ethyl-2'-[1-[(2R)-3-[[1-(3-fluoro-4-methylphenyl)-2-methylpropan-2-yl]amino]-2-hydroxypropoxy]ethyl]biphenyl-4-carboxylic acid, 2'-[1-[(2R)-3-[[1-(3-fluoro-4-methylphenyl)-2-methylpropan-2-yl]amino]-2-hydroxypropoxy]ethyl]-3-isopropylbiphenyl-4-carboxylic acid, 2-chloro-6-[2-1-[(2R)-3-[[1-(naphthalen-2-yl)-2-methylpropan-2-yl]amino]-2-hydroxypropoxy]ethyl]phenyl]pyridine-3-carboxylic acid, 2'-[1-[(2R)-3-[[1-(naphthalen-2-yl)-2-methylpropan-2-yl]amino]-2-hydroxypropoxy]ethyl]-3-propylbiphenyl-4-carboxylic acid, 2,3-dimethyl-2'-[1-[(2R)-3-[[1-(naphthalen-2-yl)-2-methylpropan-2-yl]amino]-2-hydroxypropoxy]ethyl]biphenyl-4-carboxylic acid, 2'-[1-[(2R)-3-[[1-(3-fluoro-4-methylphenyl)-2-methylpropan-2-yl]amino]-2-hydroxypropoxy]ethyl]-3-propylbiphenyl-4-carboxylic acid, 2-chloro-6-[2-[1-[(2R)-3-[[1-(3-fluoro-4-methylphenyl)-2-methylpropan-2-yl]amino]-2-hydroxypropoxy]ethyl]phenyl]pyridine-3-carboxylic acid, 3,5-dimethyl-2'-[1-[(2R)-3-[[1-(naphthalen-2-yl)-2-methylpropan-2-yl]amino]-2-hydroxypropoxy]ethyl]biphenyl-4-carboxylic acid, 2-[1-[(2R)-3-[[1-(naphthalen-2-yl)-2-methylpropan-2-yl]amino]-2-hydroxypropoxy]ethyl]-m-terphenyl-4'-carboxylic acid, 2'-[1-[(2R)-3-[[1-(3-fluoro-4-methylphenyl)-2-methylpropan-2-yl]amino]-2-hydroxypropoxy]ethyl]-2,3-dimethylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3,5-dimethylbiphenyl-4-carboxylic acid, 4-(hydroxymethyl)-2'-[1-[(2R)-3-[[1-(naphthalen-2-yl)-2-methylpropan-2-yl]amino]-2-hydroxypropoxy]ethyl]biphenyl-3-carboxylic acid, 3-isobutyl-2'-[1-[(2R)-3-[[1-(naphthalen-2-yl)-2-methylpropan-2-yl]amino]-2-hydroxypropoxy]ethyl]biphenyl-4-carboxylic acid, 2'-[1-[(2R)-3-[[1-(3-fluoro-4-methylphenyl)-2-methylpropan-2-yl]amino]-2-hydroxypropoxy]ethyl]-3-isobutylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-4-(hydroxymethyl)biphenyl-3-carboxylic acid, 2'-[1-[(2R)-3-[[1-(3-fluoro-4-methylphenyl)-2-methylpropan-2-yl]amino]-2-hydroxypropoxy]ethyl]-3-(2-methyl-1-propenyl)biphenyl-4-carboxylic acid, 2'-[1-[(2R)-3-[[1-(naphthalen-2-yl)-2-methylpropan-2-yl]amino]-2-hydroxypropoxy]ethyl]-3-hydroxybiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-hydroxybiphenyl-4-carboxylic acid, 3-ethyl-2'-[1-[(2R)-3-[[1-(4-chloro-3-fluorophenyl)-2-methylpropan-2-yl]amino]-2-hydroxypropoxy]ethyl]biphenyl-4-carboxylic acid, 2'-[1-[(2R)-3-[[1-(4-chloro-3-fluorophenyl)-2-methylpropan-2-yl]amino]-2-hydroxypropoxy]ethyl]-3-isopropylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-(1-methylpropyl)biphenyl-4-carboxylic acid, 2-methyl-2'-[1-[(2R)-3-[[1-(naphthalen-2-yl)-2-methylpropan-2-yl]amino]-2-hydroxypropoxy]ethyl]biphenyl-4-carboxylic acid, 3-methyl-2'-[1-[(2R)-3-[[1-(naphthalen-2-yl)-2-methylpropan-2-yl]amino]-2-hydroxypropoxy]ethyl]biphenyl-4-carboxylic acid, 4-fluoro-2'-[1-[(2R)-3-[[1-(naphthalen-2-yl)-2-methylpropan-2-yl]amino]-2-hydroxypropoxy]ethyl]biphenyl-3-carboxylic acid, 2'-[1-[(2R)-3-[[1-(3,4-dichlorophenyl)-2-methylpropan-2-yl]amino]-2-hydroxypropoxy]ethyl]-2-methylbiphenyl-4-carboxylic acid, 6-fluoro-2'-[1-[(2R)-3-[[1-(naphthalen-2-yl)-2-methylpropan-2-yl]amino]-2-hydroxypropoxy]ethyl]biphenyl-3-carboxylic acid, 3-fluoro-2'-[1-[(2R)-3-[[1-(naphthalen-2-yl)-2-methylpropan-2-yl]amino]-2-hydroxypropoxy]ethyl]biphenyl-4-carboxylic acid, 2'-[1-[(2R)-3-[[1-(3-chlorophenyl)-2-methylpropan-2-yl]amino]-2-hydroxypropoxy]ethyl]-3-methylbiphenyl-4-carboxylic acid, 2'-[1-[(2R)-3-[[1-(3,4-dichlorophenyl)-2-methylpropan-2-yl]amino]-2-hydroxypropoxy]ethyl]-3-methylbiphenyl-4-carboxylic acid, 2-fluoro-2'-[1-[(2R)-3-[[1-(naphthalen-2-yl)-2-methylpropan-2-yl]amino]-2-hydroxypropoxy]ethyl]biphenyl-4-carboxylic acid, 2'-[(cyclopropyl)[(2R)-3-[[1-(naphthalen-2-yl)-2-methylpropan-2-yl]amino]-2-hydroxypropoxy]methyl]-3-methylbiphenyl-4-carboxylic acid, 2'-[(cyclopropyl)[(2R)-3-[[1-(naphthalen-2-yl)-2-methylpropan-2-yl]amino]-2-hydroxypropoxy]methyl]-3-fluorobiphenyl-4-carboxylic acid, 2'-[(cyclopropyl)[(2R)-3-[[1-(naphthalen-2-yl)-2-methylpropan-2-yl]amino]-2-hydroxypropoxy]methyl]-2-fluorobiphenyl-4-carboxylic acid, 2'-[(cyclopropyl)[(2R)-3-[[1-(naphthalen-2-yl)-2-methylpropan-2-yl]amino]-2-hydroxypropoxy]methyl]-2-methylbiphenyl-4-carboxylic acid, 2'-[1-[(2R)-3-[[1-(3,4-dichlorophenyl)-2-methylpropan-2-yl]amino]-2-hydroxypropoxy]ethyl]-2-fluorobiphenyl-4-carboxylic acid, 3-chloro-2'-[1-[(2R)-3-[[1-(naphthalen-2-yl)-2-methylpropan-2-yl]amino]-2-hydroxypropoxy]ethyl]biphenyl-4-carboxylic acid, 2'-[1-[(2R)-3-[[1-(naphthalen-2-yl)-2-methylpropan-2-yl]amino]-2-hydroxypropoxy]ethyl]-3-nitrobiphenyl-4-carboxylic acid, 3-amino-2'-[1-[(2R)-3-[[1-(naphthalen-2-yl)-2-methylpropan-2-yl]amino]-2-hydroxypropoxy]ethyl]biphenyl-4-carboxylic acid, 3-(acetylamino)-2'-[1-[(2R)-3-[[1-(naphthalen-2-yl)-2-methylpropan-2-yl]amino]-2-hydroxypropoxy]ethyl]biphenyl-4-carboxylic acid, 3-chloro-2'-[1-[(2R)-3-[[1-(3-fluoro-4-methylphenyl)-2-methylpropan-2-yl]amino]-2-hydroxypropoxy]ethyl]biphenyl-4-carboxylic acid, 2'-[1-[(2R)-3-[[1-(3-methoxy-4-methylphenyl)-2-methylpropan-2-yl]amino]-2-hydroxypropoxy]ethyl]-3-methylbiphenyl-4-carboxylic acid, 2,3-dihydro-5-[2-[1-[(2R)-3-[[1-(naphthalen-2-yl)-2-methylpropan-2-yl]amino]-2-hydroxypropoxy]ethyl]phenyl]benzofuran-7-carboxylic acid, 2,6-dimethyl-2'-[1-[(2R)-3-[[1-(naphthalen-2-yl)-2-methylpropan-2-yl]amino]-2-hydroxypropoxy]ethyl]biphenyl-4-carboxylic acid, 2'-[1-[(2R)-3-[[1-(3-fluoro-4-methylphenyl)-2-methylpropan-2-yl]amino]-2-hydroxypropoxy]ethyl]-2,6-dimethylbiphenyl-4-carboxylic acid, 3-(dimethylamino)-2'-[1-[(2R)-3-[[1-(naphthalen-2-yl)-2-methylpropan-2-yl]amino]-2-hydroxypropoxy]ethyl]biphenyl-4-carboxylic acid, 2,3-dihydro-5-[2-[1-[(2R)-3-[[1-(3-fluoro-4-methylphenyl)-2-methylpropan-2-yl]amino]-2-hydroxypropoxy]ethyl]phenyl]benzofuran-7-carboxylic acid, 3-benzyl-2'-[1-[(2R)-3-[[1-(3-fluoro-4-methylphenyl)-2-methylpropan-2-yl]amino]-2-hydroxypropoxy]ethyl]biphenyl-4-carboxylic acid, 2'-[1-[(2R)-3-[[1-(3-fluoro-4-methylphenyl)-2-methylpropan-2-yl]amino]-2-hydroxypropoxy]ethyl]-3-methoxybiphenyl-4-carboxylic acid, 2'-[1-[(2R)-3-[[1-(4-chloro-2-fluorophenyl)-2-methylpropan-2-yl]amino]-2-hydroxypropoxy]ethyl]-3-methoxybiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-methoxybiphenyl-4-carboxylic acid, 2'-[1-[(2R)-3-[[1-(4-chloro-3-fluorophenyl)-2-methylpropan-2-yl]amino]-2-hydroxypropoxy]ethyl]-2-methylbiphenyl-4-carboxylic acid, 2'-[1-[(2R)-3-[[1-(4-chloro-2-fluorophenyl)-2-methylpropan-2-yl]amino]-2-hydroxypropoxy]ethyl]-2-methylbiphenyl-4-carboxylic acid, 4-methyl-2'-[1-[(2R)-3-[[1-(naphthalen-2-yl)-2-methylpropan-2-yl]amino]-2-hydroxypropoxy]ethyl]biphenyl-3-carboxylic acid, 2'-[1-[(2R)-3-[[1-(3-fluoro-4-methylphenyl)-2-methylpropan-2-yl]amino]-2-hydroxypropoxy]ethyl]-4-methylbiphenyl-3-carboxylic acid, 2'-[1-[(2R)-3-[[1-(3,5-dichlorophenyl)-2-methylpropan-2-yl]amino]-2-hydroxypropoxy]ethyl]-3-methylbiphenyl-4-carboxylic acid, 2'-[1-[(2R)-3-[[1-(2,5-difluorophenyl)-2-methylpropan-2-yl]amino]-2-hydroxypropoxy]ethyl]-3-methylbiphenyl-4-carboxylic acid, 2'-[1-[(2R)-3-[[1-(5-chloro-2-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(3-chloro-2-fluorophenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-trifluoromethylphenyl)-2-methylpropan-2-yl]amino]-2-hydroxypropoxy]ethyl]-3-methylbiphenyl-4-carboxylic acid, 2'-[1-[(2R)-3-[[1-(5-chloro-3-fluorophenyl)-2-methylpropan-2-yl]amino]-2-hydroxypropoxy]ethyl]-3-methylbiphenyl-4-carboxylic acid, 2'-[1-[(2R)-3-[[1-(3,5-ditrifluoromethylphenyl)-2-methylpropan-2-yl]amino]-2-hydroxypropoxy]ethyl]-3-methylbiphenyl-4-carboxylic acid, 2'-[1-[(2R)-3-[[1-(4-methyl-3,5-dimethoxyphenyl)-2-methylpropan-2-yl]amino]-2-hydroxypropoxy]ethyl]-3-methylbiphenyl-4-carboxylic acid, 2'-[1-[(2R)-3-[[1-(3,5-dimethoxyphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-trifluoromethylphenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-t-butylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-t-butylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-t-butylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-methoxybiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-morpholinobiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-(trifluoromethoxy)biphenyl-4-carboxylic acid, 2'-[1-[(-2R)-3-[[1-(3-trifluoromethyl-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-(hydroxymethyl)biphenyl-4-carboxylic acid, and 2'-[1-[(2R)-3-[[1-(4-chloro-3-fluorophenyl)-2-methylpropan-2-yl]amino]-2-hydroxypropoxy)ethyl]-3-carboxy]biphenyl-4-carboxylic acid, a pharmaceutically acceptable salt thereof or an optically active form thereof.

[11] A compound represented by the following formula (1''), a pharmaceutically acceptable salt thereof or an optically active form thereof:

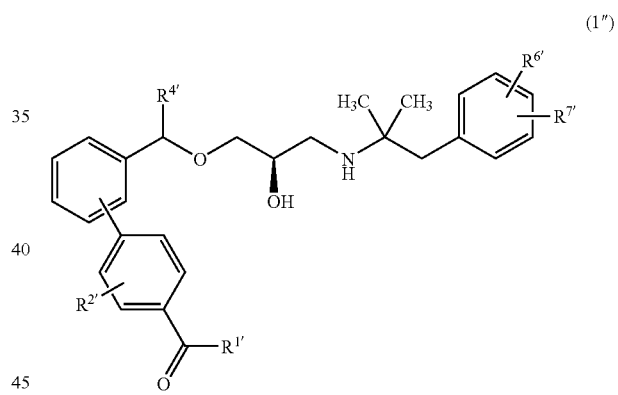

(1'')

wherein $R^{1'}$ is a hydroxyl group or a $C_{1-6}$ alkoxy group, $R^{2'}$ is a hydroxyl group, a halogen atom, an amino group, a $C_{1-7}$ acylamino group, a halo $C_{1-6}$ alkyl group, a $C_{1-6}$ alkoxy-carbonyl group, a $C_{1-6}$ alkoxy group, a halo $C_{1-6}$ alkoxy group, a $C_{1-6}$ alkyl group, a hydroxy-$C_{1-6}$ alkyl group, a di($C_{1-6}$ alkyl)amino group or a nitro group, $R^{4'}$ is a $C_{1-6}$ alkyl group or a $C_{3-6}$ cycloalkyl group, $R^{6'}$ is a halogen atom, a $C_{1-6}$ alkyl group, a $C_{1-6}$ alkoxy group or a halo $C_{1-6}$ alkyl group, or when $R^{7'}$ is adjacent, $R^{6'}$ and $R^{7'}$ are linked to form —CH=CH—CH=CH—, and $R^{7'}$ is a hydrogen atom, a halogen atom, a $C_{1-6}$ alkyl group, a $C_{1-6}$ alkoxy group or a halo $C_{1-6}$ alkyl group.

[12] A compound represented by the following formula (1'''), a pharmaceutically acceptable salt thereof or an optically active form thereof:

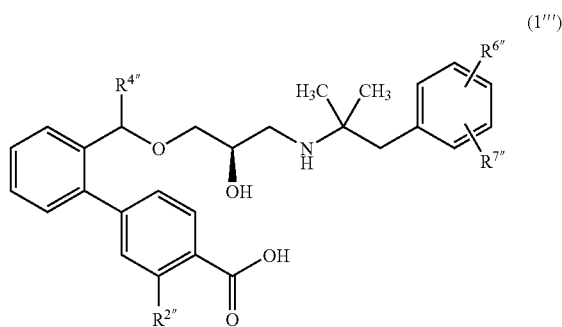

(1''')

wherein

R$^{2''}$ is a C$_{1-6}$ alkyl group,

R$^{4''}$ is a methyl group or a cyclopropyl group,

R$^{6''}$ is a halogen atom or a C$_{1-6}$ alkyl group, and

R$^{7''}$ is a hydrogen atom, a halogen atom, a C$_{1-6}$ alkyl group, a C$_{1-6}$ alkoxy group or a halo C$_{1-6}$ alkyl group.

[13] The compound of the above-mentioned [11] or [12], which is selected from the group consisting of 2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-methylbiphenyl-4-carboxylic acid, 2'-[1-[(2R)-3-[[1-(3-chloro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-2-fluorophenyl)-2-methylpropan-2-yl]amino]-2-hydroxypropoxy]ethyl]-3-methylbiphenyl-4-carboxylic acid, 2'-[1-[(2R)-3-[[1-(2-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-ethyl-3-fluorophenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-methylbiphenyl-5-carboxylic acid, 2'-[(cyclopropyl)[(2R)-3-[[1-(4-chloro-2-fluorophenyl)-2-methylpropan-2-yl]amino]-2-hydroxypropoxy]methyl]-3-methylbiphenyl-4-carboxylic acid, 2'-[(cyclopropyl)[(2R)-3-[[1-(4-chloro-3-fluorophenyl)-2-methylpropan-2-yl]amino]-2-hydroxypropoxy]methyl]-3-methylbiphenyl-4-carboxylic acid, 3-methyl-2'-[1-[(2R)-3-[[1-(3,4-dimethylphenyl)-2-methylpropan-2-yl]amino]-2-hydroxypropoxy]ethyl]biphenyl-4-carboxylic acid, 2'-[1-[(2R)-3-[[1-(4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-methoxyphenyl)-2-methylpropan-2-yl]amino]-2-hydroxypropoxy]ethyl]-3-methylbiphenyl-4-carboxylic acid, 2'-[1-[(2R)-3-[[1-(4-ethylphenyl)-2-methylpropan-2-yl]amino]-2-hydroxypropoxy]ethyl]-3-methylbiphenyl-4-carboxylic acid, 3-ethyl-2'-[1-[(2R)-3-[[1-(3-fluoro-4-methylphenyl)-2-methylpropan-2-yl]amino]-2-hydroxypropoxy]ethyl]biphenyl-4-carboxylic acid, 2'-[1-[(2R)-3-[[1-(3-fluoro-4-methylphenyl)-2-methylpropan-2-yl]amino]-2-hydroxypropoxy]ethyl]-3-isopropylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-propylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-isobutylbiphenyl-4-carboxylic acid, 3-ethyl-2'-[1-[(2R)-3-[[1-(4-chloro-3-fluorophenyl)-2-methylpropan-2-yl]amino]-2-hydroxypropoxy]ethyl]biphenyl-4-carboxylic acid, 2'-[1-[(2R)-3-[[1-(4-chloro-3-fluorophenyl)-2-methylpropan-2-yl]amino]-2-hydroxypropoxy]ethyl]-3-isopropylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-(1-methylpropyl)biphenyl-4-carboxylic acid, 2'-[1-[(2R)-3-[[1-(3-chlorophenyl)-2-methylpropan-2-yl]amino]-2-hydroxypropoxy]ethyl]-3-methylbiphenyl-4-carboxylic acid, 2'-[1-[(2R)-3-[[1-(3,4-dichlorophenyl)-2-methylpropan-2-yl]amino]-2-hydroxypropoxy]ethyl]-3-methylbiphenyl-4-carboxylic acid, 2'-[1-[(2R)-3-[[1-(3-methoxy-4-methylphenyl)-2-methylpropan-2-yl]amino]-2-hydroxypropoxy]ethyl]-3-methylbiphenyl-4-carboxylic acid, 2'-[1-[(2R)-3-[[1-(3,5-dichlorophenyl)-2-methylpropan-2-yl]amino]-2-hydroxypropoxy]ethyl]-3-methylbiphenyl-4-carboxylic acid, 2'-[1-[(2R)-3-[[1-(4-chloro-3-trifluoromethylphenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-t-butylbiphenyl-4-carboxylic acid, 2'-[1-[(2R)-3-[[1-(4-chloro-2-fluorophenyl)-2-methylpropan-2-yl]amino]-2-hydroxypropoxy]ethyl]-3-t-butylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-t-butylbiphenyl-4-carboxylic acid and 2'-[1-[(2R)-3-[[1-(3-trifluoromethyl-4-methylphenyl)-2-methylpropan-2-yl]amino]-2-hydroxypropoxy]ethyl]-3-methylbiphenyl-4-carboxylic acid a pharmaceutically acceptable salt thereof or an optically active form thereof.

[14] The compound of the above-mentioned 13, which is selected from the group consisting of 2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-methylbiphenyl-4-carboxylic acid, 2'-[1-[(2R)-3-[[1-(3-chloro-4-methylphenyl)-2-methyl-propan-2-yl]amino]-2-hydroxypropoxy]ethyl]-3-methylbiphenyl-4-carboxylic acid and 2'-[1-[(2R)-3-[[1-(4-chloro-2-fluorophenyl)-2-methylpropan-2-yl]amino]-2-hydroxypropoxy]ethyl]-3-methylbiphenyl-4-carboxylic acid, a pharmaceutically acceptable salt thereof or an optically active form thereof.

[15] 2'-[1-[(2R)-3-[[1-(3-Fluoro-4-methylphenyl)-2-methylpropan-2-yl]amino]-2-hydroxypropoxy]ethyl]-3-methylbiphenyl-4-carboxylic acid, a pharmaceutically acceptable salt thereof or an optically active form thereof.

[16] 2'-[1-[(2R)-3-[[1-(4-Chloro-3-fluorophenyl)-2-methylpropan-2-yl]amino]-2-hydroxypropoxy]ethyl]-3-methylbiphenyl-4-carboxylic acid, a pharmaceutically acceptable salt thereof or an optically active form thereof.

[17] 2'-[1-[(2R)-3-[[1-(3-Chloro-4-methylphenyl)-2-methylpropan-2-yl]amino]-2-hydroxypropoxy]ethyl]-3-methylbiphenyl-4-carboxylic acid, a pharmaceutically acceptable salt thereof or an optically active form thereof.

[18] 2'-[1-[(2R)-3-[[1-(4-Chloro-2-fluorophenyl)-2-methylpropan-2-yl]amino]-2-hydroxypropoxy]ethyl]-3-methylbiphenyl-4-carboxylic acid, a pharmaceutically acceptable salt thereof or an optically active form thereof.

[19] A pharmaceutical composition comprising a pharmaceutically acceptable carrier, and a compound of any of the above-mentioned [1] to [18], a pharmaceutically acceptable salt thereof or an optically active form thereof as an active ingredient.

[20] The pharmaceutical composition of the above-mentioned [19], wherein the active ingredient is a compound of any of the above-mentioned [3] to [6], a pharmaceutically acceptable salt thereof or an optically active form thereof.

[21] The pharmaceutical composition of the above-mentioned [19], wherein the active ingredient is a compound of any of the above-mentioned [7] to [10], a pharmaceutically acceptable salt thereof or an optically active form thereof.

[22] The pharmaceutical composition of the above-mentioned [19], wherein the active ingredient is a compound of any of the above-mentioned [11] to [18], a pharmaceutically acceptable salt thereof or an optically active form thereof.

[23] A therapeutic drug for osteoporosis, which comprises a pharmaceutically acceptable carrier, and a compound of any of the above-mentioned [1] to [18], a pharmaceutically acceptable salt thereof or an optically active form thereof, as an active ingredient.

[24] The therapeutic drug for osteoporosis of the above-mentioned [23], wherein the active ingredient is a compound of any of the above-mentioned [3] to [6], a pharmaceutically acceptable salt thereof or an optically active form thereof.

[25] The therapeutic drug for osteoporosis of the above-mentioned [23], wherein the active ingredient is a compound of any of claims [7] to [10], a pharmaceutically acceptable salt thereof or an optically active form thereof.

[26] The therapeutic drug for osteoporosis of the above-mentioned [23], wherein the active ingredient is a compound of any of the above-mentioned [11] to [18], a pharmaceutically acceptable salt thereof or an optically active form thereof.

[27] The therapeutic drug for osteoporosis of any of the above-mentioned [23] to [26], which is used for concomitant use with a different therapeutic drug for osteoporosis.

[28] The therapeutic drug for osteoporosis of the above-mentioned [25], wherein the different therapeutic drug for osteoporosis is selected from the group consisting of a calcium agent, a vitamin D preparation, a vitamin K preparation, a female hormone preparation, an estrogen antagonist preparation, an anabolic steroid preparation, a parathyroid hormone preparation, a calcitonin preparation, a bisphosphonate preparation and an ipriflavone preparation.

[29] A method for treating osteoporosis, which comprises administering an effective amount of a compound of any of the above-mentioned [1] to [18], a pharmaceutically acceptable salt thereof or an optically active form thereof to a patient with osteoporosis.

[30] A calcium receptor antagonist comprising a pharmaceutically acceptable carrier, and a compound of any of the above-mentioned [1] to [18], a pharmaceutically acceptable salt thereof or an optically active form thereof as an active ingredient.

[31] A calcium receptor antagonist of the above-mentioned [28], wherein the active ingredient is a compound of any of the above-mentioned [3] to [6], a pharmaceutically acceptable salt thereof or an optically active form thereof.

[32] The calcium receptor antagonist of the above-mentioned [28], wherein the active ingredient is a compound of any of the above-mentioned [7] to [10], a pharmaceutically acceptable salt thereof or an optically active form thereof.

[33] The calcium receptor antagonist of the above-mentioned [28], wherein the active ingredient is a compound of any of the above-mentioned [11] to [18], a pharmaceutically acceptable salt thereof or an optically active form thereof.

[34] A calcium receptor antagonist having an $IC_{50}$ value of a calcium receptor antagonistic action which is not less than 10 times the $IC_{50}$ value of an inhibitory action of metabolic enzyme P450.

[35] The calcium receptor antagonist of the above-mentioned [34], wherein the $IC_{50}$ value of the calcium receptor antagonistic action is not less than 100 times the $IC_{50}$ value of an inhibitory action of metabolic enzyme P450.

[36] The calcium receptor antagonist of the above-mentioned [34], wherein the metabolic enzyme P450 is CYP2D6.

[37] The calcium receptor antagonist of the above-mentioned [35], wherein the metabolic enzyme P450 is CYP2D6.

[38] A calcium receptor antagonist having an $IC_{50}$ value of a calcium receptor antagonistic action is not more than 0.1 μM, and an $IC_{50}$ value of an inhibitory action of the metabolic enzyme CYP2D6 is not less than 1 μM.

[39] The calcium receptor antagonist of the above-mentioned [38], wherein the $IC_{50}$ value of the calcium receptor antagonistic action is not more than 0.1 μM, and the $IC_{50}$ value of the inhibitory action of the metabolic enzyme CYP2D6 is not less than 10 μM.

[40] The calcium receptor antagonist of any of the above-mentioned [32] to [35], wherein the calcium receptor antagonist is described in any of the above-mentioned [28] to [31].

[41] A PTH secretagogue comprising a pharmaceutical acceptable carrier and a compound of any of the above-mentioned [1] to [18], a pharmaceutically acceptable salt thereof or an optically active form thereof as an active ingredient.

[42] The PTH secretagogue of the above-mentioned [41], wherein the active ingredient is a compound of any of the above-mentioned [3] to [6], a pharmaceutically acceptable salt thereof or an optically active form thereof.

[43] The PTH secretagogue of the above-mentioned [41], wherein the active ingredient is a compound of any of the above-mentioned [7] to [10], a pharmaceutically acceptable salt thereof or an optically active form thereof.

[44] The PTH secretagogue of the above-mentioned [41], wherein the active ingredient is a compound of any of the above-mentioned [11] to [18], a pharmaceutically acceptable salt thereof or an optically active form thereof.

DETAILED DESCRIPTION OF THE INVENTION

The terms used in the present specification are defined as follows.

The "halogen atom" is fluorine atom, chlorine atom, is bromine atom or iodine atom, which is preferably fluorine atom or chlorine atom, particularly preferably chlorine atom.

The "$C_{1-6}$ alkyl group" is straight chain or branched chain alkyl group having 1 to 6, preferably 1 to 4, carbon atoms. Examples thereof include $C_{1-4}$ alkyl group selected from methyl group, ethyl group, propyl group, isopropyl group, butyl group, isobutyl group, tert-butyl group, pentyl group, isopentyl group, tert-pentyl group or hexyl group and the like, preferably methyl group, ethyl group, propyl group, isopropyl group, butyl group, isobutyl group and tert-butyl group.

The "halo $C_{1-6}$ alkyl group" is the aforementioned "$C_{1-6}$ alkyl group" substituted by one or more halogen atoms of haloalkyl groups, wherein the position of substitution is free of any particularly limitation as long as it is chemically acceptable. Examples of the "halo $C_{1-6}$ alkyl group" include fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, 2-fluoroethyl group, 2,2-difluoroethyl group, 2,2,2-trifluoroethyl group, 2-chloroethyl group, 2,2-dichloroethyl group, 2,2,2-trichloroethyl group, 2-bromomethyl group, 2,2-dibromoethyl group, 2,2,2-tribromoethyl group, 3-chloropropyl group or 4-chlorobutyl group and the like, preferably halo $C_{1-2}$ alkyl group such as trifluoromethyl group and 2,2,2-trichloroethyl group, particularly preferably trifluoromethyl group.

The "hydroxy-$C_{1-6}$ alkyl group" is a hydroxyalkyl group wherein the aforementioned "$C_{1-6}$ alkyl group" is substituted by hydroxyl group, wherein the position of substitution is free of any particularly limitation as long as it is chemically acceptable. Examples of the "hydroxy-$C_{1-6}$ alkyl group" include hydroxymethyl group, 1-hydroxyethyl group, 2-hydroxyethyl group, 1-hydroxypropyl group, 2-hydroxypropyl group, 3-hydroxypropyl group, 2-hydroxy-1-methylethyl group, 1-hydroxybutyl group, 2-hydroxybutyl group, 3-hydroxybutyl group, 4-hydroxybutyl group, 3-hydroxy-2-methylpropyl group, 2-hydroxy-1,1-dimethylethyl group, 5-hydroxypentyl group or 6-hydroxyhexyl group and the like, preferably hydroxy-$C_{1-4}$ alkyl group selected from hydroxymethyl group, 2-hydroxyethyl group, 3-hydroxypropyl group and 4-hydroxybutyl group.

The "$C_{1-6}$ alkoxy group" is a straight chain or branched chain alkoxy group having 1 to 6, preferably 1 to 4, carbon atoms. Examples thereof include methoxy group, ethoxy group, propoxy group, isopropoxy group, butoxy group, tert-butoxy group, pentyloxy group, tert-pentyloxy group, hexyloxy group and the like, preferably $C_{1-4}$ alkoxy group selected from methoxy group, ethoxy group, propoxy group, isopropoxy group, butoxy group and tert-butoxy group.

The "halo $C_{1-6}$ alkoxy group" is a haloalkoxy group wherein the aforementioned "$C_{1-6}$ alkoxy group" is substituted by one or more halogen atoms. The position of substitution is free of any particularly limitation as long as it is chemically acceptable. The "halo $C_{1-6}$ alkoxy group" is, for example, fluoromethoxy group, difluoromethoxy group, trifluoromethoxy group, chloromethoxy group, dichloromethoxy group, trichloromethoxy group, bromomethoxy group, dibromomethoxy group, tribromomethoxy group, iodomethoxy group, diiodomethoxy group, triiodomethoxy group, 2-fluoroethoxy group, 2,2-difluoroethoxy group, 2,2,2-trifluoroethoxy group, 2-chloroethoxy group, 2,2-dichloroethoxy group, 2,2,2-trichloroethoxy group, 2-bromoethoxy group, 2,2-dibromoethoxy group, 2,2,2-tribromoethoxy group, 3-chloropropoxy group, 4-chlorobutoxy group and the like, preferably halo $C_{1-2}$ alkoxy group such as trifluoromethoxy group and 2,2,2-trichloroethoxy group, particularly preferably trifluoromethoxy group.

The "$C_{1-6}$ alkoxy-$C_{1-6}$ alkyl group" is alkoxyalkyl group wherein the aforementioned "$C_{1-6}$ alkyl group" is substituted by the aforementioned "$C_{1-6}$ alkoxy group". The position of substitution is free of any particularly limitation as long as it is chemically acceptable. Examples of the "$C_{1-6}$ alkoxy-$C_{1-6}$ alkyl group" include methoxymethyl group, ethoxymethyl group, propoxymethyl group, butoxymethyl group, pentyloxymethyl group, hexyloxymethyl group, 1-methoxyethyl group, 1-ethoxyethyl group, 2-methoxyethyl group, 2-ethoxyethyl group, 1-methoxypropyl group, 1-ethoxypropyl group, 2-methoxypropyl group, 2-ethoxypropyl group, 3-methoxypropyl group, 3-ethoxypropyl group, 2-methoxy-1-methylethyl group, 1-methoxybutyl group, 1-ethoxybutyl group, 2-methoxybutyl group, 2-ethoxybutyl group, 3-methoxybutyl group, 3-ethoxybutyl group, 4-methoxybutyl group, 4-ethoxybutyl group, 3-methoxy-2-methylpropyl group, 2-methoxy-1,1-dimethylethyl group, 2-ethoxy-1,1-dimethylethyl group, 5-methoxypentyl group, 6-methoxyhexyl group and the like, preferably $C_{1-4}$ alkoxy-$C_{1-4}$ alkyl group selected from methoxymethyl group, ethoxymethyl group, propoxymethyl group, butoxymethyl group, 2-methoxyethyl group, 3-methoxypropyl group and 4-methoxybutyl group.

The "$C_{1-6}$ alkoxy-carbonyl group" is alkoxy-carbonyl group wherein $C_{1-6}$ alkoxy moiety is the aforementioned "$C_{1-6}$ alkoxy group". Examples thereof include methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, hexyloxycarbonyl group and the like, preferably $C_{1-4}$ alkoxy-carbonyl group selected from methoxycarbonyl group, ethoxycarbonyl group, propoxycarbonyl group, isopropoxycarbonyl group, butoxycarbonyl group and tert-butoxycarbonyl group.

The "$C_{1-6}$ alkylamino group" is alkylamino group wherein the aforementioned "$C_{1-6}$ alkyl group" is substituted by amino group. Examples thereof include methylamino group, ethylamino group, propylamino group, isopropylamino group, butylamino group, isobutylamino group, tert-butylamino group, pentylamino group, isopentylamino group, tert-pentylamino group or hexylamino group and the like, preferably $C_{1-4}$ alkylamino group selected from methylamino group, ethylamino group, propylamino group, isopropylamino group, butylamino group, isobutylamino group and tert-butylamino group.

The "di(C$_{1-6}$ alkyl)amino group" is a dialkylamino group wherein amino group is di-substituted by the aforementioned "C$_{1-6}$ alkyl group" and the kind of alkyl group may be different. For example, dimethylamino group, ethylmethylamino group, diethylamino group, methylpropylamino group, ethylpropylamino group, dipropylamino group, diisopropylamino group, dibutylamino group, diisobutylamino group, di-tert-butylamino group, dipentylamino group, diisopentylamino group, di-tert-pentylamino group, dihexylamino group and the like can be mentioned, preferably di C$_{1-4}$ alkylamino group selected from dimethylamino group, diethylamino group, dipropylamino group, diisopropylamino group, dibutylamino group, diisobutylamino group and di-tert-butylamino group.

The "di(C$_{1-6}$ alkyl)aminocarbonyl group" is dialkylaminocarbonyl group wherein aminocarbonyl group is di-substituted by the aforementioned "C$_{1-6}$ alkyl group" and the kind of alkyl group may be different. For example, dimethylaminocarbonyl group, ethylmethylaminocarbonyl group, diethylaminocarbonyl group, methylpropylaminocarbonyl group, ethylpropylaminocarbonyl group, dipropylaminocarbonyl group, diisopropylaminocarbonyl group, dibutylaminocarbonyl group, diisobutylaminocarbonyl group, di-tert-butylaminocarbonyl group, dipentylaminocarbonyl group, diisopentylaminocarbonyl group, di-tert-pentylaminocarbonyl group, dihexylaminocarbonyl group and the like can be mentioned, preferably di(C$_{1-4}$ alkyl)aminocarbonyl group selected from dimethylaminocarbonyl group, diethylaminocarbonyl group, dipropylaminocarbonyl group, diisopropylaminocarbonyl group, dibutylaminocarbonyl group, diisobutylaminocarbonyl group and di-tert-butylaminocarbonyl group.

The "C$_{1-7}$ acyl group" is alkanoyl group, alkenoyl group or aroyl group having 1 to 7 carbon atoms, such as formyl group, acetyl group, propionyl group, butyryl group, pivaloyl group, ethenoyl group, propenoyl group, butenoyl group, benzoyl group and the like, can be mentioned, preferably formyl group, acetyl group, pivaloyl group and benzoyl group. The acyl group may be substituted by carboxyl group. Examples thereof include carboxyacetyl group, 3-carboxypropionyl group, 4-carboxybutyryl group and the like.

The "C$_{1-7}$ acylamino group" is acylamino group wherein the acyl moiety preferably has 1 to 7, more preferably 2 to 5, chains (straight chain and branched chain) or is cyclic. As the acyl portion, for example, those exemplified for the aforementioned "C$_{1-7}$ acyl group" can be mentioned. Examples of the acylamino group include alkanoylamino group such as formylamino group, acetylamino group, propionylamino group, butyrylamino group, pivaloylamino group and the like; and aroylamino group such as benzoylamino group and the like, preferably formylamino group, acetylamino group, pivaloylamino group and benzoylamino group.

The "C$_{3-6}$ cycloalkyl group" is a cyclic alkyl group having 3 to 6 carbon atoms, such as cyclopropyl group, cyclobutyl group, cyclopentyl group, cyclohexyl group, cycloheptyl group and the like, preferably C$_{3-5}$ cycloalkyl group such as cyclopropyl group, cyclobutyl group, cyclopentyl group and the like, more preferably cyclopropyl group and cyclobutyl group, particularly preferably cyclopropyl group.

The "C$_{2-6}$ alkenyl group" is an alkenyl group having 2 to 6 carbon atoms, such as vinyl group, 1-propenyl group, 2-methyl-1-propenyl group, allyl group, 1-butenyl group, 2-butenyl group, 3-butenyl group, 1-pentenyl group, 2-pentenyl group, 3-pentenyl group, 4-pentenyl group, 5-hexenyl group and the like, preferably C$_{2-4}$ alkenyl group such as vinyl group, 2-methyl-1-propenyl group, allyl group and the like.

The "C$_{1-4}$ alkylene group" is a linear or branched chain alkylene group having 1 to 4, preferably 1 to 3, carbon atoms, and, for example, methylene group, ethylene group, propylene group, butylene group,

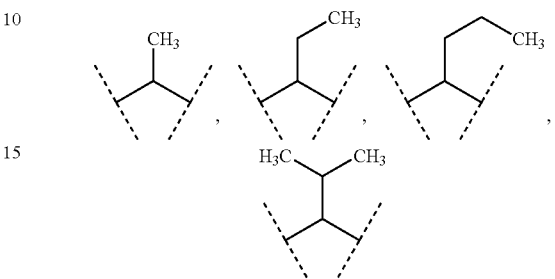

and the like can be mentioned. Preferred are methylene group, ethylene group and propylene group.

As the "C$_{1-4}$ alkylene group" contained in R$^4$,

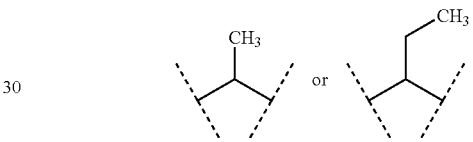

is preferable, particularly

is preferable.

The "C$_{2-4}$ alkenylene group" is an alkenylene group having 2 to 4, preferably 2 or 3, carbon atoms, such as vinylene group, 1-propenylene group, 2-propenylene group, 1-butenylene group, 2-butenylene group, 3-butenylene group and the like, preferably vinylene group, 1-propenylene or 2-propenylene group.

The "C$_{1-7}$ acylamino-C$_{1-6}$ alkyl group" is a group wherein the aforementioned "C$_{1-6}$ alkyl group" is substituted by "C$_{1-7}$ acylamino group". Examples thereof include alkanoylamino-C$_{1-6}$ alkyl group such as formylaminomethyl group, acetylaminomethyl group, propionylaminomethyl group, butyrylaminomethyl group, pivaloylaminomethyl group, formylaminoethyl group, acetylaminoethyl group, propionylaminoethyl group, butyrylaminoethyl group, pivaloylaminoethyl group, formylaminopropyl group, acetylaminopropyl group, propionylaminopropyl group, butyrylaminopropyl group, pivaloylaminopropyl group, formylaminobutyl group, acetylaminobutyl group, propionylaminobutyl group, butyrylaminobutyl group, pivaloylaminobutyl group, formylaminopentyl group, acetylaminopentyl group, propionylaminopentyl group, butyrylaminopentyl group, pivaloylaminopentyl group, formylaminohexyl group, acetylaminohexyl group, propionylaminohexyl group, butyrylaminohexyl group, pivaloylaminohexyl group and the like, and aroylamino-$C_{1-6}$ alkyl group such as benzoylaminomethyl group, benzoylaminoethyl group, benzoylaminopropyl group, benzoylaminobutyl group, benzoylaminopentyl group, benzoylaminohexyl group and the like, with preference given to acetylaminomethyl group and acetylaminoethyl group.

The "aralkyl group" is a group wherein the "$C_{1-6}$ alkyl group" is substituted by the aforementioned "aryl group". As used herein, the "aryl group" is preferably that having 6 to 14 carbon atoms. Examples thereof include phenyl group, naphthyl group, anthranyl group or biphenyl group and the like. Examples of the "aralkyl group" include benzyl group, phenethyl group, phenylbutyl group, phenylpropyl group, phenylpentyl group, phenylhexyl group, naphthylmethyl group, anthranylmethyl group, biphenylmethyl group and the like, with preference given to benzyl group.

As the "salt" of the compound of the present invention, there can be mentioned, but not limited to, inorganic acid addition salts such as hydrochloride, hydrobromide, sulfate, phosphate or nitrate and the like; organic acid addition salts such as acetate, propionate, succinate, glycolate, lactate, malate, oxalate, tartrate, citrate, maleate, fumarate, methanesulfonate, benzenesulfonate, p-toluenesulfonate or ascorbate and the like; amino acid addition salts such as aspartate or glutamate and the like; inorganic base salts with sodium, potassium, calcium, magnesium or zinc and the like; organic base salts with methylamine, dimethylamine, ethylamine, diethylamine, triethylamine, triethanolamine, trishydroxymethylaminomethane, dicyclohexylamine, ethylenediamine, guanidine, meglumine, 2-aminoethanol and the like; and base salts with amino acids such as asparagine, glutamine, arginine, histidine, lysin and the like. Preferable salts are hydrochloride, sodium salt, potassium salt and calcium salt, and hydrochloride and sodium salt are particularly preferable.

The compound of the present invention includes solvate. As used herein, a "solvate" of a compound includes solids such as crystal, amorphous form and the like, as well as those forms comprising the compound of the present invention bonded with solvent molecules such as water, alcohol and the like in a solution by a comparatively weak bond based on Van der Waals force, static interaction, hydrogen bond, charge transfer bond, coordinate bond and the like. In some cases, solvent may be incorporated into a solid state such as hydrate, alcoholate and the like. Preferable solvate is hydrate.

A "prodrug" of a compound is a derivative of the compound of the present invention, which has a chemically or metabolically decomposable group, which decomposes by hydrolysis or solvolysis, or under physiological conditions to show pharmaceutical activity. A substituent represented by $R^A$ and a substituent represented by $R^B$ in the formula (1) of the present invention are substituents directed to a prodrug, and —$COR^A$ and/or —$OR^B$ are/is substituent(s) converted to —$CO_2H$ and/or —OH in the living organism.

The "ring V" in the present invention is a ring represented by

in the formula (1), wherein $X_1$ is as defined above and "ring W" is a ring represented by

is the formula (1), wherein $X_2$ is as defined above.

The "$IC_{50}$ value of calcium receptor antagonistic action" is a value measured by the method described in Experimental Example 1 in the present specification.

The "metabolic enzyme P450" indicates cytochrome P450 existing in an animal, especially CYP2C9, CYP2D6 or CYP3A4 can be mentioned.

The "$IC_{50}$ value of inhibitory action of the metabolic enzyme CYP2D6" is a value measured by the method described in Experimental Example 4 in the present specification.

The "$IC_{50}$ value of its calcium receptor antagonistic action is not less than 10 times an $IC_{50}$ value of an inhibitory action of metabolic enzyme CYP2D6", the "$IC_{50}$ value of the calcium receptor antagonistic action is not less than 100 times the $IC_{50}$ value of the inhibitory action of the metabolic enzyme CYP2D6" refer to values calculated based on the comparison of the above-mentioned "$IC_{50}$ value of calcium receptor antagonistic action" and "$IC_{50}$ value of metabolic enzyme CYP2D6 inhibitory action".

The "$IC_{50}$ value of the compound of the calcium receptor antagonistic action is not more than 0.1 µM" means that the above-mentioned "$IC_{50}$ value of the calcium receptor antagonistic action" is 0.1 µM or below.

The "$IC_{50}$ value of a metabolic enzyme CYP2D6 inhibitory action is not less than 10 µM", and the "$IC_{50}$ value of the metabolic enzyme CYP2D6 inhibitory action is not less than 1 µM" refer to the above-mentioned "$IC_{50}$ value of the metabolic enzyme CYP2D6 inhibitory action" of not less than 10 µM and not less than 1 µM, respectively.

The compound represented by the formula (1) of the present invention has various isomers, such as optical isomers, stereoisomers, geometric isomers, tautomers and the like. The present invention encompasses all these isomers and mixtures thereof.

In the compound represented by the formula (1) of the present invention, $R^1$ is preferably a hydroxyl group or a $C_{1-4}$ alkoxy group, more preferably a hydroxyl group, a methoxy group or an ethoxy group, particularly preferably a hydroxyl group, $R^2$ and $R^3$ are each preferably a hydrogen atom, a hydroxyl group, a halogen atom (particularly preferably chlorine atom, fluorine atom), an amino group, an $C_{1-7}$ acylamino group (particularly preferably $C_{1-4}$ alkylcarbonylamino group), a halo-$C_{1-6}$ alkyl group (particularly preferably a trifluoromethyl group), a carboxyl group, a $C_{1-6}$ alkoxy group (particularly preferably $C_{1-4}$ alkoxy group), a halo-$C_{1-6}$ alkoxy group, a hydroxy-$C_{1-6}$ alkyl group (particularly preferably hydroxy-$C_{1-4}$ alkyl group), a $C_{1-7}$ acylamino-$C_{1-6}$ alkyl group (particularly preferably $C_{1-4}$ alkylcarbonylamino-$C_{1-4}$ alkyl group), a $C_{1-6}$ alkyl group (particularly preferably $C_{1-4}$ alkyl group), a $C_{2-4}$ alkenyl group, a $C_{1-6}$ alkoxy-carbonyl group, a di($C_{1-6}$ alkyl) amino group (particularly preferably di($C_{1-4}$ alkyl) amino group) or a phenyl group, or $R^2$ and $R^3$ are joined to form an ethyleneoxy group, $R^2$ is preferably a hydroxyl group, a halogen atom, an amino group, an $C_{1-7}$ acylamino group, a halo-$C_{1-6}$ alkyl group, a $C_{1-6}$ alkoxy-carbonyl group, a $C_{1-6}$ alkoxy group, a halo-$C_{1-6}$ alkoxy group, a C$_{1-6}$ alkyl group, a hydroxy-C$_{1-6}$ alkyl group, a di(C$_{1-6}$ alkyl) amino group or nitro group, more preferably a C$_{1-6}$ alkyl group, particularly preferably a C$_{1-4}$ alkyl group, X$^1$ is preferably —C═C— or —C═N—, particularly preferably —C═C—, X$^2$ is preferably —C═C—, Z is preferably —S—, —SO—, —SO$_2$—, —(CH$_2$)$_{m1}$—O—, —O—(CH$_2$)$_{m1}$—, —(CH$_2$)$_{m2}$—NH—, —NH—(CH$_2$)$_{m2}$—, —(CH$_2$)$_{m3}$—N(CH$_3$)—, —N(CH$_3$)—(CH$_2$)$_{m3}$—, C$_{1-4}$ alkylene or C$_{2-4}$ alkenylene, m1, m2 and m3 are each preferably 0 or 1, alkylene for Z is preferably methylene or ethylene, R$^4$ is preferably a C$_{1-6}$ alkyl group or a cyclopropyl group, particularly preferably a C$_{1-4}$ alkyl group such as methyl group and the like, R$^5$ is preferably a hydrogen atom, p is preferably 1, Y is preferably a carbon atom, and R$^6$, R$^7$ and R$^8$ are each preferably a hydrogen atom, a halogen atom (particularly preferably chlorine atom or fluorine atom), a C$_{1-4}$ alkyl group or a C$_{1-4}$ alkoxy group, or adjacent R$^6$ and R$^7$ are joined to form —CH═CH—CH═CH—.

The case that R$^6$ and R$^7$ are selected from the group which consist of halogen atom is particularly preferable.

The position of R$^6$ and R$^7$ is preferably

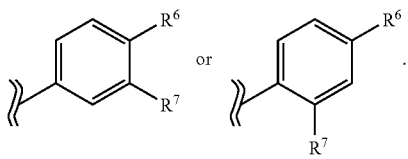

In the compound represented by the formula (1) of the present invention, when n is 1, for example, an embodiment wherein R$^1$ is a hydroxyl group or a C$_{1-6}$ alkoxy group, R$^2$ and R$^3$ are the same or different and each is a hydrogen atom, a hydroxyl group, a halogen atom, an amino group, a C$_{1-7}$ acylamino group, a trifluoromethyl group, a C$_{1-6}$ alkoxy-carbonyl group, a C$_{1-6}$ alkoxy group, a C$_{1-6}$ alkyl group, a hydroxy-C$_{1-6}$ alkyl group, a C$_{2-6}$ alkenyl group, a phenyl group, a benzyl group, a di(C$_{1-6}$ alkyl)amino group or a nitro group, or R$^2$ and R$^3$ are joined to form an ethyleneoxy group, X$^1$ is —C═C— or —C═N—, X$^2$ is —C═C—, Z is —S—, —SO—, —SO$_2$—, —(CH$_2$)$_{m1}$—O—, —O—(CH$_2$)$_{m1}$—, —(CH$_2$)$_{m2}$—NH—, —NH—(CH$_2$)$_{m2}$—, —(CH$_2$)$_{m3}$—N(CH$_3$)—, —N(CH$_3$)—(CH$_2$)$_{m3}$—, a C$_{1-4}$ alkylene group or a C$_{2-4}$ alkenylene group, wherein m1, m2 and m3 are each an integer of 0 to 2, R$^4$ is a C$_{1-6}$ alkyl group or a C$_{3-6}$ cycloalkyl group, R$^5$ is a hydrogen atom, p is 1, Y is a carbon atom or a nitrogen atom, and R$^6$, R$^7$ and R$^8$ are the same or different and each is a hydrogen atom, a halogen atom, a C$_{1-6}$ alkyl group or a C$_{1-6}$ alkoxy group, or adjacent R$^6$ and R$^7$ are joined to form —CH═CH—CH═CH— is preferable. Of such compounds, a compound wherein R$^1$ is a hydroxyl group or a C$_{1-4}$ alkoxy group, particularly a hydroxyl group, a methoxy group or an ethoxy group, R$^2$ and R$^3$ are the same or different and each is a hydrogen atom, a hydroxyl group, a halogen atom (particularly chlorine atom or fluorine atom), an amino group, a C$_{1-7}$ acylamino group (particularly C$_{1-4}$ alkylcarbonylamino group), a trifluoromethyl group, a C$_{1-4}$ alkoxy group (particularly methoxy group), a hydroxy-C$_{1-4}$ alkyl group, a C$_{1-4}$ alkyl group, a C$_{2-4}$ alkenyl group, a C$_{1-4}$ alkoxy-carbonyl group or a phenyl group, or R$^2$ and R$^3$ are joined to form an ethyleneoxy group, X$^1$ and X$^2$ are —C═C—, Z is —S—, —SO—, —SO$_2$—, —(CH$_2$)$_{m1}$—O—, —O—(CH$_2$)$_{m1}$—, —(CH$_2$)$_{m2}$—NH—, —NH—(CH$_2$)$_{m2}$—, —(CH$_2$)$_{m3}$—N(CH$_3$)—, —N(CH$_3$)—(CH$_2$)$_{m3}$—, a C$_{1-4}$ alkylene group (particularly methylene or ethylene) or a C$_{2-4}$ alkenylene group, wherein m1, m2 and m3 are each 0 or 1, R$^4$ is a C$_{1-6}$ alkyl group or a cyclopropyl group, particularly a C$_{1-4}$ alkyl group (methyl group etc.), R$^5$ is a hydrogen atom, p is 1, Y is a carbon atom, and R$^6$, R$^7$ and R$^8$ are the same or different and each is a hydrogen atom, a halogen atom (preferably chlorine atom or fluorine atom), a C$_{1-4}$ alkyl group or a C$_{1-4}$ alkoxy group, or adjacent R$^6$ and R$^7$ are joined to form —CH═CH—CH═CH— is preferable.

In the compound represented by the formula (1) of the present invention, when n is 1, for example, an embodiment wherein R$^1$ is a hydroxyl group or a C$_{1-6}$ alkoxy group (preferably methoxy group), R$^2$ and R$^3$ are the same or different and each is a hydrogen atom, a halogen atom (preferably fluorine atom or chlorine atom), a C$_{1-6}$ alkoxy group (preferably methoxy group) or a C$_{1-6}$ alkyl group (preferably methyl group, ethyl group, n-propyl group or isopropyl group), X$^1$ is —C═C—, X$^2$ is —C═C—, Z is —S—, —SO—, —SO$_2$—, —(CH$_2$)$_{m1}$—O—, —O—(CH$_2$)$_{m1}$—, —CH$_2$—NH—, —NH—CH$_2$—, —N(CH$_3$)—, methylene or vinylene, wherein m1 is 0 or 1, R$^4$ is a methyl group or a cyclopropyl group, R$^5$ is a hydrogen atom, p is 1, Y is a carbon atom or a nitrogen atom, and R$^6$, R$^7$ and R$^8$ are the same or different and each is a hydrogen atom, a halogen atom (preferably fluorine atom or chlorine atom) or a $C_{1-6}$ alkyl group (preferably methyl group), or adjacent $R^6$ and $R^7$ are joined to form —CH=CH—CH=CH— is more preferable. Of the above, an embodiment wherein $R^1$ is a hydroxyl group or a $C_{1-4}$ alkoxy group, particularly a hydrogen atom, a methoxy group or an ethoxy group, $R^2$ and $R^3$ are the same or different and each is a hydrogen atom or a $C_{1-4}$ alkyl group (particularly methyl group), $X^1$ is —C=C—, $X^2$ is —C=C—, Z is —S—, —SO—, —SO$_2$—, —(CH$_2$)$_{m1}$—O—, —O—(CH$_2$)$_{m1}$—, —$_{CH2}$—NH—, —NH—CH$_2$—, —N(CH$_3$)—, methylene or vinylene, wherein m1 is 0 or 1, $R^4$ is a methyl group or a cyclopropyl group, $R^5$ is a hydrogen atom, p is 1, Y is a carbon atom, and $R^6$, $R^7$ and $R^8$ are the same or different and each is a hydrogen atom, a halogen atom (particularly chlorine atom or fluorine atom) or a $C_{1-4}$ alkyl group (particularly methyl group), or adjacent $R^6$ and $R^7$ are joined to form —CH=CH—CH=CH— is preferable.

In the compound represented by the formula (1) of the present invention, when n is 0, for example, an embodiment wherein $R^1$ is a hydroxyl group or a $C_{1-6}$ alkoxy group, $R^2$ and $R^3$ are the same or different and each is a hydrogen atom, a hydroxyl group, a halogen atom, an amino group, a $C_{1-7}$ acylamino group, a trifluoromethyl group, a $C_{1-6}$ alkoxy-carbonyl group, a $C_{1-6}$ alkoxy group, a $C_{1-6}$ alkyl group, hydroxy-$C_{1-6}$ alkyl group, a $C_{2-6}$ alkenyl group, a phenyl group, a benzyl group, di($C_{1-6}$ alkyl)amino group or a nitro group, or $R^2$ and $R^3$ are joined to form an ethyleneoxy group, $X^1$ is —C=C— or —C=N—, $X^2$ is —C=C—, $R^4$ is a $C_{1-6}$ alkyl group or a $C_{3-6}$cycloalkyl group, $R^5$ is a hydrogen atom, p is 1, Y is a carbon atom or a nitrogen atom, and $R^6$, $R^7$ and $R^8$ are the same or different and each is a hydrogen atom, a halogen atom, a $C_{1-6}$ alkyl group or a $C_{1-6}$ alkoxy group, or adjacent $R^6$ and $R^7$ are joined to form —CH=CH—CH=CH— is preferable, and particularly, an embodiment wherein $R^1$ is a hydroxyl group or a $C_{1-4}$ alkoxy group, particularly a hydroxyl group, a methoxy group or an ethoxy group, $R^2$ and $R^3$ are the same or different and each is a hydrogen atom, a hydroxyl group, a halogen atom (particularly chlorine atom or fluorine atom), an amino group, a $C_{1-7}$ acylamino group (particularly $C_{1-4}$ alkylcarbonylamino group), a trifluoromethyl group, a $C_{1-4}$ alkoxy group (particularly methoxy group), a hydroxy-$C_{1-4}$ alkyl group, a $C_{1-4}$ alkyl group, a phenyl group, a di($C_{1-6}$ alkyl)amino group, a $C_{2-4}$ alkenyl group or a $C_{1-4}$ alkoxy-carbonyl group, or $R^2$ and $R^3$ are joined to form an ethyleneoxy group, $X^1$ is —C=C— or —C=N—, $X^2$ is —C=C—, $R^4$ is a $C_{1-6}$ alkyl group or a cyclopropyl group, particularly a $C_{1-4}$ alkyl group (methyl group etc.), $R^5$ is a hydrogen atom, p is 1, Y is a carbon atom, $R^6$, $R^7$ and $R^8$ are the same or different and each is a hydrogen atom, a halogen atom (particularly chlorine atom or fluorine atom), a $C_{1-4}$ alkyl group or a $C_{1-4}$ alkoxy group, or adjacent $R^6$ and $R^7$ are joined to form —CH=CH—CH=CH— is preferable.

In the compound represented by the formula (1) of the present invention, when n is 0, for example, an embodiment wherein $R^1$ is a hydroxyl group or a $C_{1-6}$ alkoxy group (preferably methoxy group), $R^2$ and $R^3$ are the same or different and each is a hydrogen atom, a hydroxyl group, a halogen atom (preferably fluorine atom or chlorine atom), an amino group, a $C_{1-7}$ acylamino group (preferably acetylamino group), a trifluoromethyl group, a $C_{1-6}$ alkoxy-carbonyl group (preferably methoxy-carbonyl group), a $C_{1-6}$ alkoxy group (preferably methoxy group), a $C_{1-6}$ alkyl group (preferably methyl group, ethyl group, propyl group, isopropyl group, isobutyl group), a hydroxy-$C_{1-6}$ alkyl group (preferably hydroxymethyl group), a $C_{2-6}$ alkenyl group (preferably 2-methyl-1-propenyl group), a phenyl group, a benzyl group, a di($C_{1-6}$ alkyl)amino group (preferably dimethylamino group) or a nitro group, or $R^2$ and $R^3$ are joined to form an ethyleneoxy group, $X^1$ is —C=C— or —C=N—, $X^2$ is —C=C—, $R^4$ is a methyl group or a cyclopropyl group, $R^5$ is a hydrogen atom, p is 1, Y is a carbon atom, and $R^6$, $R^7$ and $R^8$ are the same or different and each is a hydrogen atom, a halogen atom (preferably fluorine atom or chlorine atom), a $C_{1-6}$ alkyl group (preferably methyl group or ethyl group) or a $C_{1-6}$ alkoxy group (preferably methoxy group), or adjacent $R^6$ and $R^7$ are joined to form —CH=CH—CH=CH— is more preferable, and particularly, an embodiment wherein $R^1$ is a hydroxyl group or a $C_{1-4}$ alkoxy group (particularly methoxy group or ethoxy group), $R^2$ and $R^3$ are the same or different and each is a hydrogen atom, a hydroxyl group, a halogen atom (particularly chlorine atom or fluorine atom), an amino group, a $C_{1-7}$ acylamino group (particularly $C_{1-4}$ alkylcarbonylamino group (e.g., acetylamino group)), a trifluoromethyl group, a $C_{1-4}$ alkoxy group (particularly methoxy group), a hydroxy-$C_{1-4}$ alkyl group (particularly hydroxymethyl group), a $C_{1-4}$ alkyl group (particularly methyl group, ethyl group, isopropyl group, propyl group or isobutyl group), a $C_{2-4}$ alkenyl group (particularly 2-methyl-1-propenyl group), a $C_{1-4}$ alkoxy-carbonyl group (particularly acetylcarbonyl group), a benzyl group or a phenyl group, or $R^2$ and $R^3$ are joined to form an ethyleneoxy group, $X^1$ is —C=C— or —C=N—, $X^2$ is —C=C—, $R^4$ is a methyl group or a cyclopropyl group, $R^5$ is a hydrogen atom, p is 1, Y is a carbon atom, $R^6$, $R^7$ and $R^8$ are the same or different and each is a hydrogen atom, a halogen atom (particularly chlorine atom or fluorine atom), a $C_{1-4}$ alkyl group (particularly methyl group) or a $C_{1-4}$ alkoxy group (particularly methoxy group), or adjacent $R^6$ and $R^7$ are joined to form —CH=CH—CH=CH— is preferable.

The compound represented by the formula (1) of the present invention preferably has a configuration represented by the following formula (1')

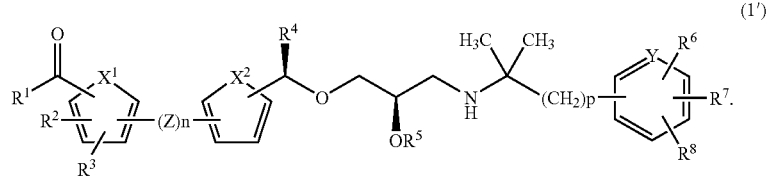

wherein each symbol is as defined above for the formula (1).

Preferable examples when n=0 are shown in the following, wherein the number placed before each compound name corresponds to Example No.

1-1
2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid 1-2
2'-[1-[(2R)-3-[[1-(4-chloro-3-fluorophenyl)-2-methylpropan-2-yl]amino]-2-hydroxypropoxy]ethyl]-3-methylbiphenyl-4-carboxylic acid 1-3
2'-[1-[(2R)-3-[[1-(3-chloro-4-methylphenyl)-2-methylpropan-2-yl]amino]-2-hydroxypropoxy]ethyl]-3-methylbiphenyl-4-carboxylic acid 1-4
2'-[1-[(2R)-3-[[1-(4-chloro-3-methylphenyl)-2-methylpropan-2-yl]amino]-2-hydroxypropoxy]ethyl]-3-methylbiphenyl-4-carboxylic acid 1-5
2'-[1-[(2R)-3-[[1-(2,3-difluoro-4-methylphenyl)-2-methylpropan-2-yl]amino]-2-hydroxypropoxy]ethyl]-3-methylbiphenyl-4-carboxylic acid 1-6
2'-[1-[(2R)-3-[[1-(4-chloro-2-fluorophenyl)-2-methylpropan-2-yl]amino]-2-hydroxypropoxy]ethyl]-3-methylbiphenyl-4-carboxylic acid 1-7
2'-[1-[(2R)-3-[[1-(2-fluoro-4-methylphenyl)-2-methylpropan-2-yl]amino]-2-hydroxypropoxy]ethyl]-3-methylbiphenyl-4-carboxylic acid 1-8
2'-[1-[(2R)-3-[[1-(4-ethyl-3-fluorophenyl)-2-methylpropan-2-yl]amino]-2-hydroxypropoxy]ethyl]-3-methylbiphenyl-4-carboxylic acid 1-9
3-methyl-2'-[1-[(2R)-3-[[1-(naphthalen-2-yl)-2-methylpropan-2-yl]amino]-2-hydroxypropoxy]ethyl]biphenyl-5-carboxylic acid 1-10
methyl 2'-[1-[(2R)-3-[[1-(naphthalen-2-yl)-2-methylpropan-2-yl]amino]-2-hydroxypropoxy]ethyl]biphenyl-3,5-dicarboxylate 1-11
2'-[(cyclopropyl)[(2R)-3-[[1-(naphthalen-2-yl)-2-methylpropan-2-yl]amino]-2-hydroxypropoxy]methyl]-3-methylbiphenyl-4-carboxylic acid 1-12, 1-13
2'-[1-[(2R)-3-[[1-(naphthalen-2-yl)-2-methylpropan-2-yl]amino]-2-hydroxypropoxy]ethyl]-3-methylbiphenyl-4-carboxylic acid 1-14
2'-[(cyclopropyl)[(2R)-3-[[1-(3-fluoro-4-methylphenyl)-2-methylpropan-2-yl]amino]-2-hydroxypropoxy]methyl]-3-methylbiphenyl-4-carboxylic acid 1-15, 1-16
2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid 1-17
2'-[1-[(2R)-3-[[1-(3-fluoro-4-methylphenyl)-2-methylpropan-2-yl]amino]-2-hydroxypropoxy]ethyl]-3-methylbiphenyl-5-carboxylic acid 1-18
2'-[(cyclopropyl)[(2R)-3-[[1-(4-chloro-2-fluorophenyl)-2-methylpropan-2-yl]amino]-2-hydroxypropoxy]methyl]-3-methylbiphenyl-4-carboxylic acid 1-19
2'-[(cyclopropyl)[(2R)-3-[[1-(4-chloro-3-fluorophenyl)-2-methylpropan-2-yl]amino]-2-hydroxypropoxy]methyl]-3-methylbiphenyl-4-carboxylic acid 1-20
2'-[1-[(2R)-3-[[1-(3-fluoro-4-methoxyphenyl)-2-methylpropan-2-yl]amino]-2-hydroxypropoxy]ethyl]-3-methylbiphenyl-4-carboxylic acid 1-21
 3-methyl-2'-[1-[(2R)-3-[[1-(3,4-dimethylphenyl)-2-methylpropan-2-yl]amino]-2-hydroxypropoxy]ethyl]biphenyl-4-carboxylic acid 1-22
 2'-[1-[(2R)-3-[[1-(4-methylphenyl)-2-methylpropan-2-yl]amino]-2-hydroxypropoxy]ethyl]-3-methylbiphenyl-4-carboxylic acid 1-23
 2'-[1-[(2R)-3-[[1-(4-chloro-3-methoxyphenyl)-2-methylpropan-2-yl]amino]-2-hydroxypropoxy]ethyl]-3-methylbiphenyl-4-carboxylic acid 1-24
 2'-[1-[(2R)-3-[[1-(4-ethylphenyl)-2-methylpropan-2-yl]amino]-2-hydroxypropoxy]ethyl]-3-methylbiphenyl-4-carboxylic acid 1-25
 2'-[1-[(2R)-3-[[1-(4-chloro-2,5-difluorophenyl)-2-methylpropan-2-yl]amino]-2-hydroxypropoxy]ethyl]-3-methylbiphenyl-4-carboxylic acid 1-26
 2'-[1-[(2R)-3-[[1-(naphthalen-2-yl)-2-methylpropan-2-yl]amino]-2-hydroxypropoxy]ethyl]-3-methoxybiphenyl-4-carboxylic acid 1-27
 2'-[1-[(2R)-3-[[1-(naphthalen-2-yl)-2-methylpropan-2-yl]amino]-2-hydroxypropoxy]ethyl]-2-methoxybiphenyl-4-carboxylic acid 1-28
 2'-[1-[(2R)-3-[[1-(naphthalen-2-yl)-2-methylpropan-2-yl]amino]-2-hydroxypropoxy]ethyl]-3-(trifluoromethyl)biphenyl-4-carboxylic acid 1-29
 2'-[1-[(2R)-3-[[1-(2-fluoro-4-methoxyphenyl)-2-methylpropan-2-yl]amino]-2-hydroxypropoxy]ethyl]-3-(trifluoromethyl)biphenyl-4-carboxylic acid 1-30
 3-ethyl-2'-[1-[(2R)-3-[[1-(naphthalen-2-yl)-2-methylpropan-2-yl]amino]-2-hydroxypropoxy]ethyl]biphenyl-4-carboxylic acid 1-31
 2'-[1-[(2R)-3-[[1-(3,4-dichlorophenyl)-2-methylpropan-2-yl]amino]-2-hydroxypropoxy]ethyl]-3-(trifluoromethyl)biphenyl-4-carboxylic acid 1-32
 2'-[1-[(2R)-3-[[1-(naphthalen-2-yl)-2-methylpropan-2-yl]amino]-2-hydroxypropoxy]ethyl]-3-isopropylbiphenyl-4-carboxylic acid 1-33
 3-ethyl-2'-[1-[(2R)-3-[[1-(3-fluoro-4-methylphenyl)-2-methylpropan-2-yl]amino]-2-hydroxypropoxy]ethyl]biphenyl-4-carboxylic acid 1-34
 2'-[1-[(2R)-3-[[1-(3-fluoro-4-methylphenyl)-2-methylpropan-2-yl]amino]-2-hydroxypropoxy]ethyl]-3-isopropylbiphenyl-4-carboxylic acid 1-35
 2-chloro-6-[2-[1-[(2R)-3-[[1-(naphthalen-2-yl)-2-methylpropan-2-yl]amino]-2-hydroxypropoxy]ethyl]phenyl]pyridine-3-carboxylic acid 1-36
 2'-[1-[(2R)-3-[[1-(naphthalen-2-yl)-2-methylpropan-2-yl]amino]-2-hydroxypropoxy]ethyl]-3-propylbiphenyl-4-carboxylic acid 1-37
 2,3-dimethyl-2'-[1-[(2R)-3-[[1-(naphthalen-2-yl)-2-methylpropan-2-yl]amino]-2-hydroxypropoxy]ethyl]biphenyl-4-carboxylic acid 1-38
 2'-[1-[(2R)-3-[[1-(3-fluoro-4-methylphenyl)-2-methylpropan-2-yl]amino]-2-hydroxypropoxy]ethyl]-3-propylbiphenyl-4-carboxylic acid 1-39
 2-chloro-6-[2-[1-[(2R)-3-[[1-(3-fluoro-4-methylphenyl)-2-methylpropan-2-yl]amino]-2-hydroxypropoxy]ethyl]phenyl]pyridine-3-carboxylic acid 1-40
 3,5-dimethyl-2'-[1-[(2R)-3-[[1-(naphthalen-2-yl)-2-methylpropan-2-yl]amino]-2-hydroxypropoxy]ethyl]biphenyl-4-carboxylic acid 1-41
 2-[1-[(2R)-3-[[1-(naphthalen-2-yl)-2-methylpropan-2-yl]amino]-2-hydroxypropoxy]ethyl]-m-terphenyl-4'-carboxylic acid 1-42
 2'-[1-[(2R)-3-[[1-(3-fluoro-4-methylphenyl)-2-methylpropan-2-yl]amino]-2-hydroxypropoxy]ethyl]-2,3-dimethylbiphenyl-4-carboxylic acid 1-43
 2'-[1-[(2R)-3-[[1-(3-fluoro-4-methylphenyl)-2-methylpropan-2-yl]amino]-2-hydroxypropoxy]ethyl]-3,5-dimethylbiphenyl-4-carboxylic acid 1-44
 4-(hydroxymethyl)-2'-[1-[(2R)-3-[[1-(naphthalen-2-yl)-2-methylpropan-2-yl]amino]-2-hydroxypropoxy]ethyl]biphenyl-3-carboxylic acid 1-45
 3-isobutyl-2'-[1-[(2R)-3-[[1-(naphthalen-2-yl)-2-methylpropan-2-yl]amino]-2-hydroxypropoxy]ethyl]biphenyl-4-carboxylic acid 1-46
 2'-[1-[(2R)-3-[[1-(3-fluoro-4-methylphenyl)-2-methylpropan-2-yl]amino]-2-hydroxypropoxy]ethyl]-3-isobutylbiphenyl-4-carboxylic acid 1-47
 2'-[1-[(2R)-3-[[1-(3-fluoro-4-methylphenyl)-2-methylpropan-2-yl]amino]-2-hydroxypropoxy]ethyl]-4-(hydroxymethyl)biphenyl-3-carboxylic acid 1-48
 2'-[1-[(2R)-3-[[1-(3-fluoro-4-methylphenyl)-2-methylpropan-2-yl]amino]-2-hydroxypropoxy]ethyl]-3-(2-methyl-1-propenyl)biphenyl-4-carboxylic acid 1-49
 2'-[1-[(2R)-3-[[1-(naphthalen-2-yl)-2-methylpropan-2-yl]amino]-2-hydroxypropoxy]ethyl]-3-hydroxybiphenyl-4-carboxylic acid 1-50
 2'-[1-[(2R)-3-[[1-(3-fluoro-4-methylphenyl)-2-methylpropan-2-yl]amino]-2-hydroxypropoxy]ethyl]-3-hydroxybiphenyl-4-carboxylic acid 1-51
  3-ethyl-2'-[1-[(2R)-3-[[1-(4-chloro-3-fluorophenyl)-2-methylpropan-2-yl]amino]-2-hydroxypropoxy]ethyl]biphenyl-4-carboxylic acid 1-52
  2'-[1-[(2R)-3-[[1-(4-chloro-3-fluorophenyl)-2-methylpropan-2-yl]amino]-2-hydroxypropoxy]ethyl]-3-isopropylbiphenyl-4-carboxylic acid 1-53
  2'-[1-[(2R)-3-[[1-(3-fluoro-4-methylphenyl)-2-methylpropan-2-yl]amino]-2-hydroxypropoxy]ethyl]-3-(1-methylpropyl)biphenyl-4-carboxylic acid 1-54
  2-methyl-2'-[1-[(2R)-3-[[1-(naphthalen-2-yl)-2-methylpropan-2-yl]amino]-2-hydroxypropoxy]ethyl]biphenyl-4-carboxylic acid 1-55
  3-methyl-2'-[1-[(2R)-3-[[1-(naphthalen-2-yl)-2-methylpropan-2-yl]amino]-2-hydroxypropoxy]ethyl]biphenyl-4-carboxylic acid 1-56
  4-fluoro-2'-[1-[(2R)-3-[[1-(naphthalen-2-yl)-2-methylpropan-2-yl]amino]-2-hydroxypropoxy]ethyl]biphenyl-3-carboxylic acid 1-57
  2'-[1-[(2R)-3-[[1-(3,4-dichlorophenyl)-2-methylpropan-2-yl]amino]-2-hydroxypropoxy]ethyl]-2-methylbiphenyl-4-carboxylic acid 1-58
  6-fluoro-2'-[1-[(2R)-3-[[1-(naphthalen-2-yl)-2-methylpropan-2-yl]amino]-2-hydroxypropoxy]ethyl]biphenyl-3-carboxylic acid 1-59
  3-fluoro-2'-[1-[(2R)-3-[[1-(naphthalen-2-yl)-2-methylpropan-2-yl]amino]-2-hydroxypropoxy]ethyl]biphenyl-4-carboxylic acid 1-60
  2'-[1-[(2R)-3-[[1-(3-chlorophenyl)-2-methylpropan-2-yl]amino]-2-hydroxypropoxy]ethyl]-3-methylbiphenyl-4-carboxylic acid 1-61
  2'-[1-[(2R)-3-[[1-(3,4-dichlorophenyl)-2-methylpropan-2-yl]amino]-2-hydroxypropoxy]ethyl]-3-methylbiphenyl-4-carboxylic acid 1-62
  2-fluoro-2'-[1-[(2R)-3-[[1-(naphthalen-2-yl)-2-methylpropan-2-yl]amino]-2-hydroxypropoxy]ethyl]biphenyl-4-carboxylic acid 1-63
  2'-[(cyclopropyl)[(2R)-3-[[1-(naphthalen-2-yl)-2-methylpropan-2-yl]amino]-2-hydroxypropoxy]methyl]-3-methylbiphenyl-4-carboxylic acid 1-64
  2'-[(cyclopropyl)[(2R)-3-[[1-(naphthalen-2-yl)-2-methylpropan-2-yl]amino]-2-hydroxypropoxy]methyl]-3-fluorobiphenyl-4-carboxylic acid 1-65
  2'-[(cyclopropyl)[(2R)-3-[[1-(naphthalen-2-yl)-2-methylpropan-2-yl]amino]-2-hydroxypropoxy]methyl]-2-fluorobiphenyl-4-carboxylic acid 1-66
  2'-[(cyclopropyl)[(2R)-3-[[1-(naphthalen-2-yl)-2-methylpropan-2-yl]amino]-2-hydroxypropoxy]methyl]-2-methylbiphenyl-4-carboxylic acid 1-67
  2'-[1-[(2R)-3-[[1-(3,4-dichlorophenyl)-2-methylpropan-2-yl]amino]-2-hydroxypropoxy]ethyl]-2-fluorobiphenyl-4-carboxylic acid 1-68
  3-chloro-2'-[1-[(2R)-3-[[1-(naphthalen-2-yl)-2-methylpropan-2-yl]amino]-2-hydroxypropoxy]ethyl]biphenyl-4-carboxylic acid 1-69
  2'-[1-[(2R)-3-[[1-(naphthalen-2-yl)-2-methylpropan-2-yl]amino]-2-hydroxypropoxy]ethyl]-3-nitrobiphenyl-4-carboxylic acid 1-70
  3-amino-2'-[1-[(2R)-3-[[1-(naphthalen-2-yl)-2-methylpropan-2-yl]amino]-2-hydroxypropoxy]ethyl]biphenyl-4-carboxylic acid 1-71
  3-(acetylamino)-2'-[1-[(2R)-3-[[1-(naphthalen-2-yl)-2-methylpropan-2-yl]amino]-2-hydroxypropoxy]ethyl]biphenyl-4-carboxylic acid 1-72
  3-chloro-2'-[1-[(2R)-3-[[1-(3-fluoro-4-methylphenyl)-2-methylpropan-2-yl]amino]-2-hydroxypropoxy]ethyl]biphenyl-4-carboxylic acid 1-73
  2'-[1-[(2R)-3-[[1-(3-methoxy-4-methylphenyl)-2-methylpropan-2-yl]amino]-2-hydroxypropoxy]ethyl]-3-methylbiphenyl-4-carboxylic acid 1-74
  2,3-dihydro-5-[2-[1-[(2R)-3-[[1-(naphthalen-2-yl)-2-methylpropan-2-yl]amino]-2-hydroxypropoxy]ethyl]phenyl]benzofuran-7-carboxylic acid 1-75
  2,6-dimethyl-2'-[1-[(2R)-3-[[1-(naphthalen-2-yl)-2-methylpropan-2-yl]amino]-2-hydroxypropoxy]ethyl]biphenyl-4-carboxylic acid 1-76
  2'-1-[(2R)-3-[[1-(3-fluoro-4-methylphenyl)-2-methylpropan-2-yl]amino]-2-hydroxypropoxy]ethyl]-2,6-dimethylbiphenyl-4-carboxylic acid 1-77
  3-(dimethylamino)-2'-[1-[(2R)-3-[[1-(naphthalen-2-yl)-2-methylpropan-2-yl]amino]-2-hydroxypropoxy]ethyl]biphenyl-4-carboxylic acid 1-78
  2,3-dihydro-5-[2-[1-[(2R)-3-[[1-(3-fluoro-4-methylphenyl)-2-methylpropan-2-yl]amino]-2-hydroxypropoxy]ethyl]phenyl]benzofuran-7-carboxylic acid 1-79
  3-benzyl-2'-[1-[(2R)-3-[[1-(3-fluoro-4-methylphenyl)-2-methylpropan-2-yl]amino]-2-hydroxypropoxy]ethyl]biphenyl-4-carboxylic acid 1-80
  2'-[1-[(2R)-3-[[1-(3-fluoro-4-methylphenyl)-2-methylpropan-2-yl]amino]-2-hydroxypropoxy]ethyl]-3-methoxybiphenyl-4-carboxylic acid 1-81
  2'-[1-[(2R)-3-[[1-(4-chloro-2-fluorophenyl)-2-methylpropan-2-yl]amino]-2-hydroxypropoxy]ethyl]-3-methoxybiphenyl-4-carboxylic acid 1-82
  2'-[1-[(2R)-3-[[1-(4-chloro-3-fluorophenyl)-2-methylpropan-2-yl]amino]-2-hydroxypropoxy]ethyl]-3-methoxybiphenyl-4-carboxylic acid 1-83
  2'-[1-[(2R)-3-[[1-(4-chloro-3-fluorophenyl)-2-methylpropan-2-yl]amino]-2-hydroxypropoxy]ethyl]-2-methylbiphenyl-4-carboxylic acid 1-84
  2'-[1-[(2R)-3-[[1-(4-chloro-2-fluorophenyl)-2-methylpropan-2-yl]amino]-2-hydroxypropoxy]ethyl]-2-methylbiphenyl-4-carboxylic acid 1-85
  4-methyl-2'-[1-[(2R)-3-[[1-(naphthalen-2-yl)-2-methylpropan-2-yl]amino]-2-hydroxypropoxy]ethyl]biphenyl-3-carboxylic acid 1-86
  2'-[1-[(2R)-3-[[1-(3-fluoro-4-methylphenyl)-2-methylpropan-2-yl]amino]-2-hydroxypropoxy]ethyl]-4-methylbiphenyl-3-carboxylic acid 1-87
  2'-[1-[(2R)-3-[[1-(3,5-dichlorophenyl)-2-methylpropan-2-yl]amino]-2-hydroxypropoxy]ethyl]-3-methylbiphenyl-4-carboxylic acid 1-89
  2'-[1-[(2R)-3-[[1-(2,5-difluorophenyl)-2-methylpropan-2-yl]amino]-2-hydroxypropoxy]ethyl]-3-methylbiphenyl-4-carboxylic acid 1-90
  2'-[1-[(2R)-3-[[1-(5-chloro-2-fluoro-4-methylphenyl)-2-methylpropan-2-yl]amino]-2-hydroxypropoxy]ethyl]-3-methylbiphenyl-4-carboxylic acid 1-91
  2'-[1-[(2R)-3-[[1-(3-chloro-2-fluorophenyl)-2-methylpropan-2-yl]amino]-2-hydroxypropoxy]ethyl]-3-methylbiphenyl-4-carboxylic acid 1-92
  2'-[1-[(2R)-3-[[1-(3-fluoro-4-trifluoromethylphenyl)-2-methylpropan-2-yl]amino]-2-hydroxypropoxy]ethyl]-3-methylbiphenyl-4-carboxylic acid 1-93
  2'-[1-([(2R)-3-[[1-(5-chloro-3-fluorophenyl)-2-methylpropan-2-yl]amino]-2-hydroxypropoxy]ethyl]-3-methylbiphenyl-4-carboxylic acid 1-94
  2'-[1-[(2R)-3-[[1-(3,5-ditrifluoromethylphenyl)-2-methylpropan-2-yl]amino]-2-hydroxypropoxy]ethyl]-3-methylbiphenyl-4-carboxylic acid 1-95
  2'-[1-[(2R)-3-[[1-(4-methyl-3,5-dimethoxyphenyl)-2-methylpropan-2-yl]amino]-2-hydroxypropoxy]ethyl]-3-methylbiphenyl-4-carboxylic acid 1-96
  2'-[1-'[(2R)-3-[[1-(3,5-dimethoxyphenyl)-2-methylpropan-2-yl]amino]-2-hydroxypropoxy]ethyl]-3-methylbiphenyl-4-carboxylic acid 1-97
  2'-[1-[(2R)-3-[[1-(4-chloro-3-trifluoromethylphenyl)-2-methylpropan-2-yl]amino]-2-hydroxypropoxy]ethyl]-3-methylbiphenyl-4-carboxylic acid 1-98
  2'-[1-[(2R)-3-[[1-(3-fluoro-4-methylphenyl)-2-methylpropan-2-yl]amino]-2-hydroxypropoxy]ethyl]-3-t-butylbiphenyl-4-carboxylic acid 1-99
  2'-[1-[(2R)-3-[[1-(4-chloro-2-fluorophenyl)-2-methylpropan-2-yl]amino]-2-hydroxypropoxy]ethyl]-3-t-butylbiphenyl-4-carboxylic acid 1-100
  2'-[1-[(2R)-3-[[1-(4-chloro-3-fluorophenyl)-2-methylpropan-2-yl]amino]-2-hydroxypropoxy]ethyl]-3-t-butylbiphenyl-4-carboxylic acid 1-101
  2'-[1-[(2R)-3-[[1-(3-fluoro-4-methylphenyl)-2-methylpropan-2-yl]amino]-2-hydroxypropoxy]ethyl]-3-methoxybiphenyl-4-carboxylic acid 1-102
  2'-[1-[(2R)-3-[[1-(3-fluoro-4-methylphenyl)-2-methylpropan-2-yl]amino]-2-hydroxypropoxy]ethyl]-3-morpholinobiphenyl-4-carboxylic acid 1-103
  2'-[1-[(2R)-3-[[1-(3-fluoro-4-methylphenyl)-2-methylpropan-2-yl]amino]-2-hydroxypropoxy]ethyl]-3-(trifluoromethoxy)biphenyl-4-carboxylic acid 1-104
  2'-[1-[(2R)-3-[[1-(3-trifluoromethyl-4-methylphenyl)-2-methylpropan-2-yl]amino]-2-hydroxypropoxy]ethyl]-3-methylbiphenyl-4-carboxylic acid 1-106
  2'-[1-[(2R)-3-[[1-(4-chloro-3-fluorophenyl)-2-methylpropan-2-yl]amino]-2-hydroxypropoxy]ethyl]-3-(hydroxymethyl)biphenyl-4-carboxylic acid 1-107
  2'-[1-[(2R)-3-[[1-(4-chloro-3-fluorophenyl)-2-methylpropan-2-yl]amino]-2-hydroxypropoxy]ethyl]-3-carboxylphenyl-4-carboxylic acid Preferable examples when n=1 are shown in the following.

2-1
  4-[2-1-[(2R)-3-[[1-(3-fluoro-4-methylphenyl)-2-methylpropan-2-yl]amino]-2-hydroxypropoxy]ethyl]phenoxy]benzoic acid 2-2
  4-[2-1-[(2R)-3-[[1-(3-fluoro-4-methylphenyl)-2-methylpropan-2-yl]amino]-2-hydroxypropoxy]ethyl]phenoxy]-3-methoxybenzoic acid 2-3
  methyl 4-[2-1-[(2R)-3-[[1-(naphthalen-2-yl)-2-methylpropan-2-yl]amino]-2-hydroxypropoxy]ethyl]phenoxy]benzoate 2-4
  4-[2-1-[(2R)-3-[[1-(naphthalen-2-yl)-2-methylpropan-2-yl]amino]-2-hydroxypropoxy]ethyl]phenoxy]benzoic acid 2-5
4-[2-[1-[(2R)-3-[[1-(quinolin-3-yl)-2-methylpropan-2-yl]amino]-2-hydroxypropoxy]ethyl]phenoxy]benzoic acid 2-6
4-[2-[1-[(2R)-3-[[1-(4-chloro-2-fluorophenyl)-2-methylpropan-2-yl]amino]-2-hydroxypropoxy]ethyl]phenoxy]benzoic acid 2-7
4-[2-[1-[(2R)-3-[[1-(3-fluoro-4-methylphenyl)-2-methylpropan-2-yl]amino]-2-hydroxypropoxy]ethyl]phenoxy]benzoic acid 2-8
3-[2-[1-[(2R)-3-[[1-(3-fluoro-4-methylphenyl)-2-methylpropan-2-yl]amino]-2-hydroxypropoxy]ethyl]phenoxy]benzoic acid 2-9
4-[2-[2-[1-[(2R)-3-[[1-(naphthalen-2-yl)-2-methylpropan-2-yl]amino]-2-hydroxypropoxy]ethyl]phenyl]vinyl]benzoic acid 2-10
3-[2-[1-[(2R)-3-[[1-(naphthalen-2-yl)-2-methylpropan-2-yl]amino]-2-hydroxypropoxy]ethyl]phenylthio]benzoic acid 2-11
4-[2-[2-[1-[(2R)-3-[[1-(3-fluoro-4-methylphenyl)-2-methylpropan-2-yl]amino]-2-hydroxypropoxy]ethyl]phenyl]vinyl]benzoic acid 2-12
4-[2-[1-[(2R)-3-[[1-(3-fluoro-4-methylphenyl)-2-methylpropan-2-yl]amino]-2-hydroxypropoxy]ethyl]phenoxy]-3,5-dimethylbenzoic acid 2-13
4-[2-[1-[(2R)-3-[[1-(4-chloro-2-fluorophenyl)-2-methylpropan-2-yl]amino]-2-hydroxypropoxy]ethyl]phenoxy]-3,5-dimethylbenzoic acid 2-14
4-[2-[1-[(2R)-3-[[1-(naphthalen-2-yl)-2-methylpropan-2-yl]amino]-2-hydroxypropoxy]ethyl]benzyl]benzoic acid 2-15
3-[2-[1-[(2R)-3-[[1-(naphthalen-2-yl)-2-methylpropan-2-yl]amino]-2-hydroxypropoxy]ethyl]benzyl]benzoic acid 2-16
4-[2-[1-[(2R)-3-[[1-(naphthalen-2-yl)-2-methylpropan-2-yl]amino]-2-hydroxypropoxy]ethyl]phenylthio]benzoic acid 2-17
4-[2-[1-[(2R)-3-[[1-(naphthalen-2-yl)-2-methylpropan-2-yl]amino]-2-hydroxypropoxy]ethyl]phenylsulfinyl]benzoic acid 2-18
4-[2-[1-[(2R)-3-[[1-(naphthalen-2-yl)-2-methylpropan-2-yl]amino]-2-hydroxypropoxy]ethyl]phenylsulfonyl]benzoic acid 2-19
4-[[2-[1-[(2R)-3-[[1-(naphthalen-2-yl)-2-methylpropan-2-yl]amino]-2-hydroxypropoxy]ethyl]phenylamino]methyl]benzoic acid 2-20
2-[[2-[1-[(2R)-3-[[1-(naphthalen-2-yl)-2-methylpropan-2-yl]amino]-2-hydroxypropoxy]ethyl]phenoxy]methyl]benzoic acid 2-21
3-[[2-[1-[(2R)-3-[[1-(naphthalen-2-yl)-2-methylpropan-2-yl]amino]-2-hydroxypropoxy]ethyl]phenoxy]methyl]benzoic acid 2-22
4-[[2-[1-[(2R)-3-[[1-(naphthalen-2-yl)-2-methylpropan-2-yl]amino]-2-hydroxypropoxy]ethyl]phenoxy]methyl]benzoic acid 2-23
3-[[2-[1-[(2R)-3-[[1-(3-fluoro-4-methylphenyl)-2-methylpropan-2-yl]amino]-2-hydroxypropoxy]ethyl]phenoxy]methyl]benzoic acid 2-24
4-[[2-[1-[(2R)-3-[[1-(3-fluoro-4-methylphenyl)-2-methylpropan-2-yl]amino]-2-hydroxypropoxy]ethyl]phenoxy]methyl]benzoic acid 2-25
3-fluoro-4-[[2-[1-[(2R)-3-[[1-(3-fluoro-4-methylphenyl)-2-methylpropan-2-yl]amino]-2-hydroxypropoxy]ethyl]phenoxy]methyl]benzoic acid 2-26
4-[[2-[1-[(2R)-3-[[1-(3-fluoro-4-methylphenyl)-2-methylpropan-2-yl]amino]-2-hydroxypropoxy]ethyl]phenoxy]methyl]-3-methylbenzoic acid 2-27
4-[2-[1-[(2R)-3-[[1-(3-fluoro-4-methylphenyl)-2-methylpropan-2-yl]amino]-2-hydroxypropoxy]ethyl]phenoxy]-3,5-dimethoxybenzoic acid 2-28
4-[2-[1-[(2R)-3-[[1-(3-fluoro-4-methylphenyl)-2-methylpropan-2-yl]amino]-2-hydroxypropoxy]ethyl]phenoxy]-3-nitrobenzoic acid 2-29
4-[2-[1-[(2R)-3-[[1-(3-fluoro-4-methylphenyl)-2-methylpropan-2-yl]amino]-2-hydroxypropoxy]ethyl]phenoxy]-2-nitrobenzoic acid 2-30
4-[2-[1-[(2R)-3-[[1-(3-fluoro-4-methylphenyl)-2-methylpropan-2-yl]amino]-2-hydroxypropoxy]ethyl]phenoxy]-3-chlorobenzoic acid 2-31
4-[2-[1-[(2R)-3-[[1-(3-fluoro-4-methylphenyl)-2-methylpropan-2-yl]amino]-2-hydroxypropoxy]ethyl]phenoxy]-2-chlorobenzoic acid 2-32
4-[2-[1-[(2R)-3-[[1-(3-fluoro-4-methylphenyl)-2-methylpropan-2-yl]amino]-2-hydroxypropoxy]ethyl]phenoxy]-2-trifluoromethylbenzoic acid 2-33
4-[2-[1-[(2R)-3-[[1-(3-fluoro-4-methylphenyl)-2-methylpropan-2-yl]amino]-2-hydroxypropoxy]ethyl]phenoxy]-3-trifluoromethylbenzoic acid 2-34
4-[2-[1-[(2R)-3-[[1-(3-fluoro-4-methylphenyl)-2-methylpropan-2-yl]amino]-2-hydroxypropoxy]ethyl]phenoxy]-3-fluorobenzoic acid 2-35
    4-[2-[1-[(2R)-3-[[1-(4-chloro-3-fluorophenyl)-2-methyl-propan-2-yl]amino]-2-hydroxypropoxy]ethyl]phenoxy]benzoic acid 2-36
    4-[2-[1-[(2R)-3-[[1-(4-chloro-3-fluorophenyl)-2-methyl-propan-2-yl]amino]-2-hydroxypropoxy]ethyl]phenoxy]-5-methylbenzoic acid The form of the compound of the present invention to be used as a pharmaceutical product is a compound itself (free form), a salt of the compound, a solvate of the compound or a prodrug of the compound. Preferable form is a free form, a salt of the compound or a solvate of the compound, particularly preferably a salt of the compound.

The compound of the present invention can be used in the form of a prodrug. In this case, for example, a compound represented by the formula (1), wherein $R^1$ is a hydroxyl group, is converted to a compound wherein $R^1$ is $R^A$, i.e., $C_{1-6}$ alkyl-OC(=O)O—$C_{1-4}$ alkylene-O—, $C_{3-6}$ cycloalkyl-OC(=O)O—$C_{1-4}$ alkylene-O— or OH—NH— and used as a prodrug, and/or a compound wherein $R^5$ is a hydrogen atom is converted to a compound wherein $R^5$ is $R^B$, i.e., a $C_{1-7}$ acyl group optionally substituted by carboxyl group and used as a prodrug.

A therapeutic drug for osteoporosis, which contains the compound of the present invention as an active ingredient can be used along with a different therapeutic drug for osteoporosis. The different therapeutic drug for osteoporosis is, for example, a calcium agent (Calcium Lactate, Calcium Gluconate, Calcium Aspartate, Calcium Chloride, Calcium Hydrogen Phosphate etc.), a vitamin D preparation (Alfacalcidol, Calcitriol, Maxacalcitol, Falecalcitriol etc.), a vitamin K preparation (Menatetrenone etc.), a female hormone preparation (Estradiol, Estriol), an estrogen antagonist preparation (Raloxifen etc.), an anabolic steroid preparation, a parathyroid hormone preparation (Teriparatide, PTH(1-84) etc.), a calcitonin preparation (Elcatonin, Calcitonin salmon etc.), a bisphosphonate preparation (Alendronate sodium hydrate, Sodium risedronate hydrate, Etidronate disodium, Pamidronate disodium, Incadronate didodium etc.), an ipriflavone preparation (Ipriflavone) and other therapeutic drug for osteoporosis such as Strontium Ranelate, a WNT inhibitors a PPAR gamma agonist, Osteopontin, a statin preparation, a RANK/RANKL inhibitor, a Src inhibitor, a Pyk2 inhibitor, Osteoprotegerin and the like. A therapeutic drug for osteoporosis containing the compound of the present invention and a different therapeutic drug for osteoporosis can be administered in an effective amount for osteoporosis patients.

The calcium receptor antagonist preferably shows an $IC_{50}$ value of its calcium receptor antagonistic action of not less than 10 times, more preferably not less than 100 times, that of the metabolic enzyme CYP2D6 inhibitory action.

In addition, the calcium receptor antagonist preferably shows an $IC_{50}$ value of its calcium receptor antagonistic action of not more than 0.1 μM and an $IC_{50}$ value of the metabolic enzyme P450, specially CYP2D6 inhibitory action of not less than 1 μM, more preferable an $IC_{50}$ value of the calcium receptor antagonistic action of not more than 0.1 μM, and an $IC_{50}$ value of metabolic enzyme P450, specially CYP2D6 inhibitory action of not less than 10 μM.

The production methods of the compound of the formula (1) of the present invention are concretely explained in the following. It is needless to say that the present invention is not limited to these production methods. For construction of the compound of the present invention, the construction may start from a moiety easily synthesized. When a reactive functional group is contained in a step, appropriate protection and deprotection may be performed, and to facilitate the reaction, any reagent other than those exemplified may be appropriately used.

The compound obtained in each step may be isolated and purified by conventional methods. In some cases, the compound may be used in the next step without isolation and purification.

The production methods of compound (1) are explained in the following separately for n=0 and n=1.

<Production Method when n=0>

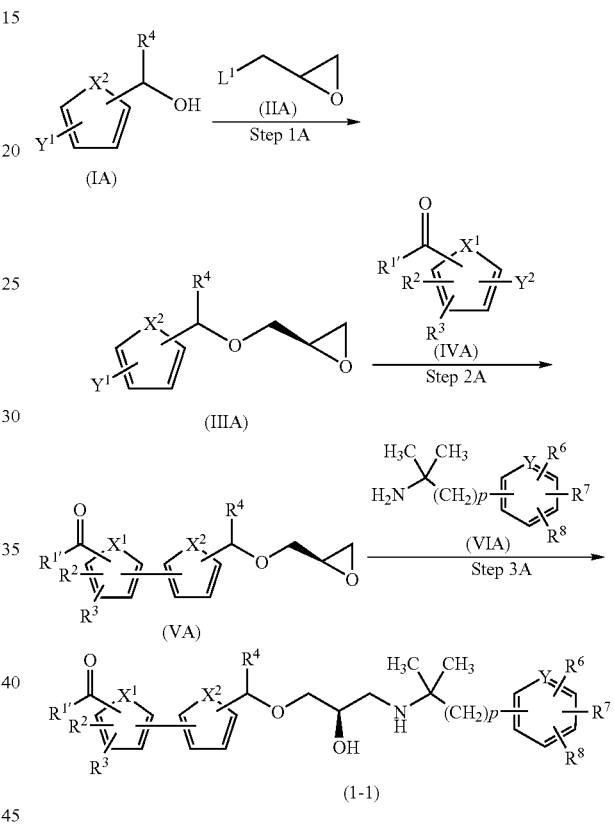

wherein $R^1$ is a $C_{1-6}$ alkoxy group, $Y^1$ and $Y^2$ are the same or different and each is a halogen atom (as defined above) or a trifluoromethanesulfonyloxy group, $L^1$ is a leaving group, such as a halogen atom (as defined above) or a sulfonyloxy group such as a 3-nitrobenzenesulfonyloxy group, a p-toluenesulfonyloxy group, a benzenesulfonyloxy group, a p-bromobenzenesulfonyloxy group, a methanesulfonyloxy group or a trifluoromethanesulfonyloxy group and the like, and other symbols are as defined above.

Step 1A

The compound (IA) is reacted with compound (IIA) in N,N-dimethylformamide, dimethyl sulfoxide, tetrahydrofuran, water and the like or a mixed solvent thereof, in the presence of a base such as sodium hydride, sodium hydroxide, potassium hydroxide, sodium carbonate, potassium carbonate, sodium hydrogencarbonate, potassium hydrogen carbonate, triethylamine, N,N-diisopropylethylamine, N-methylmorpholine, pyridine, 4-dimethylaminopyridine and the like at 0° C. to room temperature, whereby compound (IIIA) is obtained. In this case, alkylammonium hydrogensulfate such as tetrabutylammonium hydrogensulfate and the like can be added.

A stereoselective reaction can be carried out by selecting a reagent and a leaving group to be used.

For example, compound (IA) is reacted with (R)-glycidyl mesylate in N,N-dimethylformamide in the presence of sodium hydride to give compound (IIIA).

Step 2A

In this step, compound (VA) is obtained from compound (IIIA) or (IVA) by Suzuki coupling.

The compound (IVA) is reacted with bispinacolate diboron in dimethyl sulfoxide, N,N-dimethylformamide, 1,4-dioxane and the like or a mixed solvent thereof using a base such as bis(diphenylphosphino)ferrocenepalladium(II) chloride, potassium acetate and the like to give a boronic acid ester of compound (IVA), which is then reacted with compound (IIIA) in toluene, ethanol, benzene, acetone, 1,4-dioxane, tetrahydrofuran, acetonitrile, N,N-dimethylformamide, 1,2-dimethoxyethane, dimethyl sulfoxide, water and the like or a mixed solvent thereof, using a palladium catalyst such as bis(diphenylphosphino)ferrocenepalladium (II) chloride, tetrakis(triphenylphosphine)palladium(0) and the like and a base such as sodium carbonate, tripotassium phosphate ($K_3PO_4$), potassium carbonate, sodium hydrogencarbonate, potassium hydrogen carbonate and the like, whereby compound (VA) is obtained.

Alternatively, compound (IIIA) obtained in Step 1A is reacted with a palladium catalyst such as bis(diphenylphosphino)ferrocenepalladium(II) chloride, tetrakis(triphenylphosphine)palladium(0) and the like, potassium acetate and bispinacolate diboron in dimethyl sulfoxide, N,N-dimethylformamide, 1,4-dioxane and the like or a mixed solvent thereof to give a boronic acid ester of compound (IIIA), which is then reacted with compound (IVA) in toluene, ethanol, benzene, acetone, 1,4-dioxane, tetrahydrofuran, acetonitrile, 1,2-dimethoxyethane, dimethyl sulfoxide, water and the like or a mixed solvent thereof, using a palladium catalyst such as bis(diphenylphosphino)ferrocenepalladium(II) chloride, tetrakis(triphenylphosphine)palladium(0) and the like, and a base such as sodium carbonate, potassium carbonate, sodium hydrogencarbonate, potassium hydrogen carbonate, tripotassium phosphate and the like to give compound (VA).

Step 3A

The compound (VA) obtained in Step 2A is reacted with compound (VIA) in methanol, ethanol, n-propanol, isopropanol, tetrahydrofuran, 1,4-dioxane, acetonitrile, toluene and the like or a mixed solvent thereof at room temperature-reflux temperature to give compound (1-1). In this case, alkali perchlorate such as lithium perchlorate and the like is preferably added.

Hydrolysis of compound (1-1) by conventional methods results in conversion of $R^{1'}$ ($C_{1-6}$ alkoxy group) to a hydroxyl group.

The compound (VIA) used in Step 3A can be prepared by various methods. In the following, preparation methods of compound (VIA) are explained.

Preparation Method of Compound (VIA) 1

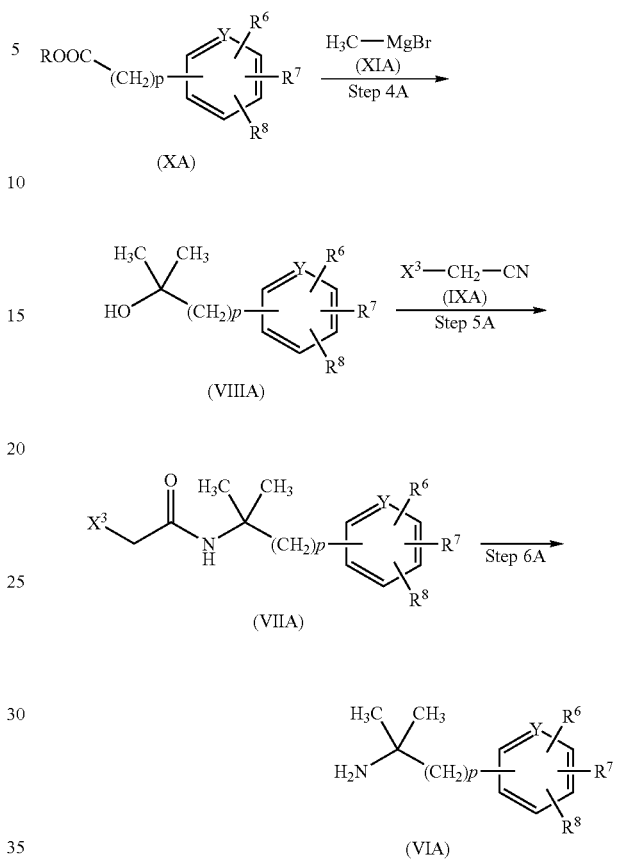

wherein $X^3$ is a hydrogen atom or a halogen atom (as defined above), R is an alkyl group (preferably a methyl group or an ethyl group), and other symbols are as defined above.

Step 4A

The compound (XA) is reacted with compound (XIA) in tetrahydrofuran or diethyl ether to give compound (VIIIA).

Step 5A

In this step, compound (VIIA) is obtained from compound (VIIIA) by Ritter reaction. The compound (VIIIA) obtained in Step 4A is reacted with compound (IXA) obtained in Step 4A in acetic acid with addition of sulfuric acid to give compound (VIIA).

Step 6A

When $X^3$ in compound (VIIA) obtained in Step 5A is a halogen atom, this step is performed under the conditions generally used for removing a haloacetyl group. For example, reaction in water, methanol, ethanol, n-propanol, isopropanol, tetrahydrofuran, 1,4-dioxane, acetic acid and the like or a mixed solvent thereof, using thiourea under heating gives compound (VIA).

When $X^3$ in compound (VIIA) is a hydrogen atom, this step is performed under the conditions generally used for removing an acetyl group. For example, reaction in water, methanol, ethanol, n-propanol, isopropanol, tetrahydrofuran, 1,4-dioxane, diethylene glycol and the like using a base such as sodium hydroxide, potassium hydroxide, lithium hydroxide and the like under heating affords compound (VIA).

Preparation Method of Compound (VIA) 2

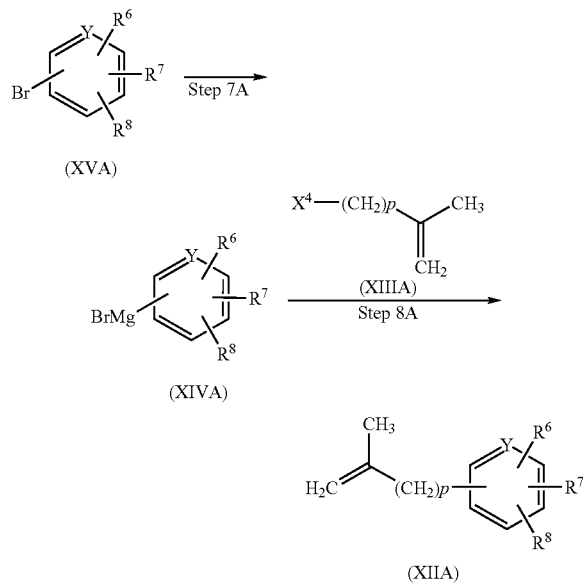

wherein $X^4$ is a halogen atom (as defined above), and other symbols are as defined above.

Step 7A

The compound (XVA) is reacted with magnesium in tetrahydrofuran or diethyl ether to give compound (XIVA).

Step 8A

The compound (XIVA) obtained in Step 7A is reacted with compound (XIIIA) in tetrahydrofuran or diethyl ether, using copper iodide as a catalyst as necessary to give compound (XIIA).

The compound (XIIA) obtained in Step 8A is subjected to a similar reaction as in Step 5A to give compound (VIIA), which is then subjected to a similar reaction as in Step 6A to give compound (VIA).

Preparation Method of Compound (VIA) 3

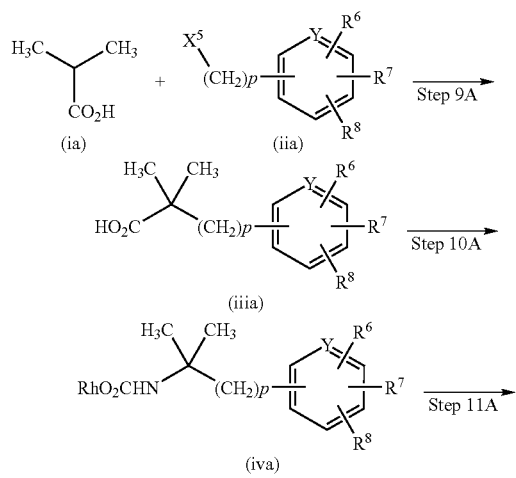

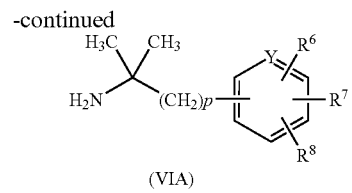

wherein $X^5$ is a halogen atom (as defined above), $RhO_2C$— is an amino-protecting group such as a benzyloxycarbonyl group, a tert-butoxycarbonyl group and the like, and other symbols are as defined above.

Step 9A

The compound (ia) is reacted with compound (iia) in a solvent such as tetrahydrofuran, n-hexane and the like in the presence of a base such as n-butyllithium and the like and hexamethylphosphoramide to give compound (iiia).

Step 10A

In this step, compound (iiia) obtained in Step 9A is subjected to Curtius rearrangement to give compound (iia). The compound (iiia) is reacted with halogenated alkyl carbonate such as chloroethyl carbonate and the like in water, acetone, methyl ethyl ketone and the like or a mixed solvent thereof, in the presence of a base such as triethylamine, N,N-diisopropylethylamine and the like. Then, sodium azide is reacted to give a compound. The obtained compound is rearranged under heating and then reacted with alcohol of the formula: Rh—OH wherein Rh is a benzyl group, a tert-butyl group and the like to give compound (iva).

Step 11A

In this step, —$CO_2Rh$ wherein —$CO_2Rh$ is as defined above of compound (iva) obtained in Step 10A is removed, which is performed by a method generally employed for deprotection of a compound wherein an amino group is protected with —$CO_2Rh$. For example, when —$CO_2Rh$ is benzyloxycarbonyl group, compound (iva) is subjected to hydrogenation using a catalyst such as palladium carbon, palladium black, palladium hydroxide on carbon, Raney-nickel and the like in a solvent such as methanol, ethanol, n-propanol, isopropanol, tetrahydrofuran, 1,4-dioxane and the like to give compound (VIA). When, for example, —$CO_2Rh$ is tert-butoxycarbonyl group, a reaction using an acid such as hydrogen chloride, sulfuric acid, hydrogen bromide and the like in water, methanol, ethanol, n-propanol, isopropanol, tetrahydrofuran, 1,4-dioxane, acetic acid and the like or a mixed solvent thereof gives compound (VIA).

Preparation Method of Compound (VIA) 4 (p=1)

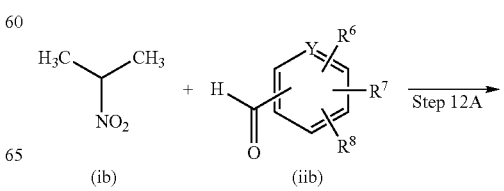

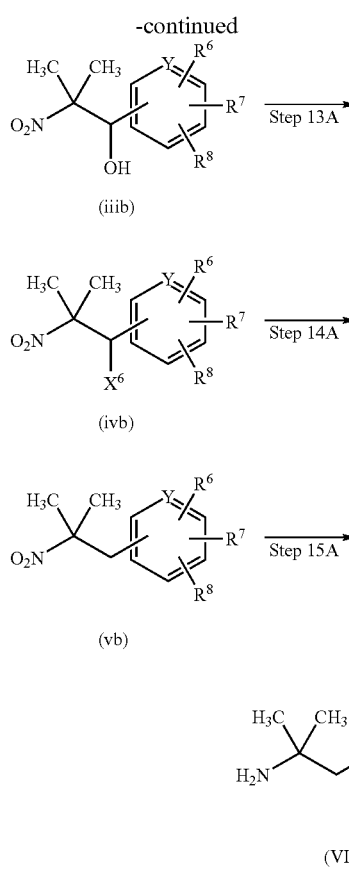

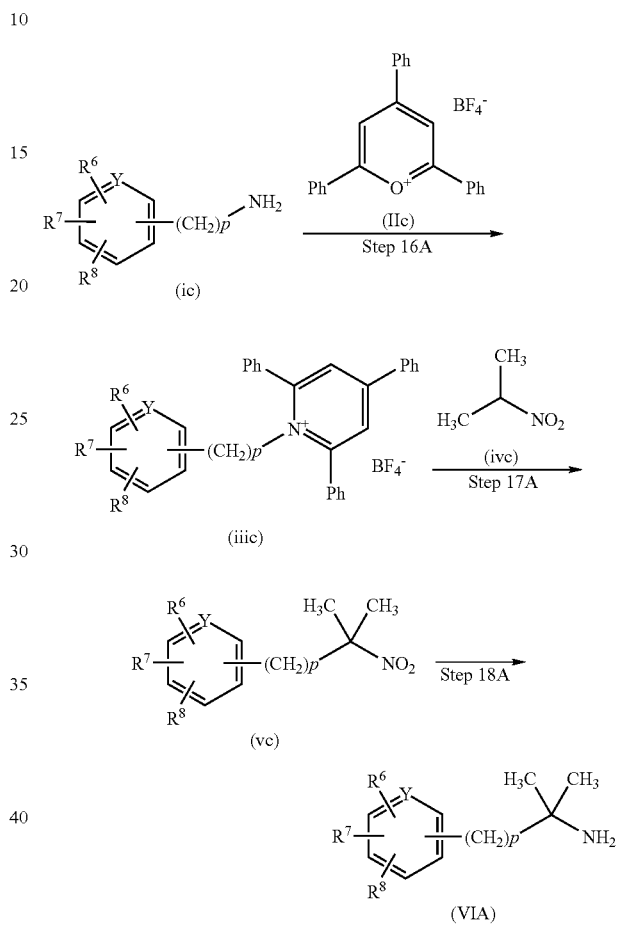

such as methanol, ethanol, n-propanol, isopropanol, tetrahydrofuran, 1,4-dioxane and the like, compound (VIA) can be obtained. In this reaction, pressurization to some extent is preferable. In addition, compound (VIA) can be also obtained by reduction with iron, tin chloride and the like in the above-mentioned solvent.

Preparation Method of Compound (VIA) 5 wherein Ph is a phenyl group, and other symbols are as defined above.

wherein $X^6$ is a halogen atom (as defined above), and other symbols are as defined above.

Step 12A

By reacting compound (iib) with compound (ib) in a solvent such as tetrahydrofuran, N,N-dimethylformamide, dimethyl sulfoxide and the like, in the presence of tetraalkylammonium halide such as tetrabutylammonium fluoride and the like and trialkylhalosilane such as tert-butyldimethylchlorosilane and the like, compound (iiib) can be obtained.

Step 13A

By subjecting compound (iiib) to be obtained in Step 12A to halogenation using a halogenating agent such as thionyl chloride, oxalyl chloride and the like, compound (ivb) can be obtained. In this reaction, the halogenating agent itself to be used may be used as a solvent, or a solvent such as dichloromethane, chloroform, 1,2-dichloroethane, tetrahydrofuran, 1,4-dioxane and the like may be used.

Step 14A

By subjecting compound (ivb) to be obtained in Step 13A to hydrogenation in a solvent such as methanol, ethanol, n-propanol, isopropanol, tetrahydrofuran, 1,4-dioxane, ethyl acetate and the like in the presence of a catalyst such as palladium carbon, palladium black, palladium hydroxide on carbon and the like, compound (vb) can be obtained. In this reaction, pressurization to some extent is preferable.

Step 15A

By subjecting compound (vb) to be obtained in Step 14A to hydrogenation using a catalyst such as Raney-nickel, platinum oxide, palladium-carbon and the like in a solvent Step 16A The compound (ic) is reacted with compound (iic) in ethanol, isopropanol, tert-butanol, acetone, water, methylene chloride, diethyl ether, N,N-dimethylformamide and the like or a mixed solvent thereof at room temperature-reflux temperature to give compound (iiic).

Step 17A

The compound (ivc) is reacted with compound (iiic) obtained in Step 16A in dimethyl sulfoxide, N,N-dimethylformamide, tetrahydrofuran, diethyl ether and the like or a mixed solvent thereof, in the presence of sodium methoxide, sodium hydride and the like to give compound (vc).

Step 18A

The compound (vc) obtained in Step 17A is subjected to a similar reaction as in Step 15A to give compound (VIA).

<Production Method When n is 1>

When Z is —O—

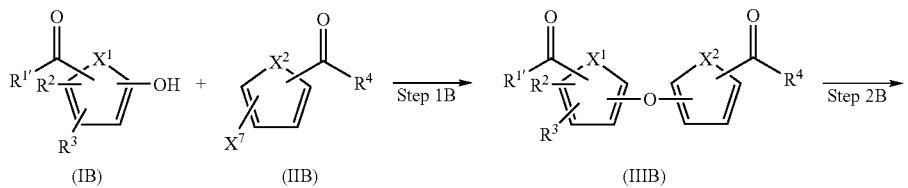

(IB)  (IIB)  Step 1B  (IIIB)  Step 2B

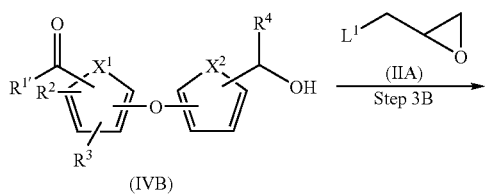

(IVB)

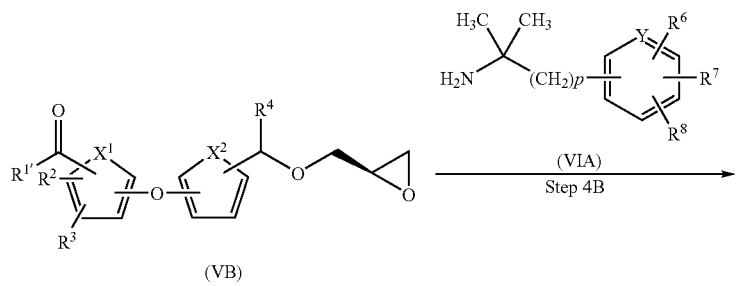

(VB)

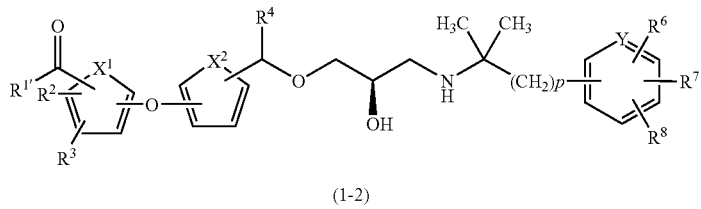

(1-2)

wherein $X^7$ is a halogen atom (as defined above), and other symbols are as defined above.

Step 1B

By reacting compound (IB) with compound (IIB) in N,N-dimethylacetamide, N,N-dimethylformamide, dimethyl sulfoxide and the like or a mixed solvent thereof, in the presence of a base such as potassium carbonate, sodium carbonate and the like, at room temperature-reflux temperature, compound (IIIB) is obtained.

Step 2B

By reduction of compound (IIIB) obtained in Step 1B with a reducing agent such as lithium aluminum hydride, sodium borohydride, lithium borohydride and the like in isopropanol, tetrahydrofuran, toluene, methanol and the like or a mixed solvent thereof, at −10° C. to room temperature, compound (IVB) can be obtained. In addition, by subjecting compound (IIIB) to reduction reaction using an asymmetric reducing agent such as B-chlorodiisopinocamphenylborane, (S)-5,5-diphenyl-2-methyl-3,4-propano-1,3,2-oxazaborolidine and the like, or to an asymmetric hydrogenation reaction using a ruthenium complex such as dichloro[(S)-2,2'-bis(diphenylphosphino)-1,1'-binaphthyl][(S)-1,1'-bis(p-methoxyphenyl)-2-isopropylethane-1,2-diamine]ruthenium (II) and the like and potassium-tert-butoxide, a stereoselective reaction proceeds to afford an R form of compound (IVB).

Step 3B

The compound (IVB) obtained in Step 2B and compound (IIA) are subjected to reactions similar to those of Step 1A to give compound (VB).

Step 4B

The compound (VB) obtained in Step 3B and compound (VIA) are subjected to reactions similar to those in Step 3A to give compound (1-2).

Hydrolysis of compound (1-2) by conventional methods affords conversion of $R^{1'}$ ($C_{1-6}$ alkoxy group) to a hydroxyl group. For example, compound (1-2) is hydrolyzed in a mixed solvent of methanol-tetrahydrofuran-water using sodium hydroxide.

The case Z is a $C_{2-4}$ alkenylene group

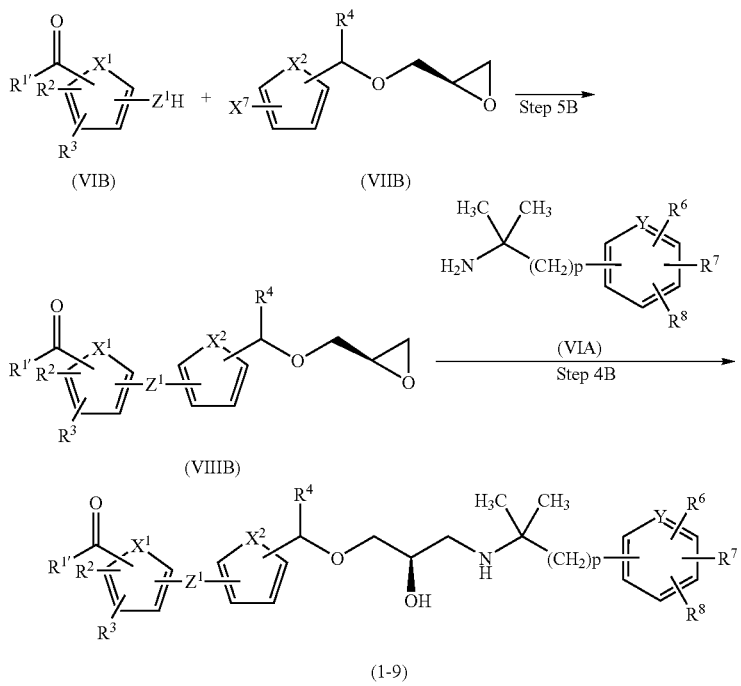

wherein $Z^1$ is a $C_{2-4}$ alkenylene group (as defined for $C_{2-4}$ alkenylene group for Z), $X^7$ is a halogen atom (as defined s above), and other symbols are as defined above.

Step 5B

By reacting compound (VIB) with compound (VIIB) in acetonitrile, N,N-dimethylformamide, toluene and the like or a mixed solvent thereof, in the presence of a base such as triethylamine, potassium carbonate, sodium carbonate and the like and tri(o-tolyl)phosphine or triphenylphosphine, using a palladium catalyst such as diacetoxypalladium, dichloropalladium and the like at room temperature-reflux temperature, compound (VIIIB) can be obtained.

By subjecting compound (VIIIB) obtained in Step 5B to a step similar to Step 4B, compound (1-9) wherein Z is a $C_{2-4}$ alkenylene group can be obtained.

The case Z is $—(CH_2)_{m2}—NH—$

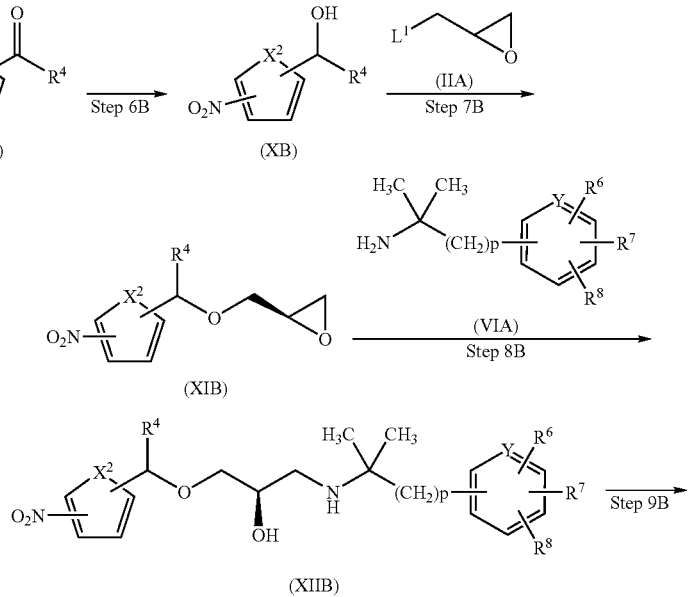

-continued
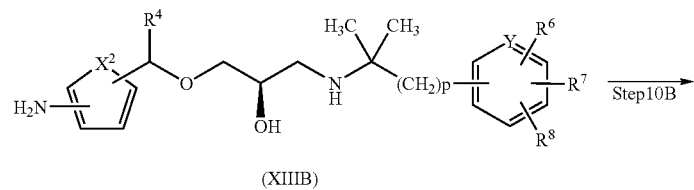
(XIIIB)
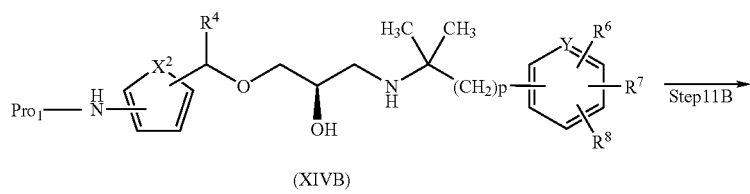
(XIVB)
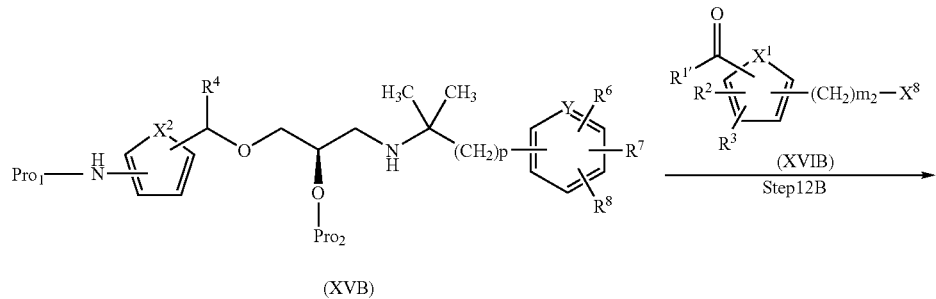
(XVB)
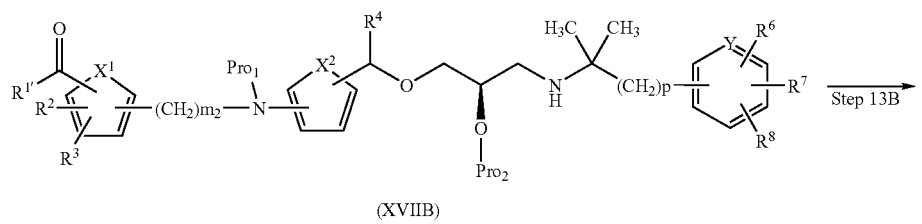
(XVIIB)
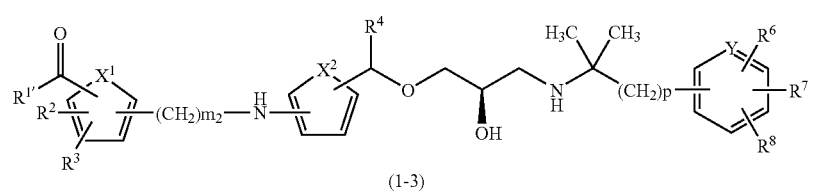
(1-3)

wherein Pro₁ is an amino-protecting group (e.g., a trifluoroacetyl group, a tert-butoxycarbonyl group and the like), Pro₂ is a hydroxyl-protecting group (e.g., an acetyl group, a benzoyl group, a chloroacetyl group, a trichloroacetyl group and the like), $X^8$ is a halogen atom (as defined above), and other symbols are as defined above.

Step 6B

By reacting compound (IXB) in methanol, ethanol, tetrahydrofuran, diethyl ether and the like or a mixed solvent thereof, using sodium borohydride, lithium borohydride and the like, compound (XB) can be obtained.

Step 7B

By subjecting compound (XB) obtained in Step 6B and compound (IIA) to a step similar to Step 1A, compound (XIB) can be obtained.

Step 8B

By subjecting compound (XIB) obtained in Step 7B and compound (VIA) to a reaction similar to Step 3A, compound (XIIB) can be obtained.

Step 9B

By reacting compound (XIIB) in tetrahydrofuran, ethanol, water, methanol and the like or a mixed solvent thereof, using iron and ammonium chloride, compound (XIIIB) can be obtained.

Step 10B

By protecting an amino group of compound (XIIIB) obtained in Step 9B by conventional methods, compound (XIVB) can be obtained. For example, when an amino group is protected with a trifluoroacetyl group, the compound is reacted with trifluoroacetic anhydride in chloroform, methylene chloride, tetrahydrofuran, toluene, ethyl acetate and the like or a mixed solvent thereof in the presence of a base such as pyridine, triethylamine and the like.

Step 11B

By protecting a hydroxyl group of compound (XIVB) obtained in Step 10B by conventional methods, compound (XVB) can be obtained. For example, when a hydroxyl group is protected with an acetyl group, the compound is reacted with acetic anhydride in chloroform, methylene chloride, tetrahydrofuran, toluene, ethyl acetate and the like or a mixed solvent thereof in the presence of a base such as pyridine, triethylamine and the like.

Step 12B

By reacting compound (XVB) obtained in Step 11B with compound (XVIB) in N,N-dimethylformamide, tetrahydrofuran, diethyl ether, dimethyl sulfoxide, acetone, acetonitrile or a mixed solvent thereof in the presence of a base such as sodium hydride, potassium carbonate, sodium carbonate and the like, compound (XVIIB) can be obtained.

Step 13B

By deprotection of compound (XVIIB) obtained in Step 12B by conventional methods, compound (1-3) can be obtained. For example, when an amino group is protected with a trifluoroacetyl group and a hydroxyl group is protected with an acetyl group, the compound is reacted in tetrahydrofuran-methanol in the presence of sodium hydroxide.

The case Z is —CONH—

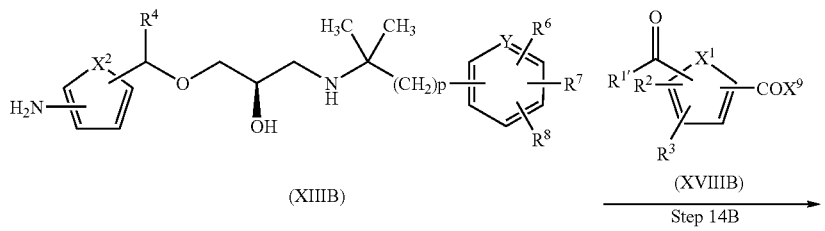

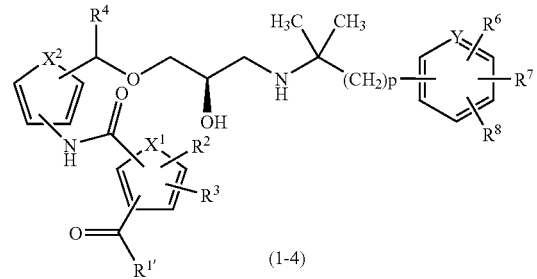

wherein $X^9$ is a halogen atom (as defined above), and other symbols are as defined above.

Step 14B

By reacting compound (XIIIB) obtained in Step 9B with compound (XVIIIB) in chloroform, methylene chloride, tetrahydrofuran, toluene, ethyl acetate, or a mixed solvent thereof, in the presence of a base such as pyridine, triethylamine, N,N-diisopropylethylamine and the like, compound (1-4) can be obtained.

Hydrolysis of compound (1-4) by conventional methods affords conversion of $R^1$ ($C_{1-6}$ alkoxy group) to a hydroxyl group. For example, compound (1-4) is hydrolyzed in a mixed solvent of methanol-tetrahydrofuran-water using sodium hydroxide.

The case Z is —S—

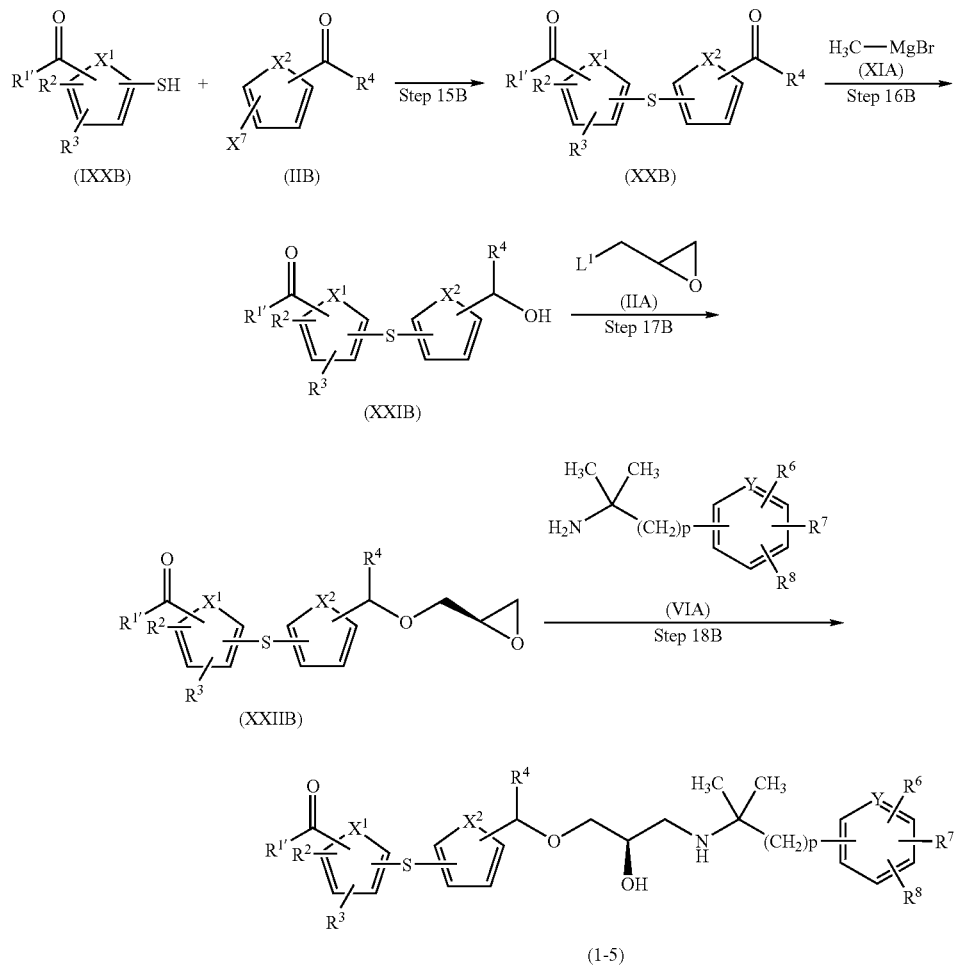

wherein each symbol is as defined above.

Step 15B

By subjecting compound (IXXB) and compound (IIB) to a reaction similar to Step 1B, compound (XXB) can be obtained.

When a compound of the formula

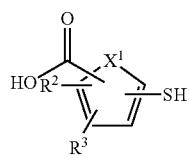

wherein each symbol is as defined above, is used as a starting material, a —CO$_2$H group is converted to a —COR$^{1'}$ group in advance to give compound (IXXB). For example, the group can be converted using concentrated sulfuric acid in C$_{1-6}$ alcohol such as methanol, ethanol and the like.

Step 16B

By subjecting compound (XXB) obtained in Step 15B and compound (XIA) to a reaction similar to Step 4A, compound (XXIB) can be obtained.

Step 17B

By subjecting compound (XXIB) obtained in Step 16B and compound (IIA) to a reaction similar to Step 1A, compound (XXIIB) can be obtained.

Step 18B

By subjecting compound (XXIIB) obtained in Step 17B and compound (VIA) to a reaction similar to Step 3A, compound (1-5) can be obtained.

Hydrolysis of compound (1-5) by conventional methods affords conversion of R$^{1'}$ (C$_{1-6}$ alkoxy group) to a hydroxyl group. For example, hydrolysis is performed in tetrahydrofuran, methanol and the like or a mixed solvent thereof in the presence of sodium hydroxide.

The case Z is a C$_{1-4}$ alkylene group

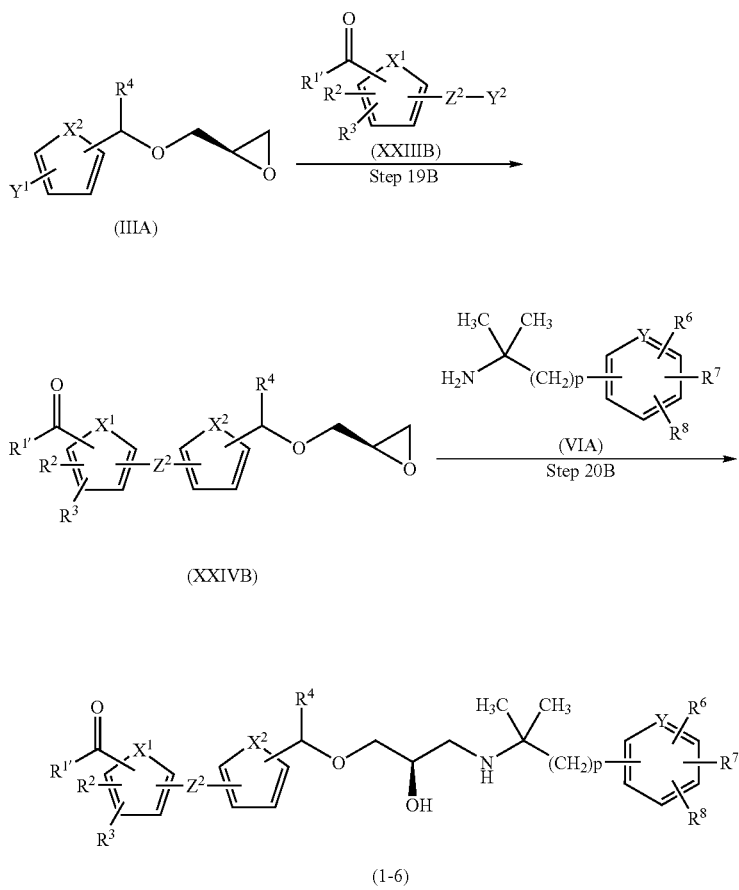

wherein Z$^2$ is a C$_{1-4}$ alkylene group (as defined for C$_{1-4}$ alkylene group for Z), and other symbols are as defined above.

Step 19B

By subjecting compound (IIIA) and compound (XXIIIB) to a reaction similar to Step 2A, compound (XXIVB) can be obtained.

Step 20B

By subjecting compound (XXIVB) obtained in Step 19B and compound (VIA) to a reaction similar to Step 3A, compound (1-6) can be obtained.

Hydrolysis of compound (1-6) by conventional methods affords conversion of R$^{1'}$ (C$_{1-6}$ alkoxy group) to a hydroxyl group. For example, compound (1-6) is hydrolyzed in tetrahydrofuran, methanol and the like or a mixed solvent thereof in the presence of sodium hydroxide.

The case Z is —(CH$_2$)$_{m1}$—O— (1)

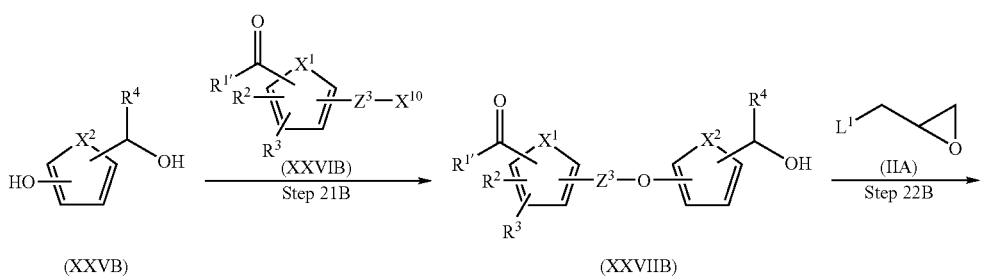

-continued

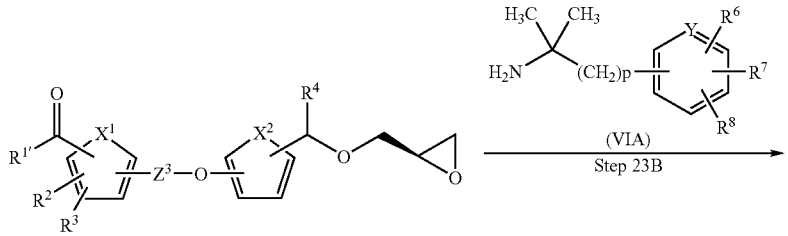

(XXVIIIB)

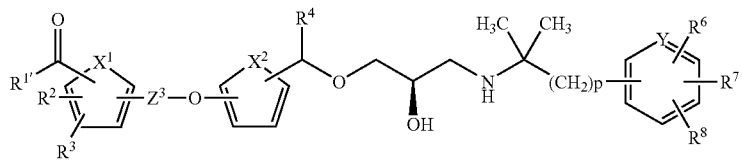

(1-7)

wherein $Z^3$ is $-(CH_2)_{m1}-$ (m1 here is as defined for m1 for Z), $X^{10}$ is a halogen atom (as defined above), and other symbols are as defined above.

Step 21B

By reacting compound (XXVB) with compound (XXVIB) in N,N-dimethylformamide, tetrahydrofuran, diethyl ether, dimethyl sulfoxide, acetone, acetonitrile and the like or a mixed solvent thereof, in the presence of a base such as sodium hydride, potassium carbonate, sodium carbonate and the like, compound (XXVIIB) can be obtained.

Step 22B

By subjecting compound (XXVIIB) obtained in Step 21B and compound (IIA) to a step similar to Step 1A, compound (XXVIIIB) can be obtained.

Step 23B

By subjecting compound (XXVIIIB) obtained in Step 22B and compound (VIA) to a step similar to Step 3A, compound (1-7) can be obtained.

Hydrolysis of compound (1-7) by conventional methods affords conversion of $R^{1'}$ ($C_{1-6}$ alkoxy group) to a hydroxyl group. For example, compound (1-7) is hydrolyzed in tetrahydrofuran, methanol and the like or a mixed solvent thereof in the presence of sodium hydroxide.

It is also possible to use an optically active compound (XXVB), and an optically active compound (XXVB) can be produced by a method as shown in the following.

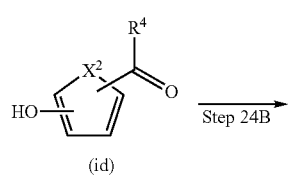

(id)

-continued

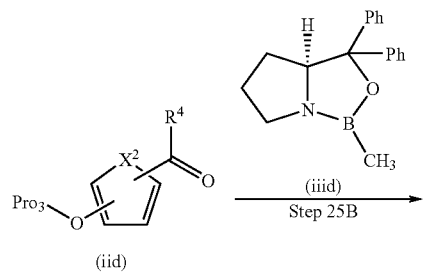

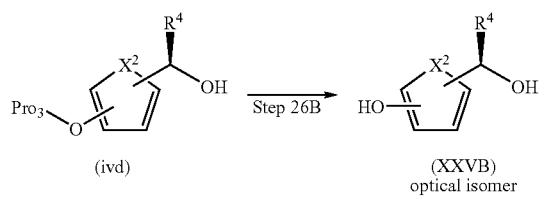

wherein $Pro_3$ is as defined for $Pro_2$, and other symbols are as is defined above.

Step 24B

By protection of a hydroxyl group of compound (id) by conventional methods, compound (iid) can be obtained. For example, when a hydroxyl group is protected with a benzyl group, the compound is reacted with benzyl halide (e.g., benzyl bromide) in N,N-dimethylformamide in the presence of a base such as potassium carbonate, sodium hydride and the like.

Step 25B

By reacting compound (iid) obtained in Step 24B with compound (iiid) in tetrahydrofuran, toluene, methylene chloride, hexane and the like or a mixed solvent thereof, in the presence of a boran dimethylsulfide complex salt, compound (ivd) can be obtained.

Step 26B

By deprotection of compound (ivd) obtained in Step 25B by conventional methods, an optically active compound (XXVB) can be obtained. For example, when a hydroxyl group is protected with a benzyl group, hydrogenation is performed in tetrahydrofuran, methanol, ethanol, ethyl acetate and the like or a mixed solvent thereof in the presence of palladium carbon.

The case Z is —$(CH_2)_{m1}$—O— (2)

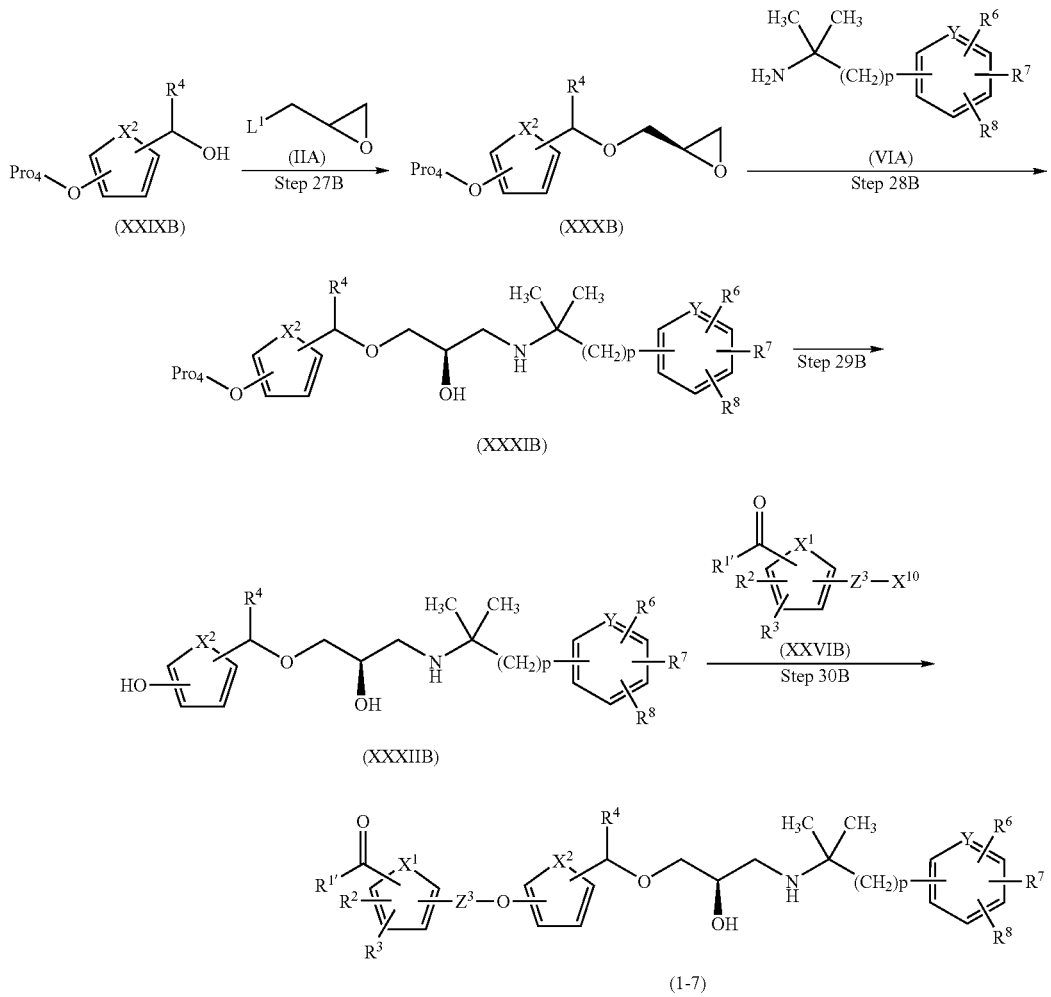

wherein $Pro_4$ is as defined for $Pro_2$ and other symbols are as defined above.

Step 27B

By subjecting compound (XXIXB) and compound (IIA) to a step similar to Step 1A, compound (XXXB) can be obtained.

Step 28B

By subjecting compound (XXXB) obtained in Step 27B and compound (VIA) to a step similar to Step 3A, compound (XXXIB) can be obtained.

Step 29B

By subjecting compound (XXXIB) obtained in Step 28B to deprotection by conventional methods, compound (XXXIIB) can be obtained. For example, when hydroxyl group of compound (XXXIB) is protected with a 2-(trimethylsilyl)ethoxymethyl group, deprotection is performed in 1,3-dimethyl-3,4,5,6-tetrahydro-2(1H)-pyrimidinone in the presence of tetrabutylammonium halide (e.g., tetrabutylammonium fluoride and the like) and MS4A.

Step 30B

By subjecting compound (XXXIIB) obtained in Step 29B and compound (XXVIB) to a reaction similar to Step 21B, compound (1-7) can be obtained.

Hydrolysis of compound (1-7) by conventional methods affords conversion of $R^{1'}$ ($C_{1-6}$ alkoxy group) to a hydroxyl group. For example, compound (1-7) is hydrolyzed in tetrahydrofuran-methanol in the presence of sodium hydroxide.

It is also possible to perform Step 27B using an optically active compound (XXIXB). For example, compound (id) is subjected to Step 24B and Step 25B, an optically active compound (XXIXB) can be obtained. For example, when an optically active compound (XXIXB), wherein a hydroxyl group is protected with a 2-(trimethylsilyl)ethoxymethyl group, is desired, compound (id) is reacted with 2-(trimethylsilyl)ethoxymethyl halide (e.g., 2-(trimethylsilyl) ethoxymethyl chloride) in Step 24B in chloroform in the presence of diisopropylethylamine.

When, in the present invention, a compound (1) wherein $R^1$ is $R^A$, particularly $R^C$—OC(=O)O—$C_{1-4}$ alkylene-O—, is desired, compound (1) wherein $R^1$ is a hydroxyl group is reacted with $R^C$—OC(=O)O—$C_{1-4}$ alkylene-$L^2$ ($L^2$ is a leaving group such as a halogen atom and the like) in N,N-dimethylformamide, tetrahydrofuran, diethyl ether, dimethyl sulfoxide, acetone, acetonitrile and the like or a mixed solvent thereof in the presence of a base such as sodium hydride, potassium carbonate, sodium carbonate and the like, whereby compound (1) wherein $R^1$ is Rc—OC(=O)O—$C_{1-4}$ alkylene-O— can be obtained.

When a compound wherein $R^1$ is $R^A$, particularly OH—NH—, is desired, compound (1) wherein $R^1$ is a hydroxyl group is reacted with trimethylsilyloxyamine in N,N-dimethylformamide, tetrahydrofuran, diethyl ether, dimethyl sulfoxide, acetone, acetonitrile and the like or a mixed solvent thereof, in the presence of a condensation agent such as dicyclohexylcarbodiimide, 1-ethyl-3-(3-dimethylaminopropyl)carbodiimide, diisopropylcarbodiimide, diphenylphosphoryl azide, 2-ethoxy-1-ethoxycarbonyl-1,2-dihydroquinoline (EEDQ) and the like and an additive such as 1-hydroxybenzotriazole, 4-dimethylaminopyridine and the like. Then, tetrabutylammonium fluoride is reacted in the above-mentioned solvent to give compound (1) wherein $R^1$ is OH—NH—.

For the production of compound (1) wherein $R^5$ is $R^B$, for example, as shown by the following formulas, compound (1-1) obtained in Step 3A is reacted with acid anhydride such as acetic anhydride, succinic anhydride, maleic anhydride and the like or acyl halide in chloroform, methylene chloride, tetrahydrofuran, toluene, ethyl acetate and the like or a mixed solvent thereof, in the presence of a base such as pyridine, triethylamine, dimethylaminopyridine and the like, whereby compound (1-8) can be obtained.

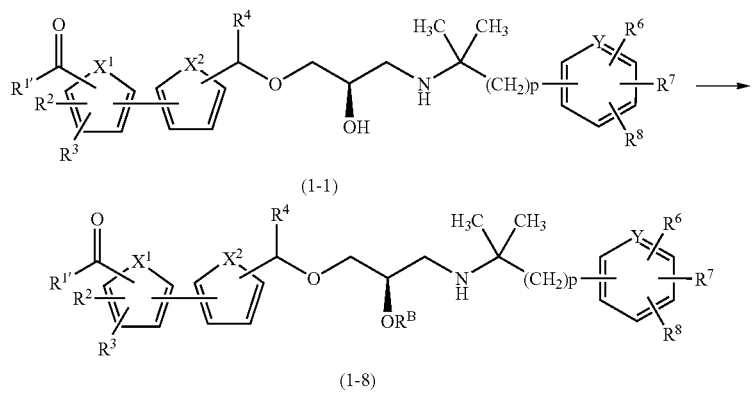

wherein each symbol is as defined above.

When a salt of a compound represented by the formula (1) is desired, known methods can be used. For example, when an acid addition salt is desired, a compound represented by the formula (1) is dissolved in water, methanol, ethanol, n-propanol, isopropanol, diethyl ether, tetrahydrofuran, 1,4-dioxane, ethyl acetate, dichloromethane, 1,2-dichloroethane, chloroform and the like or a mixed solvent thereof, the above-mentioned solvent wherein the desired acid has been dissolved is added and the precipitated crystals are collected by filtration, or concentrated under reduced pressure.

When a crystal of a salt is desired with using several solvents, a preferable method is as follows; a compound is dissolved in a solvent with high solvent power, and a solvent wherein the desired acid has been dissolved is added, and a solvent which has low solvent power is added and then the precipitated crystals are collected.

When a basic salt is desired, a compound represented by the formula (1) is dissolved in water, methanol, ethanol, n-propanol, isopropanol, tetrahydrofuran, 1,4-dioxane and the like or a mixed solvent thereof, the above-mentioned solvent wherein an equivalent amount of the desired base has been dissolved is added and the precipitated crystals are collected by filtration, or concentrated under reduced pressure.

When a crystal of a salt is desired with using several solvents, a preferable method is as follows; a compound is dissolved in a solvent with high solvent power, and a solvent wherein the desired base has been dissolved is added, and a solvent which has low solvent power is added and then the precipitated crystals are collected.

When an acid addition salt of a compound represented by the formula (1) is to be converted to a free form, acid addition salt of a compound represented by the formula (1) is added to an aqueous solution of a base such as sodium hydrogencarbonate, potassium hydrogen carbonate, sodium carbonate, potassium carbonate, sodium hydroxide, potassium hydroxide, lithium hydroxide and the like to adjust pH of the aqueous solution to neutral-weakly acidic, and the solution is separated into two layers including a solvent such as ethyl acetate, dichloromethane, 1,2-dichloroethane, chloroform, methyl ethyl ketone or toluene and the like, whereby a free form of the compound represented by the formula (1) can be obtained.

When a basic salt of a compound represented by the formula (1) is to be converted to a free form, an aqueous solution of acid such as hydrochloric acid, hydrobromic acid, sulfuric acid, acetic acid, citric acid and the like is added to an aqueous solution of a basic salt of a compound represented by the formula (1) and the precipitated solid is collected by filtration, or the solution is separated into two layers including a solvent such as ethyl acetate, dichloromethane, 1,2-dichloroethane, chloroform, methyl ethyl ketone or toluene and the like, whereby a free form of the compound represented by the formula (1) can be obtained.

When a salt of an optically active compound is desired, a compound represented by the formula (1) is suspended in methanol, ethanol, n-propanol, isoproanol, tetrahydrofuran, 1,4-dioxane, water and the like, and the suspension is heated to dissolve, and then the solution is cooled to precipitate a crystal. The crystal of the salt is obtained by the method described above with using thus obtained crystal.

The thus-obtained compound of the formula (1) of the present invention has a superior calcium receptor antagonistic action. When the compound of the present invention is to be used as a therapeutic agent of osteoporosis, hypoparathyreosis, osteosarcoma, periodontal disease, bone fracture, osteoarthrisis, chronic rheumatoid arthritis, Paget's disease, humoral hypercalcemia, autosomal dominant hypocalcemia, Parkinson's disease, dimentia and the like, it is generally administered systemically or topically, and orally or parenterally.

While the dose varies depending on age, body weight, condition, treatment effect, administration method, treatment period and the like, it is generally 0.01 mg to 10 g for an adult per day, which is given once or in several portions a day by oral or parenteral administration.

When the compound of the present invention is prepared into a solid composition for oral administration, a dosage form of tablet, pill, powder, granule and the like can be employed. In such a solid composition, one or more active ingredient is admixed with at least one inert diluent, dispersing agent, absorbent and the like, such as lactose, mannitol, glucose, hydroxypropyl cellulose, crystalline cellulose, starch, polyvinyl hydrin, magnesium aluminometasilicate, anhydrous silicic acid powder and the like. The composition may contain an additive other than diluent according to a conventional method.

For preparation of tablets or pills, gastric or enteric film of sucrose, gelatin, hydroxypropyl cellulose, hydroxymethylcellulose phthalate and the like may be applied or two or more layers may be formed. In addition, they may be prepared into capsules of gelatin or ethylcellulose.

For preparation of liquid composition for oral administration, a dosage form such as pharmaceutically acceptable emulsion, solution, suspension, syrup, elixir and the like can be employed. The diluent to be used is, for example, purified water, ethanol, vegetable oil, emulsifier and the like. This composition may contain diluent and an adjuvant other than the diluent, such as wetting agent, suspending agent, sweetener, flavor, perfume, preservative and the like.

For preparation of parenteral injection, sterile aqueous or nonaqueous solvent, solubilizer, suspending agent or emulsifier is used. Examples of the aqueous solvent, solubilizer and suspending agent include distilled water for injection, physiological saline, cyclodextrin and derivatives thereof, organic amines such as triethanolamine, diethanolamine, monoethanolamine, triethylamine and the like, inorganic alkali solution and the like.

When a water-soluble solvent is to be prepared, for example, propylene glycol, polyethylene glycol, vegetable oil such as olive oil, alcohol such as ethanol, and the like may be used. As the solubilizer, for example, surfactant (forming a mixed micelle) such as polyoxyethylene hydrogenated castor oil, sucrose esters of fatty acid and the like, lecithin or hydrogenated lecithin (forming a liposome) and the like can be used. In addition, an emulsion preparation consisting of a water-insoluble solvent such as vegetable oil and the like, and lecithin, polyoxyethylene hydrogenated castor oil, polyoxyethylene polyoxypropylene glycol and the like may be formed.

As other compositions for parenteral administration, an external liquid, liniment such as ointment, suppository, pessary and the like, containing one or more active ingredients and prepared by a method known per se may be formulated.

The form of the compound of the present invention for use as a pharmaceutical product is a compound itself (free form), a salt of the compound, a solvate of the compound or a prodrug of the compound are, wherein preferred form is a free form, a salt of the compound or a solvate of the compound, particularly preferably a salt of the compound.

EXAMPLES

The compound of the formula (1) of the present invention and its production methods are explained in detail by referring to the following Examples, which are not to be construed as limitative.

Example 1-1

2'-[(1R)-[(2R)-3-[[1-(3-Fluoro-4-methylphenyl)-2-methylpropan-2-yl]amino]-2-hydroxypropoxy]ethyl]-3-methylbiphenyl-4-carboxylic acid Step 1

(2R)-2-[((1R)-(2-Bromophenyl)ethoxy)methyl]oxirane

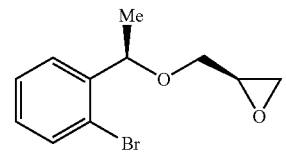

(1R)-(2-Bromophenyl)ethanol (30.0 g) and (R)-glycidyl 3-nitrobenzenesulfonate (50.3 g) were dissolved in dimethylformamide (300 ml) and sodium hydride (7.76 g, 60% in oil) was added. The mixture was stirred at room temperature for 2 hrs. 10% Aqueous citric acid solution (600 ml) was added to the reaction mixture and the mixture was extracted with ethyl acetate. The organic layer was washed successively with water and brine, dried over anhydrous sodium sulfate, and concentrated under reduced pressure. The obtained residue was purified by silica gel column chromatography (hexane:ethyl acetate=6:1) to give the title compound (32.9 g).

$^1$H-NMR (300 MHz, δppm, CDCl$_3$) 7.53-7.49(2H, m), 7.37-7.32(1H, m), 7.16-7.10(1H, m), 4.89(1H, q, J=6.4 Hz), 3.62-3.57(1H, m), 3.34-3.28(1H, m), 3.18-3.12(1H, m), 2.79-2.76(1H, m), 2.58-2.55(1H, m), 1.44(3H, d, J=6.4).

Step 2

Methyl 4-bromo-2-methylbenzoate

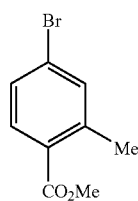

4-Bromo-2-methylbenzoic acid (75.0 g) was dissolved in methanol (500 ml) and concentrated sulfuric acid (10 ml) was added. The mixture was heated at reflux for 20 hrs. The reaction mixture was cooled to room temperature, and concentrated under reduced pressure. Water (150 ml) was added to the obtained residue, and the mixture was extracted with ethyl acetate (150 ml). The organic layer was washed successively with water, saturated aqueous sodium hydrogen carbonate solution and saturated brine, dried over sodium sulfate, and concentrated under reduced pressure to give the title compound (78.0 g).

$^1$H-NMR (400 MHz, δppm, CDCl$_3$) 8.20(1H, s), 8.86(1H, d, J=8.0 Hz), 7.30(1H, d, J=8.0 Hz), 3.91(3H, s), 2.45(3H, s).

Step 3

Methyl 3-methyl-2'-[(1R)-((R)-oxiranylmethoxy)ethyl]biphenyl-4-carboxylate

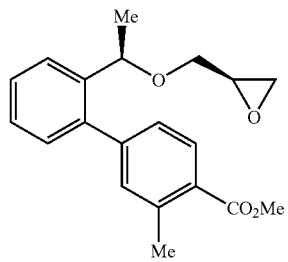

Methyl 4-bromo-2-methylbenzoate (9.16 g) obtained in Step 2 was dissolved in dimethyl sulfoxide (120 ml), and [1,1'-bis(diphenylphosphino)ferrocene]dichloropalladium (II), complex with dichloromethane(1:1) (1.46 g), potassium acetate (11.8 g) and bis(pinacolato)diboron (11.2 g) were added at 80° C. The mixture was stirred for 3 hrs. The reaction mixture was cooled to room temperature, water was added and the mixture was extracted with ethyl acetate. The organic layer was washed successively with water and brine, dried over anhydrous sodium sulfate, and concentrated under reduced pressure. The obtained residue was purified by silica gel column chromatography (hexane:ethyl acetate=9:1) and the resulting compound was dissolved in toluene (80 ml) and ethanol (80 ml). Thereto was added a solution of [1,1'-bis(diphenylphosphino)ferrocene]dichloropalladium(II),complex with dichloromethane (1:1) (1.17 g) and (2R)-2-[((1R)-(2-bromophenyl)ethoxy)methyl]oxirane (10.5 g) obtained in Step 1 in ethanol (80 ml) and 2M aqueous sodium carbonate solution (80 ml) was added. The mixture was heated under reflux for 3 hrs. The reaction mixture was allowed to return to room temperature, and extracted with diethyl ether. The organic layer was washed successively with water and saturated brine, dried over sodium sulfate, and concentrated under reduced pressure. The obtained residue was purified by silica gel column chromatography (hexane:ethyl acetate=5:1) to give the title compound (8.93 g).

$^1$H-NMR (300 MHz, δppm, CDCl$_3$) 7.96(1H, d, J=8.6 Hz), 7.60(1H, d, J=6.7 Hz), 7.43-7.28(4H, m), 7.18-7.13 (1H, m), 4.55(1H, q, J=6.4 Hz), 3.92(3H, s), 3.44-3.40(1H, m), 3.18-3.12(1H, m), 3.07-3.02(1H, m), 2.73-2.70(1H, m), 2.65(3H, s), 2.47-2.45(1H, m), 1.37(3H, d, J=6.4 Hz).

Step 4

Methyl (3-fluoro-4-methylphenyl)acetate

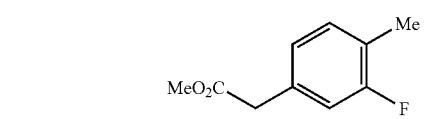

(3-Fluoro-4-methylphenyl)acetic acid (105.3 g) was dissolved in methanol (740 ml) and concentrated sulfuric acid (9.9 ml) was added. The mixture was stirred at 85° C. for 1 hr. The reaction mixture was cooled to room temperature, and concentrated under reduced pressure. Water was added to the obtained residue and the mixture was extracted with ethyl acetate (1 L). The organic layer was washed successively with water, aqueous sodium hydrogencarbonate solution, water and saturated brine, dried over anhydrous sodium sulfate, and concentrated under reduced pressure to give the title compound (114.2 g).

$^1$H-NMR (300 MHz, δppm, CDCl$_3$) 7.14-7.10(1H, m), 6.96-6.93(2H, m), 3.70(3H, s), 3.58(2H, s), 2.25-2.24(3H, s).

Step 5

1-(3-Fluoro-4-methylphenyl)-2-methylpropan-2-ol

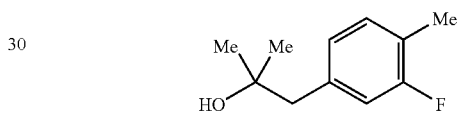

Methyl (3-fluoro-4-methylphenyl) acetate (114.2 g) obtained in Step 4 was dissolved in tetrahydrofuran (800 ml) and 1M-methylmagnesium bromide (1.56 L) was added dropwise at 0° C. under argon. The mixture was stirred at room temperature for 1 hr. The reaction mixture was ice-cooled, saturated aqueous ammonium chloride solution (155 ml) was added dropwise and magnesium sulfate (280 g) was added. The reaction mixture was filtered off and the filtrate was dried over magnesium sulfate and concentrated under reduced pressure to give the title compound (130.1 g).

$^1$H-NMR (300 MHz, δppm, CDCl$_3$) 7.11-7.08(1H, m), 6.88-6.86(2H, m), 2.71(2H, s), 2.25(3H, s), 1.22(6H, s).

Step 6

2-Chloro-N-[1-(3-fluoro-4-methylphenyl)-2-methylpropan-2-yl]acetamide

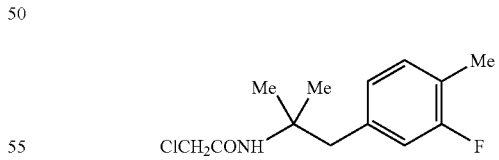

1-(3-Fluoro-4-methylphenyl)-2-methylpropan-2-ol (130.1 g) obtained in Step 5 was dissolved in chloroacetonitrile (139 ml) and acetic acid (115 ml), and concentrated sulfuric acid (33.4 ml) was added dropwise under ice-cooling. The mixture was stirred at room temperature for 2 hrs and 4N-aqueous sodium hydroxide solution (16 ml) was added dropwise under ice-cooling. The mixture was extracted twice with toluene and twice with ethyl acetate. The organic layer was washed twice with 10% brine and concentrated under reduced pressure to give the title compound (131.6 g).

¹H-NMR (300 MHz, δppm, CDCl₃) 7.10-7.06(1H, m), 6.80-6.76(2H, m), 6.19(1H, brs), 3.95(2H, s), 3.00(2H, s), 2.24(3H, s), 1.37(6H, s).

Step 7

(1-(3-Fluoro-4-methylphenyl)-2-methylpropan-2-yl)amine

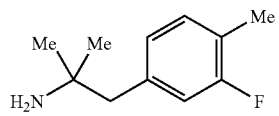

2-Chloro-N-[1-(3-fluoro-4-methylphenyl)-2-methylpropan-2-yl]acetamide (131.6 g) obtained in Step 6 was dissolved in acetic acid (200 ml) and ethanol (1 L), and thiourea (46.6 g) was added. The mixture was stirred overnight at 100° C. The reaction mixture was cooled to room temperature, and the precipitated crystals were filtered. The filtrate was concentrated under reduced pressure, and 4N-sodium hydroxide solution (300 ml) was added to the obtained residue. The mixture was extracted 3 times with toluene. The organic layer was washed with brine, and concentrated under reduced pressure. The obtained residue was dissolved in diethyl ether (1 L) and 4N-hydrochloric acid/ethyl acetate solution (255 ml) was added dropwise under ice-cooling. The mixture was stirred for 1 hr and the precipitated crystals were collected by filtration. The obtained crystals were added to a mixture of toluene and 4N-aqueous sodium hydroxide solution. The toluene layer was separated, washed twice with water, and concentrated under reduced pressure to give the title compound (57.9 g).

¹H-NMR (300 MHz, δppm, CDCl₃) 7.11-7.07(1H, m), 6.85-6.82(2H, m), 2.61(2H, s), 2.25(3H, s), 1.11(6H, s).

MS (APCI, m/z) 182(M+H)⁺.

Step 8

Methyl 2'-[(1R)-[(2R)-3-[[1-(3-fluoro-4-methylphenyl)-2-methylpropan-2-yl]amino]-2-hydroxypropoxy]ethyl]-3-methylbiphenyl-4-carboxylate

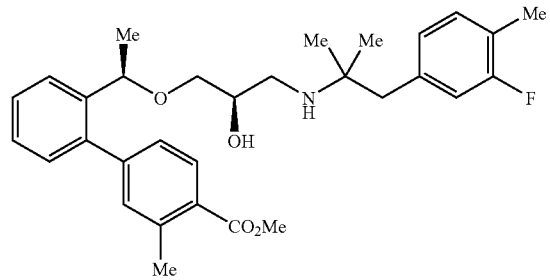

Methyl 3-methyl-2'-[(1R)-((R)-oxiranylmethoxy)ethyl] biphenyl-4-carboxylate (2.26 g) obtained in Step 3 was dissolved in toluene (50 ml). (1-(3-Fluoro-4-methylphenyl)-2-methylpropan-2-yl)amine (1.38 g) obtained in Step 7 and lithium perchlorate (815 mg) were added successively, and the mixture was stirred overnight at room temperature. The reaction mixture was washed successively with water and saturated brine, dried over sodium sulfate, and concentrated under reduced pressure. The obtained residue was purified by silica gel column chromatography (chloroform:methanol=9:1) to give the title compound (3.37 g).

¹H-NMR (400 MHz, δppm, DMSO-d₆) 7.95(1H, d, J=8.6 Hz), 7.56-7.53(1H, m), 7.41-7.37(1H, m), 7.32-7.28(1H, m), 7.17-7.12(3H, m), 7.06-7.02(1H, m), 6.80-6.77(2H, m), 4.48 (1H, q, J=6.3Hz), 3.92(3H, s), 3.66-3.63(1H, m), 3.21-3.13 (2H, m), 2.72-2.68(1H, m), 2.64(3H, s), 2.59-2.54(3H, m), 2.23(3H, m), 1.35(3H, d, J=6.3 Hz), 1.02 (3H, s), 1.00 (3H, s)

MS (ESI, m/z) 508(M+H)⁺.

Step 9

2'-[(1R)-[(2R)-3-[[1-(3-fluoro-4-methylphenyl)-2-methylpropan-2-yl]amino]-2-hydroxypropoxy]ethyl]-3-methylbiphenyl-4-carboxylic acid

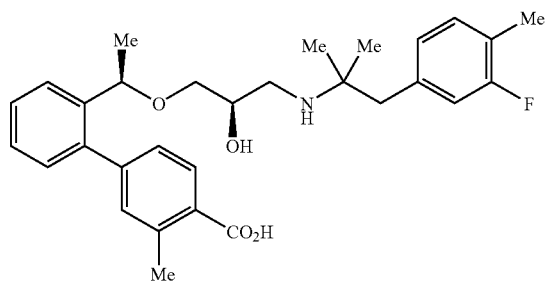

Methyl 2'-[(1R)-[(2R)-3-[[1-(3-fluoro-4-methylphenyl)-2-methylpropan-2-yl]amino]-2-hydroxypropoxy]ethyl]-3-methylbiphenyl-4-carboxylate (3.37 g) obtained in Step 8 was dissolved in methanol (25 ml) and tetrahydrofuran (25 ml), and 2N-sodium hydroxide (13.5 ml) was added. The mixture was stirred at 60° C. for 3 hrs and concentrated under reduced pressure. The obtained residue was diluted with water and the mixture was neutralized by adding 10% aqueous citric acid solution. The resulting white precipitate was collected by filtration and dried to give the title compound (3.06 g).

1H-NMR (300 MHz, δppm, DMSO-d₆) 7.85(1H, d, J=8.3 Hz), 7.56-7.53(1H, m), 7.47-7.42(1H, m), 7.37-7.32(1H, m), 7.19-7.13(4H, m), 6.97-6.89(2H, m), 4.47(1H, q, J=6.4 Hz), 3.70(1H, s), 3.14(2H, d, J=5.3 Hz), 2.85-2.80(1H, m), 2.73 (2H, s), 2.63-2.59(1H, m), 2.56(3H, s), 2.19(3H, s), 1.28(3H, d, J=6.4 Hz), 1.05(3H, s), 1.04(3H, s).

MS (ESI, m/z) 494(M+H)⁺.

Example 1-2

2'-[(1R)-[(2R)-3-[[1-(4-Chloro-3-fluorophenyl)-2-methylpropan-2-yl]amino]-2-hydroxypropoxy]ethyl]-3-methylbiphenyl-4-carboxylic acid Step 1

1-Chloro-2-fluoro-4-(2-methylallyl)benzene

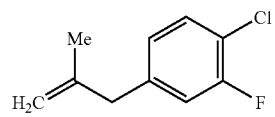

Magnesium (2.43 g) and iodine (10 mg) were added to tetrahydrofuran (40 ml) and a solution of 4-bromo-1-chloro-2-fluorobenzene (21.0 g) in tetrahydrofuran (40 ml) was added dropwise, and the mixture was stirred at room temperature for 1 hr to give a Grignard's reagent. The reaction mixture was ice-cooled and copper iodide (1.90 g) was added. 3-Chloro-2-methyl-1-propene (14.8 ml) was added and the mixture was stirred at room temperature for 1 hr. The reaction mixture was ice-cooled and saturated aqueous ammonium chloride solution (10 ml) was added. The mixture was stirred at room temperature for 20 min and magnesium sulfate (40 g) was added. The reaction mixture was filtered and the filtrate was concentrated under reduced pressure. Hexane (100 ml) was added to the obtained residue and insoluble materials were filtered off. The resulting solution was concentrated under reduced pressure to give the title compound (16.9 g).

$^1$H-NMR (300 MHz, δppm, CDCl$_3$) 7.40-7.20(1H, m), 6.99(1H, dd, J=9.9, 1.8 Hz), 6.91(1H, d, J=8.1 Hz), 4.84(1H, s), 4.73(1H, s), 3.28(2H, s), 1.66(3H, s).

Step 2

2-Chloro-N-[1-(4-chloro-3-fluorophenyl)-2-methylpropan-2-yl]acetamide

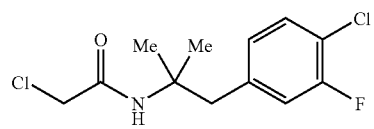

In the same manner as in Step 6 of Example 1-1, the title compound (10.1 g) was obtained from 1-chloro-2-fluoro-4-(2-methylallyl)benzene (16.9 g) obtained in Step 1.

$^1$H-NMR (400 MHz, δppm, CDCl$_3$) 7.30(1H, dd, J=7.9, 7.9 Hz), 6.92(1H, dd, J=9.9, 1.8 Hz) 6.85(1H, dd, J=8.1, 1.8 Hz), 6.14(1H, brs), 3.96(2H, s), 3.06(2H, s), 1.36(6H, s).

MS (ESI, m/z) 278(M+H)$^+$.

Step 3

1-(4-Chloro-3-fluorophenyl)-2-methylpropan-2-ylamine

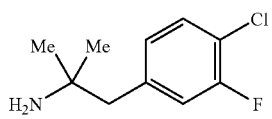

In the same manner as in Step 7 of Example 1-1, the title compound (6.90 g) was obtained from 2-chloro-N-[1-(4-chloro-3-fluorophenyl)-2-methylpropan-2-yl]acetamide (10.1 g) obtained in Step 2.

$^1$H-NMR (400 MHz, δppm, CDCl$_3$) 7.30(1H, dd, J=7.9, 7.9 Hz), 6.99(1H, dd, J=10.2, 2.0 Hz) 6.91(1H, dd, J=8.1, 1.9 Hz), 2.62(2H, s), 1.15(6H, s).

MS (ESI, m/z) 202(M+H)$^+$.

Step 4

Methyl 2'-[(1R)-[(2R)-3-[[1-(4-chloro-3-fluorophenyl)-2-methylpropan-2-yl]amino]-2-hydroxypropoxy]ethyl]-3-methylbiphenyl-4-carboxylate

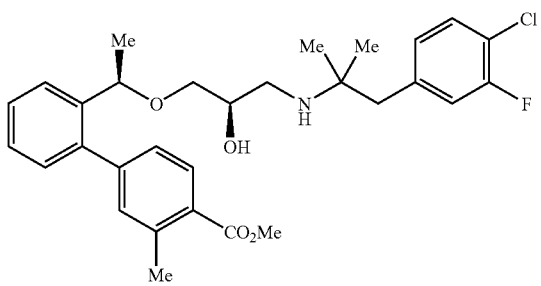

In the same manner as in Step 8 of Example 1-1, the title compound (413 mg) was obtained from methyl 3-methyl-2'-[(1R)-((R)-oxiranylmethoxy)ethyl]biphenyl-4-carboxylate (248 mg) obtained in Step 3 of Example 1-1 and 1-(4-chloro-3-fluorophenyl)-2-methylpropan-2-ylamine (170 mg) obtained in Step 3.

$^1$H-NMR (300 MHz, δppm, DMSO-d$_6$) 7.96(1H, d, J=8.4 Hz), 7.56-7.53(1H, m), 7.45-7.39(2H, m), 7.19-7.11(3H, m), 6.98-6.88(2H, m), 4.48(1H, q, J=6.6 Hz), 3.98(1H, m), 3.92(3H, s), 3.29-3.19(2H, m), 3.05-3.00(1H, m), 2.93(1H, m), 2.83(2H, s), 2.64(3H, s), 1.34(3H, d, J=6.6 Hz), 1.21(3H, s), 1.19(3H, s).

MS (ESI, m/z) 528(M+H)$^+$.

Step 5

2'-[(1R)-[(2R)-3-[[1-(4-chloro-3-fluorophenyl)-2-methylpropan-2-yl]amino]-2-hydroxypropoxy]ethyl]-3-methylbiphenyl-4-carboxylic acid

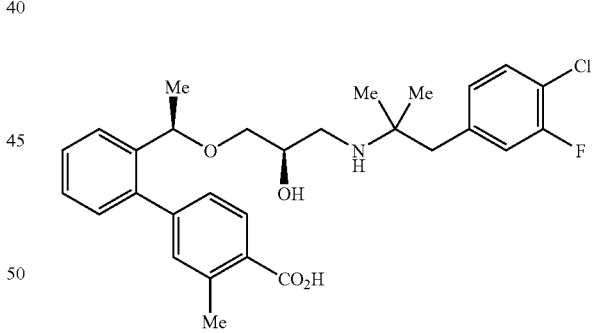

In the same manner as in Step 9 of Example 1-1, the title compound (345 mg) was obtained from methyl 2'-[(1R)-[(2R)-3-[[1-(4-chloro-3-fluorophenyl)-2-methylpropan-2-yl]amino]-2-hydroxypropoxy]ethyl]-3-methylbiphenyl-4-carboxylate (413 mg) obtained in Step 4.

$^1$H-NMR (400 MHz, δppm, DMSO-d$_6$) 7.84(1H, d, J=8.6 Hz), 7.55-7.52(1H, m), 7.47-7.41(2H, m), 7.36-7.32(1H, m), 7.25-7.22(1H, m), 7.18-7.15(3H, m), 7.05-7.03(1H, m), 4.47 (1H, q, J=6.5 Hz), 3.68(1H, m), 3.13(2H, d, J=5.5 Hz), 2.81-2.78(1H, m), 2.76(2H, s), 2.60-2.57(1H, m), 2.56(3H, s), 1.28(3H, d, J=6.2 Hz), 1.05(3H, s), 1.03(3H, s).

MS (ESI, m/z) 514(M+H)$^+$.

Examples 1-3 to 1-110

Examples 1-3 to 1-110 were obtained based on Examples 1-1 and 1-2. The results are shown in Tables 1-44.

TABLE 1

| Ex. No. | Structural formula | Property data | Reporter gene assay (μM) |
|---|---|---|---|
| 1-1 | | ¹H-NMR(300MHz, δppm, DMSO-d₆) 7.85(1H, d, J=8.3Hz), 7.56–7.53 (1H, m) 7.47–7.42(1H, m), 7.37–7.32(1H, m), 7.19–7.13(4H, m), 6.97–6.89(2H, m), 4.47(1H, q, J=6.4Hz), 3.70(1H, s), 3.14(2H, d, J=5.3Hz), 2.85–2.80 (1H, m), 2.73(2H, s), 2.63–2.59(1H, m), 2.56(3H, s),2.19(3H, s), 1.28(3H, d, J=6.4Hz), 1.05(3H, s), 1.04(3H, s), MS(ESI, m/z) 494(M+H)⁺. | 0.024 |
| 1-2 | | ¹H-NMR(400MHz, δppm, DMSO-d₆) 7.84(1H, d, J=8.6Hz), 7.55–7.52(1H, m), 7.47–7.41(2H, m), 7.36–7.32(1H, m), 7.25–7.22(1H, m), 7.18–7.15(1H, m), 7.05–7.03(1H, m), 4.47(1H, q, J=6.5Hz), 3.68(1H, m), 3.13(2H, d, J=5.5Hz), 2.81–2.78(1H, m), 2.76(2H, s), 2.60–2.57(1H, m), 2.56(3H, s), 1.28(3H, d, J=6.2Hz), 1.05(3H, s), 1.03(3H, s). MS(ESI, m/z) 514(M+H)⁺. | 0.013 |

TABLE 2

| 1-3 | | ¹H-NMR(400MHz, δppm, DMSO-d₆) 7.82(1H, d, J=8.4Hz), 7.54(1H, d, J=7.9Hz), 7.43(1H, dd, J=7.4, 7.4Hz), 7.33(1H, dd, 7.2, 7.2Hz), 7.25–7.10(5H, m), 7.04(1H, d, J=7.7Hz), 4.48(1H, q, J=6.5Hz), 3.77–3.66(1H, m), 3.14(2H, d, J=5.8Hz), 2.90–2.40(7H, m), 2.27(3H, s), 1.27(3H, d, J=6.2Hz), 1.05(3H, s), 1.04(3H, s) MS(ESI, m/z) 510(M+H)⁺. | 0.010 |
|---|---|---|---|
| 1-4 | | ¹H-NMR(400MHz, δppm, DMSO-d₆) 7.83(1H, d, J=8.4Hz), 7.54(1H, d, J=7.9Hz), 7.44(1H, dd, J=7.5, 7.5Hz), 7.34(1H, dd, 7.5, 7.5Hz), 7.28(1H, d, J=8.2Hz), 7.20–7.10(4H, m), 7.01(1H, d, J=8.1Hz), 4.48(1H, q, J=6.3Hz), 3.80–3.65(1H, m), 3.14(2H, d, J=5.6Hz), 2.90–2.40(7H, m), 1.04(3H, s), 1.03(3H, s) MS(ESI, m/z) 510(M+H)⁺. | 0.014 |

TABLE 2-continued

| 1-5 | [structure] | ¹H-NMR(400MHz, δppm, DMSO-d₆)<br>7.85(1H, d, J=8.4Hz), 7.54(1H, d, J=7.9Hz),<br>7.44(1H, dd, J=7.4, 7.4Hz),<br>7.34(1H, dd, 7.4, 7.4Hz), 7.20–7.12(3H, m),<br>7.01–6.90(2H, m), 4.47(1H, q, J=6.5Hz),<br>3.75–3.60(1H, m), 3.13(2H, d, J=5.8Hz),<br>2.90–2.70(3H, m), 2.65–2.40(4H, m),<br>2.24(3H, s), 1.27(3H, d, J=6.3Hz),<br>1.03(3H, s), 1.02(3H, s)<br>MS(ESI, m/z) 512(M+H)⁺. | 0.003 |

TABLE 3

| 1-6 | [structure] | ¹H-NMR(400MHz, δppm, DMSO-d₆)<br>7.84(1H, d, J=8.4Hz),<br>7.54(1H, dd, J=7.9, 1.2Hz),<br>7.44(1H, ddd, J=7.4, 7.4, 1.2Hz),<br>7.38–7.25(3H, m), 7.20–7.13(4H, m),<br>4.47(1H, q, J=6.2Hz), 3.75–3.60(1H, m),<br>3.12(2H, d, J=5.8Hz), 2.85–2.65(3H, m),<br>2.60–2.40(4H, m), 1.27(3H, d, J=6.2Hz),<br>1.02(3H, s), 1.00(3H, s)<br>MS(ESI, m/z) 514(M+H)⁺. | 0.020 |
| 1-7 | [structure] | ¹H-NMR(400MHz, δppm, DMSO-d₆)<br>7.84(1H, d, J=8.3Hz),<br>7.44(1H, ddd, J=7.5, 7.5, 1.2Hz),<br>7.34(1H, ddd, J=7.4, 7.4, 1.2Hz),<br>7.20–7.07(4H, m), 6.96(1H, d, J=10.9Hz),<br>6.91(1H, d, 7.9Hz), 4.48(1H, q, J=6.3Hz),<br>3.80–3.60(1H, m), 3.14(2H, d, J=5.5Hz),<br>2.95–2.70(3H, m), 2.65–2.40(4H, m),<br>2.27(3H, s), 1.27(3H, d, J=6.3Hz),<br>1.04(6H, s)<br>MS(ESI, m/z) 494(M+H)⁺. | 0.015 |

TABLE 4

| 1-8 | [structure] | ¹H-NMR(400MHz, δppm, DMSO-d₆)<br>7.83(1H, d, J=8.3Hz),<br>7.53(1H, dd, J=7.8, 1.2Hz),<br>7.43(1H, ddd, J=7.7, 7.7, 1.2Hz),<br>7.33(1H, ddd, J=7.6, 7.6, 1.2Hz),<br>7.20–7.12(4H, m), 6.98–6.87(2H, m),<br>4.48(1H, q, J=6.3Hz), 3.75–3.60(1H, m),<br>3.14(2H, d, J=5.5Hz), 2.85–2.65(3H, m),<br>2.60–2.45(6H, m), 1.27(3H, d, J=6.3Hz),<br>1.14(2H, t, J=7.5Hz) 1.03(3H, s), 1.02(3H, s)<br>MS(ESI, m/z) 508(M+H)⁺. | 0.015 |
| 1-9 | [structure] | ¹H-NMR(300MHz, δppm, DMSO-d₆)<br>7.87–7.18(14H, m), 4.45(1H, q, J=6.3Hz),<br>3.80–3.65(1H, m), 3.18(2H, d, J=5.1Hz),<br>2.95–2.80(3H, m), 2.70–2.60(1H, m),<br>2.40(3H, s), 1.26(3H, d, J=6.3Hz),<br>1.08(3H, s), 1.07(3H, s)<br>MS(ESI, m/z) 512(M+H)⁺. | 0.016 |

TABLE 4-continued
| 1-10 | 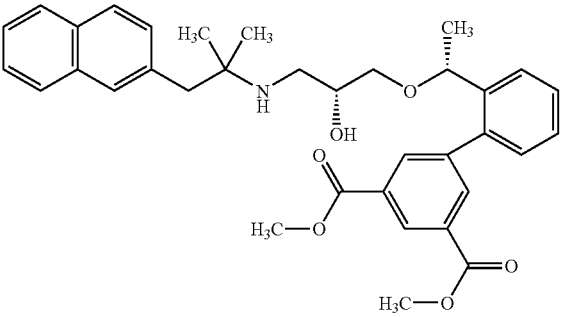 | ¹H-NMR(300MHz, δppm, CDCl₃) 8.69(1H, s), 4.43(1H, q, J=6.4Hz), 3.95(6H, s), 3.80–3.70(1H, m), 3.30–3.15(2H, m), 2.90–2.75(3H, m), 2.75–2.65(1H, m), 1.33(3H, d, J=6.4Hz), 1.12(3H, s), 1.10(3H, s). MS(ESI, m/z) 570(M+H)⁺. | 0.029 |
TABLE 5
| 1-11 | 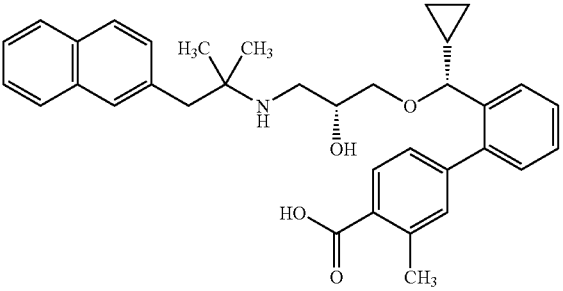 | ¹H-NMR(300MHz, δppm, DMSO-d₆) 7.88–7.16(14H, m), 3.89(1H, d, J=7.4Hz), 3.87–3.75(1H, m), 3.40–3.15(2H, m), 3.00–2.85(3H, m), 2.80–2.65(1H, m), 2.43(3H, s), 1.20–0.95(7H, m), 0.50–0.35(1H, m), 0.30–0,20(2H, m), −0.05–−0.15(1H, m). MS(ESI, m/z) 538(M+H)⁺. | 0.018 |
| 1-12 | 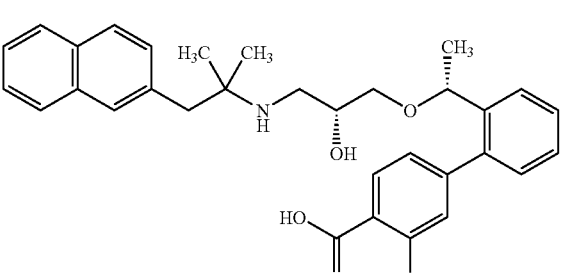 | ¹H-NMR(300MHz, δppm, DMSO-d₆) 12.7(1H, bs), 9.15(1H, bs), 8.70(1H, bs), 8.00–7.15(14H, m), 5.59(1H, bs), 4.49(1H, q, J=6.4Hz), 4.00–3.90(1H, m), 3.40–3.05(5H, m), 2.90–2.75(1H, m), 2.60(3H, s), 1.30(3H, d, J=6.3Hz), 1.25(6H, s). MS(ESI, m/z) 512(M+H−HCl)⁺ | 0.013 |
| 1-13 | 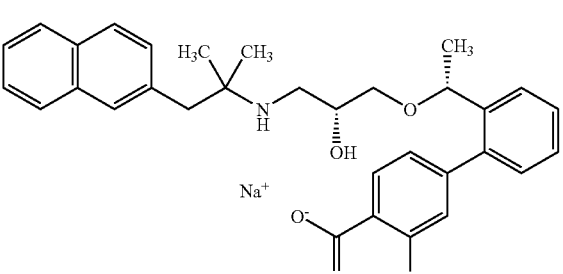 | ¹H-NMR(300MHz, δppm, DMSO-d₆) 7.90–7.70(3H, m), 7.65(1H, s), 7.60–7.25(7H, m), 7.15–7.12(1H, m), 6.96–6.93(2H, m), 4.62(1H, bs), 4.51(1H, q, J=6.4Hz), 3.55(1H, bs), 3.35–3.30(1H, m), 3.12(2H, d, J=5.7Hz), 2.80–2.60(3H, m), 2.48(3H, s), 1.24(3H, d, J=6.4Hz), 0.97(3H, s), 0.95(3H, s). MS(ESI, m/z) 512(M+2H—Na)⁺ | 0.015 |

TABLE 6

| 1-14 | 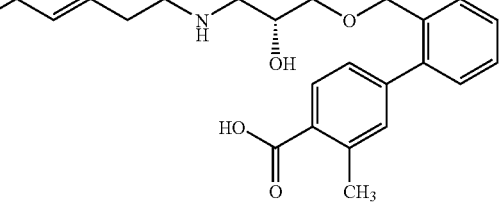 | ¹H-NMR(300MHz, δppm, DMSO-d₆) 7.85(1H, d, J=7.8Hz), 7.60(1H, d, J=6.6Hz), 7.50-7.30(2H, m), 7.20-7.10(4H, m), 7.00-6.90(2H, m), 3.86(1H, d, J=7.5Hz), 3.80-3.70(1H, m), 3.35-3.15(2H, m), 2.95-2.90(1H, m), 2.77(2H, s), 2.76-2.60(1H, m), 2.56(3H, s), 2.19(3H, s), 1.15-1.00(7H., m), 0.50-0.40(1H, m), 0.35-.020(2H, m), −0.15-−0.20(1H, m). MS(ESI, m/z) 520(M+H)⁺. | 0.006 |
|---|---|---|---|
| 1-15 | 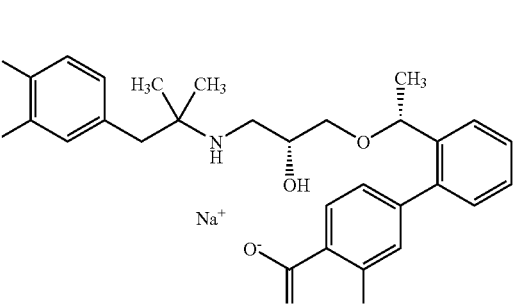 | ¹H-NMR(400MHz, δppm, DMSO-d₆) 7.55-7.45(2H, m), 7.40-7.25(2H, m), 7.15-7.05(2H, m), 6.95-6.80(4H, m), 4.49(1H, J=6.4Hz), 3.55-3.50(1H, m), 3.09(2H, s), 2.60-2.35(6H, m), 2.18(3H, s), 1.24(3H, d, J=6.4Hz), 0.89(3H, s), 0.86(3H, s). MS(ESI, m/z) 494(M+2H—Na)⁺. | 0.012 |
| 1-16 | 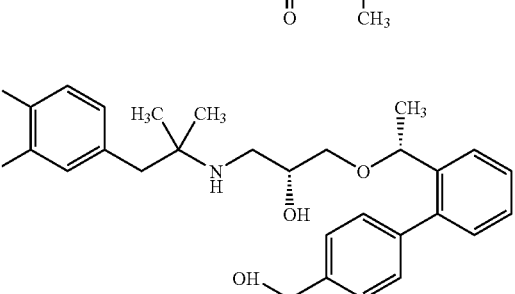 | ¹H-NMR(400MHz, δppm, DMSO-d₆) 12.7(1H, bs), 8.94(1H, bs), 8.49(1H, bs), 7.90(1H, d, J=8.0Hz), 7.60-7.15(7H, m), 7.00-6.90(2H, m), 5.55(1H, d, J=4.0Hz), 4.46(1H, q, J=6.3Hz), 3.95-3.85(1H, m), 3.20-2.65(6H, m), 2.59(3H, s), 2.21(3H, s), 1.31(3H, d, J=6.3Hz), 1.18(6H, s). MS(ESI, m/z) 494(M+M-HCl)⁺. | 0.011 |

TABLE 7

| 1-17 | 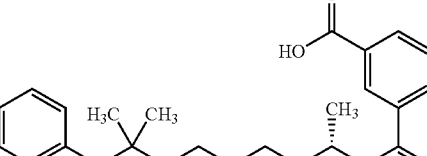 | ¹H-NMR(400MHz, δppm, DMSO-d₆) 7.76(1H, s), 7.64(1H, s), 7.60-7.10(6H, m), 7.00-6.85(2H, m), 4.43(1H, q, J=6.4Hz), 3.80-3.65(1H, m), 3.15(2H, d, J=5.1Hz), 3.80-3.55(4H, m), 2.40(3H, s), 2.18(3H, s), 1.26(3H, d, J=6.4Hz), 1.05(6H, s). MS(ESI, m/z) 494(M+N)⁺. | 0.015 |
|---|---|---|---|
| 1-18 |  | ¹H-NMR(300MHz, δppm, DMSO-d₆) 7.86(1H, d, J=8.4Hz), 7.65-7.10(9H, m), 3.85(1H, d, J=7.8Hz), 3.75-3.65(1H, m), 3.35-3.10(2H, m), 2.90-2.50(7H, m), 0.30-0.20(2H, m), −0.05-−0.20(1H, m). MS(ESI, m/z) 540(M+H)⁺. | 0.016 |

TABLE 7-continued

| 1-19 | 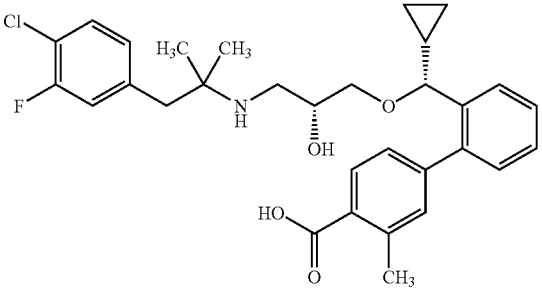 | $^1$H-NMR(400MHz, δppm, DMSO-d$_6$) 7.84(1H, d, J=8.4Hz), 7.59(1H, d, J=7.9Hz), 7.50-7.15(7H, m), 7.10-7.00(1H, m), 3.85(1H, d, J=7.4Hz), 3.75-3.65(1H, m), 3.30-3.15(2H, m), 2.90-2.75(3H, m), 2.70-2.60(1H, m), 2.56(3H, s), 1.15-1.10(7H, m), 0.50-0.40(1H, m), 0.30-0.20(2H, m), −0.15--0.15(1H, m). MS(ESI, m/z) 540(M+H)$^+$. | 0.005 |
|---|---|---|---|

TABLE 8

| 1-20 | 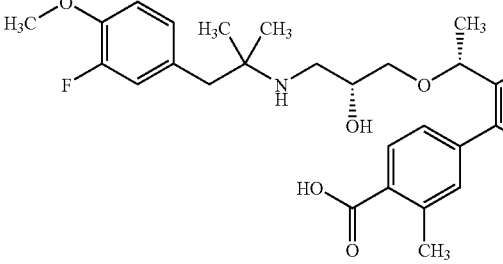 | $^1$H-NMR(300MHz, δppm, DMSO-d$_6$) 7.86(1H, d, J=8.4Hz), 7.57-7.54(1H, m), 7.47-7.42(1H, m), 7.37-7.32(1H, m), 7.19-7.13(4H, m), 6.79-6.68(2H, m), 4.48(1H, q, J=6.2Hz), 3.74(3H, s), 3.70(1H, m), 3.14(2H, d, J=5.5Hz), 2.84-2.81(1H, m), 2.71(2H, s), 2.62-2.59(1H, m), 2.56(3H, s), 1.28(3H, d, J=6.2Hz), 1.03(6H, m). MS(ESI, m/z) 510(M+H)$^+$. | 0.040 |
|---|---|---|---|
| 1-21 | 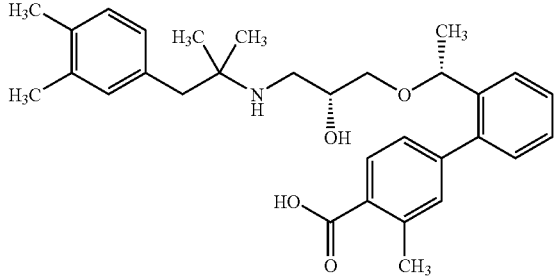 | $^1$H-NMR(400MHz, δppm, DMSO-d$_6$) 7.82-7.79(1H, m), 7.54-7.52(1H, m), 7.45-7.41(1H, m), 7.35-7.31(1H, m), 7.17-7.12(3H, m), 7.02-7.00(1H, m), 6.93(1H, s), 6.88-6.86(1H, m), 4.49(1H, q, J=6.5Hz), 3.77(1H, m), 3.15(2H, d, J=5.8Hz), 2.92-2.89(1H, m), 2.73(2H, s), 2.66-2.64(1H, m), 2.54(3H, s), 2.16(6H, s), 1.26(3H, d, J=6.2Hz), 1.06(6H, s). MS(ESI, m/z) 490(M+H)$^+$. | 0.013 |
| 1-22 | 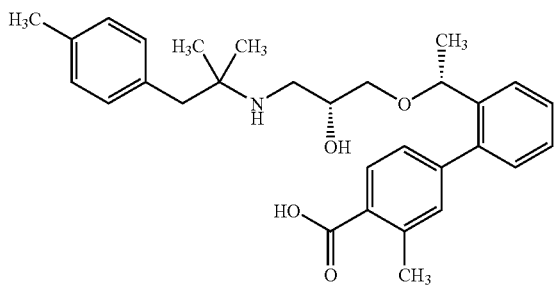 | $^1$H-NMR(400MH$^+$, δppm, DMSO-d$_6$) 7.83(1H, d, J=8.3Hz), 7.55-7.53(1H, m), 7.46-7.42(1H, m), 7.36-7.32(1H, m), 7.19-7.15(3H, m), 7.09-7.04(4H, m), 4.49(1H, q, J=6.5Hz), 3.76(1H, m), 3.16-3.14(2H, m), 2.91-2.88(1H, m), 2.76(2H, s), 2.66-2.64(1H, m), 2.56(3H, s), 2.26(3H, s), 1.27(3H, d, J=6.5Hz), 1.06(6H, s). MS(ESI, m/z) 476(M+H)$^+$. | 0.012 |

TABLE 9

| 1-23 | 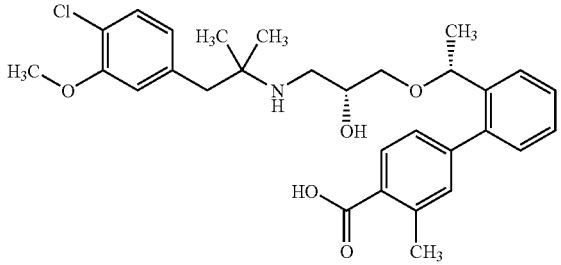 | $^1$H-NMR(400MHz, δppm, DMSO-d$_6$) 7.83(1H, d, J=8.6Hz), 7.54-7.52(1H, m), 7.46-7.42(1H, m), 7.36-7.29(2H, m), 7.19-7.14(3H, m), 6.95(1H, m), 6.78-6.75(1H, m), 4.48(1H, q, J=6.2Hz), 3.81(3H, s), 3.77-3.75(1H, m), 3.14(2H, d, J=5.8Hz), 2.89-2.87(1H, m), 2.80(2H, s), 2.66-2.61(1H, m), 2.56(3H, s), 1.28(3H, d, J=6.2Hz), 1.11(3H, m), 1.09(3H, m). MS(ESI, m/z) 526(M+H)$^+$. | 0.016 |
|---|---|---|---|

TABLE 9-continued

| | | | |
|---|---|---|---|
| 1-24 | 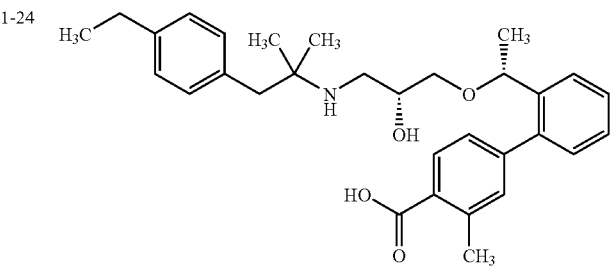 | ¹H-NMR(300MHz, δppm, DMSO-d₆) 7.85(1H, d, J=8.1Hz), 7.56-7.54(1H, m), 7.48-7.43(1H, m), 7.38-7.33(1H, m), 7.20-7.16(3H, m), 7.13-7.07(4H, m), 4.49(1H, q, J=6.2Hz), 3.75-3.74(1H, m), 3.15(2H, d, J=5.5Hz), 2.90-2.86(1H, m), 2.75(2H, s), 2.67-2.55(6H, m), 1.27(3H, d, J=6.2Hz), 1.16(3H, t, J=7.6Hz), 1.05(6H, s). MS(ESI, m/z) 490(M+H)⁺. | 0.020 |
| 1-25 | 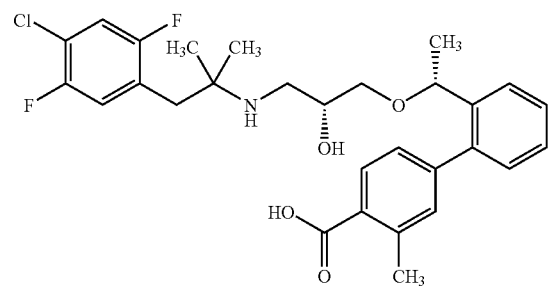 | ¹H-NMR(400MHz, δppm, DMSO-d₆) 7.84(1H, d, J=8.3Hz), 7.56-7.52(2H, m), 7.45-7.41(1H, m), 7.38-7.31(2H, m), 7.18-7.15(3H, m), 4.46(1H, q, J=6.5Hz), 3.66(1H, m), 3.12(2H, d, J=5.5Hz), 2.78-2.71(3H, m), 2.78-2.71(3H, m), 2.56(4H, m), 1.28(3H, d, J=6.5Hz), 1.04(3H, s), 1.03(3H, s). MS(ESI, m/z) 532(M+H)⁺. | 0.019 |

TABLE 10

| | | | |
|---|---|---|---|
| 1-26 | 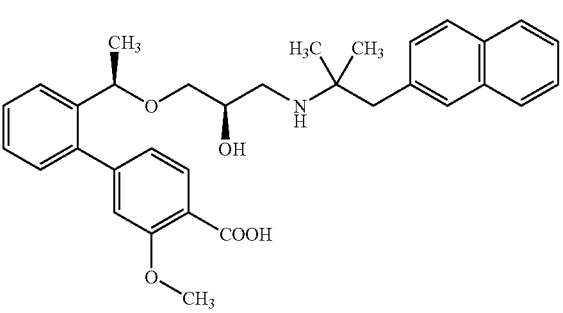 | ¹H-NMR(300MHz, δppm, DMSO-d₆) 7.89-7.81(3H, m), 7.71(1H, s), 7.66(1H, d, J=7.5Hz), 7.57-7.35(6H, m), 7.23(1H, d, J=7.5Hz), 6.95(1H, s), 6.90(1H, d, J=7.9Hz), 4.52(1H, q, J=6.4Hz), 3.81-3.75(4H, m), 3.18(2H, d, J=4.9Hz), 2.96-2.91(1H, m), 2.72-2.65(1H, m), 1.30(3H, d, J=6.4Hz), 1.11(3H, s). MS(ESI, m/z) 528(M+H)⁺. | 0.014 |
| 1-27 | 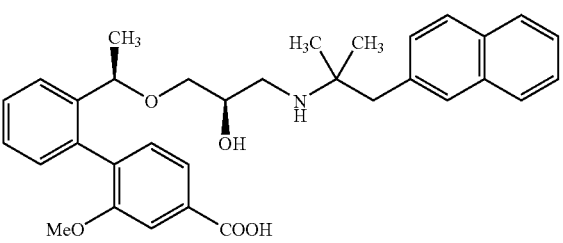 | ¹H-NMR(300MHz, δppm, DMSO-d₆) 7.93-7.88(3H, m), 7.76(1H, d, J=7.0Hz), 7.67-7.20(9H, m), 7.13-7.08(1H, m), 4.23-4.16 and 3.93-3.91(1H, m), 3.81-3.76(4H, m), 3.25-2.58(6H, m), 1.31 and 1.11(3H, d, J=6.2Hz), 1.26(3H, s), 1.22(3H, s). MS(ESI, m/z) 528(M+H)⁺. | 0.014 |
| 1-28 | 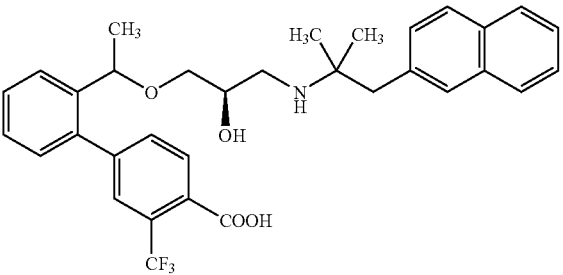 | ¹H-NMR(300MHz, δppm, DMSO-d₆) 7.90-7.84(3H, m), 7.74-7.68(2H, m), 7.63-7.57(2H, m), 7.53-7.47(4H, m), 7.41-7.36(2H, m), 7.25-7.22(1H, m), 4.556-4.47(1H, m), 3.93-3.92(1H, m), 3.26-3.07(4H, m), 2.94-2.80(2H, m), 1.31-1.22(9H, m). MS(ESI, m/z) 566(M+H)⁺. | 0.007 |

TABLE 11

| | | | |
|---|---|---|---|
| 1-29 | *(structure)* | ¹H-NMR(300 MHz, δ ppm, DMSO-d₆) 7.71(1H, d, J=8.0 Hz), 7.60-7.57(2H, m), 7.52-7.47(2H, m), 7.25-7.18(2H, m), 6.82-6.74(2H, m), 4.51(1H, q, J=6.6 Hz), 3.88-3.86(1H, m), 3.75(3H, s), 3.22-2.73(6H, m), 1.29(3H, d, J=6.6 Hz), 1.14(6H, s). MS (ESI, m/z) 564(M + H)⁺. | 0.082 |
| 1-30 | *(structure)* | ¹H-NMR(300 MHz, δ ppm, DMSO-d₆) 7.87-7.80(4H, m), 7.71(1H, s), 7.57-7.42(4H, m), 7.38-7.33(2H, m), 7.21-7.17(3H, m), 4.48(1H, q, J=6.3 Hz), 3.77-3.76(1H, m), 3.17-2.91(8H, m), 2.72-2.68(1H, m), 1.28(3H, d, J=6.3 Hz), 1.18(3H, t, J=7.4 Hz), 1.12(3H, s), 1.11(3H, s). MS(ESI, m/z) 526(M + H)⁺. | 0.007 |
| 1-31 | *(structure)* | ¹H-NMR(300 MHz, δ ppm, DMSO-d₆) 7.70(1H, d, J=7.7 Hz), 7.59-7.46(6H, m), 7.39(1H, ddd, J=7.3, 7.3, 1.4 Hz), 7.24-7.19(2H, m), 4.51(1H, q, J=6.3 Hz), 3.85-3.84(1H, m), 3.21-2.92(5H, m), 2.74-2.70(1H, m), 1.28(3H, d, J=6.3 Hz), 1.15(6H, s). MS(ESI, m/z) 584(M + H)⁺. | 0.005 |

TABLE 12

| | | | |
|---|---|---|---|
| 1-32 | *(structure)* | ¹H-NMR(300 MHz, δ ppm, DMSO-d₆) 7.87-7.77(3H, m), 7.68(1H, s), 7.50-7.31(5H, m), 7.20-7.18(2H, m), 7.10(1H, dd, J=7.7, 1.5 Hz), 4.47(1H, q, J=6.2 Hz), 3.84(1H, sept, J=7.0 Hz), 3.72-3.71(1H, m), 3.20-3.10(2H, m), 2.90(2H, s), 2.85-2.80(1H, m), 2.63-2.57(1H, m), 1.26(3H, d, J=6.2 Hz), 1.19(6H, d, J=7.0 Hz), 1.07(3H, s), 1.05(3H, s). MS (ESI, m/z) 540(M + H)⁺. | 0.002 |
| 1-33 | *(structure)* | ¹H-NMR(300 MHz, δ ppm, DMSO-d₆) 7.76(1H, d, J=8.5 Hz) 7.54(1H, dd, J=7.7, 1.1 Hz), 7.44(1H, ddd, J=7.7, 7.7, 1.1 Hz), 7.34(1H, m), 7.20-7.13(4H, m), 6.96-6.88(2H, m), 4.48(1H, q, J=6.6 Hz), 3.70-3.69(1H, m), 3.15-3.13(2H, m), 2.97(2H, q, J=7.3 Hz), 2.81-2.71(3H, m), 2.59-2.47(1H, m), 2.18(3H, s), 1.27(3H, d, J=6.6 Hz), 1.17(3H, t, J=7.3 Hz),1.02(3H, s) 1.01 (3H, s). MS (ESI, m/z) 508(M + H)⁺. | 0.005 |

TABLE 13

| | | | |
|---|---|---|---|
| 1-34 | 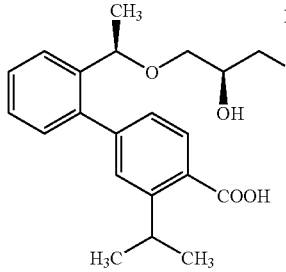 | ¹H-NMR(300 M Hz, δ ppm, DMSO-d₆) 7.64(3H, d, J=8.1 Hz), 7.54(1H, dd, J=8.1, 1.1 Hz), 7.44(1H, ddd, J=7.3, 7.3, 1:1 Hz), 7.20-7.10(4H, m), 6.96-6.88(2H, m) 4.45(1H, q, J=6.3 Hz), 3.82(1H, sept, J=6.6 Hz), 3.69-3.68(1H, m), 3.17-3.07(2H, m), 2.80-2.70(3H, m), 1.27(3H, d, J=6.3 Hz), 1.20(6H, d, J=6.6 Hz), 1.02(3H, s), 1.00(3H, s). MS(ESI, m/z) 522(M + H)⁺. | 0.005 |
| 1-35 | 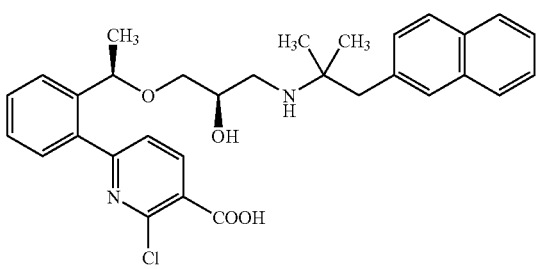 | ¹H-NMR(300 MHz, δ ppm, DMSO-d₆) 7.90-7.83(4H, m), 7.74(1H, s), 7.60-7.36(8H, m), 4.79(1H, q, J=6.1 Hz), 3.78-3.76(1H, m), 3.28-3.02(6H, m), 2.82-2.75(1H, m), 1.39(3H, d, J=6.1 Hz), 1.20(6H, s). MS(ESI, m/z) 533(M + H)⁺. | 0.010 |
| 1-36 | 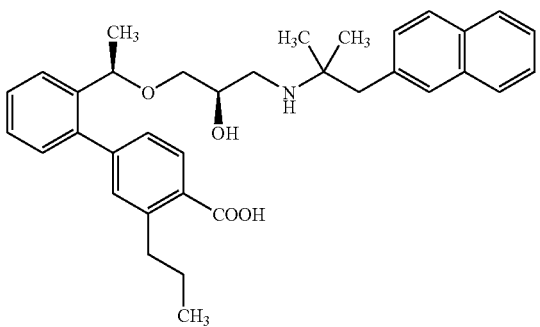 | ¹H-NMR(300 MHz, δ ppm, DMSO-d₆) 7.85-7.71(4H, m), 7.66(1H, s), 7.53-7.38(4H, m), 7.34-7.30(2H, m), 7.17-7.05(3H, m), 4.49(1H, q, J=6.3 Hz), 3.71-3.70(1H, m), 3.17-3.10(2H, m), 2.94-2.79(5H, m), 2.61-2.56(1H, m), 1.58(2H, tq, J=7.2,7.2 Hz), 1.24(3H, d, J=6.3 Hz), 1.06(3H, s), 1.04(3H, s), 0.85(3H, t, J=7.2 Hz). MS(ESI, m/z) 540(M + H)⁺. | 0.002 |

TABLE 14

| | | | |
|---|---|---|---|
| 1-37 | 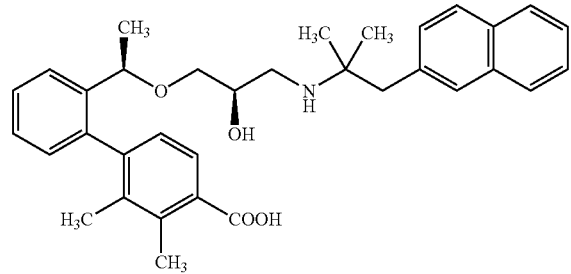 | ¹H-NMR(300 MHz, δ ppm, DMSO-d₆) 7.88-7.79(3H, m), 7.71(1H, s), 7.55-7.31(7H, m), 7.06-6.88(2H, m), 4.31-4.25 and 4.13-4.07(1H, m), 3.77-3.76(1H, m), 3.25-3.14(2H, m), 2.96-2.88(3H, m), 2.71-2.64(1H, m), 2.43(3H, s), 2.00 and 1.91(3H, s), 1.17-1.09(9H, m). MS (ESI, m/z) 526(M + H)⁺. | 0.003 |
| 1-38 | 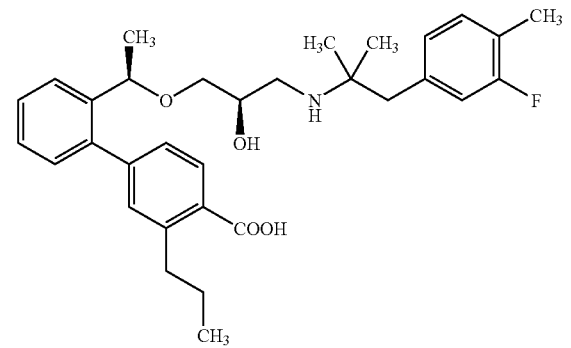 | ¹H-NMR(300 MHz, δ ppm, DMSO-d₆) 7.78(1H, d, J=7.9 Hz), 7.53(1H, dd, J=7.9, 1.2 Hz), 7.43(1H, ddd, J=7.6, 7.6, 1.4 Hz), 7.33(1H, ddd, J=7.6, 7.6, 1.4 Hz), 7.18-7.11(4H, m), 6.95-6.92(1H, m), 6.89(1H, dd, J=7.8, 1.2 Hz), 4.45(1H, q, J=6.3 Hz), 3.71-3.70(1H, m), 3.11-3.10(2H, m), 2.99-2.82(3H, m), 2.74(2H, s), 2.62-2.57(1H, m), 2.17(3H, s) 1.57(2H, tq,J=7.4, 7.4 Hz), 1.26(3H, d, J=6.3 Hz), 1.04(3H, s), 1.03(3H, s), 0.86(3H, t, J=7.4 Hz). MS(ESI, m/z) 522(M + H)⁺. | 0.002 |

TABLE 14-continued

| 1-39 | 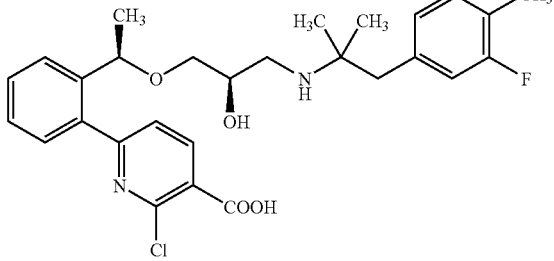 | ¹H-NMR(300 MHz, δ ppm, DMSO-d₆) 7.95(1H, d, J=7.6 Hz), 7.58-7.47(3H, m), 7.38-7.36(2H, m), 7.20(1H, dd, J=7.6,7.6 Hz), 6.99-6.91(2H, m), 4.76(1H, q, J=6.3 Hz), 3.78-3.76(1H, m), 3.23-3.12(2H, m), 2.96-2.87(2H, m), 2.79-2.73(1H, m), 2.18(3H, s), 1.39(3H, d, J=6.3 Hz), 1.15(6H, s). MS(ESI, m/z) 515(M + H)⁺. | 0.012 |

TABLE 15

| 1-40 | 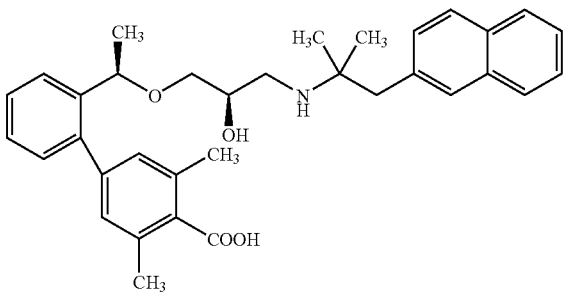 | ¹H-NMR(300 MHz, δ ppm, DMSO-d₆) 7.90-7.82(3H, m), 7.72(1H, s), 7.54-7.30(6H, m), 7.15(1H, dd, J=7.7, 1.5 Hz), 6.93(2H, s), 4.53(1H, q, J=6.3 Hz), 3.81-3.80(1H, m), 3.21-3.16(2H, m), 3.02-2.98(3H, m), 2.77-2.70(1H, m), 2.30(6H, s), 1.29(3H, d, J=6.3 Hz), 1.16(6H, s). MS(ESI, m/z) 526(M + H)⁺. | 0.003 |
| 1-41 | 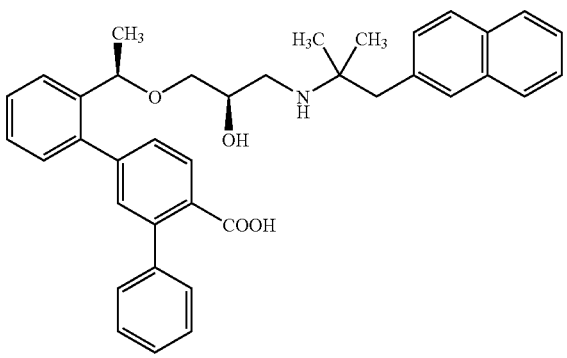 | ¹H-NMR(300 MHz, δ ppm, DMSO-d₆) 7.85-7.76(3H, m), 7.61-7.59(2H, m), 7.53(1H, dd, J=7.6, 1.0 Hz), 7.47-7.39(5H, m), 7.34-7.19(7H, m), 7.13(1H, d, J=1.6 Hz), 4.60(1H, q, J=6.3 Hz), 3.74-3.73(1H, m), 3.17-3.15(2H, m), 2.83-2.80(3H, m), 2.60-2.56(1H, m), 1.27(3H, d, J=6.3 Hz), 0.97(6H, s). MS(ESI, m/z) 574(M + H)⁺. | 0.003 |
| 1-42 | 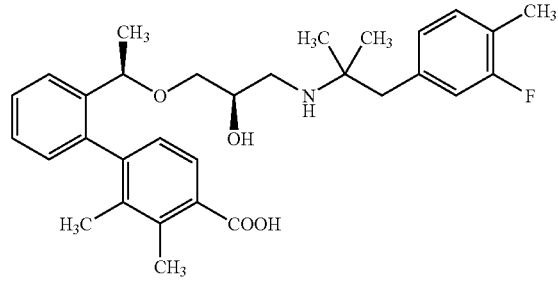 | ¹H-NMR(300 MHz, δ ppm, DMSO-d⁶) 7.53-7.39(3H, m), 7.33-7.29(1H, m), 7.15-7.11(1H, m), 7.03-6.99(1H, m), 6.95-6.86(3H, m), 4.26-4.22 and 4.08-4.03(1H, m), 3.71-3.70(1H, m), 3.20-3.10(2H, m), 2.83-2.80(1H, m), 2.73-2.71(2H, m), 2.61-2.56(1H, m), 2.41 and 2.40(3H, s), 2.16(3H, s) 1.97 and 1.89(3H, s), 1.15-1.12(3H, m), 1.04-1.01(6H, m). MS(ESI, m/z) 508(M + H)⁺. | 0.024 |

TABLE 16

| 1-43 | 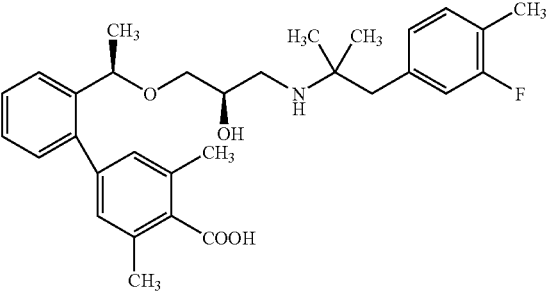 | $^1$H-NMR(300 MHz, δ ppm, DMSO-$d_6$) 7.51(1H, dd, J=7.6, 1.2 Hz), 7.40(1H, ddd, J=7.6, 7.6, 1.2 Hz), 7.31(1H, ddd, J=7.6, 7.6, 1.4 Hz), 7.20-7.16(1H, m), 7.13(1H, dd, J=7.6, 1.4 Hz), 6.98-6.89(4H, m), 4.50(1H, q, J=6.3 Hz), 3.78-3.77(1H, m), 3.18-3.10(1H, m), 2.97-2.94(1H, m), 2.82(2H, s), 2.71-2.66(1H, m), 2.27(6H, s), 2.18(3H, s), 1.28(3H, d, J=6.3 Hz), 1.10(3H, s), 1.09(3H, s). MS(ESI, m/z)508(M + H)$^+$. | 0.016 |
|---|---|---|---|
| 1-44 | 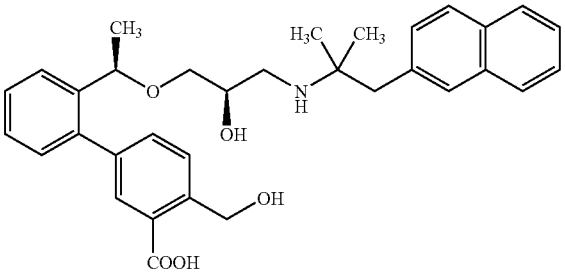 | $^1$H-NMR(300 MHz, δ ppm, DMSO-$d_6$) 7.86-7.77(3H, m), 7.70(1H, s) 7.53-7.29(8H, m), 7.26(1H, dd, J=7.9, 1.8 Hz), 4.68(1H, d, J=13.8 Hz), 4.64(1H, d, J=13.8 Hz), 4.47(1H, q, J=6.2 Hz), 3.88-3.87(1H, m), 3.22-3.21(2H, m), 3.05(2H, s), 3.00-2.96(1H, m), 2.80-2.75(1H, m), 1.26(3H, d, J=6.2 Hz), 1.16(6H, s). MS(ESI, m/z) 528(M + H)$^+$. | 0.009 |
| 1-45 | 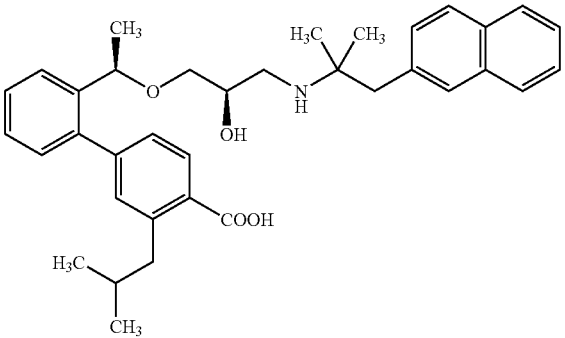 | $^1$H-NMR(300 MHz, δ ppm, DMSO-$d_6$) 7.88-7.76(3H, m), 7.68(1H, s), 7.56-7.31(7H, m), 7.19-7.13(2H, m), 7.04-7.03(1H, m), 4.50(1H, q, J=6.6 Hz), 3.71-3.70(1H, m), 3.18-3.09(2H, m), 2.93-2.78(5H, m), 2.62-2.58(1H, m), 1.91-1.84(1H, m), 1.26(3H, d, J=6.6 Hz), 1.07(3H, s), 1.05(3H, s), 0.85(3H, d, J=2.6 Hz),0.83(3H, d, J=2.6 Hz). MS(ESI, m/z) 554(M + H)$^+$. | 0.002 |

TABLE 17

| 1-46 | 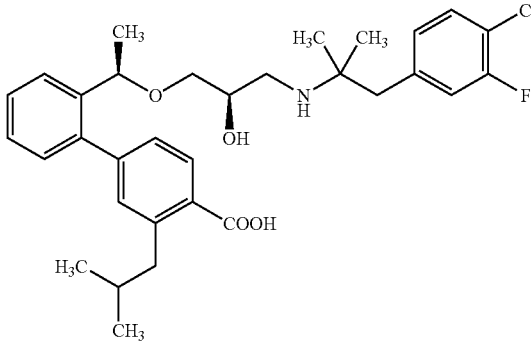 | $^1$H-NMR(300 MHz, δ ppm, DMSO-$d_6$) 7.76(1H, d, J=7.7 Hz), 7.54(1H, dd, J=7.7, 1.1 Hz), 7.43(1H, ddd, J=7.7, 7.7, 1.1 Hz), 7.34(1H, ddd, J=7.7, 7.7, 1.1 Hz), 7.18-7.04(4H, m), 6.95-6.87(2H, m), 4.48(1H, q, J=6.2 Hz), 3.65-3.64(1H, m), 3.12-3.09(2H, m), 2.93-2.78 (2H, m), 2.70-2.66(3H, m), 2.54-2.47(1H, m), 2.18(1H, s), 1.88(1H, sept, J=6.6 Hz), 1.26(3H, d, J=6.2 Hz),0.99(3H, s), 0.98(3H, s), 0.85(3H, d, J=6.6 Hz), 0.84(3H, J=6.6 Hz). MS(ESI, m/z) 536(M + H)$^+$. | 0.003 |

TABLE 17-continued

| 1-47 | 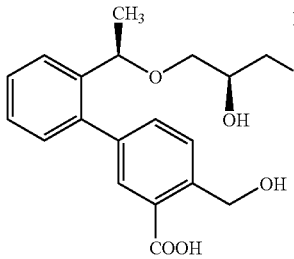 | ¹H-NMR(300 MHz, δ ppm, DMSO-d₆) 7.78(1H, d, J=1.8 Hz), 7.55(1H, dd, J=7.7, 1.2 Hz), 7.50(1H, d, J=8.0 Hz), 7.43(1H, ddd, J=7.3,7.3,1.5 Hz), 7.35(1H, ddd, J=7.3, 7.3, 1.5 Hz), 7.30(1H, dd, J=7.7, 1.2 Hz), 7.22-7.17(2H, m), 7.01-6.92(2H, m), 4.72(1H, q, J=13.5 Hz), 4.66(1H, d, J=13.5 Hz), 4.48(1H, q, J=6.3 Hz), 3.85-3.84(1H, m), 3.23-3.21(2H, m), 2.96-2.91(1H, m), 2.86(2H, s), 2.76-2.70(1H, m),2.20(3H, s), 1.29(3H, d, J=6.3 Hz), 1.12(6H, s). MS(ESI, m/z) 510(M + H)⁺. | 0.065 |

TABLE 18

| 1-48 | 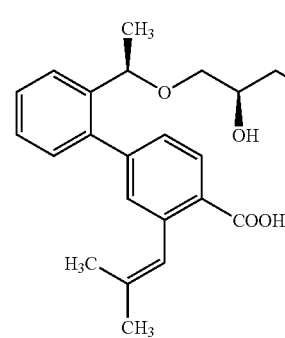 | ¹H-NMR(300 MHz, δ ppm, DMSO-d₆) 7.77(1H, d, J=7.9 Hz), 7.51(1H, dd, J=7.7, 1.1 Hz), 7.41(1H, ddd, J=7.4, 7.4, 1.4 Hz), 7.31(1H, ddd, J=7.4, 7.4, 1.1 Hz), 7.15-7.10(3H, m), 7.00(1H, d, J=1.6 Hz), 6.93-6.90(1H, m), 6.86(1H, dd, J=7.7, 1.4 Hz), 6.72(1H, s), 4.51(1H, q, J=6.5 Hz), 3.69-3.68 (1H, m), 3.10-3.08(2H, m), 2.80-2.76(1H, m), 2.70(2H, s), 2.56-2.51(1H, m), 2.16(3H, s), 1.78(3H, s), 1.67(3H, s),1.25(3H, d, J=6.5 Hz), 1.02(3H, s), 1.00(3H, s). MS(ESI, m/z) 534(M + H)⁺. | 0.002 |
| 1-49 | 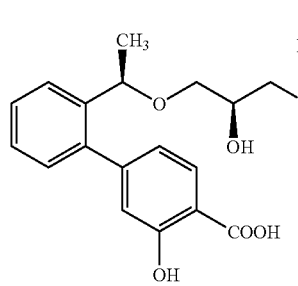 | ¹H-NMR(300 MHz, δ ppm, DMSO-d₆) 7.87-7.81(3H, m), 7.70-7.68(2H, m), 7.49-7.43(3H, m), 7.37(1H, ddd, J=7.4, 7.4, 1.4 Hz), 7.33(1H, dd, J=8.5, 1.8 Hz), 7.28(1H, ddd, J=7.4, 7.4, 1.4 Hz), 7.14(1H, dd, J=7.6, 1.4 Hz), 6.50-6.47(2H, m), 4.54(1H, q, J=6.3 Hz), 3.81-3.80(1H, m), 3.17-3.03(5H, m), 2.80-2.75(1H, m), 1.27(3H, d, J=6.3 Hz), 1.17(6H, s). MS(ESI, m/z) 514(M + H)⁺. | 0.002 |

TABLE 19

| 1-50 | 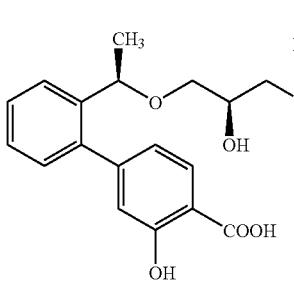 | ¹H-NMR(300 MHz, δ ppm, DMSO-d₆) 7.67(3H, d, J=7.7 Hz), 7.84(1H, dd, J=7.9,1.2 Hz), 7.37(1H, ddd, J=7.4, 7.4, 1.2 Hz), 7.28(1H, ddd, J=7.4, 7.4, 1.2 Hz), 7.17(1H, dd, J=7.9, 7.9 Hz), 7.13(1H, dd, J=7.4,1.2 Hz), 6.97-6.89(2H, m), 6.48-6.45(2H, m), 4.53(1H, q, J=6.3 Hz), 3.77-3.76(1H, m), 3.14-3.07(2H, m), 2.98-2.70(4H, m), 2.17(3H, s), 1.27(3H, d, J=6.3 Hz),1.10(6H, s). MS(ESI, m/z) 496(M + H)⁺. | 0.002 |

TABLE 19-continued

| 1-51 | 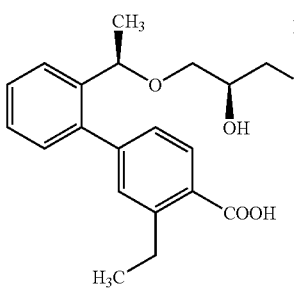 | ¹H-NMR(300 MHz, δ ppm, DMSO-d⁶)<br>7.76(1H, d, J=8.4 Hz), 7.55-7.52(1H, m),<br>7.45-7.40(2H, m),<br>7.34(1H, ddd, J=7.3, 7.3, 1.5 Hz),<br>7.24-7.12(4H, m), 7.03(1H, dd, J=8.1, 1.5 Hz),<br>4.46(1H, q, J=6.3 Hz), 3.66-3.59(1H, m),<br>3.12-3.11(2H, m), 2.96(2H, q, J=7.3 Hz),<br>2.72-2.67(3H, m), 2.53-2.47(1H, m),<br>1.26(3H, d, J=6.3 Hz), 1.17(3H, t, J=7.3 Hz),<br>0.99(3H, s),0.97(3H, s).<br>MS(ESI, m/z) 528(M + H)⁺. | 0.004 |

TABLE 20

| 1-52 | 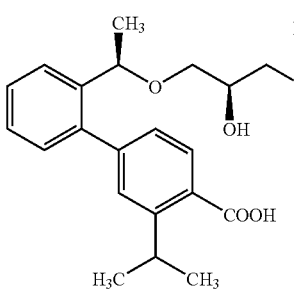 | ¹H-NMR(300 MHz, δ ppm, DMSO-d₆)<br>7.56(1H, d, J=7.9 Hz),<br>7.49(1H, dd, J=7.9, 1.4 Hz), 7.41-7.36(2H,m),<br>7.30(1H, ddd, J=7.4, 7.4, 1.4 Hz),<br>7.18(1H, dd, J=10.7, 1.8 Hz),<br>7.15-7.13(2H, m), 7.06(1H, dd, J=7.9, 1.6 Hz),<br>6.99(1H, dd, J=8.3, 1.6 Hz),<br>4.40(1H, q, J=6.3 Hz),<br>3.77(1H, sept, J=7.0 Hz), 3.63-3.57(1H, m),<br>3.11-3.03(2H, m), 2.71-2.43(4H, m),<br>1.24(3H, d, J=6.3 Hz),1.16(3H, d, J=7.0 Hz),<br>1.15(3H, d, J=7.0 Hz), 0.96(3H, s), 0.94(3H, s).<br>MS(ESI, m/z) 542(M + H)⁺. | 0.003 |
| 1-53 | 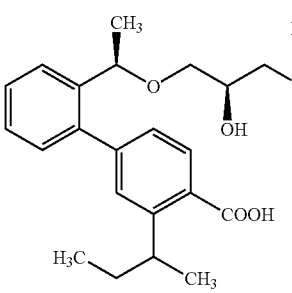 | ¹H-NMR(300 MHz, δ ppm, DMSO-d₆)<br>7.62(1H, d, J=7.7 Hz), 7.55-7.31(3H, m),<br>7.19-7.08(4H, m), 6.95-6.87(2H, m),<br>4.45(1H, q, J=6.2 Hz), 3.64-3.57(2H, m),<br>3.13-3.09(2H, m), 2.78-2.69(3H, m),<br>2.56-2.53(1H, m), 2.18(3H, s),<br>1.67-1.47(2H, m), 1.27(3H, d, J=6.2 Hz),<br>1.19(3H, d, J=1.5 Hz), 1.01(3H, s),<br>0.99(3H, s), 0.79-0.74(3H, s).<br>MS(ESI, m/z) 536(M + H)⁺. | 0.015 |

TABLE 21

| 1-54 | 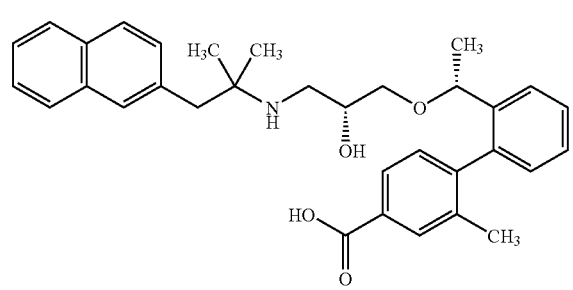 | ¹H-NMR (300 MHz, δ ppm, DMSO-d₆)<br>7.92–7.80(5H,m), 7.71(1H,s),<br>7.59–7.08(8H,m),<br>4.23and4.05(1H,q,J=6.2Hz), 3.75(1H,brs),<br>3.63–3.58(1H,m), 3.23–3.13(1H,m),<br>2.96–2.91(2H,m), 2.73–2.71(1H,m),<br>2.11and2.04(3H,s), 1.44(1H,m)<br>1.21(3H,d,J=6.2Hz), 1.11(6H,brs).<br>MS(ESI,m/z) 512(M+H)⁺. | 0.023 |

TABLE 21-continued

| | | | |
|---|---|---|---|
| 1-55 | 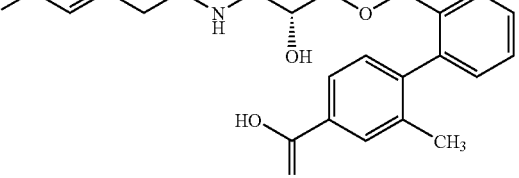 | ¹H-NMR (300 MHz, δ ppm, DMSO-d$_6$) 7.90–7.81(4H,m), 7.71(1H,s), 7.57–7.32(6H,m), 7.21–7.18(1H,s), 4.48(1H,q,J=6.3Hz), 3.72(1H,brs), 3.17–3.15(2H,m), 2.96–2.87(3H,m), 2.73–2.65(1H,m), 2.58(3H,s), 1.28(3H,d,J=6.3Hz), 1.12(3H,s), 1.11 (3H,s). MS (ESI,m/z) 512 (M+H)⁺. | 0.010 |
| 1-56 | 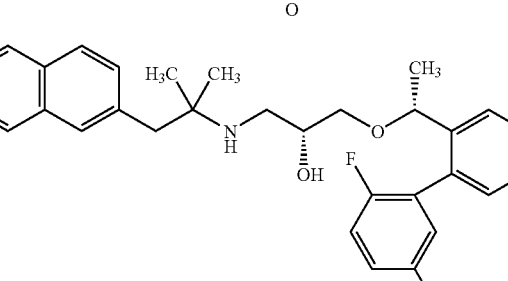 | ¹H-NMR (300 MHz, δ ppm, DMSO-d$_6$) 7.89–7.81(3H,m), 7.72(1H,s), 7.63–7.13(10H,m), 4.45(1H,q,J=6.5Hz), 3.81(1H,brs), 3.24–3.21(2H,m), 3.01(2H,s), 2.93–2.83(1H,m), 2.77–2.67(1H,m), 1.27(3H,d,J=6.5Hz), 1.14(6H,brs). MS(ESI,m/z) 516(M+H)⁺. | 0.019 |

TABLE 22

| | | | |
|---|---|---|---|
| 1-57 | 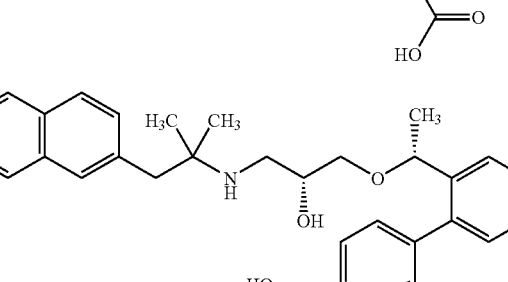 | ¹H-NMR (300 MHz, δ ppm,DMSO-d$_6$) 7.92(1H,s), 7.84(1H,t,J=6.5Hz), 7.59–7.34(5H,m), 7.27–7.08(3H,m), 4.21and4.03(1H,q,J=6.4Hz), 3.70(1H,brs), 3.62–3.58(2H,m), 3.21–3.14(2H,m), 2.80(2H,m), 2.10and2.05(3H,s), 1.22and1.16(3H,d,J=6.4Hz), 1.08(6H,brs). MS(ESI,m/z) 530(M+H)³⁰. | 0.027 |
| 1-58 | | ¹H-NMR (400 MHz, δ ppm, DMSO-d$_6$) 7.98–7.94(1H,m), 7.85–7.77(4H,m), 7.67(1H,s), 7.56–7.777(4H,m), 7.46–7.42(3H,m), 7.36–7.26(3H,m), 7.21–7.15(1H,m) , 4.25(1H,q,J=6.5Hz), 3.78(1H,brs), 3.13(2H,brs), 2.97(2H,brs), 2.93–2.85(1H,m) , 2.68–2.62(1H,m), 1.23(3H,brs), 1.10(EH,brs). MS(ESI,m/z) 516(M+H)⁺. | 0.021 |
| 1-59 | | ¹H-NMR (300 MHz, δ ppm, DMSO-d$_6$) 7.90–7.82(4H,m), 7.74(1H,s), 7.58–7.34(6H,m), 7.23–7.12(3H,m), 4.53(1H,q,J=6.3Hz), 3.86(1H,brs), 3.21–3.19(2H,m), 3.07–3.00(3H,m), 2.83–2.71(1H,m), 1.29(3H,d,J=6.3Hz), 1.19(6H,brs). MS(ESI,m/z) 516(M+H)⁺. | 0.016 |

TABLE 23

| | | | |
|---|---|---|---|
| 1-60 | [structure] | ¹H-NMR (300 MHz, δ ppm, DMSO-d₆) 7.85–7.82(1H,d,J=8.5Hz), 7.55(1H,d,J=7.7Hz), 7.44(1H,t,J=7.5Hz), 7.34(1H,t,J=7.5Hz), 7.28–7.13(7H,m), 4.48(1H,q,J=6.2Hz), 3.66(1H,brs), 3.19–3.12(3H,m), 2.77–2.71(3H,m), 2.56(3H,brs), 1.27(3H,d,J=6.2Hz), 1.01(3H,s), 1.00(3H,s), MS(ESI,m/z) 496(M+H)⁺. | 0.096 |
| 1-61 | [structure] | ¹H-NMR (300 MHz, δ ppm, DMSO-d₆) 7.83(1H,d,J=8.2Hz), 7.55–7.31(5H,m), 7.18–7.14(4H,m), 4.47(1H,q,J=6.4Hz), 3.61(1H,brs), 3.13–3.11(3H,m), 2.70–2.64(31-1,m), 2.55(3H,brs), 1.26(3H,d,J=6.4Hz), 0.98(3H,s), 0.97(3H,s), MS(ESI,m/z) 530(M+H)⁺. | 0.004 |
| 1-62 | [structure] | ¹H-NMR (300 MHz, δ ppm, DMSO-d₆) 7.89–7.82(4H,m), 7.74(2H,s), 7.59–7.35(7H,m), 7.22–7.19(1H,d,J=7.7Hz), 4.34(1H,brs), 3.84(1H,brs), 3.18(1H,brs), 3.05–2.95(2H,m), 2.80–2.68(1H,m), 2.53–2.49(2H,brs), 1.28–1.08(9H,brs). MS(ESI,m/z) 516(M+H)⁺. | 0.008 |

TABLE 24

| | | | |
|---|---|---|---|
| 1-63 | [structure] | ¹H-NMR (300 MHz, δ ppm, DMSO-d₆) 7.91–7.77(4H,m), 7.69(1H,s), 7.61–7.57(1H,m), 7.49–7.28(5H,m), 7.19–7.15(3H,m), 3.90–3.84(2H,m), 3.68(1H,brs), 3.34–3.21(2H,m), 2.89–2.75(3H,m), 2.55(3H,s), 1.07–0.97(7H,m), 0.42(1H,brs), 0.30–0.18(2H,m), −0.12(1H,brs). MS(ESI,m/z) 538(M+H)⁺. | 0.016 |
| 1-64 | [structure] | ¹H-NMR (300 MHz, δ ppm, DMSO-d₆) 7.88–7.73(5H,m), 7.63–7.60(1H,m), 7.50–7.33(5H,m), 7.22–7.04(3H,m), 3.94–3.80(2H,m), 3.42–3.24(3H,m), 3.06–3.00(2H,m), 2.88–2.75(1H,m), 1.25–1.00(7H,m), 0.44(1H,brs), 0.35–0.20(2H,m), −0.14(1H,brs). MS(ESI,m/z) 542(M+H)⁺. | 0.017 |

TABLE 24-continued

| | | | |
|---|---|---|---|
| 1-65 | 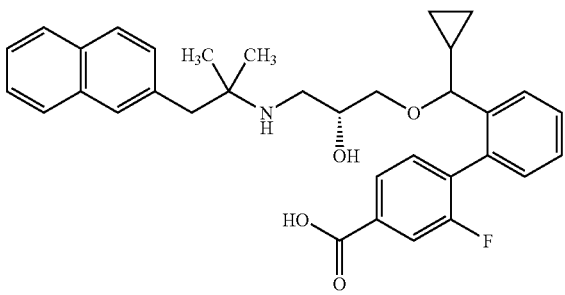 | $^1$H-NMR (300 MHz, δ ppm, DMSO-d$_6$) 7.85–7.56(7H,m), 7.47–7.23(6H,m), 7.17(1H,d,J=7.5Hz), 3.84(1H,brs), 3.74–3.72(1H,m), 3.43–3.18(3H,m), 3.07–2.90(2H,m), 2.78–2.68(1H,m), 1.16–1.13(6H,m), 0.95(1H,brs), 0.45(1H,brs), 0.22(2H,brs), 0.18 (1H,brs), MS(ESI,m/z) 542(M+H)$^+$. | 0.016 |

TABLE 25

| | | | |
|---|---|---|---|
| 1-66 | 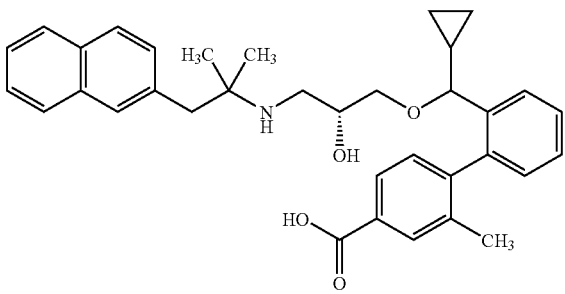 | $^1$H-NMR (300 MHz, δ ppm, DMSO-d$_6$) 7.90–7.57(7H,m), 7.50–7.33(5H,m), 7.24–7.07(2H,M), 3.87–3.85(1H,m), 3.70(1H,brs), 3.57–3.53(1H,m), 3.31–3.17(2H,m), 2.95–2.80(2H,m), 2.77–2.65(1H,r), 2.09(3H,s), 1.12–1.05(6H,brs), 0.95(1H,brs), 0.38(1H,brs), 0.30–0.20(2H,m), 0.34(1H,brs). MS (ESI,m/z) 538 (M+H)$^+$. | 0.017 |
| 1-67 | 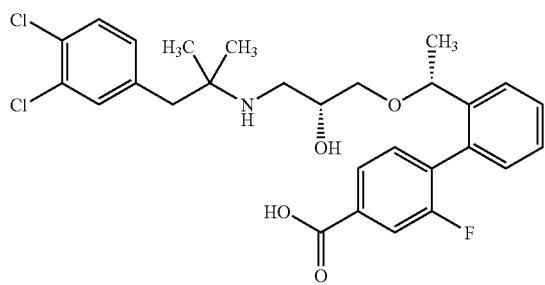 | $^1$H-NMR (300 MHz, δ ppm, DMSO-d$_6$) 7.82(1H,brs), 7.70(1H,d,J=6.8Hz), 7.58–7.47(4H,m), 7.39–7.27(2H,m), 7.19(2H,d,J=6.8Hz), 4.30(1H,brs), 3.70(1H,brs), 3.13(2H,brs), 2.88–2.75(3H,m), 2.63–2.53(1H,m), 1.22(3H,brs), 1.06(6H,brs). MS(ESI,m/z) 534(M+H)$^+$. | 0.019 |
| 1-68 | 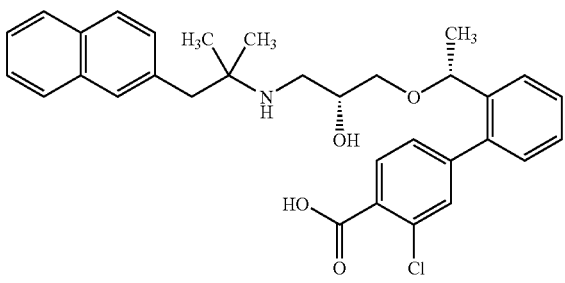 | $^1$H-NMR (300 MHz, δ ppm, DMSO-d$_6$) 7.89–7.82(3H,m), 7.73(1H,s), 7.62–7.33(7H,m), 7.25–7.18(3H,m), 4.56(1H,q,J=6.2Hz), 3.88(1H,brs), 3.24–3.17(2H,m), 3.08–3.03(3H,m), 2.82–2.72(1H,m), 1.26(3H,d,J=6.2Hz), 1.19(6H,brs). MS (ESI,m/z) 532 (M+H)$^+$. | 0.003 |

TABLE 26

| | | | |
|---|---|---|---|
| 1-69 | 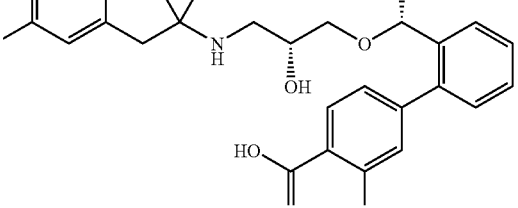 | ¹H-NMR (300 MHz, δ ppm, DMSO-d₆) 7.90–7.75(5H,m), 7.59–7.35(8H,m), 7.24(1H,d,J=7.7Hz), 4.55(1H,q,J=6.5Hz), 3.87(1H,brs), 3.24–3.23(2H,m), 3.05(3H,brs), 2.83–2.73(1H,m), 1.27(3H,d,J=6.5Hz), 1.17(6H,brs). MS(ESI,m/z) 543(M+H)⁺. | 0.002 |
| 1-70 | | ¹H-NMR (300 MHz, δ ppm, DMSO-d₆) 7.88–7.77 (4H,m), 7.69 (1H,s), 7.55–7.28(6H,m), 7.15(1H,d,J=7.7Hz), 6.61(1H,s), 6.40(1H,d,J=8.0Hz), 4.55(1H,q,J=6.6Hz), 3.70(1H,brs), 3.16–3.14(2H,m), 2.89(2H,brs), 2.84–2.83(1H,m), 2.63–2.57(1H,m), 1.26(3H,d,J=6.6Hz), 1.07(3H,s), 1.05(3H,s). MS(ESI,m/z) 513 (M+H)⁺. | 0.005 |
| 1-71 | | ¹H-NMR (400 MHz, δ ppm, DMSO-d₆) 8.42(1H,s), 8.05(1H,d,J=7.9Hz), 7.87–7.81(3H,m), 7.72(1H,s), 7.53–7.29(6H,m), 7.16(1H,d,J=7.4Hz), 6.88(1H,d,J=7.9Hz), 4.57C1H,q,J=6.3Hz), 3.84(1H,brs), 3.17–3.16(2H,m), 3.06(3H,brs), 2.81–2.79(1H,m), 2.02(3H,s), 1.29(3H,d,J=6.3Hz), 1.19(6H,brs). MS (ESI,m/z) 555 (M+H)⁺. | 0.005 |

TABLE 27

| | | | |
|---|---|---|---|
| 1-72 | 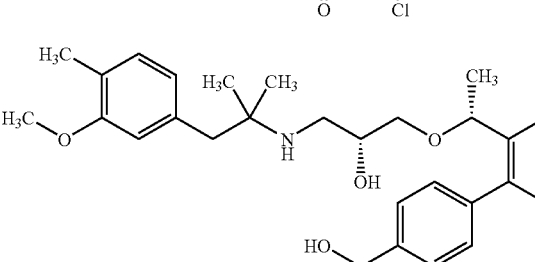 | ¹H-NMR (400 MHz, δ ppm, CDCl₃) 8.01(1H,d,J=6.7Hz), 7.60–7.54(2H,m), 7.45(1H,t,J=7.3Hz), 7.35(1H,t,J=7.5Hz), 7.24–7.17(3H,m), 6.99–6.92(2H,m), 4.55(1H,q,J=6.0Hz), 3.85(1H,brs), 3.60(1H,brs), 3.21–3.17(1H,m), 3.03–2.95C1H,m), 2.87(2H,s), 2.77–2.68(1H,m), 2.19(3H,s), 1.28(3H,d,J=6.0Hz), 1.13(6H,brs). MS(ESI,m/z) 514(M+H)⁺. | 0.015 |
| 1-73 | | ¹H-NMR (400 MHz, δ ppm, CDCl₃) 7.82(1H,d,J=8.5Hz), 7.51C1H,d,J=8.1Hz), 7.37(1H,t,J=7.7Hz), 7.30–7.25(1H,m), 7.16C1H,d,J=7.7Hz), 7.0E–7.04C3H,m), 4.56(1H,q,J=6.6Hz), 4.20(1H,brs), 3.79(3H,s), 3.38–2.78(6H,m), 2.59(3H,s), 2.16(3H,s), 1.37(3H,brs), 1.28–1.26(6H,brs). MS(ESI,m/z) 506(M+H)⁺. | 0.007 |

TABLE 27-continued

| 1-74 | 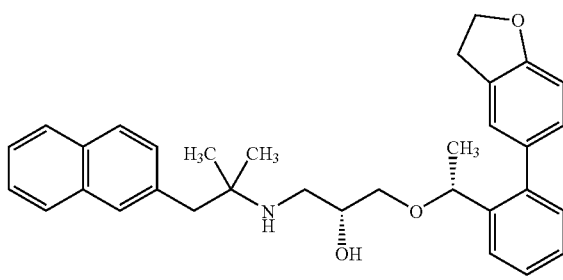 | ¹H-NMR (300 MHz, δ ppm, DMSO-d₆) 7.88–7.78(3H,m), 7.68–7.29(9H,m), 7.19–7.16(1H,d,J=7.7Hz), 4.62(2H,t,J=8.8Hz), 4.51(1H,q,J=6.2Hz), 3.71(1H,brs), 3.23(2H,t,J8.8Hz), 3.17–3.15(2H,m), 2.90(2H,s), 2.83–2.75(1H,m), 2.64–2.60(1H,m), 1.27(3H,d,J=6.2Hz), 1.07(3H,s), 1.05(3H,s). MS(ESI,m/z) 540(M+H)⁺. | 0.011 |

TABLE 28

| 1-75 | 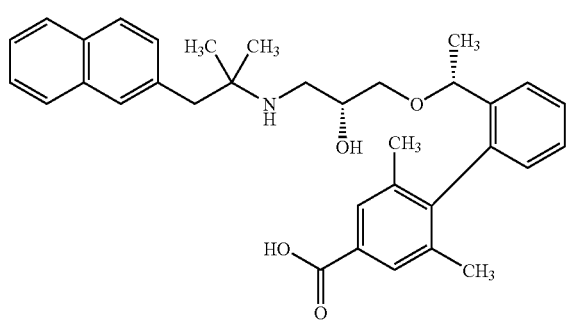 | ¹H-NMR (300 MHz, δ ppm, DMSO-d₆) 7.85–7.66(*6H, m), 7.57(1H, d, J=7.7Hz), 7.47–7.33(5H, m), 6.97(1H, d, J=7.4Hz), 3.97(1H, q, J=6.2Hz), 3.68(1H, brs), 3.21–3.15(2H, m), 2.86(2H, s), 2.81–2.77(1H, m), 2.64–2.62(1H, m), 2.01(3H, s), 1.91(3H, s), 1.09(3H, d, J=6.2Hz), 1.04(3H, s), 1.03(3H, s). MS(ESI, m/z) 526(M+H)⁺. | 0.012 |
| 1-76 | 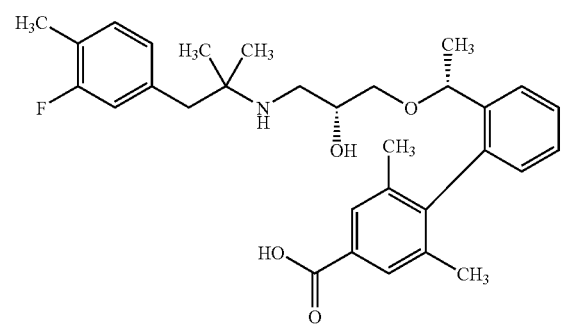 | ¹H-NMR (400 MHz, δ ppm, DMSO-d₆) 7.71(2H, d, J=7.3Hz), 7.56(1H, d, J=7.7Hz), 7.44–7.30(2H, m), 7.10(1H, t, J=8.0Hz), 6.98–6.86(3H, m), 3.94(1H, q, J=6.3Hz), 3.63(1H, brs), 3.17–3.16(2H, m), 2.75–2.71(1H, m), 2.65(2H, brs), 2.57–2.53(1H, m), 2.17(3H, s), 2.02(3H, s), 1.93(3H, s), 1.11(3H, d, J=6.3Hz), 0.99(3H, s), 0.98(3H, s). MS(ESI, m/z) 508(M+H)⁺. | 0.022 |
| 1-77 | 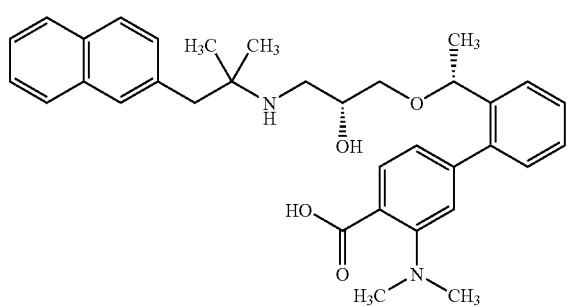 | ¹H-NMR (300 MHz, δ ppm, DMSO-d₆) 7.98(1H,d,J=8.Hz), 7.87–7.76(2H,m), 7.66(1H,s), 7.57–7.33(8H,m), 7.24–7.20(2H,m), 4.42(1H,q,J=6.2Hz), 4.06–4.02(1H,m), 3.68(2H,brs), 3.16–3.11(1H,m), 2.83–2.80(8H,m), 2.73–2.67(1H,m), 1.28(3H,d,J=6.2Hz), 1.01(3H,s), 0.99(3H,s). MS(ESI,m/z) 541(M+H)⁺. | 0.021 |

TABLE 29

| 1-78 | 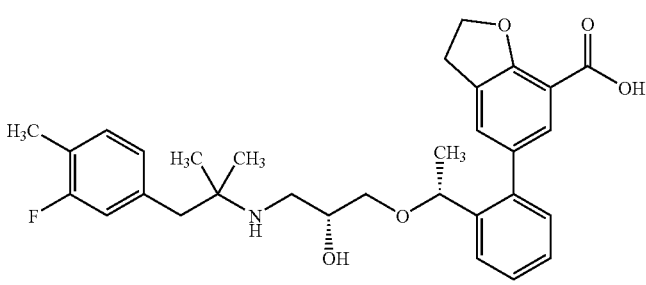 | ¹H-NMR (400 MHz, δ ppm, DMSO-d₆) 7.48–7.46(1H,d,J=7.7Hz),7.40–7.25(4H,m), 7.14–7.09(2H,m), 6.93–6.85(2H,m), 4.58(2H,q,J=8.8Hz), 4.46(1H,q,J=6.3Hz), 3.65(1H,brs), 3.20(2H,t,J=8.8Hz), 3.14–3.09(2H,m), 2.72–2.67(3H,m), 2.53–2.51(1H,m), 2.15(3H,s), 1.25(3H,d,J=6.3Hz), 0.98(3H,s), 0.97(3H,s). MS(ESI,m/z) 522(M+H)⁺. | 0.020 |
|---|---|---|---|
| 1-79 | 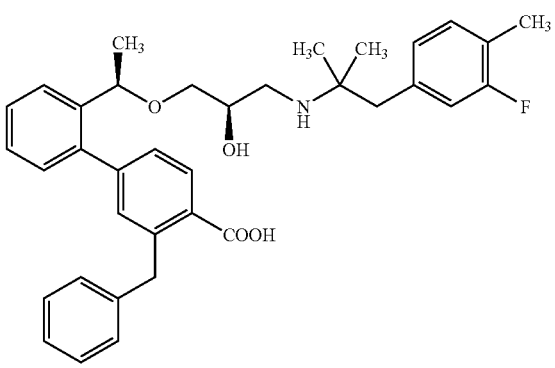 | ¹H-NMR (300 MHz, δ ppm, DMSO-d₆) 7.70(1H,d,J=7.9Hz), 7.46–7.23(3H,m), 7.22–7.04(8H,m), 6.92–6.87(2H,m), 6.83(1H,dd,J=7.7,1.2Hz), 4.44(1H,d,J=14.4Hz), 4.35(1H,q,J=6.5Hz), 4.33(1H,d,J=14.4Hz), 3.63–3.61(1H,m), 3.04–2.97(2H,m), 2.71–2.65(3H,m), 2.51–2.45(1H,m), 2.15(3H,s), 1.12(3H,d,J=6.5Hz), 0.97(3H,s), 0.96 (3H,s). MS(ESI,m/z) 570(M+H)⁺. | 0.004 |
| 1-80 | 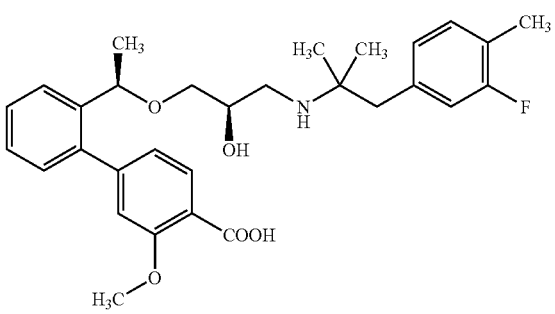 | ¹H-NMR (400 MHz, δ ppm, DMSO-d₆) 7.63 (1H,d,J=7.9Hz) , 7.53–7.41(2H,m), 7.33(1H,ddd,J=7.5,7.5,1.2Hz), 7.21–7.13(2H,m), 6.95–6.85(4H,m), 4.48(1H,q,J=6.3Hz), 3.79(3H,s), 3.71–3.70(1H,m), 3.13–3.11(2H,m), 2.88–2.86(1H,m) , 2.75(2H,s), 2.64–2.59(1H,m), 2.17(3H,s), 1.29 (3H,d,J=6.3Hz), 1.05(3H,s), 1.04(3H,s). MS(ESI,m/z) 494(M+H)⁺. | 0.027 |

TABL 30

| 1-81 | 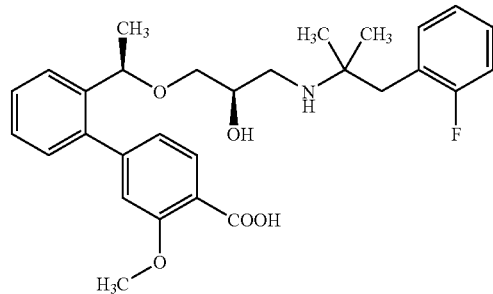 | ¹H-NMR (300 MHz, δ ppm, DMSO-d₆) 7.64(1H,d,J=7.9Hz), 7.52(1H,d,J=7.9Hz), 7.43–7.16(6H,m), 6.93(1H,s), 6.88–6.86(1H,m), 4.47(1H,q,J=6.4Hz), 3.79(3H,s), 3.66–3.64(1H,m), 3.11–3.10(2H,m), 2.80–2.74(2H,m), 2.58–2.53(1H,m), 1.28(3H,d,J=6.4Hz), 1.01(3H,s), 1.00(3H,s). MS(ESI,m/z) 530 (M+H)⁺. | 0.026 |
|---|---|---|---|

TABL 30-continued

| 1-82 | 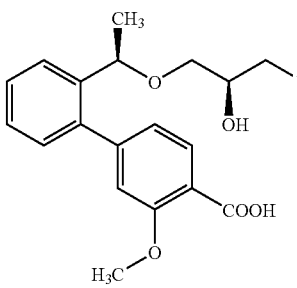 | ¹H-NMR (300 MHz, δ ppm, DMSO-d₆) 7.70(1H,d,J= 8.0Hz), 7.57–7.22(6H,m), 7.07–6.89(3H,m), 4.49(1H,q,J=6.2Hz), 3.83 (3H,s), 3.68–3.67(1H,m), 3.15–3.13(2H,m), 2.82–2.77(3H,m), 2.63–2.57(1H,m), 1.31(3H,d,J=6.2Hz), 1.05(3H,s), 1.04(3H,s). MS(ESI,m/z) 530(M+H)⁺. | 0.027 |
|---|---|---|---|
| 1-83 | 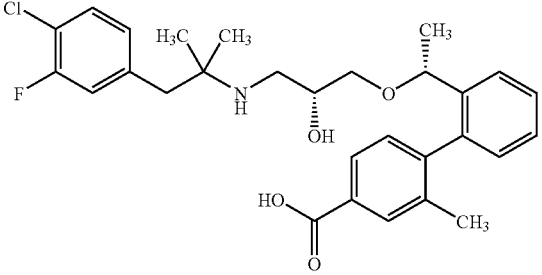 | ¹H-NMR (300MHz, δ ppm, DMSO–d₆) 7.89(1H,brs), 7.80 (1H,t,J=8.1Hz), 7.55 (1H,t,J=6.1Hz), 7.44(1H,t,J=7.5Hz), 7.37–7.24(3E,m), 7.20–7.06(3H,m), 4.20and4.02(1H,q,J=6.2Hz), 3.58(1H,brs), 3.20–3.03(3H,m), 2.66(3H,brs), 2.08and2.03(3H,s), 1.19and1.13(3H,d,J=6.2Hz), 0.96(6H,brs). MS (ESI,m/z) 514 (M+H)⁺. | 0.016 |

TABLE 31

| 1-84 | 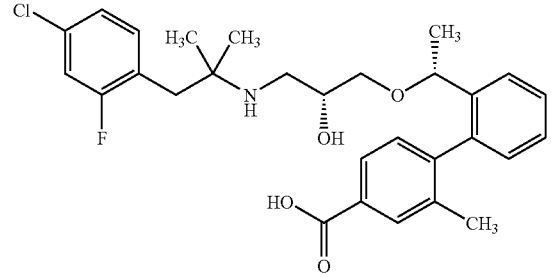 | ¹-NMR (300 MHz, δ ppm, DMSO-d₆) 7.90(1H,brs), 7.80(1H,t,J=8.5Hz), 7.55(1H,t,J=6.3Hz), 7.47–7.32(3H,m), 7.25–7.02(4H,m), 4.21and4.02(1H,q,J=6.6Hz), 3.59(1H,brs), 3.18–3.04(3H,m), 2.70–2.64(3H,m), 2.09and2.03(3H,s), 1.19and1.13(3H,d,J6.6Hz), 0.97(6H,brs). MS(ESI,m/z) 514(M+H)⁺. | 0.022 |
|---|---|---|---|
| 1-85 | 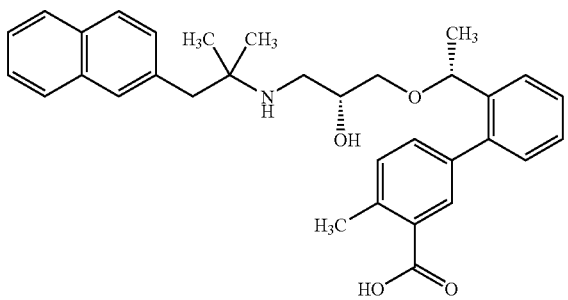 | ¹-NMR (300 MHz, δ ppm, DMSO-d₆) 7.88–7.80(3H,m), 7.69–7.68(2H,m), 7.53(1H,dd,J=7.8,1.3Hz), 7.50–7.26(7H,m), 7.18(1H,dd,J=7.5,1.3Hz), 4.48(1H,q,J=6.3Hz), 3.78(1H,m), 3.17(2H,d,J=5.6Hz), 2.98(2H,s), 2.91(1H,dd,J=12,3.5Hz), 2.69(1H,dd,J=12,8.2Hz), 2.56(3H,s), 1.28(3H,d,J=6.3Hz), 1.13(3H,s), 1.12(3H,s). MS(ESI,m/z) 512(M+H)⁺. | 0.004 |

TABLE 32

1-86

¹H-NMR (400 MHz, δ ppm, DMSO-d₆)  0.014
7.66(1H,d,J=1.9Hz),
7.53(1H,dd,J=7.7,1.3Hz),
7.42 (1H,ddd,J=7.6,7.6,1.4Hz),
7.35–7.25(3H,m), 7.18–7.14(2H,m),
6.95C1H,dd,J=11,1.2Hz),
6.90(1H,dd,J=7.7,1.4Hz),
4.46(1H,q,J=6.3Hz), 3.74(1H,m),
3.14(2H,d,J=5.EHz),
2.84(1H,dd,J=12,3.5Hz), 2.77(2H,s),
2.62(1H,dd,J=12,8.1Hz), 2.55(3H,s),
2.18(3H,s), 1.28(3H,d,J=6.3Hz),
1.06(3H,s), 1.05(3H,s).
MS(ESI,m/z) 494(M+H)⁺.

1-87

¹H-NMR (400MHz, δ ppm, DMSO-d₆)  0.014
7.85(1H,d,J=8.4Hz), 7.54(1H,d,J=7.9Hz),
7.47–7.40(2H,m),
7.33(1H,ddd,7.2,7.2,1.2Hz),
7.25(2H,d,1.9Hz), 7.20–7.13(3H,m),
4.47(1H,q,J=6.5Hz), 3.75–3.60(1H,m),
3.13(2H,d,J=5.6Hz), 2.85–2.65(3H,m),
2.60–2.55(4H,m), 1.28(3H,d,J=6.2Hz),
1.03(3H,s), 1.02(3H,s),
MS(ESI,m/z) 530(M+H)⁺.

TABLE 33

1-88

¹H-NMR (400 MHz, δppm, DMSO-d₆)  0.014
7.57(1H,d,J=8.6Hz),
7.49(1H,d,J=8.1Hz),
7.38 (2H,q,J=7.9Hz),
7.29(1H,dd,J=7.4,7.4Hz),
7.20(1H,d,J=10.7Hz),
7.13(1H,d,J=7.6Hz),
7.03–6.92(3H,m),
4.48(1H,q,J=6.3Hz),
3.57–3.49(1H,m),
3.08(2H,d,J=5.6Hz),
2.64–2.54(3H,m),
2.52–2.37 (4H,m),
1.25(3H,d,J=6.3Hz),
0.93(3H,s), 0.91(3H,s)
MS(ESI,m/z) 514(M+2H-Na)⁺.

1-89

¹H-NMR (400 MHz, δ ppm, DMSO-d₆)  0.271
7.74(1H,d,J=7.9Hz),
7.51(1H,dd,J=7.9,1.2Hz),
7.40(1H,ddd,J=7.9,7.9,1.4Hz),
7.31(1H,ddd,7.6,7.6,1.2Hz),
7.17–7.04(6H,m),
4.45(1H,q,J=6.5Hz),
3.58–3.52(1H,m),
3.09(2H,d,J=5.6Hz),
2.64–2.60(3H,m),
2.52(3H,s),
2.46–2.40(1H,m),
1.26(3H,d,J=6.5Hz),
0.96(3H,s), 0.94(3H,s)
MS(ESI,m/z) 498 (M+H)⁺.

TABLE 34
| 1-90 | 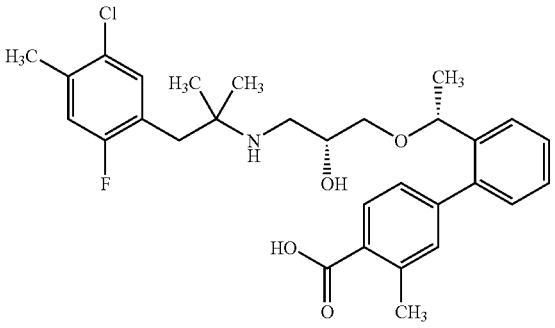 | ¹H-NMR (400MHz, δ ppm, DMSO-d₆) 7.84(1H,d,J=8.6Hz), 7.54(1H,d,J=7.0Hz), 7.43(1H,dd,J=7.7,1.4Hz), 7.35–7.29(2H,m), 7.19–7.16(4H,m), 4.47(1H,q,J=6.5Hz), 3.65(1H,m), 3.13(2H,d,J=5.8Hz), 2.76–2.67(3H,m), 2.57–2.56(4H,m), 2.28(3H,s), 1.27(3H,d,J=6.5Hz), 1.02(3H,s), 1.02(3H,s) MS(ESI,m/z) 528 (M+H)⁺. | 0.271 |
|---|---|---|---|
| 1-91 | 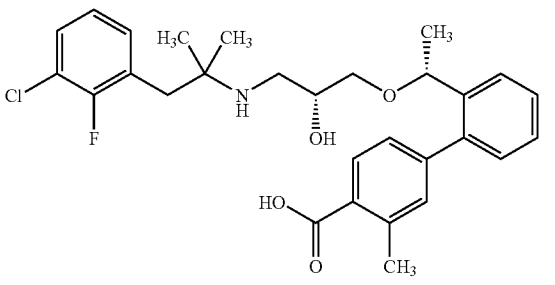 | ¹-NMR (400MHz, δppm, DMSO-d₆) 7.87(1H,d,J=8.4Hz), 7.57–7.54(1H,m), 7.47–7.42(1H,m), 7.38–7.32(1H,m), 7.27–7.09(5H,m), 4.46(1H,q,J=6.5Hz), 3.68–3.64(1H,m), 3.13(2H,d,J=5.5Hz), 2.80–2.75(3H,m), 2.59-2.57(4H,m), 1.28 (3H,d,J=6.2Hz), 1.04 (3H,s), 1.03 (3H,s) MS(ESI,m/z) 514 (M+H)⁺. | 0.028 |
TABLE 35
| 1-92 | 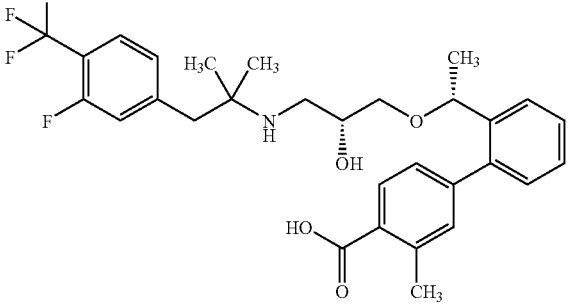 | ¹H-NMR (400 MHz, δ ppm, DMSO-d₆) 7.89–7.85(1H,m), 7.67–7.17(9H,m), 4.48(1H,q,J=6.2Hz), 3.64(1H,m), 3.13(2H,d,J=4.8Hz), 2.83–2.68(3H,m), 2.59–2.57(4H,m), 1.28(3H,d,J=6.2Hz), 1.04–0.99(6H,m) MS(ESI,m/z) 548 (M+H)⁺. | 0.022 |
|---|---|---|---|
| 1-93 | 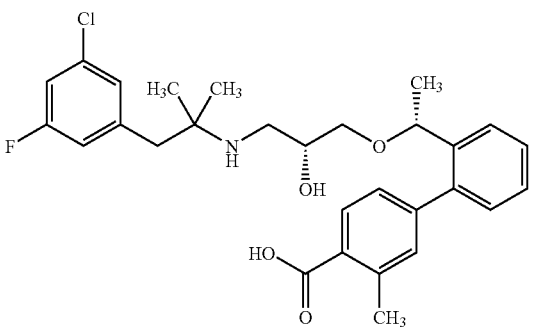 | ¹H-NMR (400 MHz, δ ppm,DMSO-d₆) 7.89–7.85(1H,m), 7.56–7.03(9H,m), 4.48(1H,q,J=6.2Hz), 3.64(1H,m), 3.13(2H,d,J=4.8Hz), 2.75–2.72(3H,m), 2.57(3H,s), 1.28(3H,d,J=6.6Hz), 1.01(3H,s), 1.00(3H,s) MS (ESI ,m/z) 514 (M+H)⁺. | 0.027 |

TABLE 36
| | | | |
|---|---|---|---|
| 1-94 | 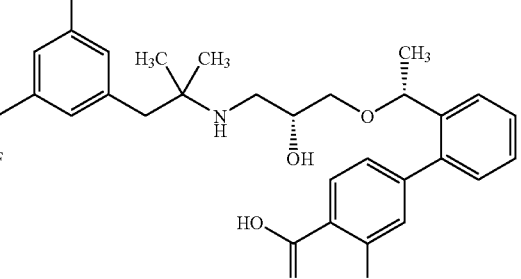 | ¹H-NMR (400MHz, δ ppm, DMSO-d₆) 7.92–7.85(4H,m), 7.55–7.31(3H,m), 7.20–7.16(3H,m), 4.46(1H,q,J=6.6Hz), 3.61(1H,m), 3.12(2H,d,J=5.1Hz), 2.92-2.68(3H,m), 2.56(3H,s), 1.26(3H,d,J=6.2Hz), 1.02-0.99(6H,m) MS(ESI,m/z) 598 (M+H)⁺. | 0.028 |
| 1-95 | 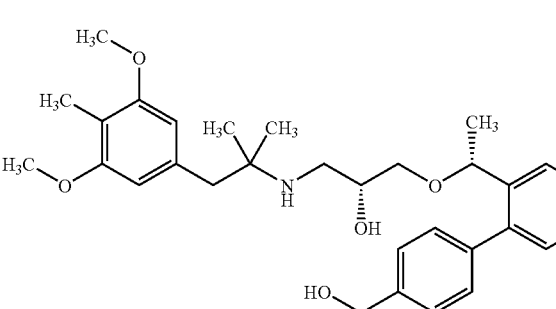 | ¹H-NMR (400 MHz, δ ppm, DMSO-d₆) 7.87–7.82(1H,m), 7.54–7.33 (3H,m), 7.20–7.15(3H,m), 6.43(2H,s), 4.48(1H,q,J=6.6Hz), 3.73 (6H,s), 3.71–3.70(1H,m), 3.14 (2H,d,J=4.4Hz), 2.91–2.72(3H,m), 2.57(3H,s), 1.95 (3H,s), 1.27 (3H,d,J=6.2Hz), 1.12(3H,s), 1.10(3H,s) MS(ESI,m/z) 536 (M+H)⁺. | |
TABLE 37
| | | | |
|---|---|---|---|
| 1-96 | 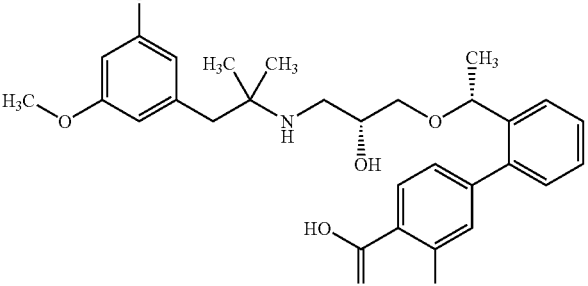 | ¹H-NMR (400 MHz, δ ppm, DMSO-d₆) 7.85–7.82(1H,m), 7.55–7.32(3H,m), 7.19–7.14(3H,m), 6.38–6.33(3H,m), 4.48(1H,m), 3.70(6H,s), 3.15–3.12(2H,m), 2.56–2.654(3H,m), 1.27(3H,t,J=6.6Hz) 1.10–1.03 (6H,m) MS(ESI,m/z) 522 (M+H)⁺. | |
| 1-97 | 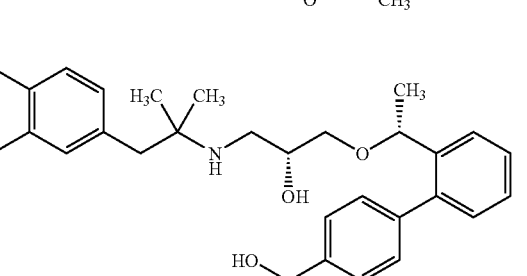 | ¹-NMR (400MHz, δppm, DMSO-d₆) 7.89–7.84(1H,m), 7.65–7.32(6H,m), 7.20–7.17(3H,m), 4.46(1H,m), 3.64(1H,m), 3.13(2H,d,J=5.1Hz), 2.89–2.72(3H,m), 2.58–2.54(4H,m), 1.27(3H,d,J=6.6Hz), 1.04(3H,s), 1.02(3H,s) MS(ESI,m/z) 564 (M+H)⁺. | 0.106 |

TABLE 38
| 1-98 | 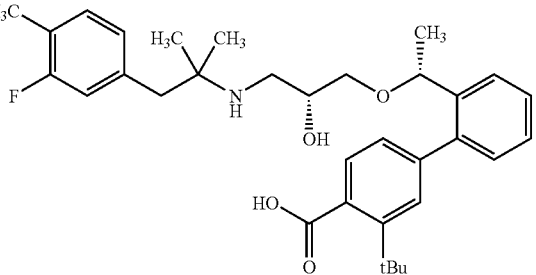 | $^1$H-NMR (400MHz, δ ppm, DMSO-d$_6$) 7.54(1H,dd,J=7.7,1.1Hz), 7.47(1H,d,J=8.1Hz), 7.44–7.31(2H,m), 7.22–7.13(4H,m), 6.99–6.91(2H,m), 4.49(1H,q,J=6.3Hz), 3.82–3.80(1H,m), 3.21–3.19(2H,m), 2.95–2.85(3H,m), 2.74–2.67(1H,m), 2.20(3H,s), 1.43(9H,s), 1.29(3H,d,J=6.3Hz), 1.12(3H,s) MS(ESI,m/z) 536 (M+H)$^+$. | 0.013 |
|---|---|---|---|
| 1-99 | 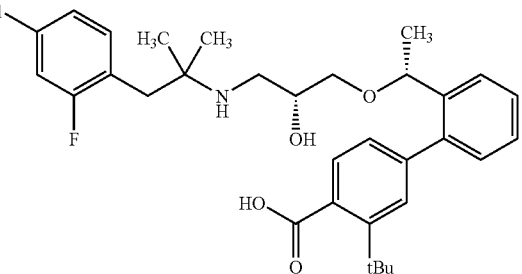 | $^1$H-NMR (400MHz, δ ppm, DMSO-d$_6$) 7.55–7.29(6H,m), 7.22–7.10(4H,m), 4.48(1H,q,J=6.4Hz), 3.77–3.75(1H,m), 3.19–2.65(GH,m), 1.43(9H,s), 1.29 (3H,d,J=6.4Hz), 1.08(6H,s) MS(ESI,m/z) 556(M+H)$^+$. | 0.023 |
TABLE 39
| 1-100 | 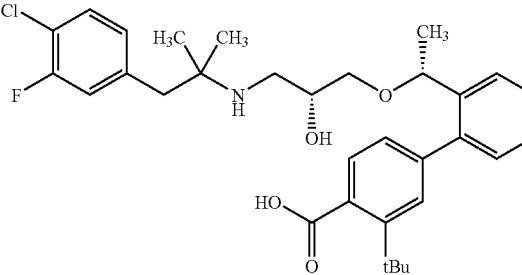 | $^1$H-NMR (400 MHz, δ ppm,DMSO-d$_6$) 7.55–7.44(9H,m), 7.08–7.06(1H,m), 4.48(1H,q,J=6.4Hz), 3.76–3.71(1H,m), 3.19–3.17(2H,m), 2.87–2.64(4H,m), 1.43(9H,s), 1.30(3H,d,J=6.4Hz), 1.11(6H,s) MS(ESI,m/z) 556 (M+H)$^+$. | 0.017 |
|---|---|---|---|
| 1-101 | 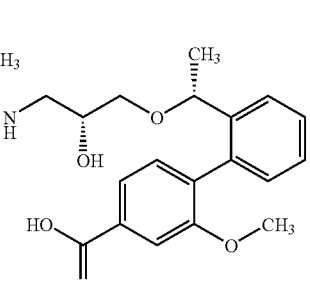 | $^1$H-NMR (400 MHz, δ ppm, DMSO-d$_6$) 7.65–7.60(2H,m), 7.53–47.29(3H,m), 7.24–6.91(5H,m), 4.19(1H,q,J=6.6Hz), 3.82–2.57(10H,m), 2.19(3H,s), 1.29(3H,d,J=6.6Hz), 1.13(3H,s), 1.07(3H,s) MS(ESI,m/z) 510(M+H)$^+$. | 0.016 |

TABLE 40

| | | | |
|---|---|---|---|
| 1-102 | 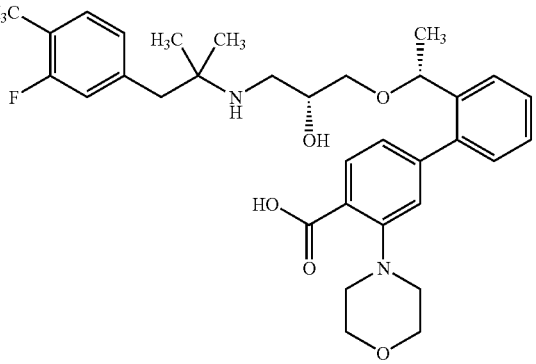 | ¹H-NMR (400MHz, δ ppm, DMSO-d₆) 7.90(1H,d,J=7.8Hz), 7.55(1H,dd,J=7.9, 1.1Hz), 7.48–7.31(3H,m), 7.23–7.12(3H,m), 6.95–6.87(2H,m), 4.43(1H,q,J=6.2Hz), 3.77–3.63(5H,m), 3.12–3.07(6H,m), 2.75–2.47(4H,m), 2.18(3H,s), 1.30(3H,d,J=6.2Hz), 1.01(3H,s), 1.00(3H,s) MS(ESI,m/z) 565 (M+H)⁺. | 0.014 |
| 1-103 | 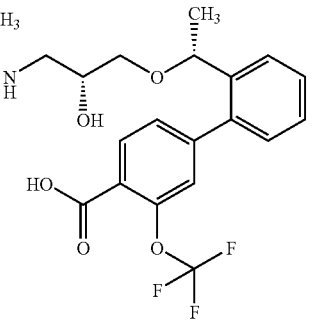 | ¹H-NMR (400 MHz, δ ppm, DMSO-d₆) 7.84(1H,d,J=7.9Hz), 7.55–7.32(4H,m), 7.21–7.15(3H,m), 6.96–6.89(2H,m), 4.47(1H,q,J=5.9Hz), 3.84–3.83(1H,m), 3.31–2.72(6H,m), 2.17(3H,s), 1.26(3H,d,J=5.9Hz), 1.12(6H,s) MS (ESI ,m/z) 564 (M+H)⁺. | 0.003 |

TABLE 41

| | | | |
|---|---|---|---|
| 1-104 | 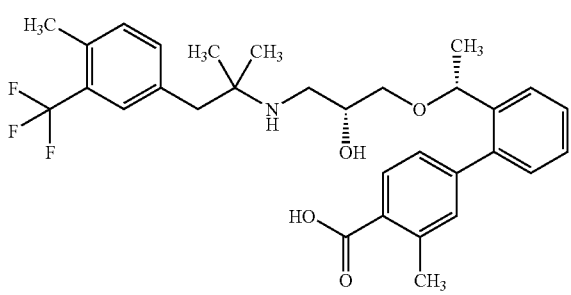 | ¹H-NMR (400MHz, δppm, DMSO-d₆) 7.84(1H, d, J=8.4Hz), 7.54(1H, d, J=6.9Hz), 7.48–7.40(2H, m), 7.37–7.28(3H, m), 7.20–7.12(3H, m), 4.46(1H, q, J=6.5Hz), 3.75–3.60(1H, m), 3.13(2H, d, J=5.6Hz), 2.85–2.75(3H, m), 2.65–2.55(4H, m) , 2.34(3H, s), 1.27(3H, d, J=6.5Hz), 1.03(3H, s), 1.02(3H, s) MS(ESI, m/z) 544(M+H)⁺. | 0.028 |
| 1-105 ½H₂SO₄ ½H₂O | 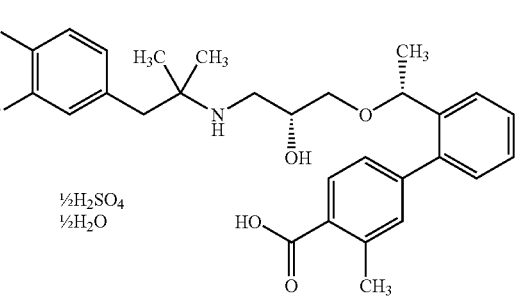 | ¹H–NMR(400MHz, δppm, DMSO-d₆) 7.87(1H, d, J=7.9Hz), 7.54(1H, d, J=7.9Hz), 7.50–7.40(2H, m), 7.35(1H, dd, 7.5, 7.5Hz), 7.25(1H, d, 10.5Hz), 7.21–7.14(3H, m), 7.05(1H, d, J=8.1Hz), 4.46(1H, q, J=6.3Hz), 3.80–3.65(1H, m), 3.13(2H, d, J=5.4Hz), 2.95–2.75(3H, m), 2.70–2.55(4H, m) , 1.29(3H, d, J=6.3Hz), 1.08(3H, s), 1.07(3H, s) MS(ESI, m/z) 514(M+H–½H₂SO₄–½H₂O)⁺. | 0.009 |

TABLE 42

| | | | |
|---|---|---|---|
| 1-106 | [structure] | ¹H-NNR(400MHz, δppm, DMSO-d₆)<br>7.87(1H, d, J=7.6Hz),<br>7.54(1H, d, J=7.7Hz),<br>7.49–7.37(3H, m),<br>7.34(1H, dd, 7.4, 7.4Hz),<br>7.25(1H, d, 10.5Hz),<br>7.22–7.13(2H, m),<br>7.05(1H, d, J=8.2Hz),<br>4.73(2H, s),<br>4.49(1H, q, J=6.3Hz),<br>3.75–3.60(1H, m),<br>3.14(2H, d, J=5.6Hz),<br>2.90–2.75(3H, m),<br>2.66–2.56(1H, m),<br>1.28(3H, d, J=6.3Hz),<br>1.07(3H, s), 1.05(3H, s)<br>MS(ESI, m/z) 530(M+H)⁺. | 0.020 |
| 1-107 | [structure] | ¹H-NMR(400MHz, δppm, DMSO-d₆)<br>8.26(1H, d, J=7.9Hz),<br>8.12(1H, d, J=1.8Hz), 7.60–<br>7.42(4H, m),<br>7.38(1H, dd, J=7.5, 7.5Hz),<br>7.29(1H, d, 10.7Hz),<br>7.23(1H, d, 7.6Hz),<br>7.07(1H, d, J=8.3Hz),<br>4.45(1H, q, J=6.3Hz), 3.83–<br>3.73(1H, m),<br>3.20–2.71(6H, m),<br>1.33(3H, d, J=6.3Hz),<br>1.14(6H, s)<br>MS(ESI, m/z) 544(M+H)⁺ | 0.200 |

TABLE 43

| | | | |
|---|---|---|---|
| 1-108 | [structure] | ¹H-NMR(400MHz, δppm, DMSO-d₆)<br>7.85(1H, d, J=8.6Hz),<br>7.55(1H, dd, J=1.1, 7.8Hz),<br>7.45(1H, ddd, J=7.4, 7.4, 0.9Hz),<br>7.35(1H, ddd, J=7.4, 7.41.4Hz),<br>7.19–7.16(4H, m), 6.98–6.90(2H, m),<br>4.48(1H, q, J=6.5Hz), 3.76(1H, m),<br>3.14(2H, d, J=5.8Hz), 2.91-2.88(1H, m),<br>2.79(2H, m), 2.66-2.61(1H, m),<br>2.56(3H, s), 2.19(s, 3H),<br>1.28(3H, d, J=6.3Hz), 1.08(3H, s),<br>1.07(3H, s)<br>MS(ESI, m/z) 494(M+H–½H₂SO₄)⁺. | 0.014 |
| 1-109<br>½H₂SO₄ | [structure] | ¹H-NNR(400MHz, δppm, DMSO-d₆)<br>7.88(1H, d, J=8.1Hz),<br>7.56(1H, dd, J=7.8, 1.2Hz),<br>7.46(1H, ddd.J=7.4, 7.4, 1.2Hz),<br>7.41-7.29(4H, m), 7.24-7.18(3H, m),<br>4.47(1H, q, J=6.3Hz), 3.74(1H, m),<br>3.13(2H, d, J=5.3Hz), 2.91-2.84(3H, m),<br>2.68-2.61(1H, m) , 2.57(3H, s),<br>1.28(3H, d, J=6.5Hz), 1.08(6H, s)<br>MS(ESI, m/z) 514(M+H–½H₂SO₄)⁺. | 0.015 |

TABLE 44

| 1-110 | 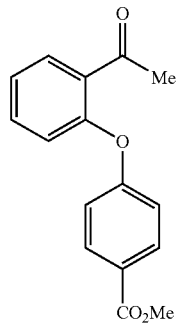 | $^1$H-NNR(400MHz, δppm, DMSO-$d_6$) 12.89(1H, s), 8.97(1H, s), 8.60(1H, s), 7.91(1H, d, J=7.6Hz), 7.58(1H, d, J=7.9Hz), 7.49-7.44(3H, m), 7.39-7.19(5H, m), 4.48(1H, q, J=6.2Hz), 3.92(1H, m), 3.20-2.97(5H, m), 2.79(1H, m), 2.59(3H.s), 2.50(3H, s), 1.32(3H, d, J=6.5Hz), 1.18(6H, m) MS(ESI, m/z) 514(M+H−HCl)$^+$. | 0.026 |
|---|---|---|---|

Example 2-1

4-[2-[(1R)-[(2R)-3-[[1-(3-fluoro-4-methylphenyl)-2-methylpropan-2-yl]amino]-2-hydroxypropoxy]ethyl]phenoxy]benzoic acid

Step 1

Methyl 4-(2-acetylphenoxy)benzoate

2'-Fluoroacetophenone (10.6 g), methyl 4-hydroxybenzoate (11.7 g) and potassium carbonate (11.2 g) were suspended in dimethylacetamide (70 ml), and the mixture was stirred at 140° C. for one day. The reaction mixture was cooled to room temperature and extracted with ethyl acetate. The organic layer was washed with brine, dried over sodium sulfate, and concentrated under reduced pressure. The obtained residue was purified by silica gel column chromatography (n-hexane:ethyl acetate=7:1) to give the title compound (8.62 g).

$^1$H-NMR (300 MHz, δppm, CDCl$_3$) 8.03(2H, d, J=6.6 Hz), 7.88(1H, m), 7.50(1H, m), 7.27(1H, m), 7.01-6.98(3H, m), 3.90(3H, s), 2.57(3H, s).

Step 2

Methyl 4-[2-((1R)-hydroxyethyl)phenoxy]benzoate

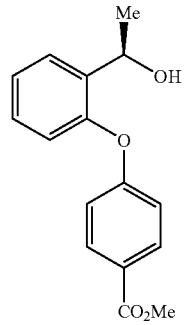

Methyl 4-(2-acetylphenoxy)benzoate (3.0 g) obtained in Step 1, dichloro[(S)-2,2'-bis(diphenylphosphino)-1,1'-binaphthyl][(S)-1,1'-bis(p-methoxyphenyl)-2-isopropylethane-1,2-diamine]ruthenium(II) (68 mg) and potassium-tert-butoxide (301 mg) were suspended in isopropanol (30 ml), and the suspension was hydrogenated (3.0 kgf/cm$^2$) at room temperature for 4.5 hrs at medium pressure. Water (150 ml) was added to the reaction mixture, and the mixture was extracted with ethyl acetate (150 ml) and washed with brine. The organic layer was dried over sodium sulfate, and concentrated under reduced pressure. The obtained residue was dissolved in tetrahydrofuran (60 ml) and methanol (60 ml) and 4N-lithium hydroxide solution (15 ml) was added. The mixture was stirred overnight at room temperature. The reaction mixture was concentrated under reduced pressure and 1N-hydrochloric acid (120 ml) was added. The mixture was extracted with ethyl acetate (150 ml). The organic layer was washed successively with water (50 ml) and saturated brine (50 ml), dried over sodium sulfate, and concentrated under reduced pressure. The obtained residue was dissolved in methanol (100 ml) and 4-dimethylaminopyridine (142 mg) and 1-ethyl-3-(3-dimethylaminopropyl)carbodiimide hydrochloride (2.49 g) were added. The mixture was stirred for 26 hrs. The reaction mixture was concentrated under reduced pressure, and the residue was purified by silica gel column chromatography (hexane:ethyl acetate=5:1-4:1) to give the title compound (2.63 g).

$^1$H-NMR (300 MHz, δppm, CDCl$_3$) 8.00(2H, d, J=7.7 Hz), 7.59(1H, m), 7.30-7.21(2H, m), 6.97-6.91(3H, m), 5.13(1H, d, J=6.5 Hz), 3.90(3H, s), 1.48(3H, d, J=6.5 Hz).

Step 3

Methyl 4-[2-[(1R)-((R)-oxiranylmethoxy)ethyl]phenoxy]benzoate

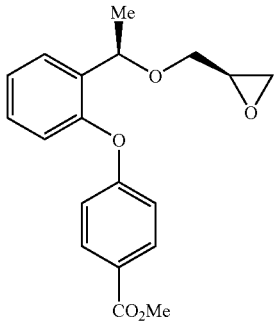

Methyl 4-[2-((1R)-hydroxyethyl)phenoxy]benzoate (3.62 g) obtained in Step 2 was dissolved in tetrahydrofuran (15 ml). The mixture was ice-cooled and sodium hydride (471 mg, 60% in oil) was added. The mixture was stirred for 3 min. Then, (R)-glycidyl 3-nitrobenzenesulfonate (3.62 g) and dimethyl sulfoxide (3 ml) were added and the mixture was stirred overnight at room temperature. 10% Aqueous citric acid solution (80 ml) was added to the reaction mixture and the mixture was extracted with ethyl acetate (150 ml). The organic layer was washed successively with water (50 ml) and saturated brine (50 ml), dried over anhydrous sodium sulfate, and concentrated under reduced pressure. The obtained residue was purified by silica gel column chromatography (hexane:ethyl acetate=4:1-3:1) to give the title compound (315 mg).

$^1$H-NMR (300 MHz, δppm, CDCl$_3$) 7.99(2H, d, J=6.6 Hz), 7.57(1H, m) 7.31-7.23(2H, m), 6.96-6.90(3H, m), 4.80(1H, d, J=6.6 Hz), 3.89(3H, s), 3.55(1H, m), 3.26(1H, m), 3.25(1H, m), 2.74(1H, m), 2.51(1H, m), 1.41(3H, d, J=6.6 Hz).

Step 4

Methyl (3-fluoro-4-methylphenyl)acetate

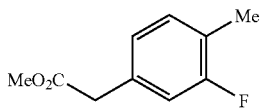

(3-Fluoro-4-methylphenyl)acetic acid (105.3 g) was dissolved in methanol (740 ml). Concentrated sulfuric acid (9.9 ml) was added and the mixture was stirred at 85° C. for 1 hr. The reaction mixture was allowed to return to room temperature, and concentrated under reduced pressure. Water was added to the obtained residue and the mixture was extracted with ethyl acetate (1 L). The organic layer was washed successively with water, saturated aqueous sodium hydrogencarbonate solution, water and brine, dried over anhydrous sodium sulfate, and concentrated under reduced pressure to give the title compound (114.2 g).

$^1$H-NMR (300 MHz, δppm, CDCl$_3$) 7.14-7.10(1H, m), 6.96-6.93(2H, m), 3.70(3H, s), 3.58(2H, s), 2.25-2.24(3H, s).

Step 5

1-(3-fluoro-4-methylphenyl)-2-methylpropan-2-ol

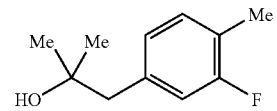

Methyl (3-fluoro-4-methylphenyl)acetate (114.2 g) obtained in Step 4 was dissolved in tetrahydrofuran (800 ml) and 1M-methylmagnesium bromide (1.56 L) was added dropwise under argon at 0° C. The mixture was stirred at room temperature for 1 hr. The reaction mixture was ice-cooled, saturated aqueous ammonium chloride solution (155 ml) was added dropwise and then magnesium sulfate (280 g) was added. The reaction mixture was filtered and the filtrate was dried over magnesium sulfate, and concentrated under reduced pressure to give the title compound (130.1 g).

$^1$H-NMR (300 MHz, δppm, CDCl$_3$) 7.11-7.08(1H, m), 6.88-6.86(2H, m), 2.71(2H, s), 2.25(3H, s), 1.22(6H, s).

Step 6

2-chloro-N-[1-(3-fluoro-4-methylphenyl)-2-methylpropan-2-yl]acetamide

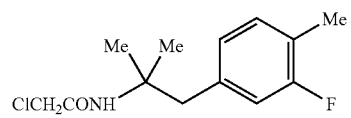

1-(3-Fluoro-4-methylphenyl)-2-methylpropan-2-ol (130.1 g) obtained in Step 5 was dissolved in chloroacetonitrile (139 ml) and acetic acid (115 ml), and concentrated sulfuric acid (33.4 ml) was added dropwise under ice-cooling. The mixture was stirred at room temperature for 2 hrs and 4N-aqueous sodium hydroxide solution (160 ml) was added dropwise under ice-cooling. The mixture was extracted twice with toluene and twice with ethyl acetate. The organic layer was washed twice with 10% brine and concentrated under reduced pressure to give the title compound (131.6 g).

$^1$H-NMR (300 MHz, δppm, CDCl$_3$) 7.10-7.06(1H, m), 6.80-6.76(2H, m), 6.19(1H, brs), 3.95(2H, s), 3.00(2H, s), 2.24(3H, s), 1.37(6H, s).

Step 7

[1-(3-fluoro-4-methylphenyl)-2-methylpropan-2-yl]amine

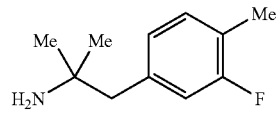

2-Chloro-N-[1-(3-fluoro-4-methylphenyl)-2-methylpropan-2-yl]acetamide (131.6 g) obtained in Step 6 was dissolved in acetic acid (200 ml) and ethanol (1 L), and thiourea (46.6 g) was added. The mixture was stirred overnight at 100° C. The reaction mixture was cooled to room temperature, and the precipitated crystals were filtered. The filtrate was concentrated under reduced pressure, and 4N-sodium hydroxide solution (300 ml) was added to the obtained residue. The mixture was extracted 3 times with toluene. The organic layer was washed with brine, and concentrated under reduced pressure. The obtained residue was dissolved in diethyl ether (1 L) and 4N-hydrochloric acid/ethyl acetate solution (255 ml) was added dropwise under ice-cooling. The mixture was stirred for 1 hr and the precipitated crystals were collected by filtration. The obtained crystals were added to a mixture of toluene and 4N-aqueous sodium hydroxide solution. The toluene layer was separated, washed twice with water, and concentrated under reduced pressure to give the title compound (57.9 g).

$^1$H-NMR (300 MHz, δppm, CDCl$_3$) 7.11-7.07(1H, m), 6.85-6.82(2H, m), 2.61(2H, s), 2.25(3H, s), 1.11(6H, s).

MS (APCI, m/z) 182(M+H)$^+$.

Step 8

Methyl 4-[2-[(1R)-[(2R)-3-[[1-(3-fluoro-4-methylphenyl)-2-methylpropan-2-yl]amino]-2-hydroxypropoxy]ethyl]phenoxy]benzoate

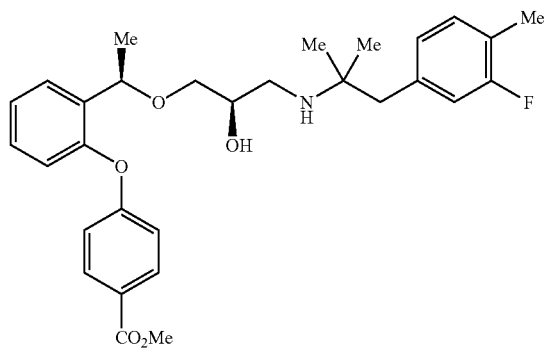

Methyl 4-[2-[(1R)-((R)-oxiranylmethoxy)ethyl]phenoxy]benzoate (109 mg) obtained in Step 3 was dissolved in toluene (3 ml), and [1-(3-fluoro-4-methylphenyl)-2-methylpropan-2-yl]amine (87 mg) obtained in Step 7 and lithium perchlorate (51 mg) were added successively. The mixture was stirred at room temperature for 15 hrs. The reaction mixture was concentrated under reduced pressure and the obtained residue was purified by silica gel column chromatography (hexane:ethyl acetate=1:1-chloroform:methanol=10:1) to give the title compound (193 mg).

$^1$H-NMR (400 MHz, δppm, CDCl$_3$) 7.99(2H, d, J=6.9 Hz), 7.49(1H, dd, J=5.4, 2.1 Hz), 7.35-7.20(2H, m), 7.15-7.10(1H, m), 7.00-6.80(5H, m), 4.72(1H, q, J=6.5 Hz), 4.20-4.10(1H, m), 3.89(3H, s), 3.50-3.35(2H, m), 3.30-3.20(1H, m), 3.10-2.80(3H, m), 2.22(3H, s), 1.40-1.20(9H, m).

MS (ESI, m/z) 510(M+H)$^+$.

Step 9

4-[2-[(1R)-[(2R)-3-[[1-(3-fluoro-4-methylphenyl)-2-methylpropan-2-yl]amino]-2-hydroxypropoxy]ethyl]phenoxy]benzoic acid

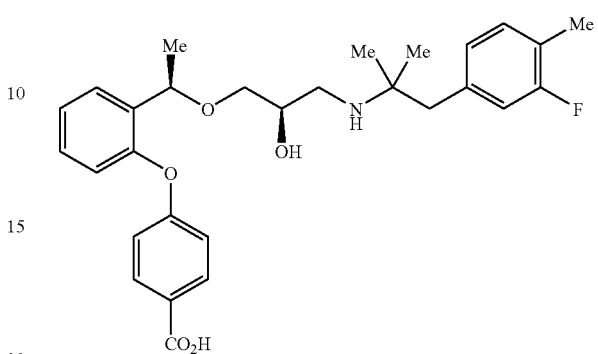

Methyl 4-[2-[(1R)-[(2R)-3-[[1-(3-fluoro-4-methylphenyl)-2-methylpropan-2-yl]amino]-2-hydroxypropoxy]ethyl]phenoxy]benzoate (185 mg) obtained in Step 8 was dissolved in methanol (3 ml) and tetrahydrofuran (3 ml), and 2N-sodium hydroxide solution (1.5 ml) was added. The mixture was stirred at room temperature for 4 hrs. The reaction mixture was concentrated under reduced pressure and the obtained residue was diluted with water. 10% Aqueous citric acid solution was added, and the resulting precipitate was collected by filtration to give the title compound (152 mg).

$^1$H-NMR (300 MHz, δppm, DMSO-d$_6$) 7.93(2H, d, J=8.7 Hz), 7.55(1H, d, J=7.5 Hz), 7.40-7.25(2H, m), 7.20-7.10 (1H, m), 7.05-6.85(5H, m), 4.68(1H, q, J=6.3 Hz), 3.80-3.65(1H, m), 3.24(2H, d, J=5.4 Hz), 2.85-2.55(4H, m), 2.19(3H, s), 1.32(3H, d, J=6.3 Hz), 1.03(3H, s), 1.02(3H, s).

MS (ESI, m/z) 496(M+H)$^+$.

Example 2-2

4-[2-[1-[(2R)-3-[[1-(3-fluoro-4-methylphenyl)-2-methylpropan-2-yl]amino]-2-hydroxypropoxy]ethyl]phenoxy]-3-methoxybenzoic acid Step 1

Methyl 4-(2-acetylphenoxy)-3-methoxybenzoate

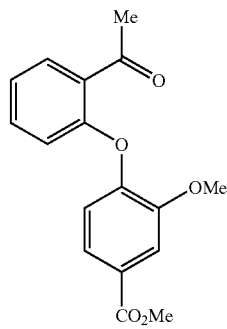

2'-Fluoroacetophenone (1.38 g) and methyl 4-hydroxy-3-methoxybenzoate (1.82 g) were dissolved in dimethylformamide (10 ml), and potassium carbonate (1.45 g) was added. The mixture was stirred at 100° C. for 15 hrs. The reaction mixture was cooled to room temperature, and water was added. The mixture was extracted with ethyl acetate. The organic layer was washed successively with water and brine and dried over sodium sulfate. The obtained residue was purified by silica gel column chromatography (hexane: ethyl acetate=5:1) to give the title compound (1.25 g).

Step 2

Methyl 4-[2-(1-hydroxyethyl)phenoxy]-3-methoxybenzoate

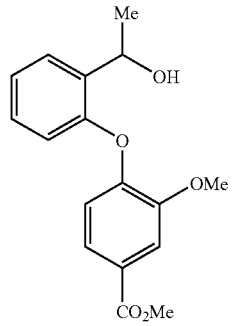

Methyl 4-(2-acetylphenoxy)-3-methoxybenzoate (1.24 g) obtained in Step 1 was dissolved in methanol (20 ml), and after ice-cooling, sodium borohydride (312 mg) was added. The mixture was stirred for 2 hrs. The reaction mixture was concentrated under reduced pressure, and water was added. The mixture was extracted with ethyl acetate. The organic layer was washed successively with 5% aqueous citric acid solution and brine, and dried over sodium sulfate. The obtained residue was purified by silica gel column chromatography (hexane:ethyl acetate=3:1) to give the title compound (834 mg).

$^1$H-NMR (300 MHz, δppm, CDCl$_3$) 7.70-7.50(3H, m), 7.25-7.10(2H, m), 6.90(1H, d, J=8.4 Hz), 6.77(1H, dd, J=6.6, 1.5 Hz), 5.25-5.15(1H, m), 3.94(3H, s), 3.93(3H, s), 2.53(1H, d, J=4.2 Hz), 1.53(3H, d, J=6.6 Hz).

Step 3

Methyl 3-methoxy-4-[2-[1-((R)-oxiranylmethoxy)ethyl]phenoxy]benzoate

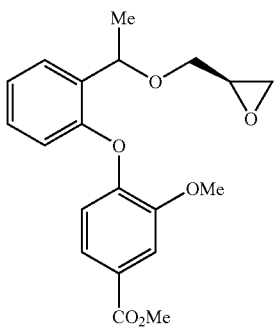

In the same manner as in Step 3 of Example 2-1, the title compound (150 mg) was obtained from methyl 4-[2-(1-hydroxyethyl)phenoxy]-3-methoxybenzoate (660 mg) obtained in Step 2.

$^1$H-NMR (400 MHz, δppm, CDCl$_3$) 7.70-7.50(3H, m), 7.25-7.15(2H, m), 6.80-6.70(2H, m), 4.87(1H, q, J=6.4 Hz), 3.91(6H, s), 3.60-3.50(1H, m), 3.40-3.25(1H, m), 3.15-3.10 (1H, m), 2.80-2.70(1H, m), 2.60-2.50(1H, m), 1.45-1.40(3H, m).

Step 4

Methyl 4-[2-[1-[(2R)-3-[[1-(3-fluoro-4-methylphenyl)-2-methylpropan-2-yl]amino]-2-hydroxypropoxy]ethyl]phenoxy]-3-methoxybenzoate

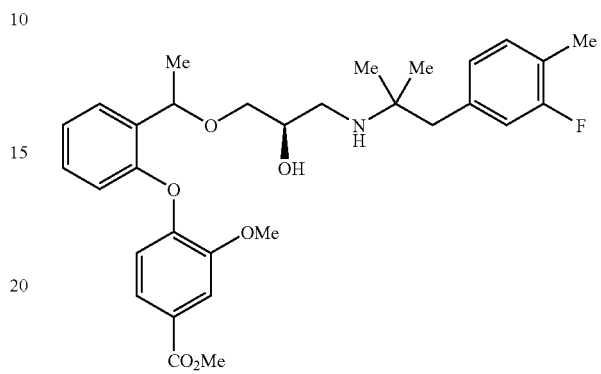

In the same manner as in Step 8 of Example 2-1, the title compound (189 mg) was obtained from methyl 3-methoxy-4-[2-[1-((R)-oxiranylmethoxy)ethyl]phenoxy]benzoate (146 mg) obtained in Step 3 and 1-(3-fluoro-4-methylphenyl)-2-methylpropan-2-ylamine (89 mg) obtained in Step 7 of Example 2-1.

$^1$H-NMR (400 MHz, δppm, CDCl$_3$) 7.65-7.45(3H, m), 7.25-7.00(3H, m), 6.85-6.70(4H, m), 4.83(1H, d, J=6.3 Hz), 3.90(6H, s), 3.80-3.70(1H, m), 3.40-3.30(2H, m), 2.85-2.55 (4H, m), 2.23(3H, s), 1.45-1.35(3H, m), 1.05(6H, s).

MS (ESI, m/z) 540(M+H)$^+$

Step 5

4-[2-[1-[(2R)-3-[[1-(3-fluoro-4-methylphenyl)-2-methylpropan-2-yl]amino]-2-hydroxypropoxy]ethyl]phenoxy]-3-methoxybenzoic acid

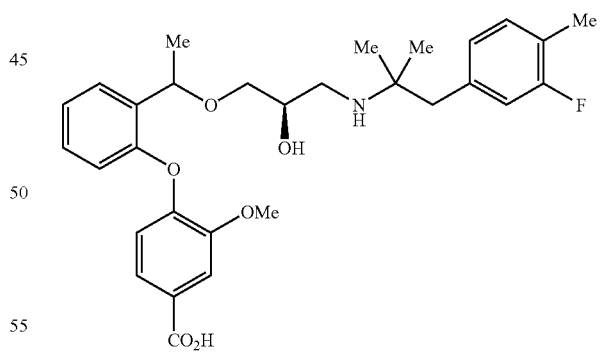

In the same manner as in Step 9 of Example 2-1, the title compound (160 mg) was obtained from methyl 4-[2-[1-[(2R)-3-[[1-(3-fluoro-4-methylphenyl)-2-methylpropan-2-yl]amino]-2-hydroxypropoxy]ethyl]phenoxy]-3-methoxybenzoate (180 mg) obtained in Step 4.

$^1$H-NMR (300 MHz, δppm, DMSO-d$_6$) 7.70-7.45(3H, m), 7.30-7.10(3H, m), 7.05-6.85(3H, m), 6.75-6.70(1H, m), 4.81(1H, q, J=6.0 Hz), 3.90-3.70(4H, m), 3.30(2H, d, J=5.1 Hz), 2.95-2.60(4H, m), 2.19(3H, s), 1.36(3H, d, J=6.0 Hz), 1.05(6H, s).

MS (ESI, m/z) 496(M+H)⁺.

Examples 2-3 to 2-36

Examples 2-3 to 2-36 were obtained based on Examples 2-1 and 2-2. The results are shown in Tables 45-60.

TABLE 45

| Ex. No. | Structural formula | Property data | Reporter gene assay (μM) |
|---|---|---|---|
| 2-1 | | ¹H-NMR(300MHz, δppm, DMSO-d₆) 7.93(2H, d, J=8.7Hz), 7.55(1H, d, J=7.5Hz), 7.40-7.25(2H, m), 7.20-7.10(1H, m), 7.05-6.85(5H, m), 4.68(1H, q, J=6.3Hz), 3.80-3.65(1H, m), 3.24(2H, d, J=5.4Hz), 2.85-2.55(4H, m), 2.19(3H, s) 1.32(3H, d, J=6.3Hz), 1.03(3H, s), 1.02(3H, s). MS(ESI, m/z) 496(M+H)⁺. | 0.015 |
| 2-2 | | ¹H-NMR(300MHz, δppm, DMSO-d₆) 7.70-7.45(3H, m), 7.30-7.10(3H, m), 7.05-6.85(3H, m), 6.75-6.70(1H, m), 4.81(1H, q, J=6.0Hz), 3.90-3.70(4H, m), 3.30(2H, d, J=5.1Hz), 2.95-2.60(4H, m), 2.19(3H, s), 1.36(3H, d, J=6.0Hz), 1.05(6H, s). MS(ESI, m/z) 496(M+H)⁺. | 0.021 |
| 2-3 | | ¹H-NMR(300MHz, δppm, DMSO-d₆) 8.00-7.75(5H, m), 7.69(1H, s), 7.65-7.25(6H, m), 7.15-6.95(3H, m), 4.66(1H, q, J=6.6Hz), 3.81(3H, s), 3.75-3.65(1H, brs), 3.30-3.15(2H, m), 3.00-2.55(4H, m), 1.40-1.30(3H, m), 1.07(6H, s) MS(ESI, m/z) 528(M+H)⁺. | 0.071 |

TABLE 46

| 2-4 |  | ¹H-NMR(300MHz, δppm, DMSO-d₆) 8.00-7.75(5H, m), 7.70(1H, s), 7.65-7.20(6H, m), 7.10-6.85(3H, m), 4.70(1H, q, J=6.41Hz), 3.90-3.70(1H, m), 3.35-3.20(2H, m), 3.00-2.40(4H, m), 1.31(3H, d, J=6.4Hz), 3.90-3.70(1H, m), 3.35-3.20(2H, m), 3.00-2.40(4H, m), 1.31(3H, d, J=6.4Hz), 1.10(6H, s) MS(ESI, m/z) 514(M+H)⁺. | 0.010 |

TABLE 46-continued
| 2-5 | 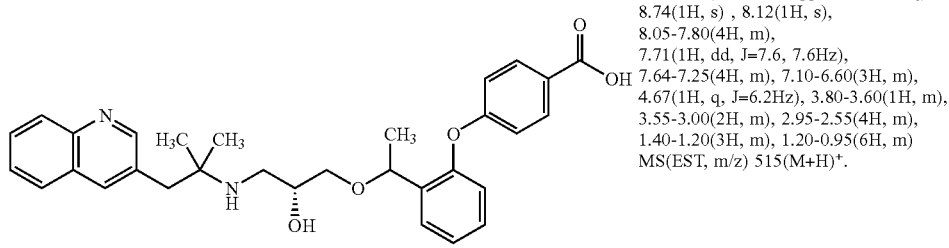 | ¹H-NMR(300MHz, δppm, DMSO-d₆) 8.74(1H, s), 8.12(1H, s), 8.05-7.80(4H, m), 7.71(1H, dd, J=7.6, 7.6Hz), 7.64-7.25(4H, m), 7.10-6.60(3H, m), 4.67(1H, q, J=6.2Hz), 3.80-3.60(1H, m), 3.55-3.00(2H, m), 2.95-2.55(4H, m), 1.40-1.20(3H, m), 1.20-0.95(6H, m) MS(EST, m/z) 515(M+H)⁺. | 0.057 |
| --- | --- | --- | --- |
| 2-6 | 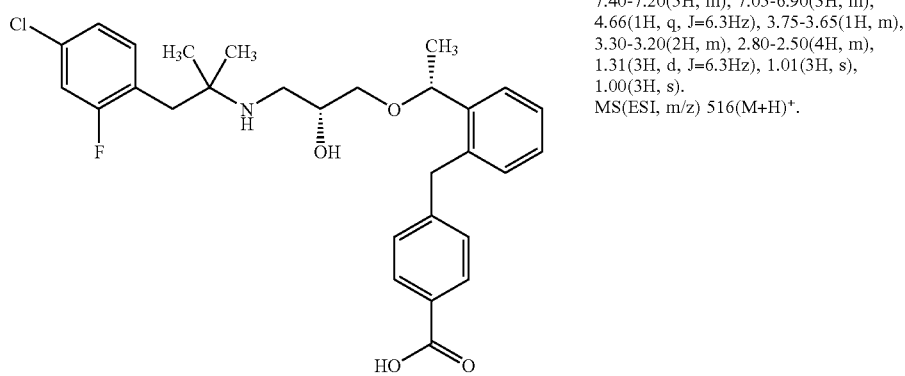 | ¹H-NMR(300MHz, δppm, DMSO-d₆) 7.93(2H, d, J=8.7Hz), 7.60-7.50(1H, m), 7.40-7.20(5H, m), 7.05-6.90(3H, m), 4.66(1H, q, J=6.3Hz), 3.75-3.65(1H, m), 3.30-3.20(2H, m), 2.80-2.50(4H, m), 1.31(3H, d, J=6.3Hz), 1.01(3H, s), 1.00(3H, s). MS(ESI, m/z) 516(M+H)⁺. | 0.022 |
| 2-7 | 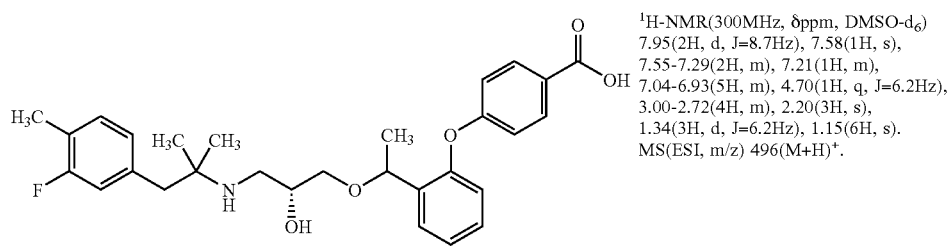 | ¹H-NMR(300MHz, δppm, DMSO-d₆) 7.95(2H, d, J=8.7Hz), 7.58(1H, s), 7.55-7.29(2H, m), 7.21(1H, m), 7.04-6.93(5H, m), 4.70(1H, q, J=6.2Hz), 3.00-2.72(4H, m), 2.20(3H, s), 1.34(3H, d, J=6.2Hz), 1.15(6H, s). MS(ESI, m/z) 496(M+H)⁺. | 0.017 |
TABLE 47
| 2-8 | 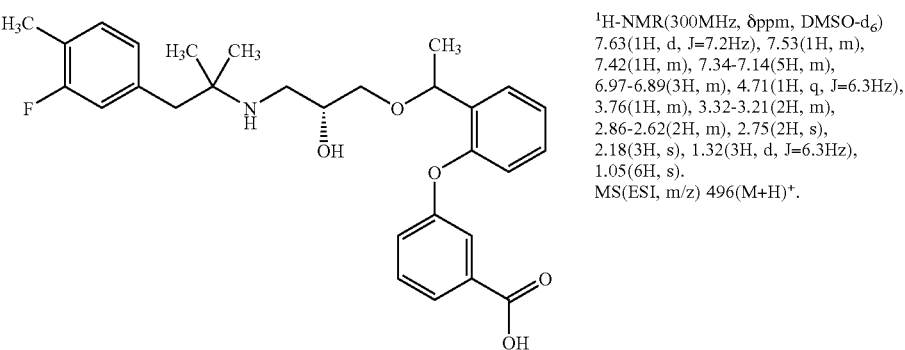 | ¹H-NMR(300MHz, δppm, DMSO-d₆) 7.63(1H, d, J=7.2Hz), 7.53(1H, m), 7.42(1H, m), 7.34-7.14(5H, m), 6.97-6.89(3H, m), 4.71(1H, q, J=6.3Hz), 3.76(1H, m), 3.32-3.21(2H, m), 2.86-2.62(2H, m), 2.75(2H, s), 2.18(3H, s), 1.32(3H, d, J=6.3Hz), 1.05(6H, s). MS(ESI, m/z) 496(M+H)⁺. | 0.054 |
| --- | --- | --- | --- |

TABLE 47-continued
| 2-9 | 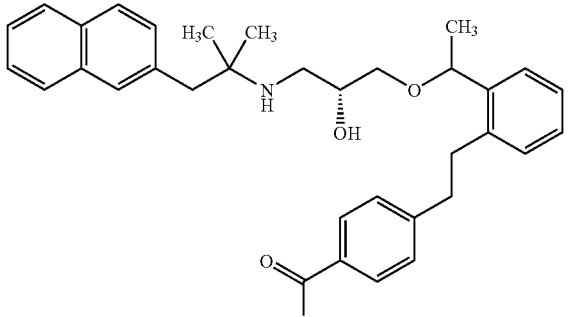 | ¹H-NMR(300MHz, δppm, DMSO-d₆) 7.95(2H, d, J=7.7Hz), 7.85-7.66(8H, m), 7.46-7.42(3H, m), 7.35-7.30(3H, m), 7.17(1H, d, J=16.2Hz), 4.99(1H, q, J=6.5Hz), 3.91(1H, m), 3.45(1H, m), 3.40(1H, m), 2.95(1H, m), 2.93(2H, s), 2.73(1H, m), 1.39(3H, d, J=6.5Hz), 1.08(6H, s). MS(ESI, m/z) 524(M+H)⁺. | 0.016 |
| --- | --- | --- | --- |
| 2-10 | 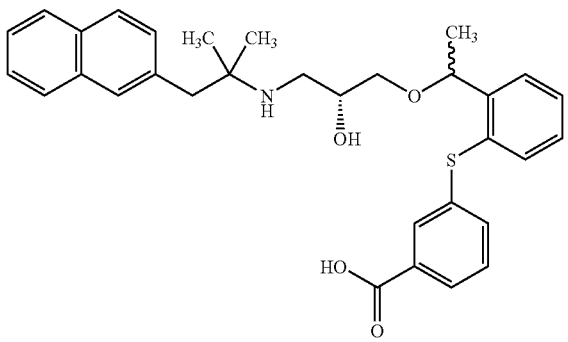 | ¹H-NMR(500 MHz, δppm, CD₃OD) 7.92-7.16 (15H, m), 5.07-5.02(1H, m), 3.96-3.90 (1H, m), 3.40-3.32(1H, m), 3.28-3.11 (4H, m), 3.04-2.98(1H, m), 1.42-1.30 (9H, m). MS(ESI, m/z) 530(M+H)⁺. | 0.027 |
TABLE 48
| 2-11 | 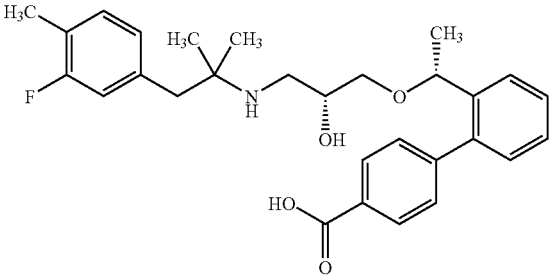 | ¹H-NMR(300MHz, δppm, DMSO-d₆) 7.95(2H, d, J=8.0Hz), 7.78-7.69(4H, m), 7.44-7.31(3H, m), 7.20-7.11(2H, m), 6.95-6.86(2H, m), 4.97(1H, q, J=6.6Hz), 3.81(1H, brs), 3.39-3.25(3H, m), 2.83-2.77(1H, m), 2.66(2H, s), 2.61-2.55(1H, m), 2.17(3H, s), 1.38(3H, d, J=6.6Hz), 0.98(6H, brs). MS(ESI, m/z) 506(M+H)⁺. | 0.021 |
| --- | --- | --- | --- |
| 2-12 | 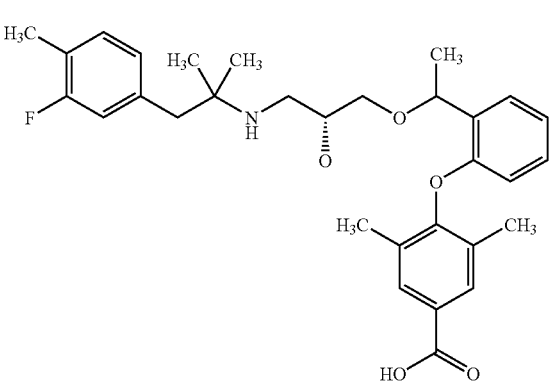 | ¹H-NMR(400MHz, δppm, DMSO-d₆) 7.74-7.69(2H, m), 7.47-7.42(1H, m), 7.13-6.87(5H, m), 6.15(1H, d, J=8.1Hz), 5.03(1H, q, J=6.3Hz), 3.75(1H, brs), 3.35-3.33(3H, m), 2.78-2.76(1H, m), 2.65-2.51(2H, m), 2.15(3H, s), 2.07(3H, s), 2.02(3H, s), 1.42(3H, d, J=6.3Hz), 0.99(6H, brs). MS(ESI, m/z) 524(M+H)⁺. | 0.005 |

TABLE 48-continued

| | | | |
|---|---|---|---|
| 2-13 | (structure: 4-Cl, 2-F benzyl-C(CH₃)₂-NH-CH₂-CH(OH)-CH₂-O-CH(CH₃)-[2-substituted phenyl]-CH₂-[3,5-dimethyl-4-yl]-benzoic acid) | ¹H-NMR(400MHz, δppm, DMSO-d₆) 7.74-7.69(2H, m), 7.48-7.42(1H, m), 7.09-6.98(2H, m), 6.15(1H, d, J=8.1Hz), 5.03(1H, q, J=6.1Hz), 3.73(1H, brs), 3.38-3.30(3H, m), 2.80-2.55(3H, m), 2.07(3H, s), 2.03(3H, s), 1.43(3H, d, J=6.1Hz), 0.98(6H, brs). MS(ESI, m/z) 544(M+H)⁺. | 0.022 |

TABLE 49

| | | | |
|---|---|---|---|
| 2-14 | (structure with 2-naphthyl group, benzoic acid at para) | ¹H-NMR(400MHz, δppm, DMSO-d₆) 7.85-7.76(5H, m), 7.66(1H, s), 7.48-7.41(2H, m), 7.39(1H, dd, J=7.5, 1.7Hz), 7.28-7.15(5H, m), 4.68(1H, q, J=6.3Hz), 4.12(1H, d, J=16Hz), 4.07(1H, d, J=16Hz), 3.68(1H, m), 3.09(2H, d, J=5.6Hz), 2.87(2H, s), 2.77(1H, dd, J=11, 3.5Hz), 2.57(1H, dd, J=11, 7.7Hz), 1.15(3H, d, J=6.3Hz), 1.05(3H, s), 1.04(3H, s). MS(ESI, m/z) 512(M+H)⁺. | 0.053 |
| 2-14' | (structure with 2-naphthyl group, benzoic acid at para) | ¹H-NMR(300MHz, δppm, DMSO-d₆) 7.90-7.70(5H, m), 7.68(1H, s), 7.55-7.10(9H, m), 4.68(1H, q, J=6.2Hz), 4.10(2H, s), 3.80-3.50(1H, m), 3.20-2.90(2H, m), 2.86(2H, d, J=2.9Hz), 2.80-2.50(2H, m), 1.15(3H, d, J=6.3Hz), 1.04(3H, s), 1.03(3H, s). MS(EST, m/z) 512(M+H)⁺. | 0.030 |
| 2-15 | (structure with 2-naphthyl group, benzoic acid at meta) | ¹H-NMR(300MHz, δppm, DMSO-d₆) 7.89-7.70(6H, m), 7.52-7.34(6H, m), 7.31-7.17(3H, m), 4.71(1H, q, J=6.2Hz), 4.10(2H, s), 3.75(1H, m), 3.16-3.07(2H, m), 2.95(2H, s), 2.84(1H, dd, J=12, 2.9Hz), 2.64(1H, dd, J=12, 7.71Hz), 1.18(3H, d, J=6.2Hz), 1.10(3H, s), 1.09(3H, s). MS(ESI, m/z) 512(M+H)⁺. | 0.016 |

TABLE 50

| 2-16 | 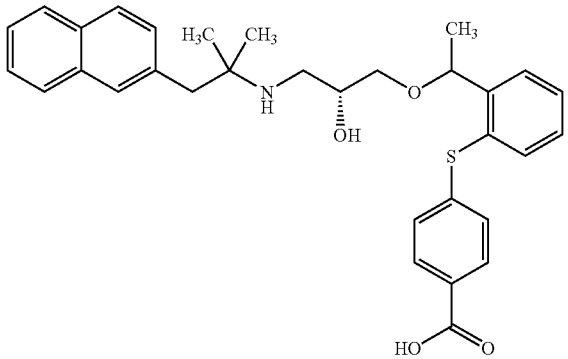 | ¹H-NMR(300MHz, δppm, DMSO-d₆) 7.88-7.80(5H, m), 7.71(1H, s), 7.63-7.58(1H, m), 7.53-7.43(4H, m), 7.39-7.33(2H, m), 7.14(2H, d, J=8.4Hz), 4.93(1H, q, J=6.6Hz), 3.81(1H, m), 3.26-3.14(2H, m), 2.96-2.87(3H, m), 2.77-2.68(1H, m), 1.27(3H, d, J=6.6Hz), 1.11(6H, s). MS(ESI, m/z) 530(M+H)⁺. | 0.014 |
| --- | --- | --- | --- |
| 2-17 | 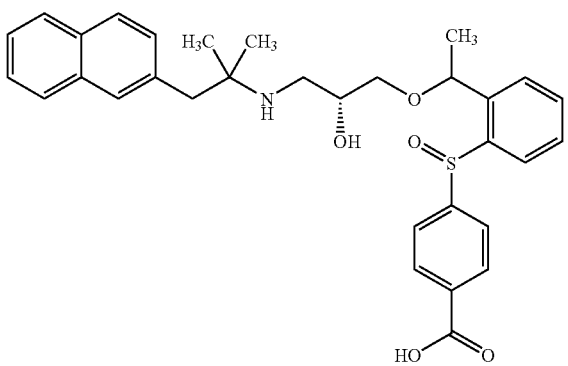 | ¹H-NMR(400MHz, δppm, DMSO-d₆) 8.12-8.03(2H, m), 7.89-7.65(7H, m), 7.58-7.44(5H, m), 7.39-7.34(1H, m), 5.21(0.25H, q, J=6.5Hz), 5.10(0.25H, q, J=6.5Hz), 4.98-4.93(0.5H, m), 3.87(1H, m), 3.25-2.68(6H, m), 1.37(1.5H, d, J=6.5Hz), 1.35(1.5H, d, J=6.5Hz), 1.20-1.15(6H, m). MS(ESI, m/z) 546(M+H)⁺. | 0.148 |
| 2-18 | 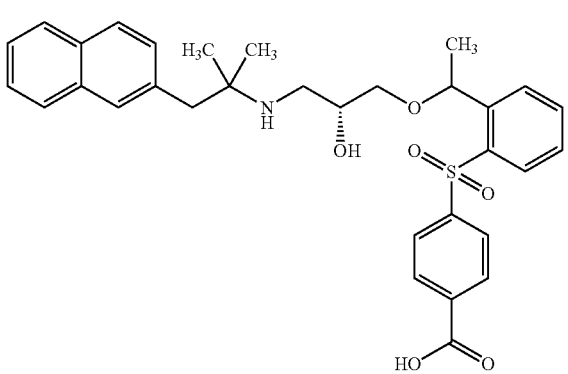 | ¹H-NMR(400MHz, δppm, DMSO-d₆) 8.16-8.07(3H, m), 7.90-7.76(6H, m), 7.73-7.67(2H, m), 7.65-7.60(1H, m), 7.50-7.44(2H, m), 7.38-7.34(1H, m), 5.16(0.5H, q, J=6.2Hz), 5.07(0.5H, q, J=6.2Hz), 3.70(1H, m), 2.97-2.82(2H, m), 2.74-2.57(2H, m), 1.26-1.18(9H, m). MS(ESI, m/z) 562(M+H)⁺. | 0.236 |

TABLE 51

| 2-19 | 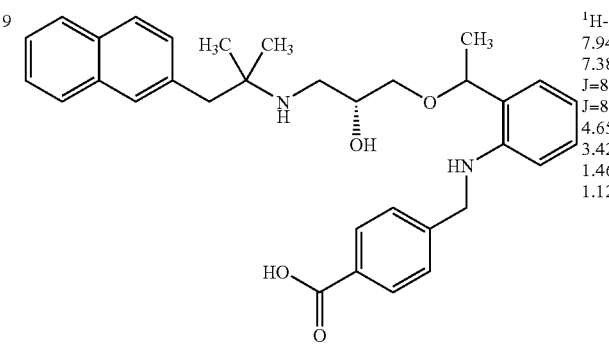 | ¹H-NMR (300 MHz, δ ppm, DMSO-d₆) 7.94–7.80(5H, m), 7.70(1H, m), 7.51–7.44(4H, m), 7.38–7.34(1H, m), 7.07(1H, d, J=7.4 Hz), 6.98(1H, ddd, J=8.1, 7.0, 1.3 Hz), 6.56(1H, dd, J=7.4, 7.0 Hz), 6.43(1H, d, J=8.1 Hz), 6.12–6.03(1H, m), 4.67(0.5H, q, J=6.6 Hz), 4.65(0.5H, q, J=6.6 Hz), 4.41(2H, m), 3.91(1H, m), 3.42–3.30(2H, m), 3.00–2.90(3H, m), 2.82–2.73(1H, m), 1.46(1.5H, d, J=6.6 Hz),1.45(1.5H, d, J=6.6 Hz), 1.12–1.10(6H, m). MS (ESI, m/z) 527 (M + H)⁺. | 0.029 |

TABLE 51-continued

| 2-20 | 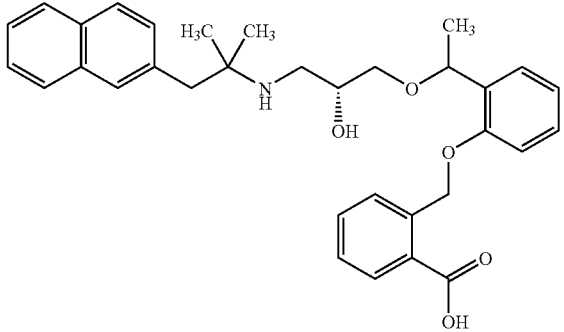 | ¹H-NMR (400 MHz, δ ppm, DMSO-d₆)<br>7.89–7.83(3H, m), 7.77–7.73(2H, m), 7.49–7.45(3H, m), 7.38–7.32(4H, m), 7.22(1H, ddd, J=8.4, 7.4, 1.8 Hz), 7.09(1H, d, J=8.4 Hz), 6.96(1H, dd, J=7.4, 7.4 Hz), 5.58(1H, d, J=11 Hz), 5.19(1H, d, J=11 Hz), 4.99(1H, q, J=6.3 Hz), 4.01(1H, m), 3.43(1H, dd, J=11, 6.8 Hz), 3.33(1H, dd, J=11, 6.1 Hz), 3.12–3.07(3H, m), 2.83(1H, dd, J=12, 6.5 Hz), 1.26(3H, d, J=6.3 Hz), 1.20(6H, s). MS (ESI, m/z) 528 (M + H)⁺. | 0.020 |

TABLE 52

| 2-20' | 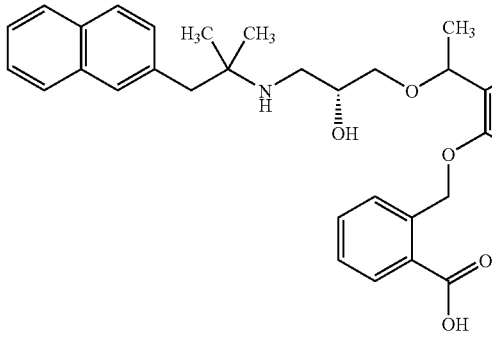 | ¹H-NMR (300 MHz, δ ppm, DMSO-d₆)<br>8.00–7.65(5H, m), 7.60–7.30(7H, m), 7.23(1H, dd, J=7.4, 7.4, Hz), 7.10(1H, d, J=8.4 Hz), 6.97(1H, dd, J=7.4, 7.4 Hz), 5.68(0.5H, d, J=10 Hz), 5.59(0.5H, d, J=10 Hz), 5.25–4.90(2H, m), 4.25–3.95(1H, m), 3.50–3.20(2H, m), 3.15–2.95(2H, m), 2.90–2.65(1H, m), 1.35–1.00(9H, m), MS (ESI, m/z) 528 (M + H)⁺. | 0.021 |
| 2-21 | 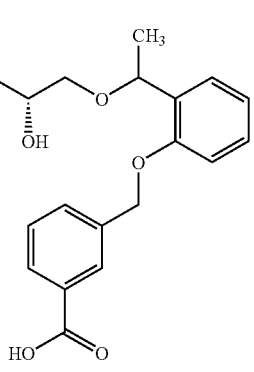 | ¹H-NNR (400 MHz, δ ppm, DMSO-d₆)<br>8.06(1H, s), 7.88–7.81(4H, m), 7.72(1H, s), 7.54–7.34(6H, m), 7.20(1H, ddd, J=8.4, 7.4, 1.8 Hz), 7.05(1H, d, J=8.4 Hz), 6.95(1H, dd, J=7.4, 7.4 Hz), 5.27(1H, d, J=13 Hz), 5.22(1H, d, J=13 Hz), 4.97(1H, q, J=6.2 Hz), 3.98(1H, m), 3.40(1H, dd, J=10, 6.1 Hz), 3.33(1H, dd, J=10, 5.3 Hz), 3.08(2H, s), 3.00(1H, dd, J=12, 3.5 Hz), 2.78(1H, dd, J=12, 7.6 Hz), 1.34(3H, d, J=6.2 Hz), 1.18(3H, s), 1.17(3H, s).<br>MS (ESI, m/z) 528 (M + H)⁺. | 0.017 |

TABLE 53

| 2-21' | 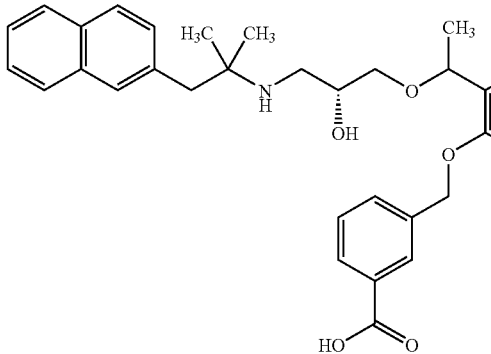 | ¹H-NMR (300 MHz, δ ppm, DMSO-d₆)<br>8.06(1H, s), 7.89–7.81(4H, m), 7.72(1H, s), 7.54–7.34(6H, m), 7.24–7.16(1H, m), 7.06(1H, d, J=8.4 Hz), 6.96(1H, m), 5.33–5.21(2H, m), 5.00(1H, m), 3.99(1H, m), 3.42–3.28(2H, m), 3.08(2H, s), 3.05(1H, s), 2.98–2.71(2H, m), 1.34(1.5H, d, J=6.2 Hz), 1.33(1.5H, d, J=6.2 Hz), 1.15(6H, s).<br>MS (ESI, m/z) 528 (M + H)⁺. | 0.026 |

TABLE 53-continued

| | | | |
|---|---|---|---|
| 2-22 | [structure] | $^1$H-NMR (400 MHz, δ ppm, DMSO-$d_6$)<br>7.97(2H, d, J=8.3 Hz), 7.86–7.78(3H, m), 7.69(1H, s),<br>7.52(2H, d, J=8.3 Hz), 7.48–7.43(2H, m), 7.37–7.34(2H, m),<br>7.22(1H, ddd, J=8.3, 7.4, 1.7 Hz), 7.06(1H, d, J=8.3 Hz),<br>6.97(1H, dd, J=7.4, 7.4 Hz), 5.20(2H, s), 4.91(1H, q, J=6.3 Hz),<br>3.84(1H, m), 3.30(2H, m), 2.94–2.90(3H, m), 2.70(1H, dd,<br>J=12, 7.9 Hz), 1.33(3H, d, J=6.3 Hz), 1.10(3H, s),<br>1.09(3H, s).MS (ESI, m/z) 528 (M + H)$^+$. | 0.017 |

TABLE 54

| | | | |
|---|---|---|---|
| 2-22' | [structure] | $^1$H-NMR (300 MHz, δ ppm, DMSO-$d_6$)<br>7.98(2H, d, J=8.3 Hz), 7.87–7.78(3H, m), 7.70(1H, s),<br>7.53(2H, d, J=8.3 Hz), 7.49–7.35(4H, m), 7.23(1H, m),<br>7.06(1H, d, J=8.3 Hz), 6.98(1H, dd, J=7.4, 7.4 Hz), 5.21(2H, s),<br>4.91(1H, q, J=6.3 Hz), 3.82(1H, m), 3.31(2H, m),<br>2.91–2.86(3H, m), 2.77–2.64(1H, m), 1.32(3H, d, J=6.3 Hz),<br>1.08(6H, s).<br>MS (ESI, m/z) 528 (M + H)$^+$. | 0.023 |
| 2-23 | [structure] | $^1$H-NNR (400 MHz, δ ppm, DMSO-$d_6$)<br>8.03(1H, s), 7.81(1H, d, J=7.7 Hz), 7.51(1H, d, J=7.7 Hz),<br>7.39(1H, dd, J=7.7, 7.7 Hz), 7.34(1H, dd, J=7.7, 1.6 Hz),<br>7.21–7.15(2H, m), 7.04(1H, d, J=7.7 Hz), 7.00–6.92(3H, m),<br>5.27(1H, d, J=13 Hz), 5.22(1H, d, J=13 Hz), 4.96(1H, q,<br>J=6.4 Hz), 3.93(1H, m), 3.38(1H, dd, J=10, 6.3 Hz), 3.30(1H,<br>dd, J=10, 5.4 Hz), 2.93–2.83(3H, m), 2.69(1H, dd, J=12,<br>7.3 Hz), 2.18(3H, s),1.33(3H, d, J=6.4 Hz), 1.10(6H, s).<br>MS (ESI, m/z) 510 (M + H)$^+$. | 0.027 |

TABLE 55

| | | | |
|---|---|---|---|
| 2-24 | [structure] | $^1$H-NMR (400 MHz, δ ppm, DMSO-$d_6$)<br>7.96(2H, d, J=8.4 Hz), 7.51(2H, d, J=8.4 Hz), 7.36(1H, dd,<br>J=7.6, 1.6 Hz), 7.22(1H, ddd, J=7.6, 7.6, 1.6 Hz), 15(1H, dd,<br>J=8.1, 8.1 Hz), 7.05(1H, d, J=8.1 Hz), 6.99–6.94(2H, m),<br>6.90(1H, dd, J=7.6, 1.4 Hz), 5.20(2H, s), 4.90(1H, q, J=6.4 Hz),<br>3.80(1H, m), 3.31–3.24(2H, m), 2.86(1H, dd, J=12, 3.2 Hz),<br>2.73(2H, s), 2.63(1H, dd, J=12, 8.1 Hz), 2.17(3H, s),1.33(3H, d,<br>J=6.4 Hz), 1.04(3H, s), 1.03(3H, s).<br>MS (ESI, m/z) 510 (M + H)$^+$. | 0.057 |

TABLE 55-continued

| No. | Structure | Data | Value |
|---|---|---|---|
| 2-25 | (structure) | ¹H-NMR (300 MHz, δ ppm, DMSO-d₆) 7.89(1H, dd, J=8.1, 1.5 Hz), 7.65(1H, dd, J=11, 1.5 Hz), 7.59(1H, dd, J=7.7, 7.7 Hz), 7.37(1H, dd, J=7.7, 1.8 Hz), 7.29–7.12(3H, m), 7.03–6.91(3H, m), 5.20(2H, s), 486(1H, q, J=6.2 Hz), 3.90(1H, m), 3.30–3.22(2H, m), 2.98(1H, dd, J=12, 2.7 Hz), 2.83 (2H, s), 2.72(1H, dd, J=12, 8.8 Hz),2.18 (3H, s), 1.30(3H, d, J=6.2 Hz), 1.11(6H, s). MS (ESI, m/z) 528 (M + H)⁺. | 0.065 |

TABLE 56

| No. | Structure | Data | Value |
|---|---|---|---|
| 2-26 | (structure) | ¹H-NMR (400 MHz, δ ppm, DMSO-d₆) 7.78–7.76(2H, m), 7.51(1H, d, J=7.4 Hz), 7.36(1H, m), 7.26–7.22(1H, m), 7.16–7.11 (2H, m), 7.00–6.88 (3H, m), 5.16(1H, d, J=13 Hz), 5.14(1H, d, J=13 Hz), 4.83(1H, m), 3.76(1H, m), 3.26(2H, m), 2.83(1H, m), 2.70(2H, s), 2.60(1H, m), 2.37(3H, s), 2.17(3H, s), 1.30(3H, d, J=6.2 Hz), 1.02(6H, s). MS (ESI, m/z) 524 (M + H)⁺. | 0.024 |
| 2-27 | (structure) | ¹H-NMR (300 MHz, δ ppm, DMSO-d₆) 7.40–7.30(1H, m), 7.29(2H, s), 7.12(1H, dd, J=7.9, 7.9 Hz), 7.03(1H, dd, J=7.9, 7.9 Hz), 6.97–6.88(3H, m), 6.31(1H, d, J=7.9 Hz), 5.05–4.95(1H, m), 3.81–3.71(7H, m), 3.37–3.31(2H, m), 2.85–2.77(1H, m), 2.70–2.55(3H, m), 2.15(3H, s), 1.40(3H, d, J=6.3 Hz), 1.01(3H, s), 1.00(3H, s). MS (ESI, m/z) 496 (M + H)⁺. | 0.027 |

TABLE 57

| No. | Structure | Data | Value |
|---|---|---|---|
| 2-28 | (structure) | ¹H-NNR (300 MHz, δ ppm, DMSO-d₆) 8.42(1H, d, J=1.9 Hz), 8.08(1H, dd, J=8.5, 1.8 Hz), 7.56(1H, dd, =7.2, 2.0 Hz), 7.36–7.27(2H, m), 7.27 (2H, m), 7.17(1H, t, J=8.1 Hz), 7.01–6.90(4H, m), 4.73(1H, q, J=6.3 Hz), 3.85–3.75(1H, m), 3.26(2H, d, J=5.5 Hz), 2.90–2.63(7H, m), 2.17(3H, s), 1.35 (3H, d, J=6.2 Hz), 1.08(3H, s), 1.08(3H, s) MS (ESI, m/z) 541 (M + H)⁺. | 0.003 |

TABLE 57-continued
2-29 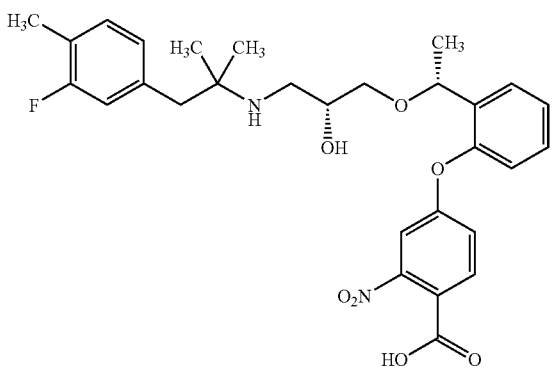
¹H-NNR (300 MHz, δ ppm, DMSO-d₆)
7.70(1H, d, J=1.9 Hz), 7.56 (1H, dd, J=7.6, 2.1 Hz),
7.41–7.29(2H, m), 7.23–7.18(2H, m),
7.08–6.94(4H, m), 4.72(1H, q, J=6.6 Hz), 3.90–3.74 (1H, m),
3.27–3.23(2H, m), 3.05–2.71(7H, m), 2.20(3H, s),
1.35 (3H, d, J=6.2 Hz), 1.12(3H, s), 1.12(3H, s)
MS (ESI, m/z) 541 (M + H)⁺.
0.011
TABLE 58
2-30 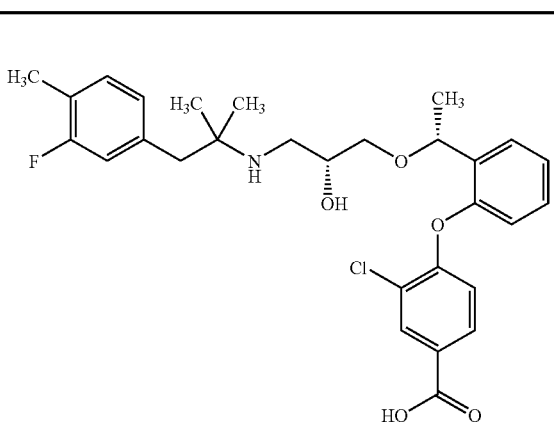
¹H-NMR (300 MHz, δ ppm, DMSO-d₆)
8.00(1H, d, J=1.9 Hz), 7.81(1H, dd, J=8.5, 1.8 Hz),
7.54(1H, dd, J=7.3, 1.8 Hz), 7.35–7.23(2H, m), 7.16(1H,
t, J=7.9 Hz), 6.98–6.85(4H, m), 4.74(1H, q, J=6.2 Hz),
3.83–3.73(1H, m), 3.27(2H, d, J=5.5 Hz), 2.89–2.62(7H, m),
2.18(3H, s), 1.36(3H, d, J=6.6 Hz), 1.06(3H, s), 1.05(3H, s)
MS (ESI, m/z) 530 (M + H)⁺.
0.003
2-31 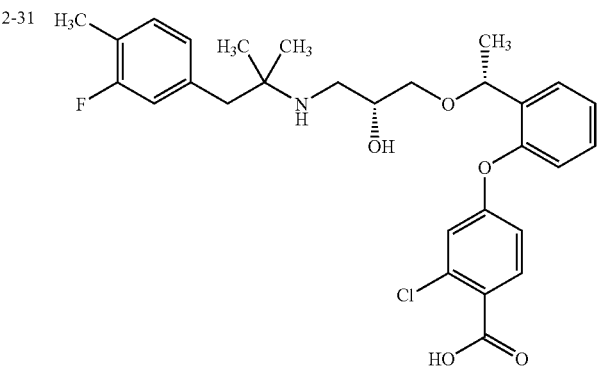
¹H-NMR (300 MHz, δ ppm, DMSO-d₆)
7.59(1H, d, J=8.8 Hz), 7.54(1H, dd, J=5.5, 1.8 Hz),
7.39–7.26(2H, m), 7.18(1H, t, J=8.3 Hz), 7.03(1H, dd, 6.6,
1.5 Hz), 6.98–6.88(3H, m), 6.81(1H, dd, J=8.5, 2.6 Hz),
4.68(1H, q, J=6.6 Hz), 3.74–3.62(1H, m), 3.28–3.16(2H, m),
2.87–2.64(7H, m), 2.19(3H, s), 1.34(3H, d, J=6.2 Hz),
1.08 (3H, s), 1.08 (3H, s) MS (ESI, m/z) 530 (M + H)⁺.
0.016

TABLE 59

| | Structure | NMR / MS | Value |
|---|---|---|---|
| 2-32 | (structure) | ¹H-NMR (300 MHz, δ ppm, DMSO-d₆) 7.57(2H, t, J=8.8 Hz), 7.40–7.28(2H, m), 7.22–7.13(2H, m), 7.09–7.02(2H, m), 6.98–6.91(2H, m), 4.71(1H, q, J=6.4 Hz), 3.81–3.71(1H, m), 3.29–3.17(2H, m), 2.96–2.67(7H, m), 2.19(3H, s), 1.35(3H, d, J=6.6 Hz), 1.12(3H, s), 1.12(3H, s) MS (ESI, m/z) 564 (M + H)⁺. | 0.014 |
| 2-33 | (structure) | ¹H-NMR (300 MHz, δ ppm, DMSO-d₆) 8.22(1H, d, J=2.2 Hz), 8.09(1H, dd, J=8.5, 1.8 Hz), 7.58(1H, dd, J=7.4, 2.2 Hz), 7.41–7.30(2H, m), 7.16(1H, t, J=8.0 Hz), 7.03–6.90(3H, m), 6.83(1H, d, J=8.4 Hz), 4.65(1H, q, J=6.2 Hz), 3.84–3.71(1H, m), 3.29–3.20(2H, m), 2.91–2.63(7H, m), 2.17(3H, s), 1.33(3H, d, J=6.6 Hz), 1.07(3H, s), 1.06(3H, s) MS (ESI, m/z) 564 (M + H)⁺. | 0.002 |

TABLE 60

| | Structure | NMR / MS | Value |
|---|---|---|---|
| 2-34 | (structure) | ¹H-NMR (300 MHz, δ ppm, DMSO-d₆) 7.79(1H, d, J=1.8 Hz), 7.71(1H, d, J=8.5 Hz), 7.53(1H, dd, J=7.4, 2.2 Hz), 7.34–7.22(2H, m), 7.16(1H, t, J=7.9 Hz), 6.98–6.87(4H, m), 4.80(1H, q, J=6.6 Hz), 3.81–3.71(1H, m), 3.28(2H, d, J=5.5 Hz), 2.85–2.58(7H, m), 2.18(3H, s), 1.36(3H, d, J=6.6 Hz), 1.04(3H, s), 1.03(3H, s) MS (ESI, m/z) 514 (M + H)⁺. | 0.006 |
| 2-35 | (structure) | ¹H-NMR (400 MHz, δ ppm, DMSO-d₆) 7.90(2H, m), 7.60–7.20(5H, m), 7.05–6.90(4H, m), 4.66(1H, q, J=6.4 Hz), 3.70–3.60(1H, m), 3.25–3.15(2H, m), 2.80–2.70(2H, m), 2.60–2.50(2H, m), 1.35–1.30(3H, m), 1.05–0.95(6H, m) MS (ESI, m/z) 516 (M + H)⁺. | 0.011 |

TABLE 60-continued

| 2-36 | ¹H-NMR (300 MHz, δ ppm, DMSO-d₆)<br>7.88(1H, s), 7.80–7.20(6H, m), 7.03(1H, d, J=7.8 Hz),<br>6.87(1H, d, J=6.6 Hz), 6.67(1H, d, J=9.0 Hz), 4.68(1H, q,<br>J=6.6 Hz), 3.70–3.60(1H, m), 3.30–3.15(2H, m)<br>2.70–2.50(4H, m), 2.31(3H, s), 1.40–1.20(3H, m),<br>1.00–0.90(6H, m) MS (ESI, m/z) 530 (M + H)⁺. | 0.013 |

Experimental Examples

The bioactivity of the compound of the present invention was examined by tests.

Experimental Example 1

Evaluation of Antagonistic Action on Calcium Receptor Using Reporter Gene

Luciferase cDNA and human calcium receptor cDNA were introduced into a cell strain derived from rat adrenal to transform the cells, and the transformed cells were cultured in a medium (80 µl, F12 medium containing 0.5% dialyzed horse serum and 0.25% dialyzed bovine fetal serum). A dimethyl sulfoxide solution containing a test compound at 0.1-10000 µM was diluted 100-fold with the medium and added to the test compound group at 10 µl per well (dimethyl sulfoxide final concentration 0.1%). In the same manner as in test compound group, dimethyl sulfoxide 100-fold diluted with medium was added to a control group and a blank group. Then, 50 mM calcium chloride-containing medium was added to every well except the blank group at 10 µl per well (final concentration 5 mM). A medium containing 50 mM calcium chloride was added to the control group at 10 µl per well, such that the final calcium concentration of the medium became 5 mM. A medium alone was added to the blank group. After culture for 4 hrs, luciferase substrate was added and the luciferase activity was measured with a photoluminometer. The inhibitory rate (%) was calculated from the obtained measured values according to the following formula.

$$\text{Inhibitory rate (\%)} = 100 - \frac{\text{measured value of compound group} - \text{measured value of blank group}}{\text{measured value of control group} - \text{measured value of blank group}} \times 100$$

Based on the results, the concentration ($IC_{50}$) showing 50% inhibitory rate was determined. The results are shown in the aforementioned Tables 1 to 60.

Experimental Example 2

PTH Secretion Action

The test compound was orally administered to 5 to 9-week-old male SD rats (Charles River Japan, Inc.) fasted for 20 hr, using a solvent (0.5% methyl cellulose solution) at a dose of 1 mg/5 ml/kg. A solvent alone was orally administered to the control group at a dose of 5 ml/kg. The blood was drawn from the tail vein immediately before and, 15 min, 30 min, 60 min and 120 min after the administration of the test compound, and serum was obtained. The serum PTH concentration was measured using rat PTH ELISA kit (Amersham Biosciences). The results are shown in Table 61.

Additionally, a compound described below was tested at a dose of 30 mg/5 ml/kg in the same manner described above as a comparative example and no PTH secretion activity was exhibited.

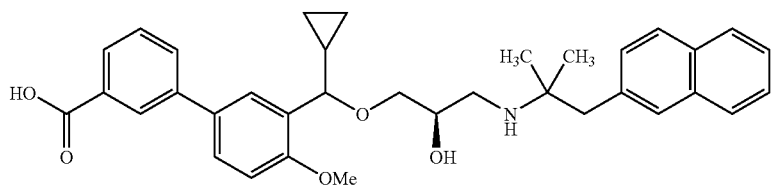

TABLE 61

| Test compound | Serum PTH concentration (pg/ml) | | | |
|---|---|---|---|---|
| | 15 min later | 30 min later | 60 min later | 120 min later |
| | Control group | | | |
| | Test compound administration group | | | |
| 1-1 | 13.2 ± 2.6 | 18.0 ± 1.5 | 14.6 ± 3.6 | 15.9 ± 2.7 |
| | 43.9 ± 2.0 | 25.0 ± 3.2 | 17.9 ± 2.0 | 14.8 ± 1.6 |
| 1-2 | 8.8 ± 1.3 | 12.5 ± 0.6 | 13.4 ± 2.7 | 13.0 ± 1.8 |
| | 28.5 ± 5.3 | 27.1 ± 2.3 | 10.5 ± 1.3 | 12.4 ± 1.6 |
| 1-3 | 8.8 ± 1.3 | 12.5 ± 0.6 | 13.4 ± 2.7 | 13.0 ± 1.8 |
| | 23.8 ± 1.6 | 25.1 ± 3.9 | 9.5 ± 0.5 | 11.6 ± 0.9 |
| 1-6 | 11.9 ± 2.4 | 15.9 ± 1.0 | 8.7 ± 1.2 | 9.4 ± 2.1 |
| | 28.9 ± 6.9 | 19.2 ± 3.1 | 10.0 ± 1.7 | 8.3 ± 0.6 |
| 1-30 | 14.9 ± 1.3 | 14.5 ± 2.7 | 12.9 ± 2.1 | 11.1 ± 2.2 |
| | 26.1 ± 2.3 | 24.2 ± 3.3 | 18.2 ± 1.3 | 13.8 ± 0.6 |

Experimental Example 3

PTH Secretion Action

The test compound was orally administered to 5 to 9-week-old male SD rats (Charles River Japan, Inc.) fasted for 20 hrs, using a solvent (0.5% methyl cellulose solution) at a dose of 1 mg/5 ml/kg. A solvent alone was orally administered to the control group at a dose of 5 ml/kg. The blood was drawn from the tail vein immediately before and 15 min, 30 min after administration of the test compound, and serum was obtained. The serum PTH concentration was measured using rat PTH ELISA kit (Amersham Biosciences). The results are shown in Table 62.

TABLE 62

| Test compound | Serum PTH concentration (pg/ml) | |
|---|---|---|
| | 15 min later | 30 min later |
| | Control group | |
| | Test compound administration group | |
| 2-1 | 13.7 ± 2.3 | 17.6 ± 3.1 |
| | 25.1 ± 2.3 | 19.1 ± 0.9 |

Experimental Example 4

Metabolic Enzyme CYP2D6 Inhibitory Activity

Using a metabolic enzyme CYP2D6 inhibition measurement kit (BD Bioscience) and following the manual of the kit, the inhibitory activity of the test compound was measured. With the enzyme activity free of the test compound as 100%, the concentration ($IC_{50}$) showing 50% inhibition was determined. The results are shown in Table 63 and Table 64, wherein ">10" means over 10 μM.

TABLE 63

| Test compound | $IC_{50}$ (μM) |
|---|---|
| 1-57 | >10 |
| 1-59 | >10 |
| 1-26 | >10 |
| 1-27 | >10 |
| 1-32 | 10.0 |
| 1-33 | >10 |
| 1-34 | >10 |
| 1-35 | >10 |
| 1-73 | >10 |

TABLE 63-continued

| Test compound | $IC_{50}$ (μM) |
|---|---|
| 1-39 | >10 |
| 1-48 | >10 |
| 1-80 | >10 |

TABLE 64

| Test compound | $IC_{50}$ (μM) |
|---|---|
| 2-5 | >10 |
| 2-20' | >10 |

Experimental Example 5

Effect of Concomitant Administration of Test Compound and Estrogen on Bone Resorption and PTH Secretion The 13-week-old ovariectomized rats were divided into 4 groups of a control group (Group A), an estrogen administration group (Group B), a test compound administration group (Group C), and a test compound and estrogen concomitant administration group (Group D). One sham control group (E group) subjected to a sham surgery was also established. Estradiol was dissolved in 5% benzyl alcohol-corn oil and subcutaneously administered to an estrogen administration groups (Group B and Group D) at the dose of 10 μg/kg. 5% Benzyl alcohol-corn oil was subcutaneously administered to groups (Group A and Group C) free from administration of estrogen. The compound of Example 1-1 was suspended in 0.5% methyl cellulose solution and orally administered to groups (Group C and Group D) to be administered with the test compound at the dose of 3 mg/kg. As regards the groups (Group A and Group B) free from administration of the test compound, 0.5% methyl cellulose solution was orally administered.

On day 13 from the start of the administration, the blood was drawn in each group from the tail vein, and serum was obtained. ICTP, which is a blood bone resorption marker, was measured using a commercially available ELISA kit ("RatLaps ELISA kit", Nordic Bioscience Diagnostics).

In addition, blood was drawn with time for the measurement of blood PTH at day 16 of administration. The blood was drawn in each group from the tail vein immediately before oral administration and 0.25, 0.5, 1, 2 and 4 hr later, and serum was obtained. For serum PTH measurement, a commercially available ELISA kit ("rat intact PTH ELISA kit", Immutopics) was used.

The measurement results of blood ICTP are shown in Table 65 and the blood PTH measurement results are shown in Table 66.

TABLE 65

| | Blood I CTP concentration (ng/ml) |
|---|---|
| Group A | 29.21 ± 5.14 |
| Group B | 20.93 ± 3.18 |
| Group C | 26.10 ± 3.45 |
| Group D | 21.77 ± 3.34 |
| Group E | 18.84 ± 2.356 | mean ± S.D., n = 5

TABLE 66

| | PTH (1–84) concentration (pg/ml) | | | | | |
|---|---|---|---|---|---|---|
| | 0 hr | 0.25 hr | 0.5 hr | 1 hr | 2 hr | 4 hr |
| Group A | 29.45 ± 8.67 | 26.74 ± 6.49 | 48.15 ± 10.13 | 33.93 ± 7.09 | 37.29 ± 14.84 | 55.83 ± 18.16 |
| Group B | 36.83 ± 14.45 | 53.65 ± 56.31 | 56.55 ± 21.71 | 35.70 ± 21.30 | 41.94 ± 20.85 | 46.84 ± 14.62 |
| Group C | 31.19 ± 16.28 | 371.21 ± 77.74 | 370.78 ± 98.28 | 177.39 ± 96.06 | 117.51 ± 123.12 | 56.50 ± 12.29 |
| Group D | 27.12 ± 4.58 | 407.35 ± 134.53 | 418.87 ± 154.78 | 279.76 ± 117.98 | 115.50 ± 74.98 | 58.84 ± 16.75 | mean ± S.D., n = 5

When osteoporosis is to be treated by increasing the blood PTH concentration based on inhibition of the action of calcium receptor, the compound to be used for this end should have at least the following properties.

(i) The compound has a sufficient antagonistic action on calcium receptors. In other words, the compound has a sufficiently low $IC_{50}$ value. In the specification of WO99/51241, it is described, "In general, a compound showing a low $IC_{50}$ value in the assay of calcium receptor inhibitor is a more superior compound. A compound showing an $IC_{50}$ value of not lower than 50 μM is considered to be inactive. A preferable compound shows an $IC_{50}$ value of not more than 10 μM, more preferably 1 μM, and most preferably not more than 0.1 μM."

(ii) Administration of the compound results in a sufficient increase in the blood PTH concentration.

(iii) The time-course concentrations in blood after administration of the compound are not sustainable. Desirably, the PTH concentration returns to the level before administration in 3-4 hr after administration of the compound.

Moreover, it is preferable to satisfy the following two aspects;

(1) Administration of the compound does not inhibit the action of bone resorption suppressants such as estrogen and the like.

(2) The PTH secretion action of the compound is not inhibited by bone resorption suppressants such as estrogen and the like.

As regards (i); as shown in Tables 1 to 60, the $IC_{50}$ value of the compound of the present invention is not more than 1 μM, and the compound has a sufficient antagonistic action on calcium receptors. The compound of the present invention is considered to be preferable in view of the $IC_{50}$ value.

As regards (ii); as shown in Tables 61 and 62, the serum PTH concentration 15 min later was 1.8-3.3 times higher (compound wherein n=0) and 1.8 times higher (compound wherein n=1) than control, and the compound of the present invention has been confirmed to have a superior PTH secretion promoting action.

As regards (iii); as shown in Table 61, PTH secretion by the compound of the present invention reached a peak at 15 min after administration, sharply decreased thereafter and returned to the blood PTH concentration before administration in about 1-2 hr. It is clear from this aspect that the compound of the present invention is superior. In contrast, as a result of the reproductive test of NPS-2143 of the reference, the sustained secretion promoting action of NPS-2143 was confirmed.

From the foregoing test results, it is clear that the compounds of the present invention satisfies the above-mentioned properties.

As regards (1); as shown in Table 65, comparison of the sham control group subjected to a sham surgery and the control group reveals an increase in ICTP due to ovary enucleation, thereby confirming promoted bone resorption. This increase was suppressed by an exclusive administration of estrogen, and concomitant administration of Example 1-1 did not show changes in the ability to suppress estrogen.

As regards (2); as shown in Table 66, there was found no difference in blood PTH value before administration between the groups. By examination of the changes with time, increase in blood PTH was not observed by estrogen exclusive administration, but a transitional increase was observed in both the Example 1-1 exclusive group and Example 1-1 and estrogen concomitant administration group.

INDUSTRIAL APPLICABILITY

As is clear from the above-mentioned Experimental Example 1, the compound of the formula (1) of the present invention has a superior calcium receptor antagonistic action. Accordingly, the compound is expected to be useful as a therapeutic drug for diseases accompanied by abnormal calcium homeostasis, such as osteoporosis, hypoparathyreosis, osteosarcoma, periodontal disease, bone fracture, osteoarthrisis, chronic rheumatoid arthritis, Paget's disease, humoral hypercalcemia, autosomal dominant hypocalcemia, Parkinson's disease, dimentia and the like. As is clear from Experimental Examples 2 and 3, the compound of the present invention has a temporary PTH secretion promoting action, and as is clear from Experimental Example 4, it has weak metabolic enzyme CYP2D6 inhibitory activity. Accordingly, the compound is particularly useful as a therapeutic agent for osteoporosis.

As is clear from Experimental Example 5, moreover, the compound of the present invention does not inhibit the action of bone resorption suppressants such as estrogen and the like, and the PTH secretion action of the compound of the present invention is not inhibited by bone resorption suppressants such as estrogen and the like. Therefore, use of the compound of the present invention and bone resorption suppressants such as estrogen and the like in combination is considered to be extremely effective for osteoporosis.

This application is based on a patent application No. 119131/2003 filed in Japan, the contents of which are hereby incorporated by reference.

The invention claimed is:

1. A compound represented by the following formula (1″):

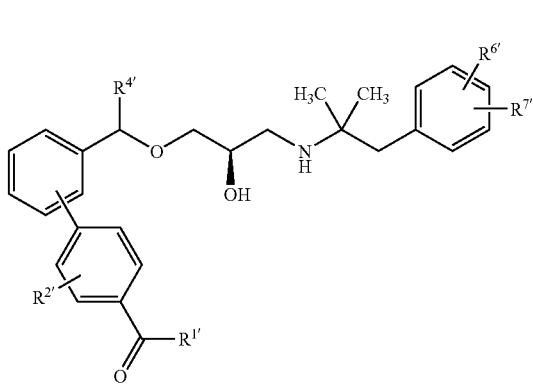

wherein
R$^{1'}$ is a hydroxyl group or a C$_{1-6}$ alkoxy group,
R$^{2'}$ is a hydroxyl group, a halogen atom, an amino group, a C$_{1-7}$ acylamino group, a halo C$_{1-6}$ alkyl group, a C$_{1-6}$ alkoxy-carbonyl group, a C$_{1-6}$ alkoxy group, a halo C$_{1-6}$ alkoxy group, a C$_{1-6}$ alkyl group, a hydroxy-C$_{1-6}$ alkyl group, a di(C$_{1-6}$ alkyl)amino group or a nitro group,
R$^{4'}$ is a C$_{1-6}$ alkyl group or a C$_{3-6}$ cycloalkyl group,
R$^{6'}$ is a halogen atom, a C$_{1-6}$ alkyl group, a C$_{1-6}$ alkoxy group or a halo C$_{1-6}$ alkyl group, or when R$^{7'}$ is adjacent, R$^{6'}$ and R$^{7'}$ are linked to form —CH═CH—CH═CH—, and
R$^{7'}$ is a hydrogen atom, a halogen atom, a C$_{1-6}$ alkyl group, a C$_{1-6}$ alkoxy group or a halo C$_{1-6}$ alkyl group,
an optically active form thereof, a pharmaceutically acceptable salt thereof, or an optically active form of the salt thereof.

2. A compound represented by the following formula (1‴):

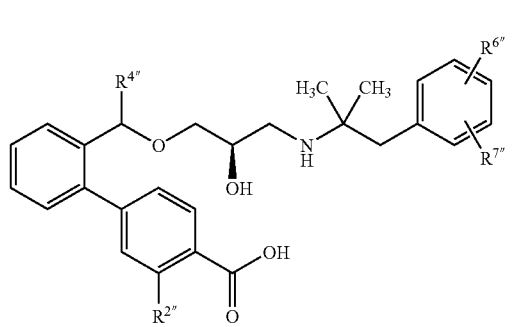

wherein
R$^{2″}$ is a C$_{1-6}$ alkyl group,
R$^{4″}$ is a methyl group or a cyclopropyl group,
R$^{6″}$ is a halogen atom or a C$_{1-6}$ alkyl group, and
R$^{7″}$ is a hydrogen atom, a halogen atom, a C$_{1-6}$ alkyl group, a C$_{1-6}$ alkoxy group or a halo C$_{1-6}$ alkyl group,
an optically active form thereof, a pharmaceutically acceptable salt thereof, or an optically active form of the salt thereof.

3. The compound of claim 1 or 2, which is selected from the group consisting of
2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid,
2'-[1-[(2R)-3-[[1-(4-chloro-3-fluorophenyl)-2-methylpropan-2-yl]amino]-2-hydroxypropoxy]ethyl]-3-methylbiphenyl-4-carboxylic acid,
2'-[1-[(2R)-3-[[1-(3-chloro-4-methylphenyl)-2-methylpropan-2-yl]amino]-2-hydroxypropoxy]ethyl]-3-methylbiphenyl-4-carboxylic acid,
2'-[1-[(2R)-3-[[1-(4-chloro-3-methylphenyl)-2-methylpropan-2-yl]amino]-2-hydroxypropoxy]ethyl]-3-methylbiphenyl-4-carboxylic acid,
2'-[1-[(2R)-3-[[1-(4-chloro-2-fluorophenyl)-2-methylpropan-2-yl]amino]-2-hydroxypropoxy]ethyl]-3-methylbiphenyl-4-carboxylic acid,
2'-[1-[(2R)-3-[[1-(2-fluoro-4-methylphenyl)-2-methylpropan-2-yl]amino]-2-hydroxypropoxy]ethyl]-3-methylbiphenyl-4-carboxylic acid,
2'-[1-[(2R)-3-[[1-(4-ethyl-3-fluorophenyl)-2-methylpropan-2-yl]amino]-2-hydroxypropoxy]ethyl]-3-methylbiphenyl-4-carboxylic acid,
2'-[1-[(2R)-3-[[1-(3-fluoro-4-methylphenyl)-2-methylpropan-2-yl]amino]-2-hydroxypropoxy]ethyl]-3-methylbiphenyl-4-carboxylic acid,
2'-[1-[(2R)-3-[[1-(3-fluoro-4-methylphenyl)-2-methylpropan-2-yl]amino]-2-hydroxypropoxy]ethyl]-3-methylbiphenyl-5-carboxylic acid,
2'-[(cyclopropyl)[(2R)-3-[[1-(4-chloro-2-fluorophenyl)-2-methylpropan-2-yl]amino]-2-hydroxypropoxy]methyl]-3-methylbiphenyl-4-carboxylic acid,
2'-[(cyclopropyl)[(2R)-3-[[1-(4-chloro-3-fluorophenyl)-2-methylpropan-2-yl]amino]-2-hydroxypropoxy]methyl]-3-methylbiphenyl-4-carboxylic acid,
3-methyl-2'-[1-[(2R)-3-[[1-(3,4-dimethylphenyl)-2-methylpropan-2-yl]amino]-2-hydroxypropoxy]ethyl]biphenyl-4-carboxylic acid,
2'-[1-[(2R)-3-[[1-(4-methylphenyl)-2-methylpropan-2-yl]amino]-2-hydroxypropoxy]ethyl]-3-methylbiphenyl-4-carboxylic acid,
2'-[1-[(2R)-3-[[1-(4-chloro-3-methoxyphenyl)-2-methylpropan-2-yl]amino]-2-hydroxypropoxy]ethyl]-3-methylbiphenyl-4-carboxylic acid,
2'-[1-[(2R)-3-[[1-(4-ethylphenyl)-2-methylpropan-2-yl]amino]-2-hydroxypropoxy]ethyl]-3-methylbiphenyl-4-carboxylic acid,
3-ethyl-2'-[1-[(2R)-3-[[1-(3-fluoro-4-methylphenyl)-2-methylpropan-2-yl]amino]-2-hydroxypropoxy]ethyl]biphenyl-4-carboxylic acid,
2'-[1-[(2R)-3-[[1-(3-fluoro-4-methylphenyl)-2-methylpropan-2-yl]amino]-2-hydroxypropoxy]ethyl]-3-isopropylbiphenyl-4-carboxylic acid,
2'-[1-[(2R)-3-[[1-(3-fluoro-4-methylphenyl)-2-methylpropan-2-yl]amino]-2-hydroxypropoxy]ethyl]-3-propylbiphenyl-4-carboxylic acid,
2'-[1-[(2R)-3-[[1-(3-fluoro-4-methylphenyl)-2-methylpropan-2-yl]amino]-2-hydroxypropoxy]ethyl]-3-isobutylbiphenyl-4-carboxylic acid,
3-ethyl-2'-[1-[(2R)-3-[[1-(4-chloro-3-fluorophenyl)-2-methylpropan-2-yl]amino]-2-hydroxypropoxy]ethyl]biphenyl-4-carboxylic acid,
2'-[1-[(2R)-3-[[1-(4-chloro-3-fluorophenyl)-2-methylpropan-2-yl]amino]-2-hydroxypropoxy]ethyl]-3-isopropylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-(1-methylpropyl)biphenyl-4-carboxylic acid, 2'-[1-[(2R)-3-[[1-(3-chlorophenyl)-2-methylpropan-2-yl]amino]-2-hydroxypropoxy]ethyl]-3-methylbiphenyl-4-carboxylic acid, 2'-[1-[(2R)-3-[[1-(3,4-dichlorophenyl)-2-methylpropan-2-yl]amino]-2-hydroxypropoxy]ethyl]-3-methylbiphenyl-4-carboxylic acid, 2'-[1-[(2R)-3-[[1-(3-methoxy-4-methylphenyl)-2-methylpropan-2-yl]amino]-2-hydroxypropoxy]ethyl]-3-methylbiphenyl-4-carboxylic acid, 2'-[1-[(2R)-3-[[1-(3,5-dichlorophenyl)-2-methylpropan-2-yl]amino]-2-hydroxypropoxy]ethyl]-3-methylbiphenyl-4-carboxylic acid, 2'-[1-[(2R)-3-[[1-(4-chloro-3-trifluoromethylphenyl)-2-methylpropan-2-yl]amino]-2-hydroxypropoxy]ethyl]-3-methylbiphenyl-4-carboxylic acid, 2'-[1-[(2R)-3-[[1-(3-fluoro-4-methylphenyl)-2-methylpropan-2-yl]amino]-2-hydroxypropoxy]ethyl]-3-t-butylbiphenyl-4-carboxylic acid, 2'-[1-[(2R)-3-[[1-(4-chloro-2-fluorophenyl)-2-methylpropan-2-yl]amino]-2-hydroxypropoxy]ethyl]-3-t-butylbiphenyl-4-carboxylic acid, 2'-[1-[(2R)-3-[[1-(4-chloro-3-fluorophenyl)-2-methylpropan-2-yl]amino]-2-hydroxypropoxy]ethyl]-3-t-butylbiphenyl-4-carboxylic acid and 2'-[1-[(2R)-3-[[1-(3-trifluoromethyl-4-methylphenyl)-2-methylpropan-2-yl]amino]-2-hydroxypropoxy]ethyl]-3-methylbiphenyl-4-carboxylic acid an optically active form thereof, a pharmaceutically acceptable salt thereof or an optically active form of the salt thereof.

4. 2'-[1-[(2R)-3-[[1-(3-Fluoro-4-methylphenyl)-2-methylpropan-2-yl]amino]-2-hydroxypropoxy]ethyl]-3-methylbiphenyl-4-carboxylic acid, an optically active form thereof, a pharmaceutically acceptable salt thereof or an optically active form of the salt thereof.

5. 2'-[1-[(2R)-3-[[1-(4-Chloro-3-fluorophenyl)-2-methylpropan-2-yl]amino]-2-hydroxypropoxy]ethyl]-3-methylbiphenyl-4-carboxylic acid, an optically active form thereof, a pharmaceutically acceptable salt thereof or an optically active form of the salt thereof.

6. 2'-[1-[(2R)-3-[[1-(3-Chloro-4-methylphenyl)-2-methylpropan-2-yl]amino]-2-hydroxypropoxy]ethyl]-3-methylbiphenyl-4-carboxylic acid, an optically active form thereof, a pharmaceutically acceptable salt thereof or an optically active form of the salt thereof.

7. 2'-[1-[(2R)-3-[[1-(4-Chloro-2-fluorophenyl)-2-methylpropan-2-yl]amino]-2-hydroxypropoxy]ethyl]-3-methylbiphenyl-4-carboxylic acid, an optically active form thereof, a pharmaceutically acceptable salt thereof or an optically active form of the salt thereof.

8. A pharmaceutical composition comprising a pharmaceutically acceptable carrier, and a compound of any of claims 1-2 or 4-7, an optically active form thereof, a pharmaceutically acceptable salt thereof or an optically active form of the salt thereof as an active ingredient.

9. A method for treating osteoporosis, which comprises administering an effective amount of a composition comprising a pharmaceutically acceptable carrier, and a compound of any one of claims 1-2 and 4-7, an optically active form thereof, a pharmaceutically acceptable salt thereof or an optically active form of the salt thereof, as an active ingredient.

10. The method of claim 9, further comprising concomitant administration of said composition with a different therapeutic drug for osteoporosis.

11. The method of claim 10, wherein the different therapeutic drug for osteoporosis is selected from the group consisting of a calcium agent, a vitamin D preparation, a vitamin K preparation, a female hormone preparation, an estrogen antagonist preparation, an anabolic steroid preparation, a parathyroid hormone preparation, a calcitonin preparation, a bisphosphonate preparation and an ipriflavone preparation.

12. A calcium receptor antagonist comprising a pharmaceutically acceptable carrier, and a compound of any one of claims 1-2 and 4-7, an optically active form thereof, a pharmaceutically acceptable salt thereof or an optically active form of the salt thereof as an active ingredient.

13. A PTH secretagogue comprising a pharmaceutical acceptable carrier and a compound of any one of claims 1-2 and 4-7, an optically active form thereof, a pharmaceutically acceptable salt thereof or an optically active form of the salt thereof as an active ingredient.

* * * * *

UNITED STATES PATENT AND TRADEMARK OFFICE
CERTIFICATE OF CORRECTION

| | | |
|---|---|---|
| PATENT NO. | : 7,304,174 B2 | |
| APPLICATION NO. | : 10/830480 | |
| DATED | : December 4, 2007 | |
| INVENTOR(S) | : Yuko Shinagawa et al. | |

It is certified that error appears in the above-identified patent and that said Letters Patent is hereby corrected as shown below:

COLUMN 9

Line 14, "osteoarthrisis" should read --osteoarthritis--; and
    Line 56, "$R_A$," should read --$R^A$,--.

COLUMN 10

Line 27, "was improved a" should read --has an improved--.

COLUMN 14

Line 64, "and $R^6$" should read --and $R^8$--.

COLUMN 16

Line 34, "2'-(1-[(2R)-3-[(1" should read --2'-[1-[(2R)-3-[[1--.

COLUMN 20

Line 18, ")ethyl]-3-carboxy]" should read --]ethyl]-3-carboxy--.

COLUMN 22

Line 52, "acid" should read --acid,--.

COLUMN 23

Line 3, "acid" should read --acid,--.

COLUMN 25

Line 17, "atom, is" should read --atom,--.

COLUMN 30

Line 1, "$X_1$" should read --$X^1$--;
    Line 10, "$X_2$" should read --$X^2$--; and
    Line 52, "group, an" should read --group, a--.

UNITED STATES PATENT AND TRADEMARK OFFICE
CERTIFICATE OF CORRECTION

| | |
|---|---|
| PATENT NO. | : 7,304,174 B2 |
| APPLICATION NO. | : 10/830480 |
| DATED | : December 4, 2007 |
| INVENTOR(S) | : Yuko Shinagawa et al. |

It is certified that error appears in the above-identified patent and that said Letters Patent is hereby corrected as shown below:

COLUMN 33

Line 14, "$_{-CH2}$-NH-," should read -- -$CH_2$-NH-,--.

COLUMN 41

Line 51, "2'-[1-([(2R)" should read --2'-[1-[(2R)--; and
　　　Line 65, "2'-[1-'[(2R)" should read --2'-[1-[(2R)--.

COLUMN 50

Line 25, "(iia)." should read --(iva).--.

COLUMN 55

Line 33, "s" (second occurrence) should be deleted.

COLUMN 66

Line 49, "is" should be deleted.

COLUMN 69

Line 14, "Rc-OC" should read --$R^c$-OC--.

COLUMN 71

Line 3, "isoproanol," should read --isopropanol,--; and
　　　Line 13, "osteoarthrisis," should read --osteoarthritis,--.

COLUMN 75

Line 5, "(1-(3-Fluoro-4-methylphenyl)-2-methylpropan-2-yl)amine," should
　　　　　read --[1-(3-Fluoro-4-methylphenyl)-2-methylpropan-2-yl]amine,--; and
　　　Line 58, "(1-(3-Fluoro-4-methylphenyl)-2-methylpropan-2-yl)amine," should
　　　　　read --[1-(3-Fluoro-4-methylphenyl)-2-methylpropan-2-yl]amine,--.

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

COLUMN 76

Lines 4-5, "1.02 (3H, s), 1.00 (3H,s)" should read --1.02(3H, s), 1.00(3H, s).--; and
Line 37, "1H-NMR" should read --$^1$H-NMR--.

COLUMN 77

Line 44, "1-(4-Chloro-3-fluorophenyl)-2-methylpropan-2-ylamine" should read --[1-(4-Chloro-3-fluorophenyl)-2-methylpropan-2-yl]amine--.

COLUMN 78

Line 24, "1-(4-chloro-3-fluorophenyl)-2-methylpropan-2-ylamine" should read --[1-(4-Chloro-3-fluorophenyl)-2-methylpropan-2-yl]amine--.

COLUMN 80

Table 1, "$^1$H-NMR" should read --$^1$H-NMR--; "1.04(3H, s)," should read --1.04(3H, s).--;
Table 2, "1.04(3H, s)" (first occurrence) should read --1.04(3H, s).--; "2.90-2.40(7H, m)," (second occurrence) should read --2.90-2.40(7H, m), 2.28(3H, s), 1.27(3H, d, J=6.2Hz),--; and "1.03(3H, s)" should read --1.03(3H, s).--.

COLUMN 82

Table 3, "7.84(1H, d, J=8.3Hz)," should read --7.84(1H, d, J=8.3Hz), 7.54(1H, dd, J=7.9, 1.2Hz),--;
Table 4, "1.02(3H, s)" should read --1.02(3H, s).--; and "1.07(3H, s)," should read --1.07(3H, s).--.

COLUMN 84

Table 4-cont., "8.69(1H, s)," should read --8.69(1H, s), 8.16(1H, d, J=1.6Hz), 7.78-7.17(11H, m),--; and
Table 5, "0.30-0,20(2H, m)," should read --0.30-0.20(2H, m),--.

UNITED STATES PATENT AND TRADEMARK OFFICE
CERTIFICATE OF CORRECTION

PATENT NO.       : 7,304,174 B2
APPLICATION NO.  : 10/830480
DATED            : December 4, 2007
INVENTOR(S)      : Yuko Shinagawa et al.

It is certified that error appears in the above-identified patent and that said Letters Patent is hereby corrected as shown below:

COLUMN 85

Table 6, " 1-16 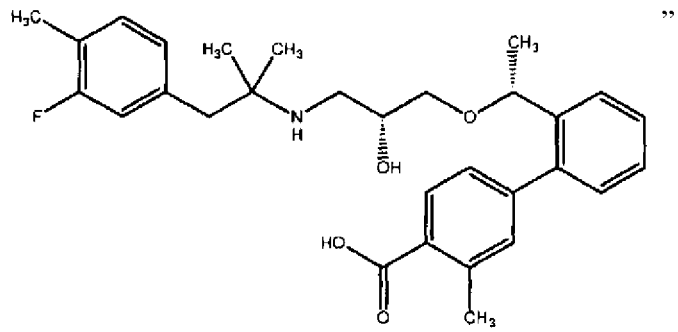 "

should read

-- 1-16 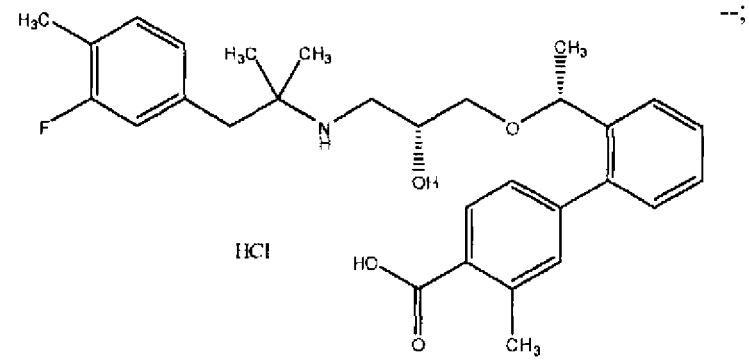 --;

and

Table 7, " 1-18 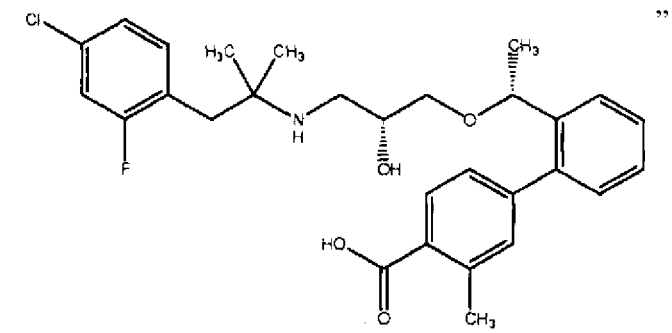 "

should read

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

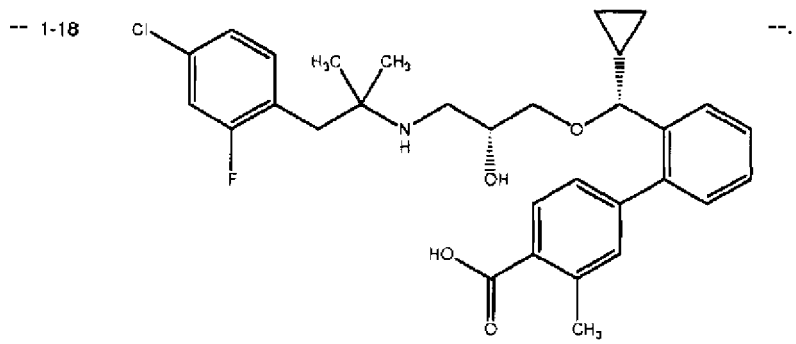

COLUMN 86

Table 6, "1.15-1.00(7H., m)," should read --1.15-1.00(7H, m),--; "0.35-.020(2H, m), -0.15--0.20(1H, m)." should read --0.35-0.20(2H, m), -0.15--0.20(1H, m).--; "4.49(1H, J=6.4Hz)," should read --4.49(1H, q, J=6.4Hz),--; and
Table 7, "2.90-2.50(7H, m)," should read --2.90-2.50(7H, m), 1.15-0.95(7H, m), 0.50-0.40(1H, m),--.

COLUMN 88

Table 8, "(400MH$^+$," should read --(400MHz,--.

COLUMN 90

Table 10, "2.96-2.91(1H, m)," should read --2.96-2.91(3H, m),--; and "4.556-4.47(1H, m)," should read --4.56-4.47(1H, m),--.

COLUMN 92

Table 12, "7.68(1H, s)," should read --7.68(1H, s), 7.62(1H, d, J=8.1Hz), 7.54(1H, m),--; and "1.02(3H, s)" should read --1.02(3H, s),--.

COLUMN 94

Table 13, "1:1 Hz)," should read --1.1 Hz), 7.34(1H, ddd, J=7.3, 7.3, 1.1 Hz),--; "6.96-6.88(2H, m)" should read --6.96-6.88(2H, m),--; and "2.80-2.70(3H, m)," should read --2.80-2.70(3H, m), 2.58-2.51(1H, m), 2.18(3H, s),--.

UNITED STATES PATENT AND TRADEMARK OFFICE
CERTIFICATE OF CORRECTION

| | |
|---|---|
| PATENT NO. | : 7,304,174 B2 |
| APPLICATION NO. | : 10/830480 |
| DATED | : December 4, 2007 |
| INVENTOR(S) | : Yuko Shinagawa et al. |

It is certified that error appears in the above-identified patent and that said Letters Patent is hereby corrected as shown below:

COLUMN 96

Table 15, "754-7.30(6H, m)," should read --7.54-7.30(6H, m),--; "DMSO-d$^6$)" should read --DMSO-d$_6$)--; and "2.16(3H, s)" should read --2.16(3H, s),--.

COLUMN 98

Table 16, "1.8Hz)," should read --1.8Hz), 7.18(1H, dd, J=7.6, 1.4 Hz),--; and Table 17, "0.84(3H, J=6.6 Hz)." should read --0.84(3H, d, J=6.6 Hz).--.

COLUMN 102

Table 19-cont., "DMSO-d$^6$)" should read --DMSO-d$_6$)--.

COLUMN 104

Table 21-cont., "7.21-7.18(1H,s)," should read --7.21-7.18(3H,m),--; Table 22, "53O(M+H)$^{30}$" should read --530(M+H)$^+$.--; "7.56-7.777(4H,m)," should read --7.56-7.50(4H,m),--; and "1.10(EH,brs)." should read --1.10(6H,brs).--.

COLUMN 106

Table 23, Ex. No. 1-60, "1.00(3H,s)," should read --1.00(3H,s).--; "2.70-2.64(31-I,m)," should read --2.70-2.64(3H,m),--; and "0.97(3H,s)," should read --0.97(3H,s).--.

COLUMN 108

Table 24-cont., "(300 MHz," should read --(400 MHz,--; and "0.18 (1H,brs)," should read --0.18(1H,brs).--; Table 25, "7.24-7.07(2H,M)," should read --7.24-7.07(2H,m),--; "2.77-2.65(1H,r)," should read --2.77-2.65(1H,m),--; and "0.34(1H,brs)." should read -- –0.34(lH,brs).--.

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

COLUMN 110

Table 26, "4.57C1H,q,J=6.3Hz)," should read --4.57(1H,q,J=6.3Hz),--;
    Table 27, "3.03-2.95C1H,m)," should read --3.03-2.95(1H,m),--;
        "(400 MHz," (second occurrence) should read --(300 MHz,--;
        "7.51C1H,d,J=8.1Hz)," should read --7.51(1H,d,J=8.1Hz),--; and
        "7.16C1H,d,J=7.7Hz), 7.0E-7.04C3H,m)," should read
        --7.16(1H,d,J=7.7Hz), 7.06-7.04(3H,m),--.

COLUMN 112

Table 27-cont., "3.23(2H,t,J8.8Hz)," should read --3.23(2H,t,J=8.8Hz),--;
    Table 28, "(300 MHz," (first occurrence) should read --(400 MHz,--;
        "7.85-7.66(*6H, m)," should read --7.85-7.66(6H, m),--; and
        "7.98(1H,d,J=8.Hz)," should read --7.98(1H,d,J=8.1Hz),--.

COLUMN 114

Table 29, "(400 MHz," (second occurrence) should read --(300 MHz,--;
        "3.71-3.70(1H,rn)," should read --3.71-3.70(1H,m),--.

COLUMN 116

Table 31, "$^1$-NMR" (both occurrences) should read --$^1$H-NMR--; and
        "(3H,d,J6.6Hz)," should read --(3H,d,J=6.6Hz),--.

COLUMN 118

Table 32, "6.95C1H,dd,J=11,1.2Hz)," should read --6.95(1H,dd,J-11, 1.2Hz),--;
        "3.14(2H,d,J=5.EHz)," should read --3.14(2H,d,J=5.6Hz),--; and
        "1.02(3H,s)," should read --1.02(3H,s).--.

COLUMN 120

Table 34, "$^1$-NMR (400MHz, 6ppm," should read --$^1$H-NMR (400MHz, δppm,--.

COLUMN 122

Table 37, "2.56-2.654(3H,m)," should read --2.56-2.54(3H,m),--; and "$^1$-NMR
        (400MHz, 8ppm," should read --$^1$H-NMR (400MHz, δppm,--.

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

COLUMN 124

Table 38, "1.12(3H,s)" should read --1.12(6H,s)--; "3.19-2.65(GH,m)," should read --3.19-2.65(6H,m),--; and
Table 39, "7.53-47.29(3H,m)," should read --7.53-7.29(3H,m),--.

COLUMN 126

Table 40, "7.48-7.31(3H.m)," should read --7.48-7.31(3H,m),--.

COLUMN 127

Table 43, " 1-108 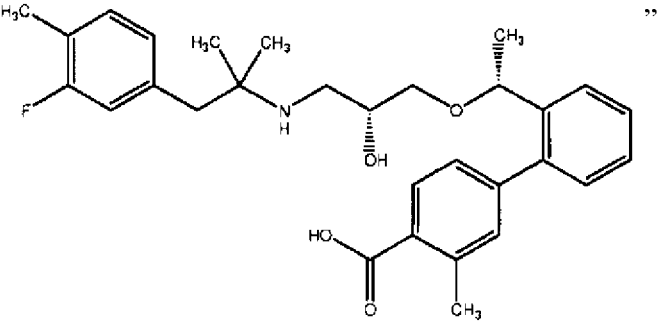 "

should read

-- 1-108 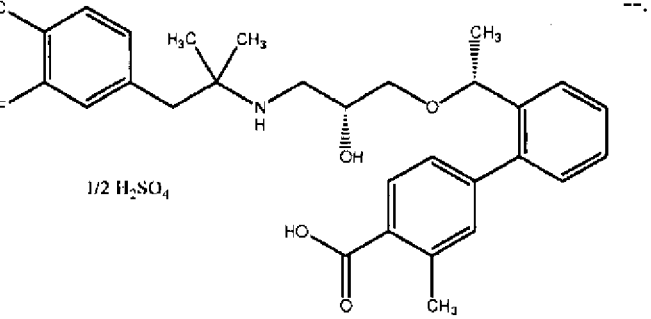 --.

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

COLUMN 128

Table 42, "$^1$H-NNR" should read --$^1$H-NMR--; "544(M+H)$^+$" should read --544(M+H)$^+$.--;
Table 43, "J=7.4, 7.41.4Hz)," should read --J=7.4, 7.4, 1.4Hz),--; "2.19(s, 3H)," should read --2.19(3H, s),--; "$^1$H-NNR" should read --$^1$H-NMR--; and "7.46(1H, ddd.J=7.4," should read --7.46(1H, ddd, J=7.4,--.

COLUMN 130

Table 44, "$^1$H-NNR" should read --$^1$H-NMR--; and "2.59(3H.s)," should read --2.59(3H,s),--.

COLUMN 136

Line 29-30, "1-(3-fluoro-4-methylphenyl)-2-methylpropan-2-ylamine" should read --[1-(3-fluoro-4-methylphenyl)-2-methylpropan-2-yl]amine--.

COLUMN 137

Table 45, " 2-2 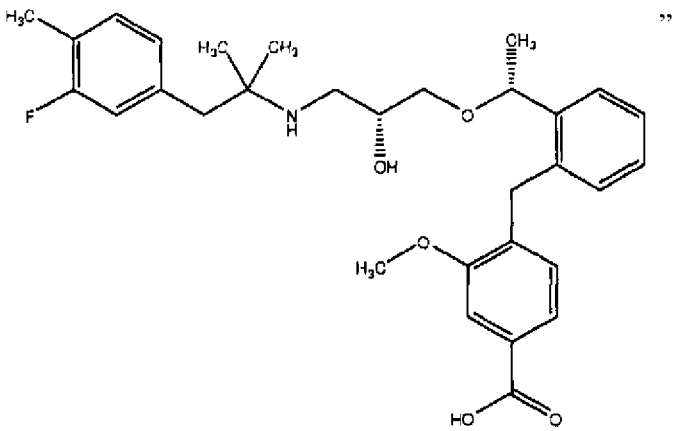 "

should read

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

-- 2-2 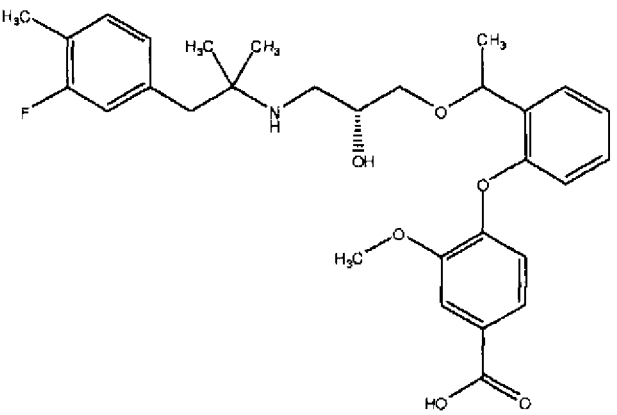 --; and

" 2-3 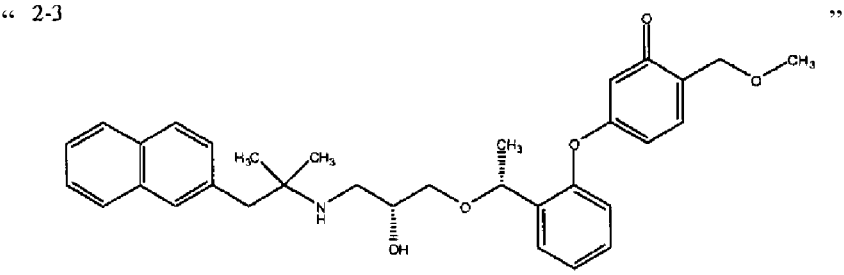 "

should read

-- 2-3 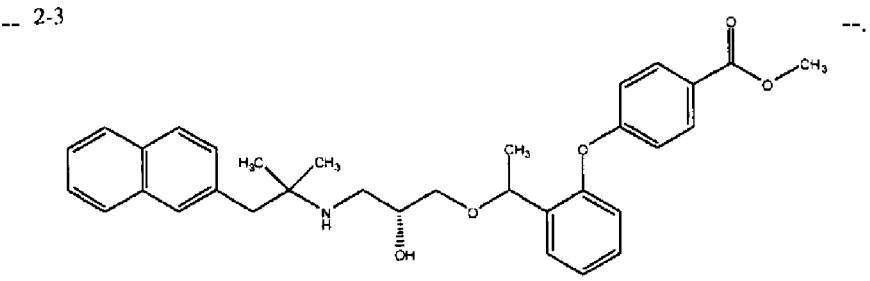 --.

COLUMN 138

Table 46, "J=6.41Hz" should read --J=6.4Hz--; and "3.90-3.70(1H, m), 3.35-3.20(2H, m), 3.00-2.40(4H, m), 1.31(3H, d, J=6.4Hz)," (second occurrence) should be deleted.

UNITED STATES PATENT AND TRADEMARK OFFICE
CERTIFICATE OF CORRECTION

PATENT NO.         : 7,304,174 B2
APPLICATION NO.    : 10/830480
DATED              : December 4, 2007
INVENTOR(S)        : Yuko Shinagawa et al.

It is certified that error appears in the above-identified patent and that said Letters Patent is hereby corrected as shown below:

COLUMN 139

Table 46-cont., " 2-6 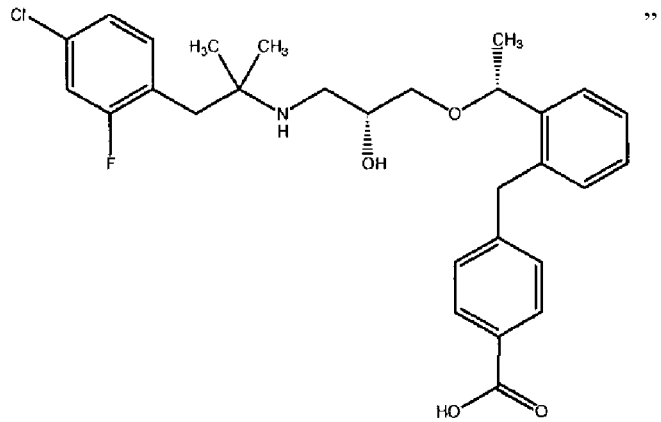 "

should read

-- 2-6 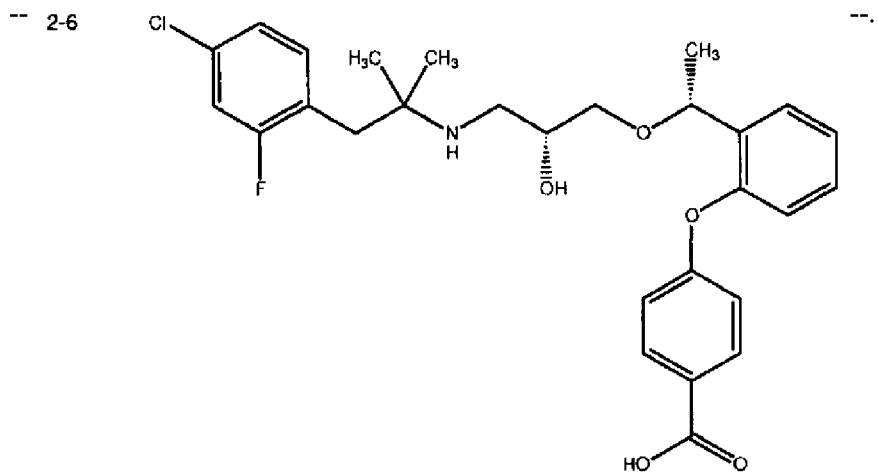 --.

COLUMN 140

Table 46-cont., "(6H, m) MS(EST, m/z)" should read --(6H, m). MS(ESI, m/z)--; and "4.70(1H, q, J=6.2Hz)," should read --4.70(1H, q, J=6.2Hz), 3.90(1H, m), 3.30-3.26(2H, m),--.

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

COLUMN 141

Table 47-cont., " 2-9 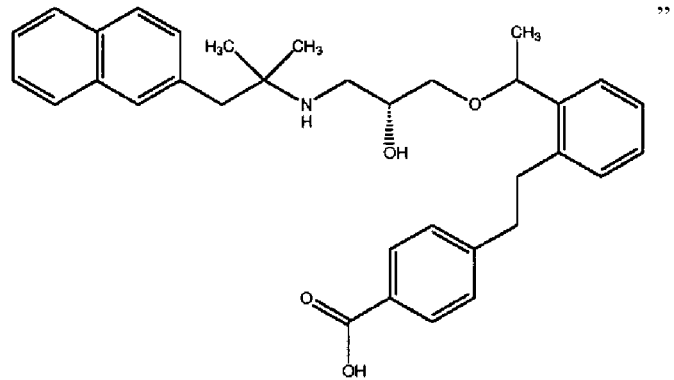 "

should read

-- 2-9 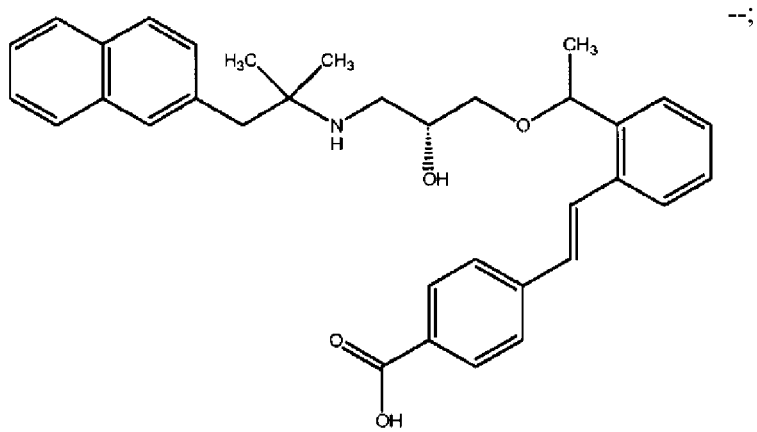 --;

UNITED STATES PATENT AND TRADEMARK OFFICE
CERTIFICATE OF CORRECTION

PATENT NO. : 7,304,174 B2  Page 13 of 17
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

Table 48, " 2-11 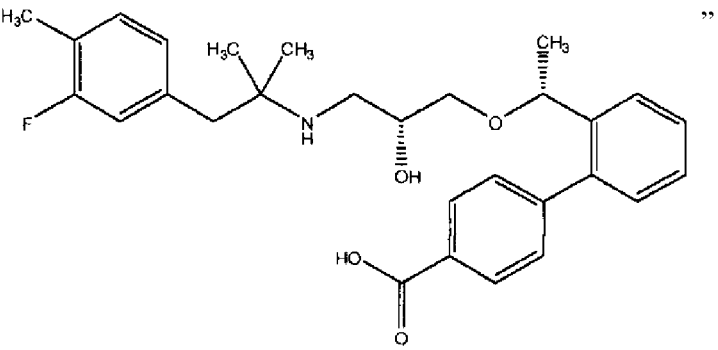 "

should read

-- 2-11 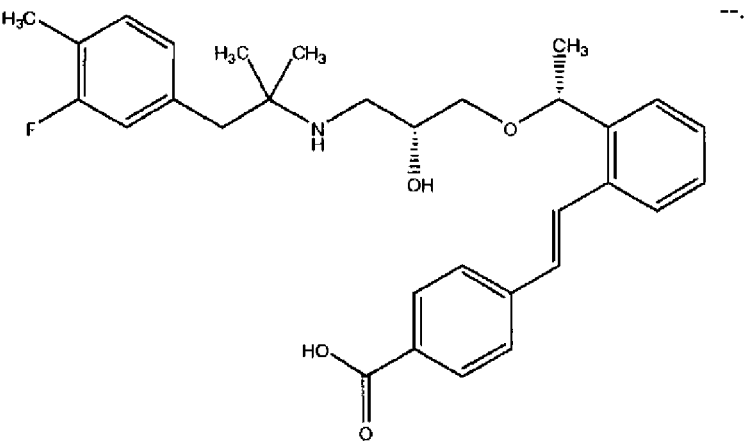 --.

COLUMN 143

Table 48-cont., " 2-13 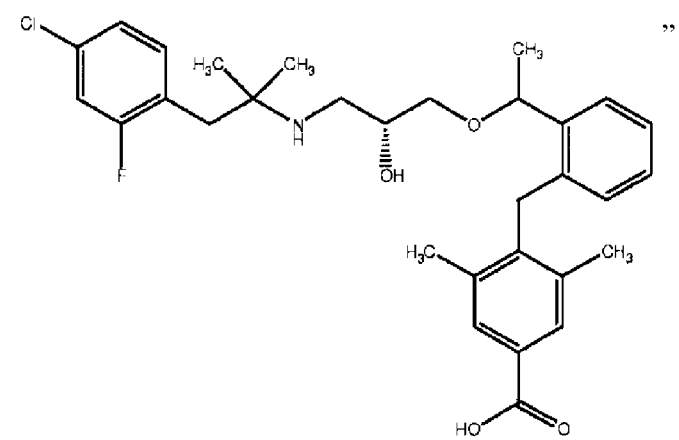 "

UNITED STATES PATENT AND TRADEMARK OFFICE
CERTIFICATE OF CORRECTION

PATENT NO. : 7,304,174 B2  Page 14 of 17
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

should read
-- 2-13

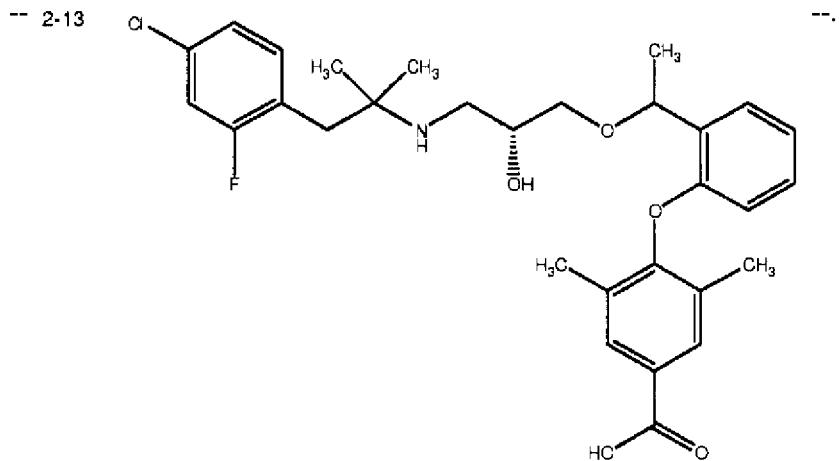

--.

COLUMN 144

Table 48-cont., "7.48-7.42(1H, m)," should read --7.48-7.42(1H, m), 7.32-7.26(2H, m), 7.16-7.13(1H, m),--;
Table 49, "7.39(1H, dd, J=7.5, 1.7Hz)," should read --7.39(1H, dd, J=7.5, 1.7Hz), 7.33(1H, dd, J=8.4, 1.6Hz),--; "MS(EST, m/z)" should read --MS(ESI, m/z)--; and "2.64(1H, dd, J=12, 7.71Hz)," should read --2.64(1H, dd, J=12, 7.7Hz),--.

COLUMN 146

Table 50, "3.70(1H, m)," should read --3.70(1H, m), 3.09(2H, d, J=7.4Hz),--.

UNITED STATES PATENT AND TRADEMARK OFFICE
CERTIFICATE OF CORRECTION

PATENT NO.        : 7,304,174 B2
APPLICATION NO.   : 10/830480
DATED             : December 4, 2007
INVENTOR(S)       : Yuko Shinagawa et al.

It is certified that error appears in the above-identified patent and that said Letters Patent is hereby corrected as shown below:

COLUMN 147

Table 51-cont., " 2-20 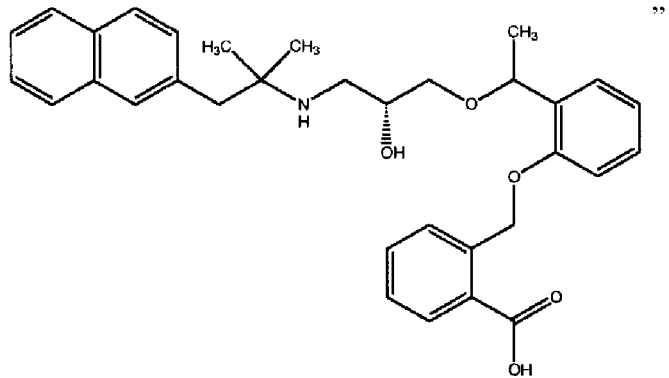 "

should read

-- 2-20 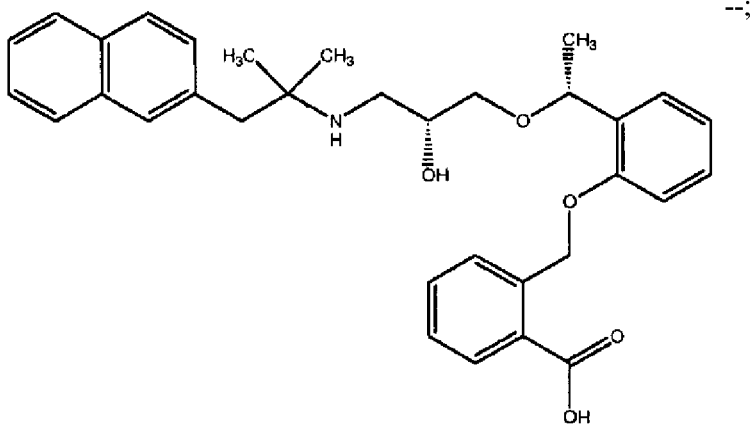 --;

and

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

Table 52, " 2-21

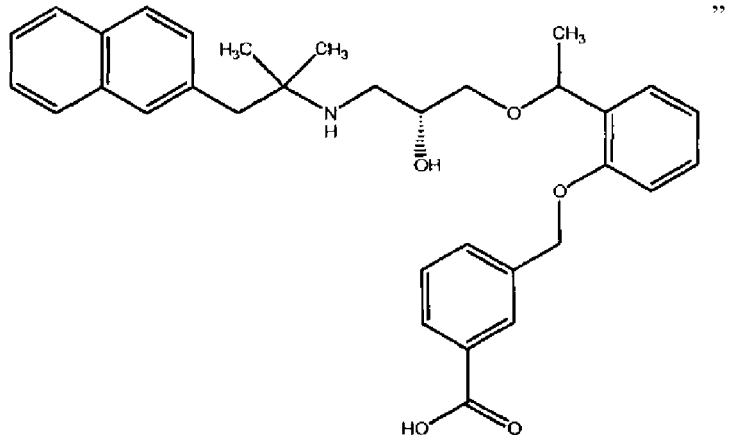

"

should read

-- 2-21

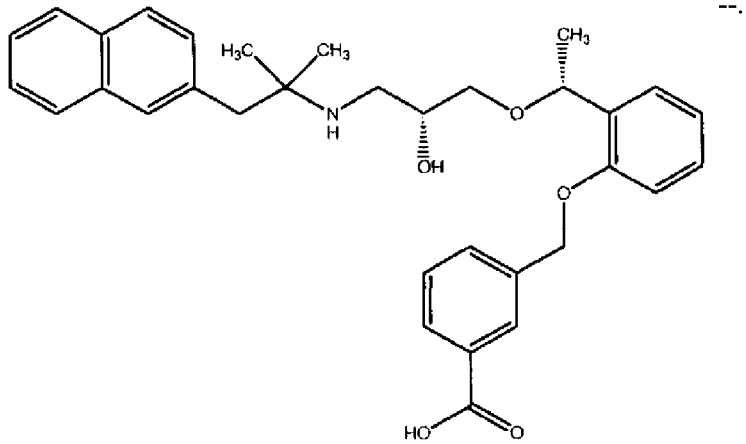

--.

COLUMN 148

Table 52, "$^1$H-NNR" should read --$^1$H-NMR--.

UNITED STATES PATENT AND TRADEMARK OFFICE
CERTIFICATE OF CORRECTION

PATENT NO. : 7,304,174 B2
APPLICATION NO. : 10/830480
DATED : December 4, 2007
INVENTOR(S) : Yuko Shinagawa et al.

It is certified that error appears in the above-identified patent and that said Letters Patent is hereby corrected as shown below:

COLUMN 150

Table 54, "$^1$H-NNR" should read --$^1$H-NMR--; and
Table 55, "15(1H, dd," should read --7.15(1H, dd,--.

COLUMN 152

Table 57, "$^1$H-NNR" should read --$^1$H-NMR--; "dd, =7.2," should read --dd, J=7.2,--; and "7.27(2H,m)" should be deleted.

COLUMN 154

Table 57-cont., "$^1$H-NNR" should read --$^1$H-NMR--; and
Table 58, "dd, 6.6," should read --dd, J=6.6,--.

COLUMN 161

Line 37, "aspects;" should read --aspects:--.

COLUMN 162

Line 44, "osteoarthrisis," should read --osteoarthritis,--.

Signed and Sealed this

Twenty-ninth Day of December, 2009

David J. Kappos
*Director of the United States Patent and Trademark Office*